United States Patent [19]

Harpold et al.

[11] Patent Number: 5,429,921
[45] Date of Patent: Jul. 4, 1995

[54] ASSAYS FOR AGONISTS AND ANTAGONISTS OF RECOMBINANT HUMAN CALCIUM CHANNELS

[75] Inventors: Michael M. Harpold; Steven B. Ellis, both of San Diego; Mark E. Williams, Carlsbad; Daniel H. Feldman, San Diego; Ann F. McCue, La Mesa, all of Calif.; Robert Brenner, Austin, Tex.

[73] Assignee: The Salk Institute Biotechnology/Industrial Assoc. Inc., La Jolla, Calif.

[21] Appl. No.: 745,206

[22] Filed: Aug. 15, 1991

Related U.S. Application Data

[63] Continuation-in-part of Ser. No. 620,250, Nov. 30, 1990, abandoned, Ser. No. 482,384, Feb. 20, 1990, Pat. No. 5,386,025, and Ser. No. 603,751, Apr. 4, 1989, abandoned, which is a continuation-in-part of Ser. No. 176,899, Apr. 4, 1988, abandoned, said Ser. No. 620,250, is a continuation-in-part of Ser. No. 176,899, Apr. 4, 1988.

[51] Int. Cl.$^6$ ............................................. C12Q 1/02
[52] U.S. Cl. .................................. 435/4; 435/69.1; 435/240.2; 435/7.2
[58] Field of Search .............. 435/7.21, 69.1, 91, 435/172.1, 172.3, 240.1, 320.1; 530/350, 395; 536/23.2

[56] References Cited

U.S. PATENT DOCUMENTS

| | | | |
|---|---|---|---|
| 4,788,135 | 11/1988 | Davis et al. | 435/6 |
| 4,912,202 | 3/1990 | Campbell et al. | 530/387 |
| 4,954,436 | 9/1990 | Froehner et al. | 435/7 |
| 5,024,939 | 6/1991 | Gorman | 435/69.1 |

FOREIGN PATENT DOCUMENTS

| | | |
|---|---|---|
| 0507170 | 3/1992 | European Pat. Off. |
| 0556651 | 4/1993 | European Pat. Off. |
| 8907608 | 8/1989 | WIPO |
| 8909834 | 10/1989 | WIPO |

OTHER PUBLICATIONS

Pragnell, et al., "Cloning and tissue-specific expression of the brain calcium channel β-subunit," *FEBS Letters*. 291:253 (1991).

DeJongh, et al., "Subunits of purified calcium channels," *J. Biol. Chem.*, 265 (25): 14738–14741 (1990). (Best available copy, sufficiently leigible for applicant to read).

Carbone, et al., "Ca currents in human neuroblastoma IMR32 cells: kinets, permeability and pharmacology," *Pfluegers Arch.* 416:170–179 (1990). (Best available copy, sufficiently legible for applicant to read).

Bosse, et al., "The cDNA and deduced amino acid sequence of the γsubunit of the L-type calcium channel from rabbit skeletal muscle," FEBS 267 (1) 153–156 (1990).

Burns, et al., "Calcium channel activity of purified human synexin and structure of the human synexin gene," *P.N.A.S.* 86:3798–3802 (1989).

Campbell, et al., "32,000–Dalton subunit of the 1,4–dihydropyridine receptor," *Ann. N.Y. Acad. Sci.* 560:251–257 (1989).

Dascal, N., "The use of Xenopus oocytes for the study of ion channels," *CRC Critical Rev. Biochem.* 22 (4): 317–387 (1987).

De Jongh, et al., "Subunits of purified calcium channels," *J. Bio. Chem.* 265 (25)14738–14741 (1990).

Jay, et al., "Primary structure of the γ subunit of the DHP–sensitive calcium channel from skeletal muscle," *Science* 248: 490–492 (1990).

Jay et al., "Structural characterization of the dihydropyridine–sensitive calcium channel αhd 2–subunit and the associated δ peptides," *J. Bio. Chem.* 266 (5) 3287–3293 (1991).

(List continued on next page.)

Claudio, T. (1987) Proc. Natl. Acad. Sci. USA 84:5967–71.

*Primary Examiner*—Garnette D. Draper
*Assistant Examiner*—David L. Fitzgerald
*Attorney, Agent, or Firm*—Brown, Martin, Haller & McClain

[57] ABSTRACT

Human calcium channel $\alpha_1$-, $\alpha_2$-, $\beta$- and $\gamma$-subunit encoding cDNAs, and related compositions and methods, are provided.

29 Claims, 14 Drawing Sheets

OTHER PUBLICATIONS

Leung, et al., "Monoclonal antibody characterization of the 1, 4–dihydrophyridine receptor of rabbit skeletal muscle," *Ann. N.Y. Acad. Sci.* 522: 43–46 (1988).

Starr, et al., "Primary structure of a calcium channel that is highly expressed in the rat cerebellum," *P.N.A.S.* 88: 5621–5625 (1991).

Vaghy, et al., "Mechanism of Action of Calcium Channel Modulator Drugs," *Ann. N.Y. Acad. Sci.* 522: 176–186 (1988).

Ahlijanian et al., "Subunit structure and localization of dihydropyridine-sensitive calcium channels in mammalian brain, spinal cord, and retina," *Neuron*, 4: 819–832 (1990).

Blount et al., "Assembly Intermediates of the Mouse Muscle Nicotinic Acetylcholine Receptor in Stably Transfected Fibroblasts," *J. Cell. Biol.*, 111: 2601 (1990).

Carbone et al., "Ca currents in human neuroblastoma IMR32 cells: kinetics, permeability and pharmacology," *Pfugers Arch.*, 416: 170–179 (1990).

Dascal et al., "Expression of modulation of voltage-gated calcium channels after RNA injection in Xenopus oocytes," *Science*, 231: 1147–1150 (1986).

Hess et al., "Calcium channels in vertebrate cells," *Ann. Rev. Neurosci.*, 13: 337–356 (1990).

Stanley et al., "Characterization of a Calcium Current in a Vertebrate Cholinergic Presynaptic Nerve Terminal," *J. Neurosci.*, 11:985 (1991).

Wei, et al., "Heterologous regulation of the cardiac $Ca^{2+}$ channel $\alpha_1$ subunit by skeletal muscle $\beta$ and $\gamma$ subunits," *J. Biol. Chem.* 266: 21943–21947 (1991).

Koch, et al., "cDNA Cloning of a Dihydropyridine-sensitive Calcium Channel from Rat Aorta," *J. Bio. Chem.* 265 (29): 17786–17791 (1990).

Sher, et al., "$\omega$-Conotoxin binding and effects on calcium channel function in human neuroblastoma and rat pheochromocytoma cell lines," *FEBS* 235 (1, 2):178–182 (1988).

Sher, et al., "Voltage-operated Calcium Channels in Small Cell Lung Carcinoma Cell Lines: Pharmacological, Functional, and Immunological Properties," *Cancer Res.* 50 (13): 3892–3896 (1990).

Powers et al. (1991) Assignment of the Human Gene for the $\alpha_1$ Subunit of the Cardiac DHP-Sensitive $Ca^{2+}$ Channel (CCHL1A1) to Chromosome 12p12-pter *Genomics* 10: 835–839.

Vaghy et al., "Identification of a novel 1,4–dihydropyridine– and phenylalkylamine–binding polypeptide in calcium channel preparation," *J. Biol. Chem.*, 262 (29): 14337–14342 (1987).

Leung et al., "Structural characterization of the 1,4–dihydropyridine receptor of the voltage-dependent $Ca^{2+}$ channel from rabbit skeletal muscle," *J. Biol. Chem.*, 262 (17): 7943–7946 (1987).

Sharp et al., "Identification and characterization of the dihydropyridine–binding subunit of the skeletal muscle dihydropyridine receptor," *J. Biol. Chem.*, 62 (25): 12309–12315 (1987).

Takahashi et al., "Subunit structure of dihydropyridine-sensitive calcium channels from skeletal muscle," *Proc. Natl. Acad. Sci (USA)*, 84:5478–5482 (1987).

Takahashi and Catterall, "Dihydropyridine-sensitive calcium channels in cardiac and skeletal muscle membranes: studies with antibodies against the $\alpha$-subunits," *Biochemistry*, 26 (17): 5518–5526 (1987).

Morton and Froehner, "Monoclonal antibody identifies a 200-kDA subunit of the dihydropyridine-sensitive calcium channel," *J. Biol. Chem.*, 262 (25): 11904–11907 (1987).

Barhanin et al., "The calcium channel antagonists receptor from rabbit skeletal muscle: reconstitution after purification and subunit characterization," *Eur. J. Biochem.*, 164: 525–531 (1987).

Sieber et al., "The 165-kDa peptide of the purified skeletal muscle dihydropyridine receptor contains the known regulatory sites of the calcium channel," *Eur. J. Biochem.*, 167: 117–122 (1987).

Kim et al., "IgG from patients with Lambert–Eaton syndrome blocks voltage-dependent calcium channels," *Science*, 239: 405–409 (1988).

Claudio et al., "Genetic reconstitution of functional acetylcholine receptor channels in mouse fibroblasts," *Science*, 238: 1688–1694 (1987).

Tanabe et al., "Primary structure of the receptor for calcium channel blockers from skeletal muscle," *Nature*, 328: 313–318 (1987).

Nakayama et al., "Purification of a putative $Ca^{2+}$ channel protein from rabbit skeletal muscle," *J. Biol. Chem.*, 262: 6572–6576 (1987).

(List continued on next page.)

OTHER PUBLICATIONS

Lang et al., "The effect of myasthenic syndrome antibody on presynaptic calcium channels in the mouse," *J. Physiol.*, 390:257–270 (1987).

Curran and Morgan, "Barium modules c-fos expression and post-translational modification," *Proc. Natl. Acad. Sci.*, 83: 3521–8524 (1986).

Fisch et al., "c-fos sequences necessary for basal expression and induction by epidermal growth factor, 12-0-tetradecanoyl phorbol-13-acetate, and the calcium ionophore," *Mol. Cell. Biol.*, 7 (10): 3490–3502 (1987).

Noda et al., "Existence of distinct sodium channel messenger RNAs in rat brain," *Nature*, 320: 188–192 (1986).

Noda et al., "Expression of functional sodium channels from cloned cDNA," *Nature*, 322: 826–828 (1986).

Mierendorf et al., "Gene isolation by screening kgt11 libraries with antiboides," *Methods in Enz.*, 152: 458–469 (1986).

Gustin et al., "Ion channels in yeast," *Science*, 233: 1195–1197 (1986).

Striessnig et al., "Photoaffinity labelling of the phenylalkylamine receptor of the skeletal muscle transverse-tubule calcium channel," *FEBS Letters*, 212: (2) 247–253 (1987).

Froehner, "New insights into the molecular structure of the dihydropyridine-sensitive calcium channel,": *TINS*, 11 (3): 90–92 (1988).

Catterall et al., "Molecular properties of dihydropyridine-sensitive calcium channels in skeletal muscle," *J. Bio. Chem.*, 263 (8): 3535–3538 (1988).

Curtis et al., "Purification of the calcium antagonist receptor of the voltage-sensitive calcium channel from skeletal muscle transverse tubules," *Biochemistry*, 23 (10): 2113–2118 (1984).

Borsotto et al., "The 1,4-dihydropyridine receptor associated with the skeletal muscle voltage-dependent $Ca^{2+}$ channel," *J. Biol. Chem.*, 260 (26): 14255–14263 (1985).

Cooper et al., "Purification and characterization of the dihydropyridine-sensitive voltage-dependent calcium channel from cardiac tissue," *J. Biol. Chem.*, 262 (2): 509–512 (1987).

Wood, "Gene cloning based on long oligonucleotide probes," *Methods in Enzymology, 152: 443–447 (1987).*

Schmid et al., "Immunochemical analysis of subunit structure of 1, 4-dihydropyridine receptors associated with voltage-dependent $Ca^{2+}$ channels in skeletal, cardiac, and smooth muscles," *Biochemistry*, 25:3492–3495 (1986).

Mishina et al., "Location of functional regions of acetylcholine receptor α-subunit by site-directed mutagenesis," *Nature*, 313: 369 (1985).

Hamill et al., "Improved patch-clamp techniques for high-resolution current recording from cells and cell-free membrane patches," *Pfluger Archive. European Journal of Physiology*, 391: 85–100 (1981).

Hess et al., "Different modes of Ca channel gating behvior favored by dihydropyridine Ca agonist and antagonists," *Nature*, 311: 538–544 (1984).

Leung et al., "Biochemical and ultrastructural characterization of the 1,4 -dihydropyridine receptor from rabbit skeletal muscle," *J. of Biol. Chem.*, 263 (2): 994–1001 (1988).

Imagawa et al., "Phosphorylation of the 1,4-dihydropyridine receptor of the voltage-dependent $Ca^{2+}$ channel by an intrinsic protein kinase in isolated triads from rabbit skeletal muscle," *J. of Biol. Chem.*, 262 (17): 8333–8339 (1987).

Miller, "Multiple calcium channels and neuronal function," *Science*, 235: 46–52 (1987).

Kozak, "An analysis of 5'-noncoding dequences from 699 vertebrate messenger RNAs," *Nucleic Acids Research*, 15 (20): 8125–8148 (1987).

von Heijne, "Signal sequences: the limits of variation," *Jour. of Mol. Biol.*, 184: 99–105 (1985).

Hubbard et al., "Synthesis and processing of asparagine-linked oligosaccharides[1,2]," *Ann. Rev. Biochem.*, 50:555–583 (1981).

Feramisco et al., "Optimal spatial requirements for the location of basic residues in peptide substrates for the cyclic AMP-dependent protein kinase," *Journal of Biological Chemistry*, 255(9):4240–4245 (1980).

Takahashi et al., "Identification of an α subunit of dihydropyridine-sensitive brain calcium channels," *Science*, 236:88–91 (1987).

Hofmann et al., "Regulation of the L-type calcium channel," *TIPS*, 8:393–398 (1987).

Curtis et al., "Reconstitution of the voltage-sensitive calcium channel purified from skeletal muscle transverse tubules," *Biochemistry*, 25:3077–3083 (1986).

Smith et al., "Calcium channel activity in a purified dihydropyridine-receptor preparation of skeletal muscle," *Biochemistry*, 26:7182–7188 (1987).

(List continued on next page.)

OTHER PUBLICATIONS

Meshi et al., "Nucleotide sequence of the 30K protein cistron of cowpea strain of tobacco mosaic virus," *Nucleic Acids Research*, 10(19):6111–6117 (1982).

Nikaido et al., "Molecular cloning of cDNA encoding human interleukin-2 receptor," *Nature*, 311:631–636 (1984).

Roberts et al., "Paraneoplastic myasthenic syndrome IgG inhibits $^{45}Ca^{2+}$ flux in a human small cell carcinoma line," *Nature*, 317:737–739 (1985).

Starr et al., Primary structure of a calcium channel that is highly expressed in rat cerebellum," *Proc. Natl. Acad. Sci. USA*, 88:5621–5625 (1991).

Snutch et al., "Distinct calcium channels are generated by alternative splicing and are differentially expressed in the mammalian CNS," *Neuron*, 7:45–57 (1991).

Hui et al., "Molecular cloning of multiple sybtypes of a novel brain isoform of the $a_1$ subunit of the voltage-dependent calcium channel," *Neuron*, 7:35–44 (1991).

Bean et al., "Classes of calcium channels in vertebrate cells," *Annu. Rev. Physiol.*, 51:367–384 (1989).

Swandulla et al., "Do calcium channel classifications account for neuronal calcium channel diversity?" *TINS*, 14(2):46–51 (1991).

Ruth et al., "Primary structure of the $\beta$ subunit of the DHP-sensitive calcium channel from skeletal muscle," *Science*, 245:1115–1118 (1989).

Mikami et al., "Primary structure and functional expression of the cardiac dihydropyridine-sensitive calcium channel," *Nature*, 340:230–233 (1989).

Biel et al., "Primary structure and functional expression of a high voltage activated calcium channel from rabbit lung," *FEBS Letters*, 269(2):409–412 (1990).

Mori et al., "Primary structure and functional expression from complementary DNA of a brain calcium channel," *Nature*, 350:398–402 (1991).

Snutch et al., "Rat brain expresses a heterogeneous family of calcium channels," *Proc. Natl. Acad. Sci. USA*, 87:3391–3395 (1990).

Perez-Reyes et al., "Molecular diversity of L-type calcium channels," *J. of Biol. Chem.*, 265(33):20430–20436 (1990).

Perez-Reyes, et al., "Induction of calcium currents by the expression of the $\alpha_1$-subunit of the dihydropyridine receptor from skeletal muscle," *Nature*, 340:233–236 (1989).

Koch et al., "Characterization of cDNA clones encoding two putative isoforms of the $\alpha_1$-subunit of the dihydropyridine-sensitive voltage-dependent calcium channel isolated from rat brain and rat aorta," *FEBS Letters*, 250(2):386–388 (1989).

Slish et al., "Evidence for the existence of a cardiac specific isoform of the $\alpha_1$-subunit of the voltage dependent calcium channel," *FEBS Letters*, 250(2):509–514 (1989).

Varadi et al., "Developmental regulation of expression of the $\alpha_1$ and $\alpha_2$ subunits mRNAs of the voltage-dependent calcium channel in a differentiating myogenic cell line," *FEBS Letters*, 250(2)CE:515–518 (1989).

Ruth et al., "Primary structure of the $\beta$-subunit of the DHP-sensitive calcium channel from skeletal muscle," *Science*, 245:1115–1118 (1989).

Jongh et al., Subunits of purified calcium channels: a 212-kDa form of $\alpha_1$ and partial amino acid sequence of a phosphorylation site of an independent $\beta$-subunit," *Proc. Natl. Acad. Sci. USA*, 86:8585–8589 (1989).

Hamilton et al., "Subunit composition of the purified dihydropyridine binding protein from skeletal muscle," *Biochemistry*, 28:7820–7828 (1989).

Nunoki et al., "Activation of purified calcium channels by stoichiometric protein phosphorylation," *proc. Natl. Acad. Sci. USA*, 86:6816–6820 (1989).

Ichida et al., "Photoaffinity labeling with dihydropyridine derivatives of crude membranes from rat skeletal, cardiac, ileal, and uterine muscles and whole brain," *J. Biochem.*, 105:767–774 (1989).

Sharp and Campbell, "Characterization of the 1,4-dihydropyridine receptor using subunit-specific polyclonal antibodies," *J.Bio. Chem.*, 264(5):2816–2825 (1989).

Campbell et al., "The biochemistry and molecular biology of the dihydropyridine-sensitive calcium channel," *TINS*, 11(10):425–430 (1988).

Pelzer et al., "Properties and regulation of calcium channels in muscle cells," *Rev. Physiol. Biochem. Pharmacol.*, 114:107–207 (1990).

Kim et al., "Studies on the structural requirements for the activity of the skeletal muscle dihydropyridine receptor/slow $Ca^{2+}$ channel," *J. Biol. Chem.*, 265(20):11858–11863 (1990).

(List continued on next page.)

OTHER PUBLICATIONS

Lotan et al., "Specific block of calcium channel expression by a fragment of dihydropyridine receptor cDNA," *Science*, 243:666–669 (1989).

Rampe et al., "[$^3$H]Pn200–110 binding in a fibroblast cell line transformed with the $\alpha_1$ subunit of the skeletal muscle L-type Ca$^{2+}$ channel," *Biochem. and Biophys. Research Communications*, 169(3):825–831 (1990).

Adams et al., "Intramembrane charge movement restored in dysgenic skeletal muscle by injection of dihydropyridine receptor cDNAs," *Nature*, 346:569–572 (1990).

Tanabe et al., "Cardiac-type excitation-contraction coupling in dysgenic skeletal muscle injected with cardiac dihydropyridine receptor cDNA," *Nature*, 344:451–453 (1990).

Tanabe et al., "Regions of the skeletal muscle dihydropyridine receptor critical for excitation-contraction coupling," *Nature*, 346:567–569 (1991).

Regulla et al., "Identifidation of the site of interaction of the dihydropyridine channel blockers nitrendipine and azidopine with the calcium-channel $\alpha_1$ subunit," *EMBO Journal*, 10(1):45–49 (1991).

Spedding, M., et al. (1984) Life Sci. 35:575–87.

Seagar, M. J., et al. (1988) Ann. N.Y. Acad. Sci. 522:162–75.

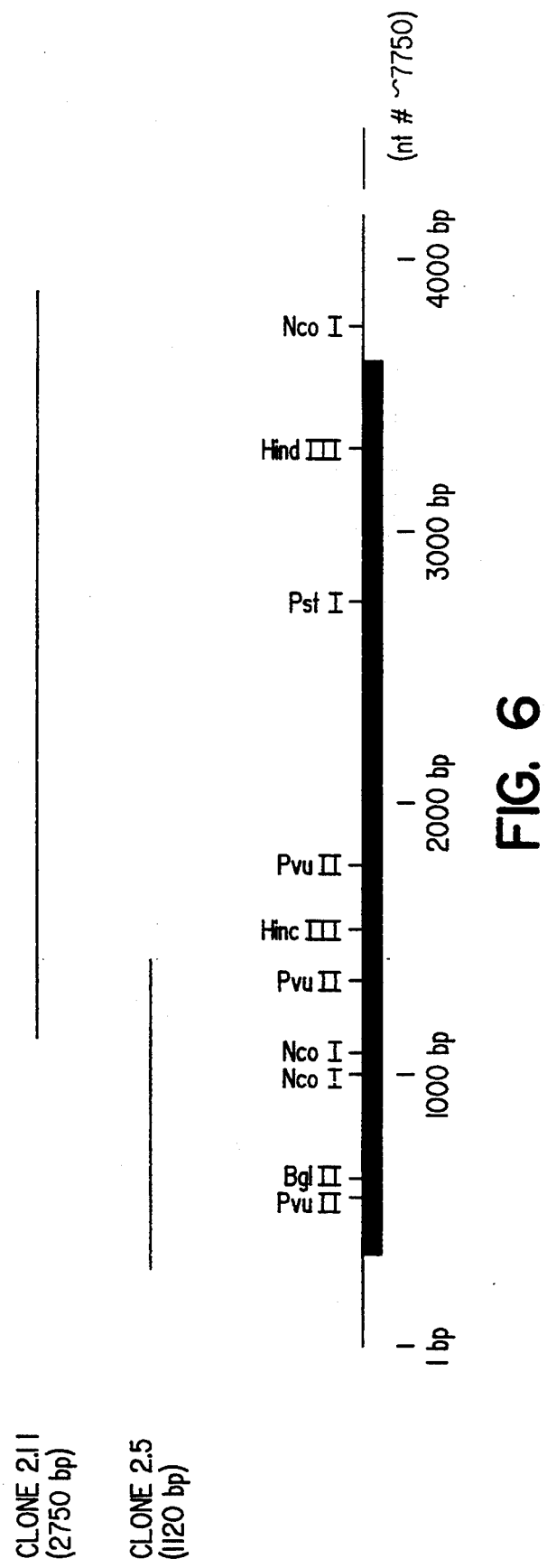

FIG. 7A

```
R.SK(β1)  PPASG NEMTNLAFEL EPLDLEEDEA ELGEQSGSAK TSVSSVTTPP PHGTRIPFFK KTEHV
          ||||| |||||||||| |||||||||| |||||||||| |||||||||||  |||||||||  ||  |||||
H.SK(β1)  PPASG NEMTNLAFEL DPLELEEEA  ELGEQSGSAK TSVSSVTTPP PHGKRIPFFK KTEHV
          |||||
H.BR(β2)  PPASA KQKQKS.... .......... .......... .......... .......... .TEHV
          ||||
H.AO(β4)  PPAS. .......... .......... .......... .......... .......... .TEHV
```

FIG. 7B

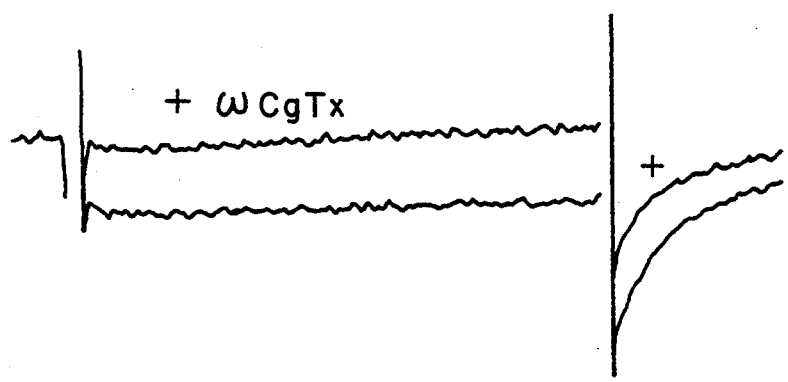
FIG. 10D  100 nA / 20 ms
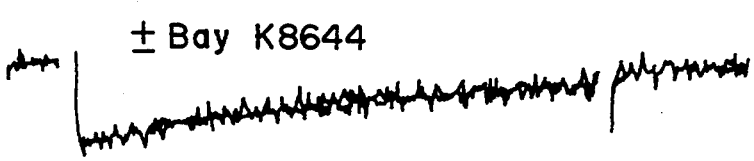
FIG. 10E  100 nA / 20 ms
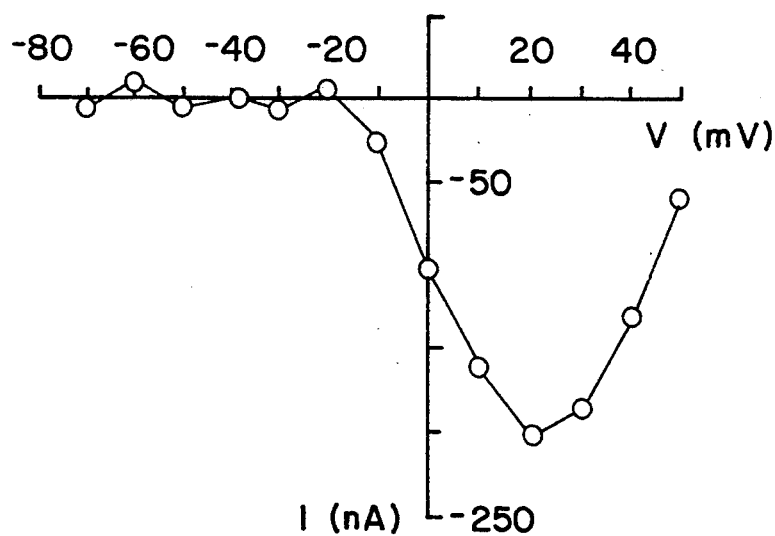
FIG. 10F

ASSAYS FOR AGONISTS AND ANTAGONISTS OF RECOMBINANT HUMAN CALCIUM CHANNELS

This application is a continuation-in-part of U.S. Ser. No. 620,250, filed Nov. 30, 1990, now abandoned, which is a continuation-in-part of U.S. Ser. No. 176,899, filed Apr. 4, 1988, now abandoned, and is also a continuation-in-part of U.S. Ser. No. 482,384, filed Feb. 20, 1990, now U.S. Pat. No. 5,386,025, and is also a continuation-in-part of U.S. Ser. No. 603,751, filed Apr. 4, 1989 as PCT/US89/01408 (U.S. application filed under 35 U.S.C. § 371 on Nov. 8, 1990), now abandoned, which is also a continuation-in-part of said application Ser. No. 176,899.

TECHNICAL FIELD

The present invention relates to molecular biology and pharmacology.

More particularly, the invention relates to calcium channel compositions and methods of making and using same.

BACKGROUND OF THE INVENTION

Calcium channels are membrane-spanning, multi-subunit proteins that allow controlled entry of $Ca^{2+}$ ions into cells from the extracellular fluid. Cells throughout the animal kingdom, and at least some bacterial, fungal and plant cells, possess one or more types of calcium channel.

The most common type of calcium channel is voltage dependent. In a voltage-dependent channel, the "opening" to allow an influx of $Ca^{2+}$ ions into the cells to begin, requires a depolarization to a certain level of the potential difference between the inside of the cell bearing the channel and the extracellular medium bathing the cell. The rate of influx of $Ca^{2+}$ into the cell depends on this potential difference. All "excitable" cells in animals, such as neurons of the central nervous system, peripheral nerve cells, and muscle cells, including those of skeletal muscles, cardiac muscles, and venous and arterial smooth muscles, have voltage-dependent calcium channels.

Calcium channels are physiologically important because the channels have a central role in regulating intracellular $Ca^{2+}$ levels. These levels are important for cell viability and function. Thus, intracellular $Ca^{2+}$ concentrations are implicated in a number of vital processes in animals, such as neurotransmitter release, muscle contraction, pacemaker activity, and secretion of hormones and other substances.

The rabbit skeletal muscle calcium channel is the most well-characterized of the calcium channels identified to date. Biochemical analysis of the calcium channel purified from rabbit skeletal muscle revealed that it consists of two large subunits, of between about 130 and about 200 kilodaltons ("kD") in molecular weight, and a number (generally thought to be one to three) of different smaller subunits, of less than about 60 kD in molecular weight. At least one of the larger subunits and possibly some of the smaller are glycosylated. Some of the subunits are capable of being phosphorylated.

The two large subunits of voltage-dependent calcium channels are designated herein the "$\alpha_1$-subunit" and the "$\alpha_2$-subunit".

The rabbit skeletal muscle calcium channel $\alpha_1$-subunit is not detectably changed in molecular weight when treated with dithiothreitol ("DTT") or with enzymes which catalyze removal of N-linked sugar groups from glycosylated proteins. The $\alpha_1$-subunit has a molecular weight of about 150 to about 170 kD when analyzed by sodium dodecylsulfate ("SDS")-polyacrylamide gel electrophoresis ("PAGE") after isolation from mammalian muscle tissue and has specific binding sites for various 1,4-dihydropyridines ("DHPs") and phenylalkylamines.

The molecular weight of the $\alpha_2$-subunit of the rabbit skeletal muscle calcium channel is at least about 130-150 kD, as determined by SDS-PAGE analysis in the presence of DTT after isolation from muscle tissue. However, in SDS-PAGE under non-reducing conditions (in the presence of N-ethylmaleimide), the $\alpha_2$-subunit migrates with a band of about 160-190 kD. The smaller fragments (of about 30 kD), which appear to be released upon reduction, are derived from the primary translation product of the $\alpha_2$ subunit transcript. There is evidence that the $\alpha_2$-subunit and the corresponding fragment produced under reducing conditions are glycosylated with at least N-linked sugars and do not have specified binding sites for 1,4-dihydropyridines and phenylalkylamines that are known to bind to the $\alpha_1$-subunit.

The $\beta$-subunit of the rabbit skeletal muscle calcium channel has recently been characterized as having an apparent molecular mass of 52–65 kD (as determined by SDS-PAGE analysis). It is comprised of consensus phosphorylation sites and has been shown by biochemical methods to be phosphorylated. This subunit is insensitive to reducing conditions.

The $\gamma$-subunit of the calcium channel has not been observed in all purified preparations, depending on the source of material analyzed, the investigating laboratory, and so on. The native material appears to be a glycoprotein with an apparent molecular mass of 30–33 kD, as determined by SDS-PAGE analysis. The native protein is believed to be glycosylated since its apparent molecular mass decreases after digestion with neuraminidase followed by endoglycosidase F.

Multiple types of calcium channels have been detected based on electrophysiological and pharmacological studies of various mammalian cells from various tissues (e.g., skeletal muscle, cardiac muscle, lung, smooth muscle and brain) [Bean, B. P., *Annu. Rev. Physiol.* 51:367–384 (1989) and Hess, P., *Annu. Rev. Neurosci.* 56:337 (1990)]. These different types of calcium channels have been broadly categorized into four classes, L-, T-, N-, and P-type, distinguished by current kinetics, holding potential sensitivity and sensitivity to calcium channel agonists and antagonists. Four subtypes of neuronal voltage-dependent calcium channels have been proposed [Swandulla, D. et al., *Trends Neurosci* 14:46 (1991)].

Characterization of a particular type of calcium channel by analysis of whole cells is severely restricted by the presence of mixed populations of different types of calcium channels in the majority of cells. This hindrance is also a drawback in attempting to discern whether a calcium current with properties that preclude categorization on the basis of these four broad classes is generated by a new type or subtype of calcium channel or a previously classified channel that is obscured by contaminating currents. Although single-channel recording methods can be used to examine individual calcium channels, such analysis reveals nothing about the molecular structure or biochemical composition of the channel. Furthermore, in this type of analysis, the channel is isolated from other cellular constituents that might be important for natural functions and pharmacological interactions.

Structural features of calcium channels can also be used in evaluation and characterization of different types of calcium channels. However, large amounts of pure channel protein are required to understand, at the molecular level, the nature of the subunits and their various interactions, for example, with one another, with the cell membranes across which the channels allow $Ca^{2+}$ ions to pass, with $Ca^{2+}$ and other ions, and with low molecular weight compounds such as drugs (pharmacological agents) that affect channel function. Due to the complex nature of these multi-subunit proteins, the varying levels of calcium channels in tissue sources of the protein, the presence of mixed populations of calcium channels in tissues, and the modifications of the native protein that can occur during the isolation procedure, it is extremely difficult to obtain large amounts of highly purified, completely intact calcium channel protein.

Characterization of the gene or genes encoding calcium channels provides another means of characterization of different types of calcium channels. The amino acid sequence determined based on the complete nucleotide sequence of the coding region of a gene encoding a calcium channel protein represents the actual primary structure of the protein. Furthermore, secondary structure of the calcium channel protein and the relationship of the protein to the membrane may be predicted based on analysis of the primary structure. For instance, hydropathy plots of the $\alpha 1$ subunit protein of the rabbit skeletal muscle calcium channel indicate that it contains four internal repeats, each containing six putative transmembrane regions. [Tanabe, T. et al., *Nature* 328:313 (1987).]

The cDNA and corresponding amino acid sequences of the $\alpha 1$, $\alpha 2$, $\beta$ and $\gamma$ subunits of the rabbit skeletal muscle have been determined [see Tanabe et al., *Nature* 328:313–318 (1987), Ellis et al., PCT Publication No. WO 89/09834, Ruth et al., *Science* 245:1115–1118 (1989), and allowed U.S. patent application Ser. No. 482,384, filed Feb. 20, 1990, (the disclosure of which is hereby incorporated by reference), respectively]. In addition, the cDNA and corresponding amino acid sequences of $\alpha 1$ subunits of rabbit cardiac muscle [Mikami, A. et al., *Nature* 340:230–233 (1989)] and lung [Biel, M., *FEBS Letters* 269:409–412 (1990)] calcium channels have been determined. Recently, a rabbit brain calcium channel (designated the BI channel) cDNA was isolated [Mori, Y. et al., *Nature* 350:398–402 (1991)]. The amino acid sequences deduced from the rabbit skeletal muscle, rabbit cardiac muscle, and rabbit lung cDNAs and the rabbit brain BI cDNA indicate that these proteins share some general structural features. However, the sequences share, at most, ~60% homology and appear to be encoded by a minimum of three distinct genes. These findings correlate with the varied intensities of hybridization of the rabbit skeletal muscle calcium channel $\alpha 1$ subunit cDNA to rabbit genomic DNA fragments as reported by Ellis et al., *Science* 241:1661–1664 (1988).

Interestingly, partial cDNAs encoding portions of several different subtypes of the calcium channel $\alpha 1$ subunit have been isolated from rat brain [Snutch, T. et al., *Proc. Natl. Acad. Sci U.S.A.* 87:3391–3395 (1990)]. These are referred to as rat brain class A, B, C and D cDNAs. More recently full-length rat brain class A [Starr, T. et al., *Proc. Natl. Acad. Sci. U.S.A.* 88:5621–5625 (1991)] and class C [Snutch, T. et al., *Neuron* 1:45–57 (1991)] cDNAs have been reported. Although the amino acid sequence encoded by the rat brain class C cDNA is approximately 95% identical to that encoded by the rabbit cardiac muscle calcium channel $\alpha 1$ subunit cDNA, the amino acid sequence encoded by the rat brain class A cDNA shares only 33% sequence identity with the amino acid sequences encoded by the rabbit skeletal or cardiac muscle $\alpha 1$ subunit cDNAs. A cDNA encoding another calcium channel $\alpha 1$ subunit was also recently reported [Hui, A. et al., *Neuron* 7:35–44 (1991)]. The amino acid sequence encoded by this cDNA is ~70% homologous to the proteins encoded by the rabbit skeletal and cardiac muscle calcium channel cDNAs.

A cDNA closely related to the rat brain class C $\alpha 1$ subunit cDNA and partial cDNA sequences closely related to other cDNAs encoding apparently different calcium channel $\alpha 1$ subunits have also been described [see Snutch, T. et al., *Neuron* 7:45–57 (1991), Perez-Reyes, E., Wei, X., Castellano, A. and Birnbaumer, L., *J. Biol. Chem.* 365:20430 (1990), and Hui, A. et al, *Neuron* 7:35–44 (1991)]. Evidence suggests that the closely related cDNA sequences, which are identical to some of the previously isolated $\alpha 1$ subunit cDNAs except in certain limited areas, represent variants generated by alternative splicing of a primary gene transcript.

Although the existence of numerous types and subtypes of calcium channel $\alpha 1$ subunits with a broad range of homologies is of interest, this information may be of limited utility in the absence of the knowledge of the functional characteristics of the calcium channels containing these different $\alpha 1$ subunits. Insufficient information is available to predict or discern, based on the primary structure of the $\alpha_1$ subunits, the functional or pharmacological properties of voltage-dependent calcium channels containing the different $\alpha_1$ subunits. Therefore, attempts to recombinantly express mammalian calcium channel $\alpha 1$ subunits have been reported.

To date, successful recombinant expression has been reported for only three of the six or seven different rabbit or rat $\alpha_1$ subunit cDNAs referred to in the preceding paragraphs. Perez-Reyes et al., *Nature* 340:233–236 (1989) have described the presence of voltage-dependent calcium currents in murine L cells transfected with the rabbit skeletal muscle calcium channel $\alpha 1$ subunit cDNA. These currents were enhanced in the presence of Bay K8644 (a known calcium channel agonist). Bay K8644-sensitive $Ba^{2+}$ currents have been detected in oocytes injected with in vitro transcripts of the rabbit cardiac muscle calcium channel $\alpha 1$ subunit cDNA [Mikami, A. et al., *Nature* 340:230–233 (1989)]. These currents were substantially reduced in the presence of the calcium channel antagonist nifedipine. Significantly, the barium currents of an oocyte co-injected with transcripts of the rabbit cardiac muscle calcium channel $\alpha 1$ subunit cDNA and the rabbit skeletal muscle calcium channel $\alpha 2$ subunit cDNA were more than 2-fold larger than those of oocytes injected with transcripts of the rabbit cardiac calcium channel $\alpha 1$ subunit cDNA. Similar results were obtained when oocytes were co-injected with transcripts of the rabbit lung calcium channel $\alpha 1$ subunit cDNA and the rabbit skeletal muscle calcium channel $\alpha 2$ subunit cDNA, i.e., the barium current was enhanced relative to that detected in oocytes injected with transcripts of the rabbit lung calcium channel $\alpha 1$ subunit cDNA only [Biel, M. et al,

*FEBS Letters* 269:409–412 (1990)]. Most recently, Mori et al., *Nature* 350:398–402 (1991) report the presence of inward barium currents in oocytes injected with in vitro transcripts of the rabbit brain BI channel cDNA. These currents were increased by two orders of magnitude when in vitro transcripts of the rabbit skeletal muscle calcium channel $\alpha 2$-, $\beta$-, or $\alpha 2$-, $\beta$- and $\gamma$-subunits were co-injected with transcripts of the BI cDNA. Barium currents in oocytes co-injected with transcripts of the BI cDNA and the rabbit skeletal muscle calcium channel $\alpha 2$ and $\beta$ cDNAs were unaffected by the calcium channel antagonists nifedipine or $\omega$-CgTx and inhibited by Bay K8644 and crude venom from *Agelenopsis aperta*.

The results of studies of recombinant expression of rabbit calcium channel $\alpha 1$ subunit cDNAs and transcripts of the cDNAs indicate that the $\alpha 1$ subunit forms the pore through which calcium enters cells. However, the relevance of the barium currents generated in these recombinant cells to the actual current generated by calcium channels containing as one component the respective $\alpha 1$ subunits in vivo is unclear. Because addition of in vitro transcripts of rabbit skeletal muscle calcium channel $\alpha 2$ and/or $\beta$ and $\gamma$ cDNAs significantly enhanced the barium currents in the recombinant cells, it appears that to completely and accurately characterize and evaluate different calcium channel types, it is essential to examine the functional properties of recombinant channels consisting of all the subunits as found in vivo. However, cDNAs encoding $\alpha 2$-, $\beta$- and $\gamma$-subunits from any of the rabbit or rat tissues besides rabbit skeletal muscle tissue are not available for use in such studies. The usefulness of rabbit skeletal muscle calcium channel $\alpha 2$- and $\beta$-subunit cDNAs in attempting to recombinantly evaluate different calcium channel types is extremely limited. Although others have suggested that the $\beta$- and $\alpha 2$-subunits of rabbit calcium channels from different tissues are essentially identical [Mori, Y. et al., *Nature* 350:398 (1991)], as described herein, different forms of $\alpha 2$-and $\beta$-subunits, arising from alternative splicing of the corresponding genes, are expressed in human brain, skeletal muscle and aorta. Therefore, in evaluating specific calcium channel types by examination of recombinantly expressed channels, it is most valuable to express cDNAs encoding calcium channel subunits from the same type of tissue.

It appears that calcium channels, specifically human calcium channels, can be relevant in certain disease states. A number of compounds useful in treating various cardiovascular diseases in animals, including humans, are thought to exert their beneficial effects by modulating functions of voltage-dependent calcium channels present in cardiac and/or vascular smooth muscle. Many of these compounds bind to calcium channels and block, or reduce the rate of, influx of $Ca^{2+}$ into the cells in response to depolarization of the cell membrane.

An understanding of the pharmacology of compounds that interact with calcium channels in other organ systems, such as the central nervous system ("CNS"), and the ability to rationally design compounds that will interact with these specific subtypes of human calcium channels to have desired therapeutic, e.g., treatment of neurodegenerative disorders, effects have been hampered by an inability to independently determine how many different types of calcium channels exist or the molecular nature of individual subtypes, particularly in the CNS, and the unavailability of pure preparations of specific channel subtypes, i.e., systems to evaluate the specificity of calcium channel-effecting compounds.

SUMMARY OF THE INVENTION

In accordance with the present invention, we have discovered, isolated and purified DNAs which encode $\alpha_1$-subunits of voltage-dependent human calcium channels (type II, type III and type IV, hereinafter VDCC II, VDCC III and VDCC IV); DNAs which encode $\alpha_2$-subunits of human calcium channels; DNAs which encode $\beta$-subunits of human calcium channels; and DNAs which encode $\gamma$-subunits of human calcium channels.

In accordance with one aspect of the present invention there is provided for the first time the isolation and characterization of full length cDNAs (and corresponding RNAs) encoding $\alpha_1$ VDCC III-, $\alpha_2$- and $\beta$-subunits of human calcium channels. Also provided are cDNAs encoding significant portions of $\alpha_1$ VDCC II-, $\alpha 1$ VDCC IV-, and $\gamma$-subunits of voltage-dependent human calcium channels from which full length cDNAs encoding types II and IV $\alpha_1$- and $\gamma$-subunits may be readily isolated, cloned and used, for example, to express recombinant human calcium channels. In still another aspect the invention concerns nucleic acid probes comprising at least about 14 contiguous nucleotides of an $\alpha_1$ VDCC III-, $\alpha_1$ VDCC II-, $\alpha_1$ VDCC IV-, $\alpha_2$-, $\beta$- or $\gamma$-subunit DNA of the invention which may be used for the isolation and cloning of additional calcium channel subunit encoding cDNAs, including splice variants within tissues and inter-tissue variants.

In another aspect of the invention there is provided a eukaryotic cell which is transfected or injected with DNA or transcripts of DNA comprising at least one or more of the novel subunit-encoding cDNAs of the invention which are expressed such that the cell possesses a calcium channel comprising at least one or more human calcium channel subunits of the present invention. These eukaryotic cells of the invention have functional, heterologous calcium channels (hereinafter referred to as "foreign" or "heterologous" or "recombinant" calcium channels) which are capable of gating the passage of calcium channel selective ions and/or binding a compound, present at a physiological concentration, which is capable of affecting the ability of the recombinant calcium channel to pass such ions. The heterologous calcium channels of such cells are distinguishable from endogenous calcium channels of the host cell. In one aspect, the invention includes a eukaryotic cell which is transfected with a cDNA (or injected with RNA transcripts thereof) encoding a human calcium channel $\alpha_1$-subunit of the invention, preferably an $\alpha_1$ VDCC III subunit, and more preferably additional cDNAs encoding human $\beta$, $\alpha_2$ or $\gamma$-subunits, such that the cell expresses a recombinant calcium channel which is capable of regulating the passage of calcium channel selective ions and is sensitive to compounds which are agonists or antagonists of human calcium channel activity. In other aspects, the invention entails a eukaryotic cell stably or transiently transfected with any combination of one, two, three or four of the subunit-encoding cDNAs of the present invention (e.g., $\alpha_1$, $\alpha_1+\beta$, $\alpha_1+\beta+\alpha_2$, etc.) which cells may be used in functional assays of the invention or, in the case of cells transformed with fewer subunit-encoding nucleic acids than necessary to constitute a functional recombinant human calcium channel, such cells may be employed as intermediates in the production of cells having additional subunits of the invention, the additional subunits being provided by subsequently transfecting such a cell with one or more cDNAs encoding a human calcium channel subunit of which the transfected cell is devoid.

In an especially preferred embodiment, the invention entails a eukaryotic cell comprising a recombinant calcium channel consisting essentially of human subunits, said recombinant channel being capable of binding agonist or antagonist compounds and/or passing calcium channel selective ions. In another of its aspects the invention employs a eukaryotic cell which expresses on its surface functional heterologous calcium channels of the invention in methods for identifying agonists and antagonists of calcium channel activity in humans and/or assessing the contribution of the various calcium channel subunits to the transport and regulation of calcium ions.

In still another aspect the invention is a purified human calcium channel subunit which is obtained from a eukaryotic cell transfected with a DNA comprising a cDNA of the invention which encodes the subunit.

BRIEF DESCRIPTION OF THE FIGURES

FIG. 6 is a restriction map a nucleic acid sequence encoding a human neuronal $\alpha_2$ calcium channel subunit, and the various cDNA clones used to derive the complete coding sequence;

FIG. 7 presents a comparison of a portion of the nucleic acid sequences and deduced amino acid sequences of (1) a rabbit skeletal muscle $\beta$ subunit, (2) a human skeletal muscle $\beta$-subunit, (3) a human neuronal $\beta$-subunit, and (4) a human aortic $\beta$-subunit;

DETAILED DESCRIPTION OF THE INVENTION

Figure 1:
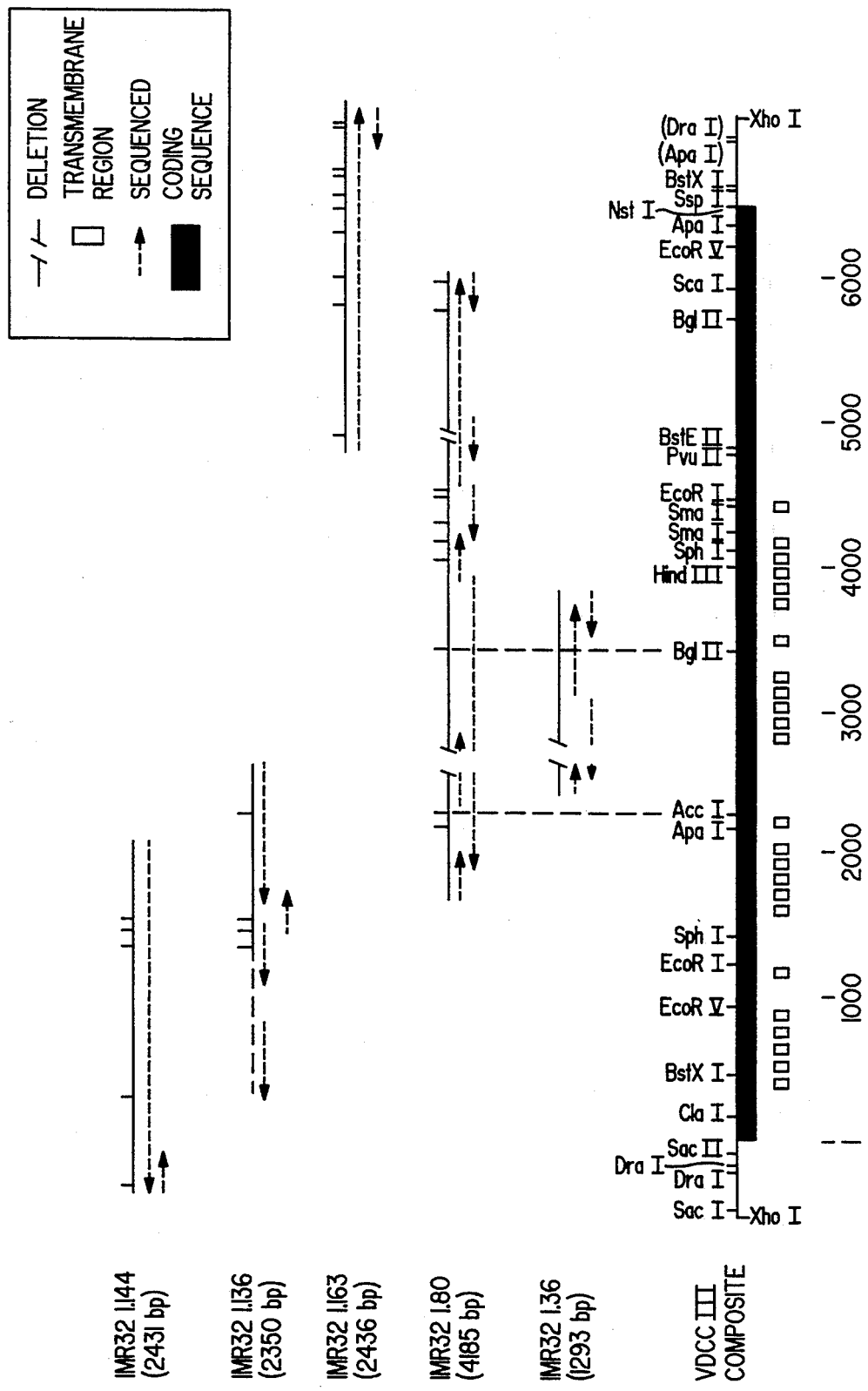
FIG. 1 represents a restriction map of a nucleic acid sequence encoding a human neuronal $\alpha_1$ calcium channel subunit (VDCC III), and the DNA sequencing strategy of various partial cDNAs used to derive the complete coding sequence.

For the first time there is provided DNAs for making recombinant human calcium channels and in vitro methods for testing compounds for calcium channel agonist and antagonist activity using eukaryotic cells that express such recombinant human calcium channels. The DNAs of the present invention and eukaryotic cells expressing these DNAs allow for the first time drug screening assays for calcium channel agonists and antagonists which are specific for human calcium channels expressed in a controlled system. The assay methods of the invention are highly accurate for predicting the relative efficacy of a compound in humans. Such assays may be advantageously used, for example, in screening methods used in conjunction with "designing" agonists and antagonists where it is important to accurately predict efficacy, with human calcium channels, between test compounds which differ slightly in structure (e.g., stereoisomers, etc.). The compositions and recombinant cells of the inventions thus allow the study of human calcium channel functions in recombinant cell systems.

Moreover, there are provided $\alpha_1$-subunits of voltage-dependent calcium channels types II, III and IV, and subtypes thereof, which types (and subtypes thereof) differ with respect to their sensitivity to known classes of calcium channel agonists and antagonists such as dihydropyridines, phenylalkylamines, omega conotoxin and pyrazonoylguanidines. Further provided are variant forms of human calcium channel $\alpha_2$ and $\beta$ subunits, some of which appear to be tissue-specific variants. Thus, the present invention advantageously allows human calcium channel subtype specific drugs to be identified.

Thus, in one of its aspects, the invention is a DNA which comprises a cDNA which codes for an $\alpha_1$-subunit of a human calcium channel, and the RNA, coding for such a subunit, made upon transcription of such a DNA according to the invention.

In another of its aspects, the invention is a DNA which comprises a cDNA which codes for an $\alpha_2$-subunit of a human calcium channel, and the RNA, coding for such a subunit, made upon transcription of such a DNA according to the invention.

In a further of its aspects, the invention is a DNA which comprises a cDNA which codes for a $\beta$-subunit of a human calcium channel, and the RNA, coding for such a subunit, made upon transcription of such a DNA according to the invention.

In another of its aspects, the invention is a DNA which comprises a cDNA which codes for a $\gamma$-subunit of a human calcium channel, and the RNA, coding for such a subunit, made upon transcription of such a DNA according to the invention.

In a further of its aspects, the invention is a eukaryotic cell comprising at least one heterologous DNA selected from the group consisting of: a DNA which comprises a nucleotide sequence which can be expressed to make an $\alpha_1$-subunit of a human calcium channel; a DNA which comprises a nucleotide sequence which can be expressed to make an $\alpha_2$-subunit of a human calcium channel; a DNA which comprises a nucleotide sequence which can be expressed to make a $\beta$-subunit of a human calcium channel; and a DNA which comprises a nucleotide sequence which can be expressed to make a $\gamma$-subunit of a human calcium channel. Preferably, said nucleotide sequence is comprised of a cDNA. cDNAs having nucleotide sequences which code for divergent, but nearly identical, amino acid sequences of a subunit of the invention are referred to herein as "splice variants." A splice variant refers to differential processing of a primary transcript of the genomic DNA to give more than one type of mRNA. Splice variants may be found within a single tissue type or between tissues (tissue-specific variants).

In particularly preferred aspects, the invention entails a recombinant eukaryotic cell comprising at least one heterologous DNA which comprises a cDNA which can be expressed to make a subunit of the present invention which at least one subunit, when expressed in the host cell, provides recombinant functional calcium channel activity of a calcium channel type that is absent from the untransfected host cell or that is of a magnitude not exhibited in the untransfected cell. "Functional" as used herein in reference to a recombinant or heterologous calcium channel means that the channel is able to provide for and regulate entry of calcium channel selective ions (e.g., $Ca^{2+}$ or $Ba^{2+}$) in response to a stimulus and/or bind ligands with affinity for the channel, and that such calcium channel activity is distinguishable (e.g., electrophysiologically, pharmacologically, etc.) from any identified endogenous calcium channel activity that might be present in the host cell. In accordance with one preferred embodiment of the invention the at least one heterologous DNA which comprises a cDNA which can be expressed to make a subunit of the present invention encodes a human calcium channel $\alpha_1$-subunit By the term "calcium channel selective ion" is meant an ion that is capable of flowing through, or being blocked from flowing through, a calcium channel which spans a cellular membrane under conditions which would substantially similarly permit or block the flow of $Ca^{2+}$. $Ba^{2+}$ is an example of an ion which is a calcium channel selective ion.

In another of its aspects, the invention entails a eukaryotic cell with a heterologous calcium channel, said cell made by a process comprising administering to said cell a first which composition, which comprises at least one RNA which is translatable in said cell for the expression of the corresponding at least one subunit of a human calcium channel. Preferably said at least one RNA encodes an $\alpha_1$-subunit of a human calcium channel. More preferably said composition comprising at least one RNA is a composition which contains an RNA which encodes an $\alpha_1$-subunit of a human calcium channel and further comprises (1) an RNA which encodes a $\beta$ subunit of a human calcium channel and/or (2) an RNA which encodes an $\alpha_2$-subunit of a human calcium channel. Especially preferred is the administration to such cell of an RNA encoding an $\alpha_1$-, an RNA encoding a $\beta$- and an RNA encoding an $\alpha_2$- human calcium channel subunit of the invention, and, optionally, an RNA encoding a $\gamma$-subunit of a human calcium channel. Preferred cells for expressing RNAs which, when expressed in combination, yield functional heterologous human calcium channels are *Xenopus laevis* oocytes.

Methods employed in making cells of the invention, i.e., transforming a eukaryotic cell with suitable heterologous DNAs, to be maintained in the cell as episomes or (preferably) integrated into chromosomal DNA of the cell, and then culturing transformants or subculturing (or passaging, in the case of mammalian cells) from such a culture or a subculture thereof, or injecting a eukaryotic cell with transcripts of the heterologous DNAs to be translated within the cell, are well known to those of ordinary skill. Preferred as host cells for preparing cells of the present invention which express heterologous calcium channels are cells of mammalian origin, such as COS cells, mouse L cells, CHO cells (e.g., DG44 cells), human embryonic kidney cells (e.g., HEK293 cells), African green monkey cells and the like, amphibian cells, such as *Xenopus laevis* oocytes, or those of yeast such as *S. cerevisiae* or *P. pastoris*.

Preferred among such cells of the invention is a recombinant eukaryotic cell with a functional heterologous calcium channel, said calcium channel made by a process comprising expressing a first cDNA, which can be expressed to make an $\alpha_1$-subunit of a human calcium channel, more preferably further comprising expressing, along with said first cDNA, a second cDNA, which can be expressed to make a $\beta$-subunit of a human calcium channel and/or a third cDNA which can be expressed to make an $\alpha_2$-subunit of a human calcium channel. Especially preferred is the expression in such a recombinant cell of each of the $\alpha_1$-, $\beta$- and $\alpha_2$-subunit-encoding cDNAs, and optionally a fourth cDNA encoding a $\gamma$-subunit of a human calcium channel, or transcripts of heterologous DNAs encoding these four subunits. Preferred host cells for expressing such cDNAs are mammalian cells such as COS cells, mouse L cells, CHO cells (e.g., DG44 cells), human embryonic kidney cells (e.g., HEK293 cells), African green monkey cells and the like, and yeast cells such as *S. cerevisiae* or *P. pastoris*.

In another of its aspects, a method of the invention entails a ligand binding assay for testing a compound for capacity to specifically bind to a calcium channel which method comprises contacting the cell membrane of a eukaryotic cell of the invention which expresses at least one subunit of a human calcium channel, preferably at least an $\alpha_1$-subunit of a human calcium channel, with the test compound and measuring the capacity of the test compound to specifically bind to the membrane. More preferably such an assay employs a recombinant cell which has a calcium channel comprising an $\alpha_1$-subunit of a human calcium channel in combination with a $\beta$-subunit of a human calcium channel and/or an $\alpha_2$-subunit of a human calcium channel. Especially preferred for use in such an assay is a recombinant cell expressing heterologous calcium channels comprising each of the $\alpha_1$-, $\beta$- and $\alpha2$- human subunits of the invention, and, optionally, a $\gamma$-subunit of a human calcium channel.

In another of its aspects, a method of the invention entails a functional assay for testing a compound for calcium channel agonist or antagonist activity which method comprises measuring the calcium channel activity of a eukaryotic cell of the invention having a heterologous, functional calcium channel (that is, the amount of current which flows through the recombinant channel in response to a stimulus) when such cell is exposed to a solution containing the compound being tested for agonist or antagonist activity, and comparing the measured calcium channel activity to the calcium channel activity of the same cell or a substantially identical control cell in a solution not containing the test compound. In the method, such a cell is maintained in a solution having a concentration of calcium channel selective ions sufficient to provide an inward current when the channels open. Especially preferred for use is a recombinant cell expressing calcium channels comprising each of the $\alpha_1$-, $\beta$- and $\alpha_2$- human subunits of the invention, and, optionally, a $\gamma$-subunit of a human calcium channel. For similar methods applied with *Xenopus laevis* oocytes and acetylcholine receptors, see e.g., Mishina et al., *Nature* 313:364 (1985) and, with such oocytes and sodium channels, see Noda et al., *Nature* 322:826–828 (1986). Such a cell having heterologous functional calcium channels is thus employed in the method of the invention to measure functionally (e.g., electrophysiologically) the ability of the test compound to potentiate or antagonize the magnitude and duration of the flow of calcium channel selective ions, such as $Ca^{++}$ or $Ba^{++}$, through the heterologous functional channel. For similar studies which have been carried out with the acetylcholine receptor, see Claudio et al., *Science* 238:1688–1694 (1987). The amount of current which flows through the recombinant calcium channels of a cell may be determined directly, electrophysiologically or by monitoring an independent reaction which occurs intracellularly and which is directly influenced in a calcium (or other) ion dependent manner.

In one embodiment of the method for testing a compound for calcium channel agonist or antagonist activity, in which method the amount of current is measured by its modulation of a reaction which is sensitive to calcium channel selective ions, a eukaryotic cell of the present invention further comprises another heterologous gene, which comprises a transcriptional control element linked operatively for expression to a structural gene for an indicator protein. The transcriptional control element employed to drive transcription of the indicator gene is responsive in the cell to a calcium channel selective ion (e.g., $Ca^{2+}$). Such methods for testing a compound for ion channel activity are disclosed in commonly owned U.S Ser. No. 563,751, filed Aug. 7, 1990, and in commonly-owned PCT International Patent Publication No. WO 92/02639, filed Aug. 7, 1991, which claims priority to U.S. Ser. No. 563,751, the contents of which applications are hereby incorporated by reference herein.

As clearly understood by those skilled in the art, assay methods for determining whether a compound is an agonist or an antagonist of a given functional activity requires comparison to a control. One type of a "control" cell or "control" culture is a cell or culture that is, and is treated, substantially the same as the culture exposed to the compound being assayed except that the control culture is not exposed to the compound being assayed. Another type of a "control" cell or "control" culture is a cell or a culture of cells which are identical to the cells according to the invention, except the cells employed for the control culture do not express functional calcium channels. In this situation, the response of test cell to the compound being assayed is compared to the response (or lack of response) of the receptor-negative cell to the compound being assayed, when cells or cultures of each type of cell are exposed to substantially the same reaction conditions in the presence of the compound being assayed. In methods of the invention utilizing patch clamp electrophysiological procedures, the same cell can be tested in the presence and absence of the test compound, by changing the external solution bathing the cell as known in the art.

In yet another of its aspects, the invention is a substantially pure subunit of a human calcium channel selected from the group consisting of an $\alpha_1$-subunit of a human calcium channel, an $\alpha_2$-subunit of a human calcium channel, a $\beta$-subunit of a human calcium channel and a $\gamma$-subunit of a human calcium channel.

By a "substantially pure" subunit or protein is meant a subunit or protein that is sufficiently free of other polypeptide contaminants to be considered homogeneous by SDS-PAGE or to be unambiguously sequenced.

In yet another aspect the invention entails immunoglobulins obtained from the serum of an animal immunized with a substantially pure preparation of a human calcium channel subunit (or epitope containing fragment thereof) of the present invention or monoclonal antibodies produced using a calcium channel subunit of the invention (or epitope containing fragment thereof) as immunogen. *E.coli* fusion proteins comprising a fragment of a human calcium channel subunit may also be used as immunogen. Such fusion proteins may consist of e.g., *E.coli* TrpE protein fused to a peptide based on selected nucleotide sequences of a subunit cDNA of the invention. The immunoglobulins of the present invention have among other properties the ability to specifically bind and/or cause the immunoprecipitation of a human calcium channel or a subunit thereof which may be present in a biological sample or a solution derived from such a biological sample. Another aspect of the invention is a diagnostic method for determining the presence of Lambert Eaton Syndrome (LES) in a human based on immunological reactivity of LES immunoglobulin G (IgG) with a human calcium channel subunit of the present invention or a eukaryotic cell of the invention which expresses a recombinant human calcium channel a subunit of the invention.

In a still further aspect, the invention is an immunoassay method for diagnosing Lambert-Eaton Syndrome in a person, which method comprises combining serum from the person (test serum) with $\alpha_1$-subunit of a human calcium channel and $\alpha_2$-subunit of a human calcium channel and ascertaining whether antibodies in the test serum react with one or both of the subunits, or a recombinant cell of the invention which expresses one or both of the subunits to a greater extent than antibodies in control serum (e.g., from a person or group of persons known to be free of the Syndrome). Any immunoassay procedure known in the art for detecting antibodies against a given antigen in serum can be employed in the method.

The invention entails also a labeled (e.g., radioactively or enzymatically labeled) RNA or single-stranded DNA of at least 14 bases in length in a sequence which comprises a sequence of at least 14 (preferably at least 30) contiguous bases of a nucleic acid which encodes at least a portion of a human calcium channel subunit, the sequence of which nucleic acid corresponds to a segment of a nucleic acid sequence of the present invention disclosed herein by reference to a Sequence ID No. Such nucleic acid segments may be used as probes. See, generally, Sambrook et al., *Molecular cloning: A Laboratory Manual*, 2d, Cold Spring Harbor Laboratory Press, 1989.

Finally, the invention entails a method to identify DNA encoding $\alpha_1$-, $\alpha_2$-, $\beta$- or $\gamma$-subunits of human calcium channels. This is accomplished by hybridizing, under appropriate hybridization conditions (e.g., high stringency), restriction enzyme-digested human DNA with a labeled probe having at least 14 nucleotides and derived from any contiguous sequence taken from the sequences set forth herein by sequence identification number. Once a fragment of interest is identified in the hybridization reaction, it can be cloned employing standard cloning techniques which are known by those of skill in the art. This method can be employed to identify varying transcripts encoding human calcium channel subunits (i.e., splice variants) generated by alternative splicing of the primary transcript of the genomic subunit DNA. For instance, a subunit cDNA isolated by hybridization to a DNA sequence of the invention can be characterized (e.g., restriction mapping, DNA sequencing) and compared to cDNAs of the invention to identify heterogeneity or divergences in the sequences indicative of alternative splicing of the transcript from which the cDNAs were derived. Oligonucleotides corresponding to divergent sequences can be used to isolate, by hybridization, the full-length splice variant cDNA. In addition, nucleic acid amplification techniques, which are well known in the art, can be used to locate splice variants of calcium channel subunits by employing oligonucleotides based on DNA sequences surrounding the divergent sequence of a cDNA as primers to amplify human RNA or genomic DNA. Size and sequence determinations of the amplification products can reveal splice variants. Furthermore, isolation of human genomic DNA sequences by hybridization to cDNAs of the invention can yield DNAs containing multiple exons, separated by introns, that correspond to different splice variants of transcripts encoding human calcium channel subunits.

A preferred strategy for cloning cDNAs encoding an $\alpha_1$-, $\alpha_2$-, $\beta$- or $\gamma$-subunits of voltage-dependent human calcium channels is to screen human cDNA libraries prepared from isolated poly A+ mRNA from cell lines or tissue of human origin having such calcium channels. Among the sources of such cells or tissue for obtaining mRNA are brain tissue or a cell line having neural origin such as a neuroblastoma cell line, human skeletal muscle or smooth muscle cells, and the like. Methods of preparing cDNA libraries are well known in the art [see generally Ausubel et al., *Current Protocols in Molecular Biology*, Wiley-Interscience, New York (1987); and Davis et al., *Basic Methods in Molecular Biology*, Elsevier Science Publishing Co., New York (1986)].

With respect to each of the respective subunits of a human calcium channel ($\alpha_1$-, $\alpha_2$-, $\beta$- or $\gamma$), once a channel subunit is found by a nucleic acid screening method, the clone may be used for further screening to identify overlapping clones. These cloned DNA fragments can be subcloned into an appropriate vector such as pIBI24/25 (IBI, New Haven, Conn.) or M13mp18/19, pGEM4, pGEM3, pGEM7Z, pSP72 or the like, and characterized by DNA sequencing and restriction enzyme mapping. A sequential series of overlapping clones may be thus generated for each of the subunits until a full-length clone can be prepared as determined by identification of translation initiation (start) and translation termination (stop) codons. Also, the 5' noncoding sequence of such a clone may be replaced with an efficient ribosome binding site as known in the art. Examples II-VI below describes in detail the cloning of each of the various subunits of the present invention as well as subtypes and splice variants, including tissue-specific variants thereof. And, where partial sequences of a subunit are disclosed, it is well within the skill of art, in view of the teaching herein to obtain the corresponding full-length nucleotide sequence encoding the subunit, subtype or splice variant thereof.

Briefly, as pertains to the isolation of the VDCC III $\alpha_1$-subunit cDNA, fragments of the rabbit skeletal muscle calcium channel $\alpha_1$-subunit cDNA were used as a probe to screen a cDNA library of the human neuroblastoma cell line, IMR32 to obtain clone $\alpha$1.36. This clone was used as a probe to screen additional IMR32 cell cDNA libraries to obtain overlapping clones, which overlapping clones were then employed in screening until a sufficient series of clones to span the length of the nucleotide sequence encoding the human VDCC III $\alpha_1$ subunit was obtained. Full-length VDCC III cDNAs were constructed by, inter alia ligating portions of partial VDCC III clones as described in Example I. The various cDNA clones from which the coding sequence for the $\alpha_1$-subunit was derived are set forth in FIG. 1. In the Figure, the heavy line represents the $\alpha_1$ coding sequence. Overlapping clones from which the complete sequence was derived are shown above the composite restriction map. The sequence of an alternative exon encoding the IS6 transmembrane domain is included in portions of the sequences of IMR32 1.157 (nt 57 to 89, Sequence ID #9; nt 1 to 67, Sequence ID #6), IMR32 1.66 (nt 100 to 132, Sequence ID #8; nt 1 to 67, Sequence ID #6), and the rabbit lung CaCB-receptor sequence, nt −33 to 67 [M. Biel. et al., (1990) *FEBS Lett.* 269, 409] [see Tanabe, T., et al. (1987), *Nature* 328:313–318 for a description of transmembrane domain terminology of the VDCC III $\alpha_1$-subunit].

Sequence ID No. 1 shows the 7,125 nucleotide sequence of the cDNA encoding the VDCC III $\alpha_1$-subunit. There is a 6,483 nucleotide sequence reading frame which encodes a sequence of 2,161 amino acids (as shown in Sequence ID No. 1).

Sequence ID No. 2 shows the 2,161 amino acid sequence deduced from the cDNA of the VDCC III $\alpha_1$ subunit of the human neuronal calcium channel. The complete sequence yields a calculated Mr of 245,163 for the VDCC III $\alpha_1$ protein. The amino acid sequence determined and reported here is about 70% identical to that described by Tanabe et al., supra. The VDCC III $\alpha_1$-subunit of the calcium channel contains four putative internal repeated sequence regions. Four internally repeated regions represent twenty-four putative transmembrane segments and the amino- and carboxyl-termini extend intracellularly.

A description of the cloning of cDNAs encoding portions of $\alpha_1$ VDCC II and $\alpha_1$ VDCC IV subunits of the invention are given in Example I. A VDCC II $\alpha_1$ subunit is encoded by a nucleotide sequence which encodes an amino acid sequence comprising the sequence represented by sequence ID No. 7 or sequence ID No. 11; and a VDCC IV $\alpha_1$ subunit is encoded by a nucleotide sequence which encodes an amino acid sequence comprising sequences represented by sequence ID No. 15 and/or sequence ID No. 17.

With respect to the $\beta$ subunit, a human hippocampus cDNA library was plated with an appropriate strain of *E. coli* and $3 \times 10^5$ plaques were screened by hybridization to a cDNA sequence encoding rabbit skeletal muscle calcium channel $\beta$ subunit to identify a positive clone which was in turn used to isolate overlapping clones until the entire sequence for the human calcium channel $\beta$ subunit was determined. The cDNA sequence encoding a $\beta$ subunit of rabbit skeletal muscle calcium channel is 20 disclosed in commonly owned U.S. application Ser. No. 482,384, filed Feb. 20, 1990 (now allowed), the contents of which are incorporated herein by reference. A detailed example of the cloning of cDNAs which encode human neuronal calcium channel $\beta$ subunits is given in Example III.

Sequence ID No. 18 shows the nucleotide sequence of a cDNA encoding one variant of the β-subunit. Sequence ID No. 22 represents the sequence of a cDNA encoding the major portion including a unique exon which is included in another splice variant of a β-subunit. Both of these splice variants encode human neuronal β-subunits. A cDNA sequence distinctive for a portion of a β-subunit of a human aortic calcium channel is shown in Sequence ID No. 31.

A cDNA encoding a human neuronal calcium channel $\alpha_2$-subunit was isolated in a manner substantially similar to that used for isolating $\alpha_1$ subunit cDNAs, except that a human genomic DNA library was probed under low and high stringency conditions with a fragment of the rabbit skeletal muscle calcium channel $\alpha_2$ subunit cDNA having the sequence corresponding to the nucleotide sequence between nucleotides 43 and 272 inclusive of rabbit back skeletal muscle calcium channel $\alpha_2$ subunit cDNA as disclosed in PCT International Patent Application Publication No. WO 89/09834, incorporated herein by reference. Example IV describes in detail the isolation of cDNA clones encoding an $\alpha_2$ subunit of a human calcium channel from a human DNA library using genomic DNA and cDNA identified by hybridization to the genomic DNA as probes.

Sequence ID No. 24 shows a cDNA sequence encoding the $\alpha_2$-subunit. As described in Example V, PCR analysis of RNA from human skeletal muscle, brain tissue and aorta using oligonucleotide primers specific for a region of the human neuronal $\alpha_2$-subunit cDNA that diverges from the rabbit skeletal muscle calcium channel $\alpha_2$-subunit cDNA (which divergence was discoverable only by first obtaining novel human calcium channel $\alpha_2$-subunit cDNAs) identified novel splice variants of the human calcium channel $\alpha_2$-subunit transcript.

A cDNA encoding a human neuronal calcium channel γ-subunit may be isolated as described in detail in the Example VI. Sequence ID No. 29 shows the nucleotide sequence at the 3'-end of this DNA which has a reading frame encoding a sequence of 43 amino acid residues.

A nucleotide sequence disclosed herein which encodes at least a portion of a subunit of a human calcium channel, (e.g., a tissue-specific exon) may be used to clone a full length gene encoding said human calcium channel subunit, which can then be expressed in a host cell, using methods described in the following examples or other procedures well known to those ordinarily skilled in the art. Incorporation of a cloned gene into a suitable expression vector, transfection of eukaryotic cells with a plasmid vector or a combination of plasmid vectors, each encoding one or more distinct genes, and selection of transfected cells are also well known in the art. (See, Sambrook, et al., *Molecular Cloning: A Laboratory Manual, Second Edition* (Cold Spring Harbor Laboratory Press (1989).) Cloned full-length cDNAs encoding any of the subunits of a human calcium channel of the present invention may be introduced into a plasmid vector for expression in a eukaryotic cell. Such a vector is an example of a DNA which comprises a cDNA with a sequence which codes for a subunit of a human calcium channel. Host cells may be transfected with one or a combination of said vectors, each of which encodes a calcium channel subunit. While the DNAs of the invention may be expressed in any eukaryotic cell including yeast cells such as *Pichia pastoris* (see e.g., Cregg, et al., *Bio/Technology* 5, 479 (1987)) it is preferred to use mammalian expression systems for expression of the calcium channel subunits of the present invention because of the ability of such expression systems to effect post-translational modifications such as glycosylation, phosphorylation, specific proteolysis and the like.

Furthermore, in vitro transcription of a cloned gene and injection of the resulting RNA into eukaryotic cells are also well known in the art. Transcripts of any of the full-length cDNAs encoding any of the subunits of a human calcium channel of the present invention may be injected alone or in combination into eukaryotic cells for expression in said cells. Amphibian oocytes are particularly preferred for expression of in vitro transcripts of the human calcium channel subunit cDNAs of the present invention.

Among the uses for eukaryotic cells which recombinantly express one or more subunits of the present invention are assays for determining whether a test compound has calcium channel agonist or antagonist activity. Desirably, a host cell for the expression of calcium channel subunits of the present invention will not produce endogenous calcium channel subunits of the type or in an amount that will substantially interfere with the detection of heterologous calcium channel subunits in ligand binding assays or detection of heterologous calcium channel function (e.g., generation of calcium current) in functional assays.

With respect to ligand binding assays, the host cells preferably should not produce endogenous calcium channels which are able to bind a ligand having, at physiological concentrations (e.g., nanomolar or picomolar amounts), affinity for one or a combination of the heterologous calcium channel subunits of the present invention. Preferred among the mammalian host cells which may be employed to express one or more of the human calcium channel subunits of the present invention for such expression are Chinese hamster ovary (CHO) cells, COS cells, mouse L cells, human embryonic kidney (HEK) cells.

With respect to ligand binding assays for identifying a compound which has affinity for calcium channels, cells are employed which express, preferably, at least a heterologous $\alpha_1$ subunit. Transfected eukaryotic cells of the present invention which express at least an $\alpha_1$-subunit of the invention may be used to determine the capacity of a test compound to specifically bind to, and likely affect the function of, a calcium channel. Such ligand binding assays may be performed on intact transfected cells or membranes prepared therefrom.

The capacity of a test compound to bind to membranes comprising heterologous calcium channels or subunits thereof may be determined by any appropriate competitive binding analysis (e.g., Scatchard plots), wherein the binding capacity of such membranes is determined in the presence and absence of one or more concentrations a compound having known affinity for the calcium channel. As a control, these results may be compared to an identically treated membrane preparation from host cells which were not transfected with one or more subunit-encoding nucleic acids (i.e., a negative control).

Stably or transiently transfected cells or injected cells of the present invention which express voltage-dependent human calcium channels comprising one or more of the subunits of a human calcium channel desirably may be used in functional assays to identify agents which are agonists or antagonists of calcium channel activity. Functionally testing activity of test compounds, including compounds having unknown activity, for calcium channel agonist or antagonist activity to determine if a test compound can potentiate or inhibit the flow of calcium through a human calcium channel entails a method which comprises (a) maintaining a eukaryotic cell which is transformed or injected to express a heterologous functional calcium channel capable of regulating the flow of calcium channel selective ions into the cell in a medium comprising calcium channel selective ions (i) in the presence of and (ii) in the absence of a test compound; (b) maintaining the cell under conditions such that the heterologous calcium channels are substantially closed and endogenous calcium channels of the cell are substantially inhibited (c) depolarizing the membrane of the cell maintained in step (b) to an extent and for an amount of time sufficient to cause (preferably, substantially only) the heterologous calcium channels to become permeable to the calcium channel selective ions; and (d) comparing the amount and duration of current flow into the cell in the presence of the test compound to that of the current flow into the cell, or a substantially similar cell, in the absence of the test compound.

Functional calcium channels as used herein may preferably comprise at least an $\alpha_1$ subunit and a $\beta$-subunit of a human calcium channel. Eukaryotic cells expressing these two subunits have exhibited voltage dependent calcium channel activity. The $\alpha_2$-subunit may potentiate calcium channel function (i.e., eukaryotic cells expressing heterologous calcium channels comprising an $\alpha_2$ subunit in addition to the $\alpha_1$ subunit and a $\beta$ subunit have been shown to exhibit increased calcium selective ion flow across the cellular membrane in response to depolarization). Eukaryotic cells which express heterologous calcium channels comprising at least a human $\alpha_1$-subunit, a human $\beta$-subunit and a human $\alpha_2$-subunit are preferred eukaryotic cells of the present invention. However, eukaryotic cells transformed with a composition consisting essentially of a cDNA-containing vector or an RNA of the invention which encodes an $\alpha_1$-subunit alone or in combination with a $\beta$- and/or an $\alpha_2$ subunit may be used to give functional calcium channels. Since recombinant cells expressing human calcium channels consisting essentially of human subunits are especially preferred, it is desirable to inject or transform such host cells with a sufficient concentration of the subunit-encoding nucleic acids of the invention to promote expression of calcium channels consisting essentially of human subunits.

With respect to measurement of functional heterologous calcium channels, preferably, endogenous ion channel activity and hybrid channel activity of a host cell can be inhibited to a significant extent by chemical (i.e., pharmacological) and/or electrophysiological means (e.g., differential holding potential) to increase the S/N ratio of the measured heterologous calcium channel activity.

Particularly preferred vectors for transfection of mammalian cells are the pSV2dhfr expression vectors (which comprises the SV40 early promoter, mouse dhfr gene, SV40 polyadenylation and splice sites and sequences necessary for maintaining the vector in bacteria), pCDNA1 or pCMV-based vectors which comprise the cytomegalovirus promoter or MMTV promoter-based vectors or the vector pCMV. A cloned calcium channel subunit gene of the present invention may be inserted in the vector pCDNA1 at a position immediately following the CMV promoter. The expression of functional, voltage-dependent calcium channels in HEK 293 cells transfected with calcium channel subunit cDNAs contained in vector pCDNA1 is described in Example VII.

Stably transfected mammalian cells may be made as known in the art by transfecting cells with an expression vector having a selectable marker gene such as the gene for thymidine kinase, dihydrofolate reductase, neomycin resistance or the like, and growing the transfected cells under conditions selective for cells expressing the marker gene.

Electrophysiological procedures for measuring the current across an ion-selective membrane of a cell are well known. A preferred method for the determination of the amount and duration of the flow of calcium selective ions through heterologous calcium channels of a recombinant cell of the invention employs electrophysiological recordings using a voltage clamp, such as the whole-cell patch clamp technique. It is known to eliminate non-calcium currents and, preferably, substantially reduce calcium currents resulting from endogenous calcium channels (i.e., pharmacologically, electrophysiologically) when measuring calcium currents through recombinant channels.

A further aspect of the invention provides for a diagnostic assay for Lambert Eaton Syndrome (LES). LES is an autoimmune disease characterized by an insufficient release of acetylcholine from motor nerve terminals which normally are responsive to nerve impulses. A recent publication (Kim and Neher, *Science* 239, 405–408 (1988)) demonstrates that IgGs from LES patients block individual voltage-dependent calcium channels and thus prevent function. A diagnostic assay for LES based on immunological reactivity of LES IgG with calcium channel $\alpha_1$-subunit alone or in combination with $\beta$-subunit is thus provided for. For example, such an assay may be based on immunoprecipitation of LES IgG by the calcium channel subunits of the invention.

The invention will now be described in greater detail by reference to the following non-limiting examples.

EXAMPLE I: cDNA Libraries used to Isolate cDNAs Encoding Human Neuronal Voltage-Dependent Calcium Channel Subunits A. RNA Isolation 1. IMR32 Cells IMR32 cells were obtained from the American Type Culture Collection (ATCC #CCL127, Rockville, Md.) and grown in DMEM, 10% fetal bovine serum, 1% penicillin/streptomycin (GIBCO, Grand Island, N.Y.) plus 1.0 mM dibutyryl cAMP (dbcAMP) for ten days. Total RNA was isolated from the cells according to the procedure described by H. C. Birnboim [*Nucleic Acids Research* 16:1487–1497 (1988)]. Poly(A+) RNA was selected according to standard procedures (see J. Sambrook, E. F. Fritsch, T. Maniatis, in: *Molecular Cloning, A Laboratory Manual*, Cold Spring Harbor Laboratory Press, 1989; pg. 7.26–7.29).

2. Human Thalamus Tissue

Human thalamus tissue (2.34 g), obtained from the National Neurological Research Bank, Los Angeles, Calif., that had been stored frozen at −70° C. was pulverized using a mortar and pestle in the presence of liquid nitrogen and the cells were lysed in 12 ml of lysis buffer (5M guanidinium isothiocyanate, 50 mM TRIS, pH 7.4, 10 mM EDTA, 5% $\beta$-mercaptoethanol). Lysis buffer was added to the lysate to yield a final volume of 17 ml. N-laurylsarcosine and CsCl were added to the mixture to yield final concentrations of 4% and 0.01 g/ml, respectively, in a final volume of 18 ml.

The sample was centrifuged at 9,000 rpm in a Sorvall SS34 rotor for 10 min at room temperature to remove the insoluble material as a pellet. The supernatant was divided into two equal portions and each was layered onto a 2-ml cushion of a solution of 5.7M CsCl, 0.1M EDTA contained in separate centrifuge tubes to yield approximately 9 ml per tube. The samples were centrifuged in an SW41 rotor at 37,000 rpm for 24 h at 20° C.

After centrifugation, each RNA pellet was resuspended in 3 ml ETS (10 mM TRIS, pH 7.4, 10 mM EDTA, 0.2% SDS) and combined into a single tube. The RNA was precipitated with 0.25M NaCl and two volumes of 95% ethanol.

The precipitate was collected by centrifugation and resuspended in 4 ml PK buffer (0.05M TRIS, pH 8.4, 0.14M NaCl, 0.01M EDTA, 1% SDS). Proteinase K was added to the sample to a final concentration of 200 μg/ml. The sample was incubated at 22° C. for 1 h, followed by extraction with an equal volume of phenol:chloroform:isoamylalcohol (50:48:2) two times, followed by one extraction with an equal volume of chloroform: isoamylalcohol (24:1). The RNA was precipitated with ethanol and NaCl. The precipitate was resuspended in 400 μl of ETS buffer. The yield of total RNA was approximately 1.0 mg. Poly A+ RNA (30 μg) was isolated from the total RNA according to standard methods as stated in Example I.A.1.

B. cDNA Library Construction

Double strand cDNA was synthesized according to standard methods (J. Sambrook, E. F. Fritsch, T. Maniatis, IN: *Molecular Cloning, A Laboratory Manual*, Cold Spring Harbor Laboratory Press, 1989, Chapter 8). Differences occurred in the construction of the cDNA libraries due to 1) the oligonucleotide used to prime the first strand cDNA synthesis, 2) the adapters that were attached to the double strand cDNA, 3) the method used to remove the free or unused adapters, and 4) the size of the fractionated cDNA ligated into the λ phage vector. Each cDNA library constructed is described below with these points highlighted.

1. IMR32 cDNA Library #1

Single strand cDNA was synthesized using IMR32 poly(A+) RNA (Example I.A.1.) as a template. The synthesis was primed using oligo (dT)$_{12-18}$ (Collaborative Research Inc., Bedford, Mass.). The single strand cDNA was converted to double strand cDNA and the yield was approximately 2 μg. EcoRI adapters,

| | |
|---|---|
| 5'-AATTCGGTACGTACACTCGAGC-3' | = 22-mer |
| 3'-     GCCATGCATGTGAGCTCG-5' | = 18-mer, | also containing SnaBI and XhoI restriction sites were then added to the double strand cDNA according to the following procedure.

a. Phosphorylation of 18-mer

The 18-mer was phosphorylated by combining the following reagents and incubating at 37° C. for 15 minutes:

| | |
|---|---|
| 225 pmoles 18 mer plus water = | 6.8 μl |
| 10x kinase buffer* | 1.2 μl |
| [$^{32}$P]γ-ATP (7000 Ci/mmole) | 1.0 μl |
| kinase (2 U/μl) | 1.0 μl |
| | 10 μl |

*See J. Sambrook et al., (supra).

The following two reagents were added to the above mixture and incubated at 37° C. for 15 minutes:

| | |
|---|---|
| 10 mM ATP | 1 μl |
| kinase (2 U/ml) | *p1326X1 μl |
| | 12 μl (total) |

The enzyme was then inactivated by boiling for 10 minutes.

b. Hybridization of 22-mer

The 22-mer was hybridized to the phosphorylated 18-mer by addition of 225 pmoles of the 22-mer (plus water to bring volume to 15 μl), and incubation at 65° C. for 5 minutes. The reaction was then allowed to slow cool to room temperature.

The adapters were thus present at a concentration of 15 pmoles/μl, and were ready for cDNA-adapter ligation.

c. Ligation of Adapters to cDNA

The following were combined:

| | |
|---|---|
| Double-strand cDNA (collected as a pellet by ethanol precipitation) plus | |
| hybridized adapters (15 pmol/μl) excess plus | 50-fold molar over ds cDNA |
| water = | 16 μl |
| 10x ligase buffer* | 2 μl |
| ligase (10 U/μl) | 2 μl |
| | 20 μl |

*See J. Sambrook et al., (supra).
The reaction was incubated at 37° C. for 60 minutes.

After the EcoRI, SnaBI, XhoI adapters were added to the double strand cDNA by incubating for 60 minutes, the ligase was inactivated by heating the mixture to 72° C. for 15 minutes. The following reagents were added to the cDNA ligation reaction and heated at 37° C. for 30 minutes:

| | |
|---|---|
| cDNA ligation reaction | 20 μl |
| water | 24 μl |
| 10x kinase buffer | 3 μl |
| 10 mM ATP | 1 μl |
| kinase (2 U/μl) | 2 μl |
| | 50 μl |

The reaction was stopped by the addition of 2 μl 0.5M EDTA, followed by one phenol/chloroform extraction and one chloroform extraction.

d. Size Selection and Packaging of cDNAs

The double strand cDNA with the EcoRI, naBI, XhoI adapters ligated was purified away from the free or nligated adapters using a 5 ml Sepharose CL-4B column (Sigma, St. Louis, Mo.). 100 μl fractions were collected and those containing the cDNA, determined by monitoring the radioactivity, were pooled, ethanol precipitated, resuspended in TE buffer and loaded onto a 1% agarose gel. After the electrophoresis, the gel was stained with ethidium bromide and the 1 to 3 kb fraction was cut from the gel. The cDNA embedded in the agarose was eluted using the "Geneluter Electroelution System" (Invitrogen, San Diego, Calif.). The eluted cDNA was collected by ethanol precipitation and resuspended in TE buffer at 0.10 pmol/μl. The cDNA was ligated to 1 μg of EcoRI digested, dephosphorylated λt11 in a 5 μl reaction volume at a 2- to 4-fold molar excess ratio of cDNA over the λgt11 vector. The ligated λgt11 containing the cDNA insert was packaged into λ phage virions in vitro using the Gigapack (Stratagene, La Jolla, Calif.) kit. The packaged phage were plated on an *E. coli* Y1088 bacterial lawn in preparation for screening.

2. IMR32 cDNA Library #2

This library was prepared as described (Example I.B.1.) with the exception that 3 to 9 kb cDNA fragments were ligated into the λgt11 phage vector rather than the 1 to 3 kb fragments.

3. IMR32 cDNA Library #3

IMR32 cell poly(A+) RNA (Example I.A.1.) was used as a template to synthesize single strand cDNA. The primers for the first strand cDNA synthesis were random primers (hexadeoxy-nucleotides [pd(N)$_6$] Cat #5020-1 Clontech, Palo Alto, Calif.). The double strand cDNA was synthesized (Example I.B.1.), EcoRI, SnaBI, XhoI adapters were added to the cDNA (Example I.B.1.), the unligated adapters were removed (Example I.B.1.), and the double strand cDNA with the ligated adapters was fractionated on an agarose gel (Example I.B.1.). The cDNA fraction greater than 1.8 kb was eluted from the agarose (Example I.B.1.), ligated into λgt11, packaged, and plated into a bacterial lawn of Y1088 (Example I.B.1.).

4. IMR32 cDNA Library #4

IMR32 cell poly(A+) RNA (Example I.A.1.) was used as a template to synthesize single strand cDNA. The primers for the first strand cDNA synthesis were oligonucleotides 89-365a specific for the VDCC III type $\alpha_1$-subunit (see Example II.A.) coding sequence (the complementary sequence of nt 2417 to 2446, Sequence ID #1), 89-495 specific for the VDCC II type $\alpha_1$-subunit (see Example II.B.) coding sequence (the complementary sequence of nt 52 to 873, Sequence ID #6), and 90-12 specific for the VDCC II type $\alpha_1$-subunit coding sequence (the complementary sequence of nt 2496 to 2520, Sequence ID #6). The cDNA library was then constructed as described (Example I.B.3) with the exception that the cDNA size-fraction greater than 1.5 kb was eluted from the agarose rather than the greater than 1.8 kb fraction.

5. IMR32 cDNA Library #5

The cDNA library was constructed as described (Example I.B.3.) with the exception that the size-fraction greater than 1.2 kb was eluted from the agarose rather than the greater than 1.8 kb fraction.

6. Human Thalamus cDNA Library #6

Human thalamus poly (A+) RNA (Example I.A.2.) was used as a template to synthesize single strand cDNA. Oligo (dT) was used to prime the first strand synthesis (Example I.B.1.). The double strand cDNA was synthesized (Example I.B.1.) and EcoRI, KpnI, NcoI adapters of the following sequence

```
5' CCATGGTACCTTCGTTGACG 3' = 20 mer
3' GGTACCATGGAAGCAACTGCTTAA 5' = 24 mer
``` were ligated to the double strand cDNA as described (Example I.B.1.) with the 20-mer replacing the 18-mer and the 24-mer replacing the 22-mer. The unligated adapters were removed by passing the cDNA-adapter mixture through a 1 ml Bio Gel A-50 (Bio-Rad Laboratories, Richmond, Calif.) column. Fractions (30 μl) were collected and 1 μl of each fraction in the first peak of radioactivity was electrophoresed on a 1% agarose gel. After electrophoresis, the gel was dried on a vacuum gel drier and exposed to x-ray film. The fractions containing cDNA fragments greater than 600 bp were pooled, ethanol precipitated, and ligated into λgt11 (Example I.B.1.). The construction of the cDNA library was completed as described (Example I.B.1.).

c. Hybridization and Washing Conditions

Hybridization of radiolabelled nucleic acids to immobilized DNA for the purpose of screening cDNA libraries, DNA Southern transfers, or northern transfers was routinely performed in standard hybridization conditions [5×SSPE, 5×Denhardt's, 50% deionized formamide, 200 μg/ml sonicated herring sperm DNA (Cat #223646, Boehringer Mannhelm Biochemicals, Indianapolis, Ind.)]. The recipes for SSPE and Denhart's and the preparation of deionized formamide are described by J. Sambrook et al. (Example I.A.1. provides the complete reference). In some hybridizations, lower stringency conditions were used in that 10% deionized formamide replaced 50% deionized formamide described for the standard hybridization conditions.

The washing conditions for removing the non-specific probe from the filters was either high, medium, or low stringency as described below:
1) high stringency: 0.1×SSPE, 0.1% SDS, 65° C.
2) medium stringency: 0.2×SSPE, 0.1% SDS, 50° C.
3) low stringency: 1.0×SSPE, 0.1% SDS, 50° C.

EXAMPLE II: Human Neuronal Calcium Channel $\alpha_1$ Subunit cDNAs

At least three voltage-dependent calcium channel $\alpha_1$-subunit genes are expressed in the human central nervous system. These genes have been designated VDCC II, VDCC III and VDCC IV (VDCC: voltage-dependent calcium channel). Human neuronal cDNA sequences corresponding to all three VDCC genes have been isolated. The isolation and characterization of sequences corresponding to the three human neuronal VDCC $\alpha_1$ subunit genes are described in detail in this example.

A. VDCC III cDNAs

1. Reference List of Partial VDCC III cDNAs

Numerous VDCC III-specific cDNAs were isolated in order to characterize the complete VDCC III coding sequence plus portions of the 5' and 3' untranslated sequences. Sequence ID #1 shows the complete VDCC III DNA coding sequence, plus 642 nucleotides of 3' untranslated sequence. Also shown in Sequence ID #1 is the deduced amino acid sequence. Sequence ID #3 shows 510 nucleotides of VDCC III 5' untranslated sequence ending in the guanidine nucleotide adjacent to the adenine nucleotide of the proposed initiation of translation. Shown below is a list of partial cDNAs used to characterize the VDCC III sequence and the nucleotide position of each clone relative to the full-length VDCC III cDNA sequence (i.e., sequence ID No. 1). Restriction maps of the partial VDCC III cDNAs are shown in FIG. 1. The isolation and characterization of these clones are described below (Example II.A.2.).

| IMR32 | 1.144 | nt. 1 to 510 of 5' untranslated sequence, nt. 1 to 1921, | Sequence ID #3 Sequence ID #1 |
|---|---|---|---|
| IMR32* | 1.136 | nt. 1117 to 2478, nt. 1 to 104 of, additional exon, | Sequence ID #1 Sequence ID #4 |
| IMR32@ | 1.80 | nt. 1573 to 5958, | Sequence ID #1 |
| IMR32# | 1.36 | nt. 2347 to 3771, | Sequence ID #1 |
| IMR32 | 1.163 | nt. 4690 to 7125, | Sequence ID #1 |

*5' of nt 1117, IMR32 1.136 encodes an intron and an additional exon described in Example II.A.2.d.
@IMR32 1.80 contains two deletions, nt 2474 to 2621 and nt 4793 to 4839 (Sequence ID #1). The 148 nt deletion (nt. 2474 to 2621) was corrected by performing a polymerase chain reaction described in Example II.A.3.b.
IMR32 1.36 contains a 132 nt deletion (nt. 2571 to 2702).

2. Isolation and Characterization of Individual Clones Listed in Example II.A.1.

a. IMR32 1.36

Two million recombinants of the IMR32 cDNA library #1 (Example I.B.1.) were screened in duplicate at a density of approximately 200,000 plaques per 150 mm plate using a mixture of radiolabelled fragments of the coding region of the rabbit skeletal muscle calcium channel α1 cDNA [for the sequence of the rabbit skeletal muscle calcium channel α1 subunit cDNA, see, Tanabe et al. (1987). *Nature* 328:313–318]:

| Fragment | Nucleotides |
|---|---|
| Kpn-EcoRI | −78 to 1006 |
| EcoRI-XhoI | 1006 to 2653 |
| ApaI-ApaI | 3093 to 4182 |
| BglII-SacI | 4487 to 5310 |

The hybridization was performed using low stringency hybridization conditions (Example I.C.) and the filters were washed under low stringency (Example I.C.). Only one VDCC III-specific recombinant (IMR32 1.36) of the two million screened was identified. IMR32 1.36 was plaque purified by standard methods (J. Sambrook et al., supra) subcloned into pGEM3 (Promega, Madison, Wisc.) and characterized by DNA sequencing.

b. IMR32 1.80

Approximately $1 \times 10^6$ recombinants of the IMR32 cDNA library #2 (Example I.B.2.) were screened in duplicate at a density of approximately 100,000 plaques per 150 mm plate using the IMR32 1.36 cDNA fragment (II.A.1) as a probe. Standard hybridization conditions were used (Example I.C), and the filters were washed under high stringency (Example I.C.). Three positive plaques were identified one of which was IMR32 1.80. IMR32 1.80 was plaque purified by standard methods, restriction mapped, subcloned, and characterized by DNA sequencing.

c. IMR32 1.144

Approximately $1 \times 10^6$ recombinants of the IMR32 cDNA library #3 (Example I.B.3) were screened with the EcoRI-PvuII fragment (nt 1573 to 2008, Sequence ID #1) of IMR32 1.80. The hybridization was performed using standard hybridization conditions (Example I.C.) and the filters were washed under high stringency (Example I.C.). Three positive plaques were identified one of which was IMR32 1.144. IMR32 1.144 was plaque purified, restriction mapped, and the cDNA insert was subcloned into pGEM7Z (Promega, Madison, Wisc.) and characterized by DNA sequencing. This characterization revealed that IMR32 1.144 has a series of ATG codons encoding seven possible initiating methionines (nt 1 to 21, Sequence ID #1). PCR analysis, and DNA sequencing of cloned PCR products encoding these seven ATG codons confirmed that this sequence is present in the VDCC III transcript expressed in dbcAMP-induced IMR32 cells.

d. IMR32 1.136

Approximately $1 \times 10^6$ recombinants of the IMR32 cDNA library #4 (Example I.B.4) were screened with the EcoRI-PvuII fragment (nt 1573 to 2008, Sequence ID #1) of IMR32 1.80 (Example II.A.1.). The hybridization was performed using standard hybridization conditions (Example I.C.) and the filters were washed under high stringency (Example I.C.). Six positive plaques were identified one of which was IMR32 1,136. IMR32 1,136 was plaque purified, restriction mapped, and the cDNA insert was subcloned into a standard plasmid vector, e.g., pSP72 (Promega, Madison, Wisc.), and characterized by DNA sequencing. This characterization revealed that IMR32 1.136 encodes an incompletely spliced VDCC III transcript. The clone contains nucleotides 1117 to 2478 of Sequence ID #1 preceded by an approximate 640 bp intron. This intron is then preceded by a 104 nt exon (Sequence ID #4) which is an alternative exon encoding the IS6 transmembrane domain [see Tanabe et al. (1987) *Nature* 328:313–318 for a description of the IS1 to IVS6 transmembrane terminology) of the VDCC III $α_1$ subunit and is proposed to be capable of replacing nt 1117 to 1220, Sequence ID #1, in a completely spliced VDCC III transcript.

e. IMR32 1.163

Approximately $1 \times 10^6$ recombinants of the IMR32 cDNA library #3 (I.B.3.) were screened with the NcoI-XhoI fragment of IMR32 1.80 (Example II.A.1.) containing nt 5301 to 5958 (Sequence ID #1). The hybridization was performed using standard hybridization conditions (Example I.C.) and the filters were washed under high stringency (Example I.C.). Three positive plaques were identified one of which was IMR32 1,163. IMR32 1,163 was plaque purified, restriction mapped, and the cDNA insert was subcloned into a standard plasmid vector, e.g., pSP72 (Promega, Madison, Wisc.), and characterized by DNA sequencing. This characterization revealed that IMR32 1,163 contains the VDCC III termination codon, nt 6484 to 6486 (Sequence ID #1).

3. Construction of a Full-Length VDCC cDNA [pVDCC III (A)]

VDCC III cDNA clones IMR32 1,144, IMR32 1.136, IMR32 1.80, and IMR32 1,163 (Example II.A.2.) overlap to comprise the entire VDCC III coding sequence, nt 1 to 6483 (Sequence ID #1), with the exception of a 148 bp deletion, nt 2474 to 2621 (Sequence ID #1). Portions of these partial cDNAs were ligated to generate a full-length VDCC III cDNA contained within a eukaryotic expression vector. The resulting vector was called pVDCCIII(A). The construction of pVDCCIII(A) was performed in four steps described in detail below: (1) the construction of pVDCCIII/5' using portions of IMR32 1,144, IMR32 1,136, and IMR32 1.80, (2) the construction of pVDCCIII/5'.3 that corrects the 148 nt deletion in the IMR32 1.80 portion of pVDCCIII/5', (3) the construction of pVDCCIII/3'.1 using portions of IMR32 1.80 and IMR32 1,163, and (4) the ligation of a portion of the pVDCCIII/5'.3 insert, the insert of pVDCCIII/3'.1 and pcDNA1 (Invitrogen, San Diego, CA.) to form pVDCCIII(A). pcDNA1 is a eukaryotic expression vector containing a cytomegalovirus (CMV) promoter which is a constitutive promoter that can be used to control the recombinant expression of a VDCC III cDNA in mammalian host cells.

Each of the DNA fragments used in preparing the full-length construct was purified by electrophoresis through an agarose gel onto DE81 filter paper (Whatman, Clifton, N.J.) and elution from the filter paper using 1.0M NaCl, 10 mM TRIS, pH 8.0, 1 mM EDTA. The ligations routinely were performed in a 10 μl reaction volume with an equal molar ratio of insert fragment and a two-fold molar excess of the total insert relative to the vector. The mass of DNAs used was normally 50 ng to 100 ng.

a. pVDCC III/5'

To construct pVDCC III/5', IMR32 1,144 (Example II.A.2.c.) was digested with XhoI and EcoRI and the fragment containing the vector (pGEM7Z), VDCC III nt 1 to 510 (Sequence ID #3), and VDCC III nt 1 to 1222 (Sequence ID #1) was isolated by gel electrophoresis. The EcoRI-ApaI fragment of IMR32 1.136 (Example II.A.2.d.) nucleotides 1222 to 2157 (Sequence ID #1) was isolated, and the ApaI-HindIII fragment of IMR32 1.80 (Example II.A.2.b.), nucleotides 2157 to 3982 (Sequence ID #1) was isolated. The three DNAs were ligated together to form pVDCC III/5' containing nt 1 to 510 (5' untranslated sequence; Sequence ID #3) and nt 1 to 3982 (Sequence ID #1).

b. pVDCCIII/5'.3

At the time pVDCCIII/5' was being constructed, a comparison of the IMR32 1.36 and IMR32 1.80 DNA sequences revealed that these two cDNAs differ through the VDCC III coding sequence, nucleotides 2474 to 2702. PCR analysis of IMR32 1.80 and dbcAMP-induced (1.0 mM, 10 days) IMR32 cytoplasmic RNA (isolated according to Ausubel, F. M. et al. (1988) (Eds) *Current Protocols in Molecular Biology*, John Wiley and Sons, New York) revealed that IMR32 1.80 had a 148 nt deletion, nt 2474 to 2621 (Sequence ID #1), and that IMR32 1.36 had a 132 nt deletion, nt 2571 to 2702. To perform the PCR analysis, amplification was primed with VDCC III-specific oligonucleotides 112 (nt 2038 to 2062, Sequence ID #1) and 311 (the complementary sequence of nt 3418 to 3447, Sequence ID #1). These products were then reamplified using VDCC III-specific oligonucleotides 310 (nt 2073 to 2098 Sequence ID #1) and 312 (the complementary sequence of nt 3373 to 3399). Contained within this reamplified product are AccI and BglII restriction sites (FIG. 1). The reamplified PCR product was restriction digested with AccI and BglII and the AccI-BglII fragment, nt 2254 to 3380 (Sequence ID #1) was cloned into AccI-BglII digested pVDCCIII/5' to replace the AccI-BglII pVDCCIII/5' fragment that had the deletion. This new construct was named pVDCCIII/5'.3. DNA sequence determination of pVDCC III/5'.3 through the amplified region confirmed the 148 nt deletion in IMR32 1.80.

c. pVDCCIII/3'.1

To construct pVDCCIII/3'.1, the cDNA insert of IMR32 1.163 (Example II.A.2.e.) was subcloned into pBluescript II (Stratagene, La Jolla, Calif.) as an XhoI fragment. The XhoI sites on the cDNA fragment were furnished by the adapters used to construct the cDNA library (I.B.3.). The insert was oriented such that the translational orientation of the insert of IMR32 1.163 was opposite to that of the lacZ gene present in the plasmid, as confirmed by analysis of restriction enzyme digests of the resulting plasmid. This was done to preclude the possibility of expression of α1 sequences in DH5α cells transformed with this plasmid due to fusion with the lacZ gene. This plasmid was then digested with HindIII and BglII and the HindIII - BglII fragment (the HindIII site comes from the vector and the BglII site is at nt 5710, Sequence ID #1) was removed, thus deleting nt 4690 to 5710 (Sequence ID #1) of the IMR32 1.163 clone and releasing the 3' BglII - XhoI fragment, nt 5710 to 7125 (Sequence ID #1). pVDCCIII/3'.1 was then made by splicing together the HindIII-PvuII fragment from IMR32 1.80 (nucleotides 3982-4784, Sequence ID #1), the PvuII - BglII fragment of IMR32 1.163 (nucleotides 4784 to 5710, Sequence ID #1) and the HindIII-BglII-digested pBluescript plasmid containing the 3' BglII/XhoI IMR32 1.163 fragment (nt 5710 to 7125, Sequence ID #1).

d. pVDCCIII(A): the Full-Length VDCC III Construct

To construct pVDCCIII(A), the DraI-HindIII fragment (5' untranslated sequence nt 327 to 510, Sequence ID #3 and coding sequence nt 1 to 3982, Sequence ID #1) of pVDCCIII/5'.3 (Example II.A.3.b.) was isolated; the HindIII-XhoI fragment pf pVDCCIII/3'.1 (containing nt 3982 to 7125, Sequence ID #1, plus the XhoI site of the adapter) (Example II.A.3.c.) was isolated; and the plasmid vector, pcDNA1, was digested with EcoRV and XhoI and isolated on an agarose gel. These three DNAs were ligated together and MC1061-P3 (Invitrogen, San Diego, Calif.) was transformed. Isolated clones were analyzed by restriction mapping and DNA sequencing and pVDCCIII(A) was identified which had the fragments correctly ligated together: DraI-HindIII, HindIII-XhoI, XhoI-EcoRV with the blunt-end DraI and EcoRV site ligating together to form the circular plasmid.

Due to the unusual primary structure of the amino-terminus of the VDCC III subunit, which is encoded by the seven consecutive 5' methionine codons (nt 1 to 21, Sequence ID #1), this 5' nt sequence plus nt 22 to 27, encoding two lysine residues, were deleted from pVDCCIII(A) and replaced with an efficient ribosomal binding site (5'-ACCACC-3') to form pVDCCIII.RB-S(A). Expression experiments in which transcripts of this construct were injected into *Xenopus laevis* oocytes did not result in an enhancement in the recombinant voltage-dependent calcium channel expression level relative to the level of expression in oocytes injected with transcripts of pVDCCIII(A).

B. VDCC II cDNAs

1. Reference List of Partial VDCC II cDNAs

Figure 2:
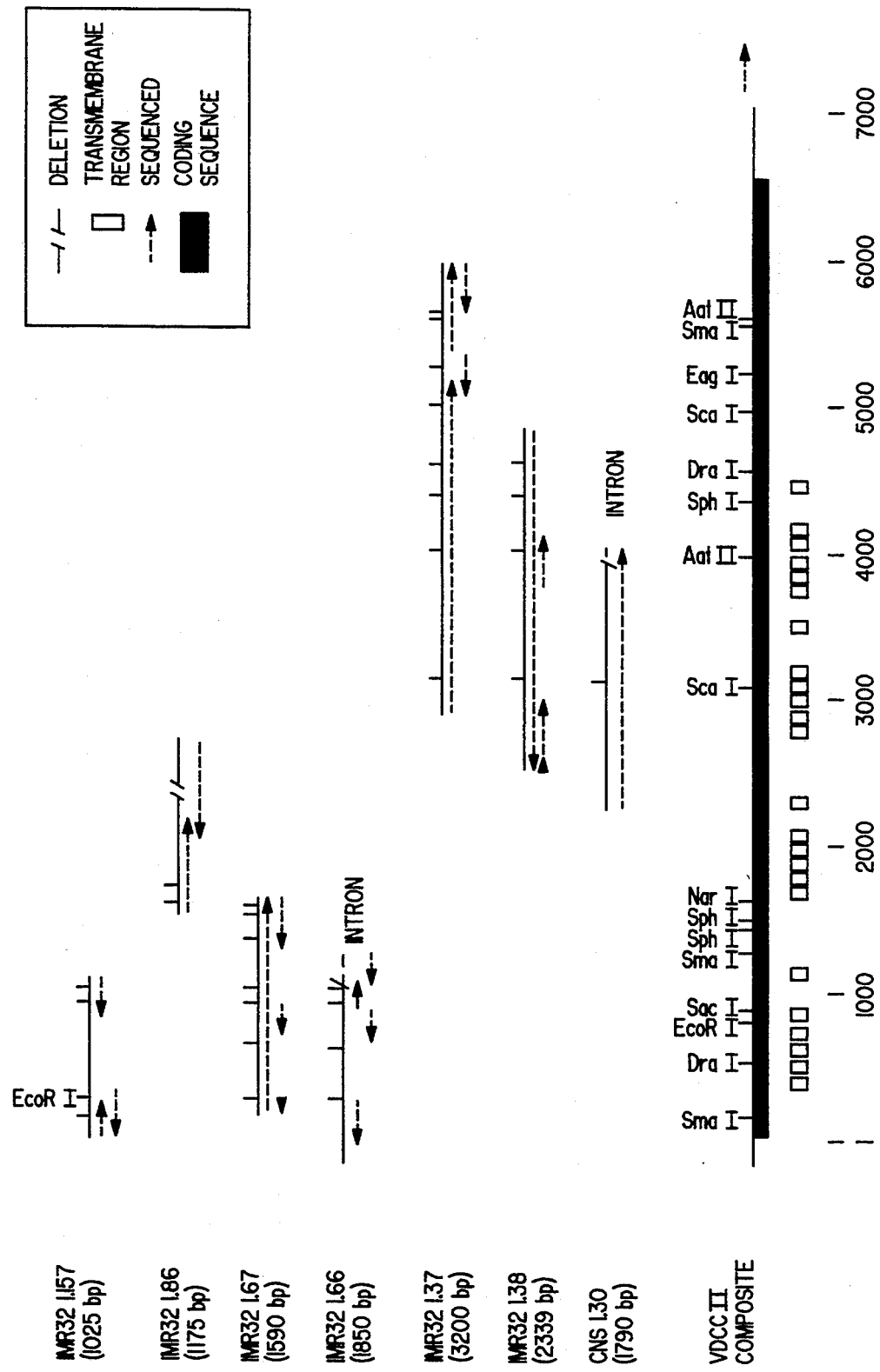
FIG. 2 represents a restriction map of a nucleic acid sequence encoding the majority of a human neuronal $\alpha_1$ calcium channel subunit (VDCC II), and the DNA sequencing strategy of various cDNA clones used to derive the coding sequence.

Numerous VDCC II-specific cDNAs were isolated in order to characterize the VDCC II coding sequence, the VDCC II initiation of translation, and an alternatively spliced region of VDCC II. Sequence ID #6 shows the characterized VDCC II coding sequence (nt 1 to 5904). Also shown in Sequence ID #6 is the deduced amino acid sequence. Sequence ID #8 and #9 encode two possible amino terminal ends of the VDCC II protein. Sequence ID #10 encodes an alternative exon for the IV S3 transmembrane domain. Shown below is a list of clones used to characterize the VDCC II sequence and the nucleotide position of each clone relative to the characterized VDCC II sequence (Sequence ID #6). Restriction maps of the partial VDCC II cDNAs are shown in FIG. 2. The isolation and characterization of these cDNAs are described below (Example II.B.2).

| IMR32 | 1.66 | nt 1 to 916, Sequence ID #6 |
| | | nt 1 to 132, Sequence ID #8 |
| IMR32 | 1.157 | nt 1 to 873, Sequence ID #6 |
| | | nt 1 to 89, Sequence ID #9 |
| IMR32 | 1.67 | nt 50 to 1717, Sequence ID #6 |
| *IMR32 | 1.86 | nt 1366 to 2583, Sequence ID #6 |
| @1.16G | | nt 758 to 867, Sequence ID #6 |
| IMR32 | 1.37 | nt 2804 to 5904, Sequence ID #6 |
| CNS | 1.30 | nt 2199 to 3903, Sequence ID #6 |
| | | nt 1 to 84 of alternative exon, Sequence ID #10 |
| IMR32 | 1.38 | nt 2448 to 4702, Sequence ID #6 |
| | | nt 1 to 84 of alternative exon, Sequence ID #10 |

*IMR32 1.86 has a 73 nt deletion compared to the rabbit cardiac muscle calcium channel $\alpha_1$-subunit cDNA sequence.
@1.16G is a VDCC II genomic clone.

2. Isolation and Characterization of Individual cDNAs and DNAs Listed in Example II.B.1 a. CNS 1.30

Approximately one million recombinants of the human thalamus cDNA library #6 (Example I.B.6.) were screened with fragments of the rabbit skeletal muscle calcium channel α1 cDNA described in Example II.A.2.a. The hybridization was performed using standard hybridization conditions (Example I.C.) and the filters were washed under low stringency (Example I.C.). Six positive plaques were identified, one of which was CNS 1.30. CNS 1.30 was plaque purified, restriction mapped, subcloned, and characterized by DNA sequencing. CNS 1.30 encodes VDCC II-specific sequence nt 2199 to 3903 (Sequence ID #6) followed by nt 1 to 84 of one of two identified alternative VDCC II exons (Sequence ID #10). 3' of Sequence ID #10, CNS 1.30 contains an intron and, thus, CNS 1.30 encodes a partially spliced VDCC II transcript.

b. 1.16G

Approximately one million recombinants of a λEMBL3-based human genomic DNA library (Cat #HL1006d Clontech Corp., Palo Alto, Calif.) were screened using a rabbit skeletal muscle cDNA fragment (nt −78 to 1006, Example II.A.2.a.). The hybridization was performed using standard hybridization conditions (Example I.C.) and the filters were washed under low stringency (Example I.C.). Fourteen positive plaques were identified, one of which was 1.16G. Clone 1.16G was plaque purified, restriction mapped, subcloned, and portions were characterized by DNA sequencing. DNA sequencing revealed that 1.16G encodes VDCC II-specific sequence as described in Example II.A.1.

c. IMR32 1.66 and IMR32 1.67

Approximately one million recombinants of IMR32 cDNA library #5 (Example I.B.5.) were screened with a 151 bp KpnI-SacI fragment of 1.16G (Example II.B.2.b.) encoding VDCC II sequence (nt 758 to 867, Sequence ID #6). The hybridization was performed using standard hybridization conditions (Example I.C.). The filters were then washed in 0.5×SSPE at 65° C. Of the positive plaques, IMR32 1.66 and IMR32 1.67 were identified. The hybridizing plaques were purified, restriction mapped, subcloned, and characterized by DNA sequencing. Two of these cDNAs, IMR32 1.66 and 1.67, encode VDCC II sequences as described (Example II.A.1.). In addition, IMR32 1.66 encodes a partially spliced VDCC II transcript marked by a GT splice donor dinucleotide beginning at the nucleotide 3' of nt 916 (Sequence ID #6). The intron sequence within 1.66 is 101 nt long. IMR32 1.66 encodes the VDCC II initiation of translation, nt 1 to 3 (Sequence ID #6) and 132 nt of 5' untranslated sequence (Sequence ID #8) precede the start codon in IMR32 1.66.

d. IMR32 1.37 and IMR32 1.38

Approximately two million recombinants of IMR32 cDNA library #1 (Example I.B.1.) were screened with the CNS 1.30 cDNA fragment (Example II.B.2.a.). The hybridization was performed using low stringency hybridization conditions (Example I.C.) and the filters were washed under low stringency (Example I.C.). Four positive plaques were identified, plaque purified, restriction mapped, subcloned, and characterized by DNA sequencing. Two of these characterized cDNAs were IMR32 1.37 and IMR32 1.38 encoding VDCC II-specific sequence as described in Example II.B.1.

Figure 3:
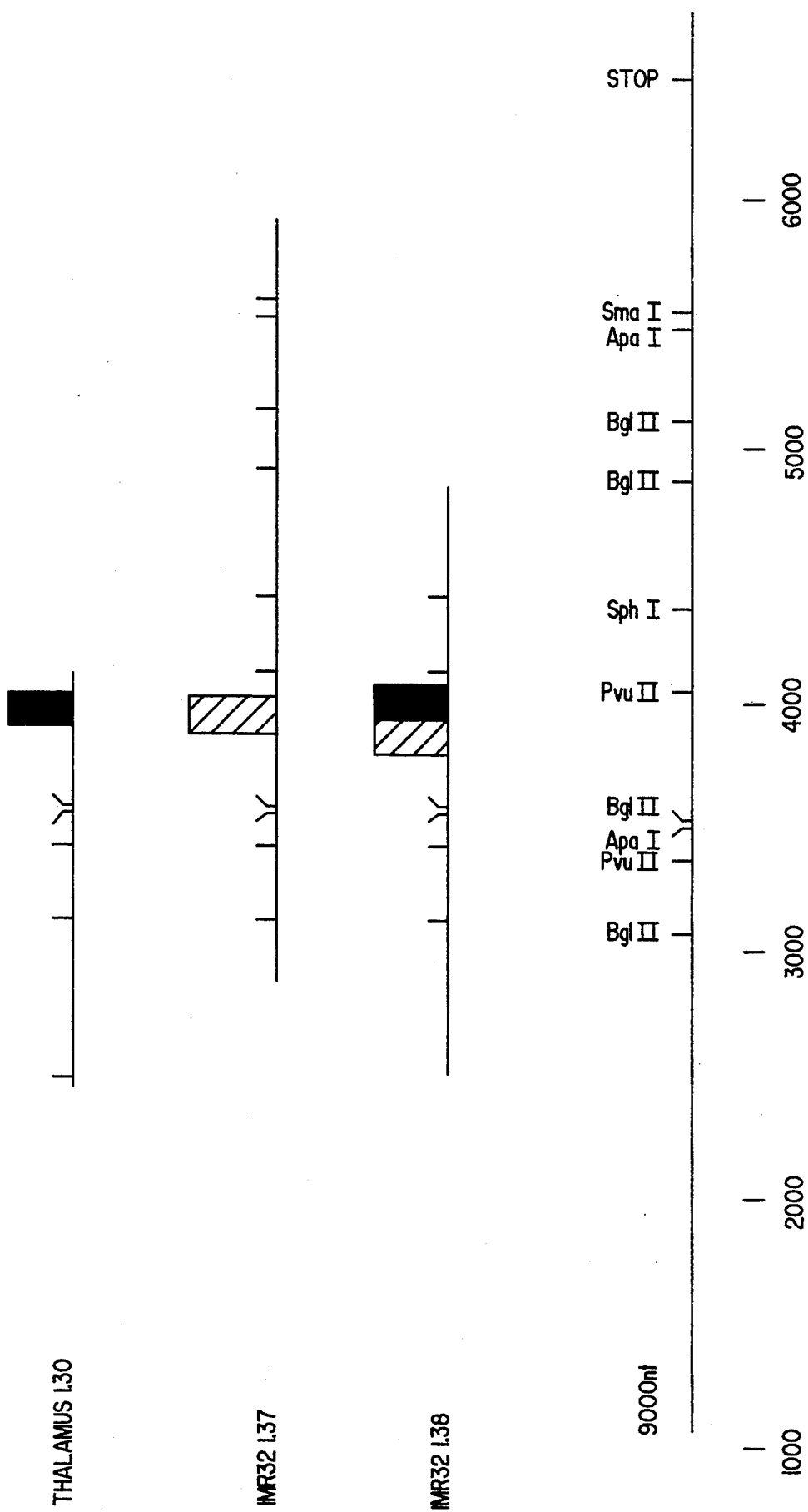
FIG. 3 depicts an alternative splicing strategy of a nucleic acid sequence encoding a human neuronal $\alpha_1$ calcium channel subunit (VDCC II)

DNA sequence comparison of IMR32 1.37 and IMR32 1.38 revealed that the VDCC II transcript has two exons that encode the IVS3 transmembrane domain. IMR32 1.37 has a single exon, nt 3904 to 3987 (Sequence ID #6) and IMR32 1.38 appears to be anomolously spliced to contain both exons juxtaposed, nt 3904 to 3987 (Sequence ID #6) followed by nt 1 to 84 (Sequence ID #10). The alternative splice of the VDCC II transcript to contain either of the two exons encoding the IVS3 region was confirmed by comparing the CNS 1.30 sequence to the IMR32 1.37 sequence. CNS 1.30 contains nt 1 to 84 (Sequence ID #10) preceded by the identical sequence contained in IMR32 1.37 for nt 2199 to 3903 (Sequence ID #6). Described in Example II.B.2.a., an intron follows nt 1 to 84 (Sequence ID #10). Regardless, two alternative exons have been spliced adjacent to nt 3903 (Sequence ID #6) represented by CNS 1.30 and IMR32 1.37. The alternative splicing of this region is schematically depicted in FIG. 3. The solid box represents nt 1 to 84 (Sequence ID #10) and the striped box represents nt 3904 to 3987 (Sequence ID #6).

e. IMR32 1.86

IMR32 cDNA library #1 (Example I.B.1.) was screened in duplicate using oligonucleotide probes 90-9

(nt 1462 to 1491, Sequence ID #6) and 90-12 (nt 2496 to 2520, Sequence ID #6). These oligonucleotide probes were chosen in order to isolate a clone that encodes the VDCC II sequence between the 3' end of IMR32 1.67 (nt 1717, Sequence ID #6) and the 5' end of CNS 1.30 (nt 2199, Sequence ID #6). The hybridization conditions were standard hybridization conditions (Example I.C.) with the exception that the 50% deionized formamide was reduced to 20%. The filters were washed under low stringency (Example I.C.). Three positive plaques were identified one of which was IMR32 1.86. IMR32 1.86 was plaque purified, subcloned, and characterized by restriction mapping and DNA sequencing. IMR32 1.86 encodes VDCC II sequences as described in Example II.B.1. Characterization by DNA sequencing revealed that IMR32 1.86 contains a 73 nt deletion when compared to the rabbit cardiac muscle calcium channel $\alpha_1$ subunit cDNA sequence [A. Mikami et al., Nature 340:230 (1989)], nt 2191 to 2263. These missing nucleotides correspond to nt 2176-2248 of Sequence ID #6. Because the 5'-end of CNS 1.30 overlaps the 3'-end of IMR32 1.86, some of these missing nucleotides, i.e., nt 2205-2248 of Sequence ID #6, are accounted for by CNS 1.30. The remaining missing nucleotides of the 73 nucleotide deletion in IMR32 1.86 (i.e., nt 2176-2204 Sequence ID #6) are represented by the letter "N" in Sequence ID #6. The 73 nt deletion is a frame-shift mutation and, thus, needs to be corrected. This can be accomplished by screening either IMR32 cDNA libraries or human CNS cDNA libraries with oligonucleotides 90-9 and 90-12, described above and isolating and characterizing positive plaques. The exact human sequence through this region then can be determined and the deletion can be corrected by standard methods, e.g., replacement of a restriction fragment or site-directed mutagenesis.

f. IMR32 1.157

One million recombinants of IMR32 cDNA library #4 (Example I.B.4.) were screened with an XhoI-EcoRI fragment of IMR32 1.67 encoding VDCC II nt 50 to 774 (Sequence ID #6). The hybridization was performed using standard hybridization conditions (Example I.C.). The filters were washed under high stringency (Example I.C.). One of the positive plaques identified was IMR32 1.157. This plaque was purified, the insert was restriction mapped and subcloned to a standard plasmid vector (e.g., pGEM7Z, Madison, Wisc.). The cDNA was characterized by DNA sequencing. IMR32 1.157 possibly encodes an alternative 5' portion of the VDCC II sequence beginning with nt 1 to 89 (Sequence ID #9) which is then followed by nt 1 to 873 (Sequence ID #6). Analysis of the 1.66 and 1.157 5' sequence is described below (Example II.B.3.).

3. Characterization of the VDCC II Initiation of Transition

The human sequences represent possible alternative 5' ends of the VDCC II transcript encoding the region of initiation of translation. IMR32 1.66 closely matches the CaCB-receptor sequence and diverges from the CaCB-receptor sequence in the 5' direction beginning at nt 122 (Sequence ID #8). The start codon identified in the CaCB-receptor sequence is enclosed in a box and is the same start codon used to describe the VDCC II coding sequence, nt 1 to 3 (Sequence ID #6). The functional significance of the IMR32 1.157 sequence, nt 1 to 89 (Sequence ID #9), is unknown, however, chimeric sequence between 1.157 and the VDCC II coding sequence 1.158 and the VDCC II coding sequence can be constructed and functional differences can be tested. IMR32 1.157 does not contain an initiation codon, however, one can be cloned by screening IMR32 cell cDNA libraries using probes corresponding to Sequence ID #9.

C. VDCC IV cDNAs

Five VDCC IV-specific cDNAs were isolated in order to characterize portions of the VDCC IV coding sequence. Sequence ID #12 shows the VDCC IV sequence characterized. The deduced amino acid sequence of VDCC IV (Sequence ID #12) revealed two regions, Sequence ID #14 and Sequence ID #16, with noteworthy sequence homology to the rabbit BI-2 deduced amino acid sequence [Mori et al., Nature 350:398 (1991)]. The deduced amino acid sequence shown in Sequence ID #14 (corresponding to nt 144-2612 of Sequence ID #12) is 80.3% identical to the rabbit BI-2 sequence (amino acid 1 to 827). The deduced amino acid sequence shown in Sequence ID #16 (corresponding to nt 3855-4811 of Sequence ID #12) is 85.8% identical to the rabbit BI-2 sequence (amino acid 1343 to 1660). The reading frame of the deduced amino acid sequences shown as Sequence ID #14 and Sequence ID #16 begins with the adenine nucleotide at position 144 (Sequence ID #12). Beginning at nt 144 (Sequence ID #12) an open reading frame is not maintained through the remaining 5323 nucleotides. Fourteen termination codons are contained in the region of Sequence ID #12 between nucleotides encoding Sequence ID #14 and Sequence ID #16 (i.e., between nt 2612-3855 of Sequence ID #12). Several possibilities exist for the absence of an open reading frame through this region. It could be the result of a partially spliced transcript and, thus, a portion of this region could encode an intron; it could be a cloning artifact or bacterial rearrangement of the sequence during purification of the cDNA; or it could simply be a sequence error. These possibilities can be pursued by using nucleotides encoding Sequence ID #14 and #16 as probes to isolate independent cDNAs. The nucleotide sequence 3' of nt 4811 (Sequence ID #12) residue 1556 also encodes several termination codons. Independent isolates of VDCC IV cDNAs encoding this region can be characterized for the reasons described above.

Figure 4:
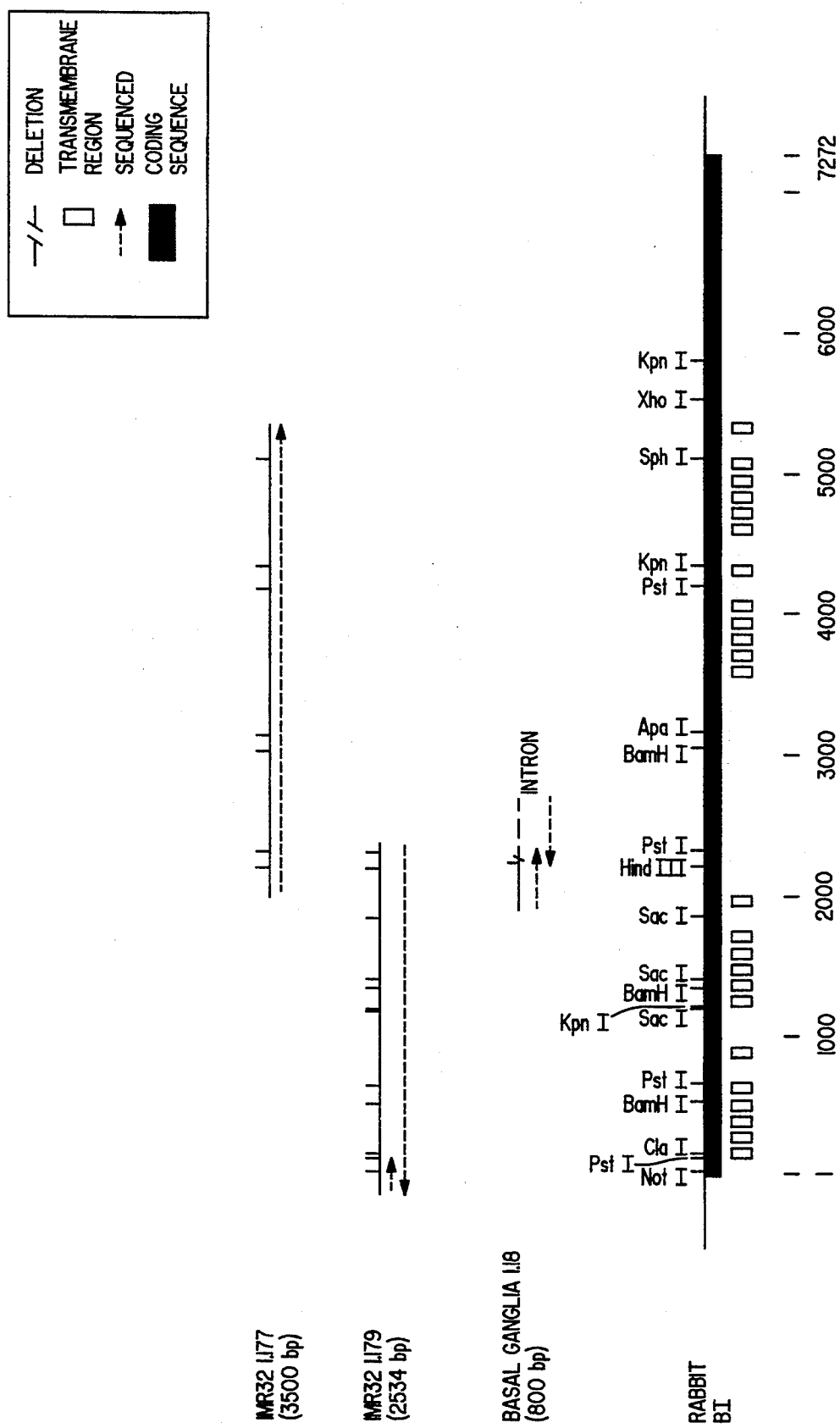
FIG. 4 presents restriction maps of a cDNA encoding the majority of a human neuronal $\alpha_1$ calcium channel VDCC IV as compared to a restriction map of the rabbit BI cDNA coding sequence.

Restriction maps of the partial VDCC IV cDNAs are shown in FIG. 4. The isolation and characterization of these clones are described below (Example II.C.2.).

| | | |
|---|---|---|
| CNS | 1.18 | contains an approximately 800 bp insert beginning at nt 2012 of Sequence ID #12 |
| *IMR32 | 1.179 | nt 1 to 2537 Sequence ID #12 |
| IMR32 | 1.177 | nt 2154 to 5467 Sequence ID #12 |
| *IMR32 | 1.177 | contains a CAG triplet between nt 2410 and nt 2414 of Sequence ID #12 that is not contained in IMR32 1.179. Therefore, IMR32 1.179 is actually 2534 nt long. |

2. Isolation and Characterization of VDCC IV cDNAs a. CNS 1.18

A human basal ganglia cDNA library obtained from the American Type Culture Collection (ATCC #37433, Rockville, Md.) were screened with the rabbit skeletal muscle $\alpha_1$-subunit cDNA fragments (see Example II.A.2.a. for description of fragments). The hybridization and washing conditions were low stringency (Example I.C.). CNS 1.18 was one of the positive clones identified. Restriction mapping and DNA sequencing revealed that it contains an approximate 800 bp insert beginning at nt 2012 (Sequence ID #12). CNS 1.18 represents a partially spliced VDCC IV transcript with the intron beginning after nt 2410 (Sequence ID #12).

b. IMR32 1.177

Approximately $1 \times 10^6$ recombinants of IMR32 cDNA library #3 (Example I.B.3.) were screened with an EcoRI-HindIII fragment of CNS 1.18 (nt 2012 to 2338). The hybridization was performed under high stringency (Example I.C.), and the filters were washed under high stringency (Example I.C.). One of the positive plaques identified was IMR32 1.177. The plaque was purified, subcloned, and sequenced. DNA sequence characterization revealed that IMR32 1.177 encoded nt 2154 to 5467 (Sequence ID #12).

c. IMR32 1.179

IMR32 1.179 was identified and characterized as described in Example II.C.2.b. DNA sequence characterization revealed that it encodes nt 1 to 2537 (Sequence ID #12).

EXAMPLE III: Isolation of cDNAs Encoding the Human Neuronal Calcium Channel β-Subunit The results of cDNA cloning, PCR analysis, and DNA sequencing have identified four alternatively spliced forms of the human calcium channel β-subunit transcript. These forms are designated $\beta_1$ expressed in skeletal muscle; $\beta_2$, expressed in the central nervous system; $\beta_3$, a second β form found in the CNS; and $\beta_4$, expressed in aorta tissue. Described in this example is the characterization of these forms and the construction of a full-length cDNA encoding the complete $\beta_2$ coding sequence. Restriction maps of the partial human neuronal cDNAs are shown in FIG. 6. Shown in FIG. 6 (Example V) is the result of PCR analysis that identifies the $\beta_1$, $\beta_2$, and $\beta_4$ alternative forms.

A. Reference List of Partial Subunit cDNAs

| | | |
|---|---|---|
| CNS β1 | nt 69 to 1546 | Sequence ID #18 |
| | nt 1 to 448 | Sequence ID #21 |
| CNS β1.18 | nt 1 to 65 | Sequence ID #20 |
| | nt 1 to 325 | Sequence ID #18 |
| CNS β4 | nt 216 to 1515 | Sequence ID #18 |

The full-length B2 coding sequence plus a portion of the 3' untranslated sequence is shown as Sequence ID #18. A portion of the 5' untranslated sequence is shown as Sequence ID #20. Encoded in CNS β1 is a 448 nt intron shown as Sequence ID #21. CNS β4 encodes an alternative splice form of the human neuronal β transcript. Nucleotides 1 to 1086 of CNS cDNA β4 (Sequence ID #22) are identical to nucleotides 246-1332 of CNS cDNA β1 (Sequence ID #18). However, CNS cDNA β4 then diverges from CNS cDNA β1 at nt 1087–1515 (Sequence ID #22).

B. Isolation and Characterization of Individual Clones

Approximately 300,000 plaques of a human hippocampus cDNA library obtained from Stratagene (CAT #936205, La Jolla, Calif.) were plated on agar plates as described by the supplier and screened with the rabbit skeletal muscle calcium channel β-subunit cDNA fragment (nt 441 to 1379) [for isolation and sequence of the rabbit skeletal muscle calcium channel β-subunit cDNA, see U.S. patent application Ser. No. 482,384 or Ruth et al. (1989) Science 245:1115]. The hybridization was performed using standard hybridization conditions (Example I.C.), and the filters were washed under low stringency (Example I.C.). Several positive plaques were identified, plaque purified and excised from the phage vector via the in vivo excision method performed according to the supplier's (Stratagene) instructions to yield cDNAs contained in the pBluescript II plasmid vector. The cDNA inserts were characterized by restriction mapping and DNA sequencing and compared to the rabbit skeletal muscle calcium channel β-subunit cDNA sequence.

a. CNS β1

Figure 5:
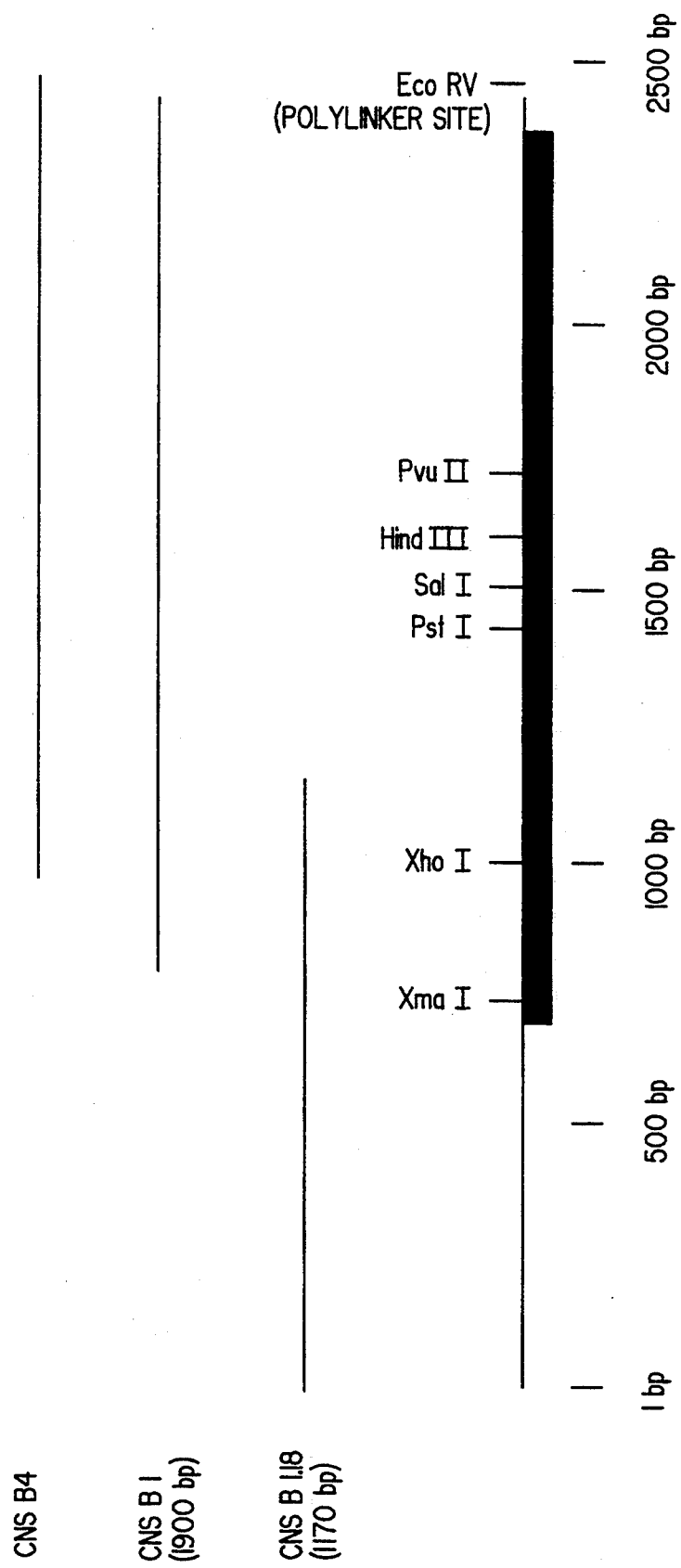
FIG. 5 is a restriction map of a nucleic acid sequence encoding a human neuronal calcium channel $\beta$-subunit, and the various cDNA clones used to derive the complete coding sequence.
Figure 8A:
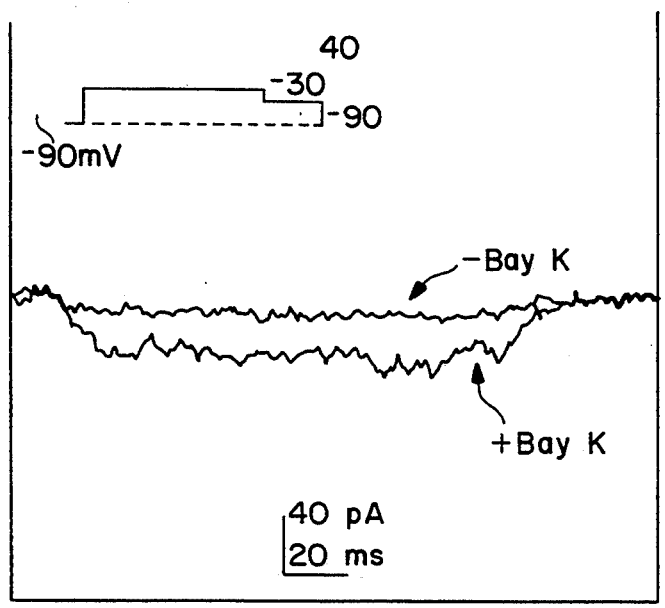
FIG. 8 shows recordings and IV curve depicting currents measured in an HEK cell transiently transfected with $\alpha_1$-, $\alpha_2$-, and $\beta$-subunit-encoding cDNAs.
Figure 8B:
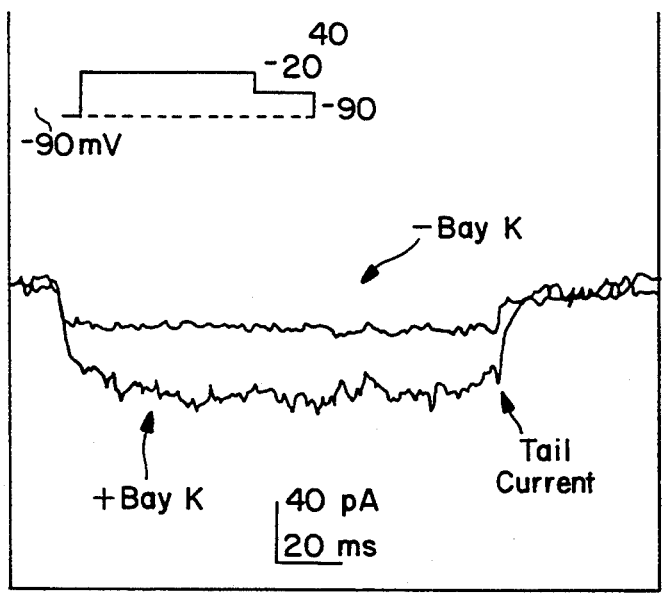
Figure 8C:
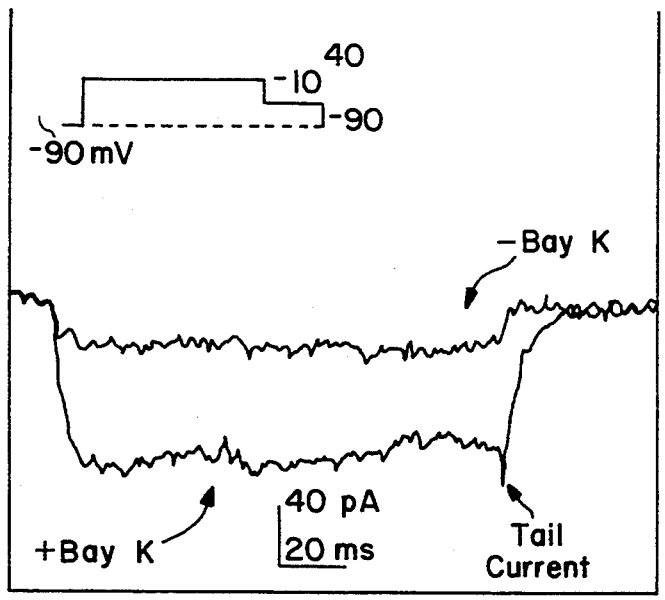
Figure 8D:
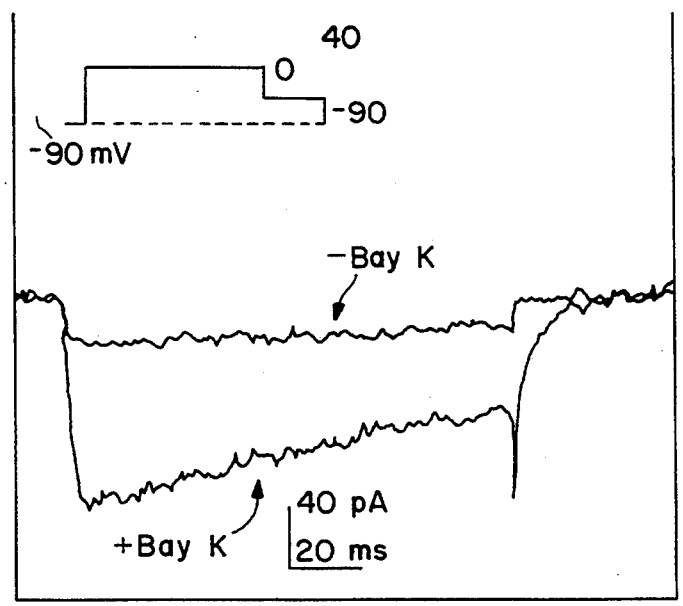
Figure 8E:
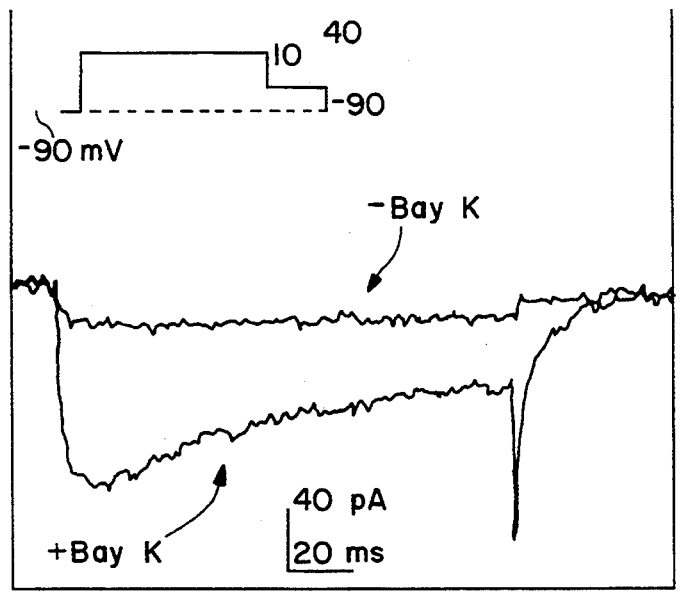
Figure 8F:
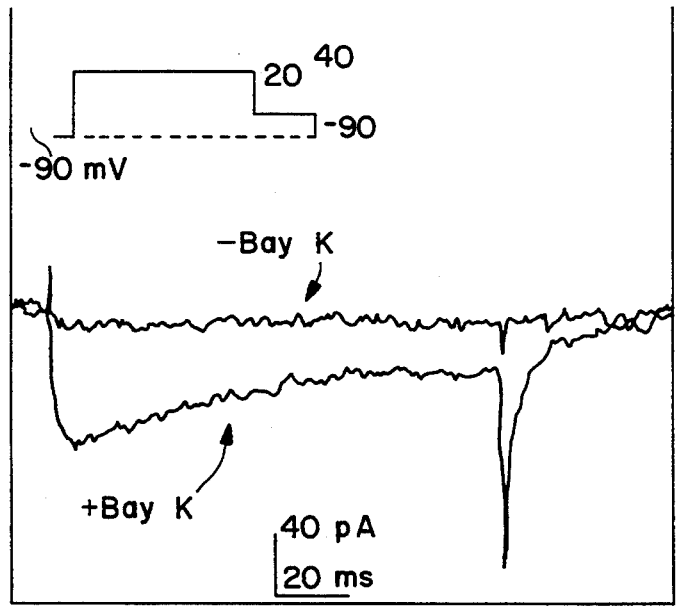
Figure 8G:
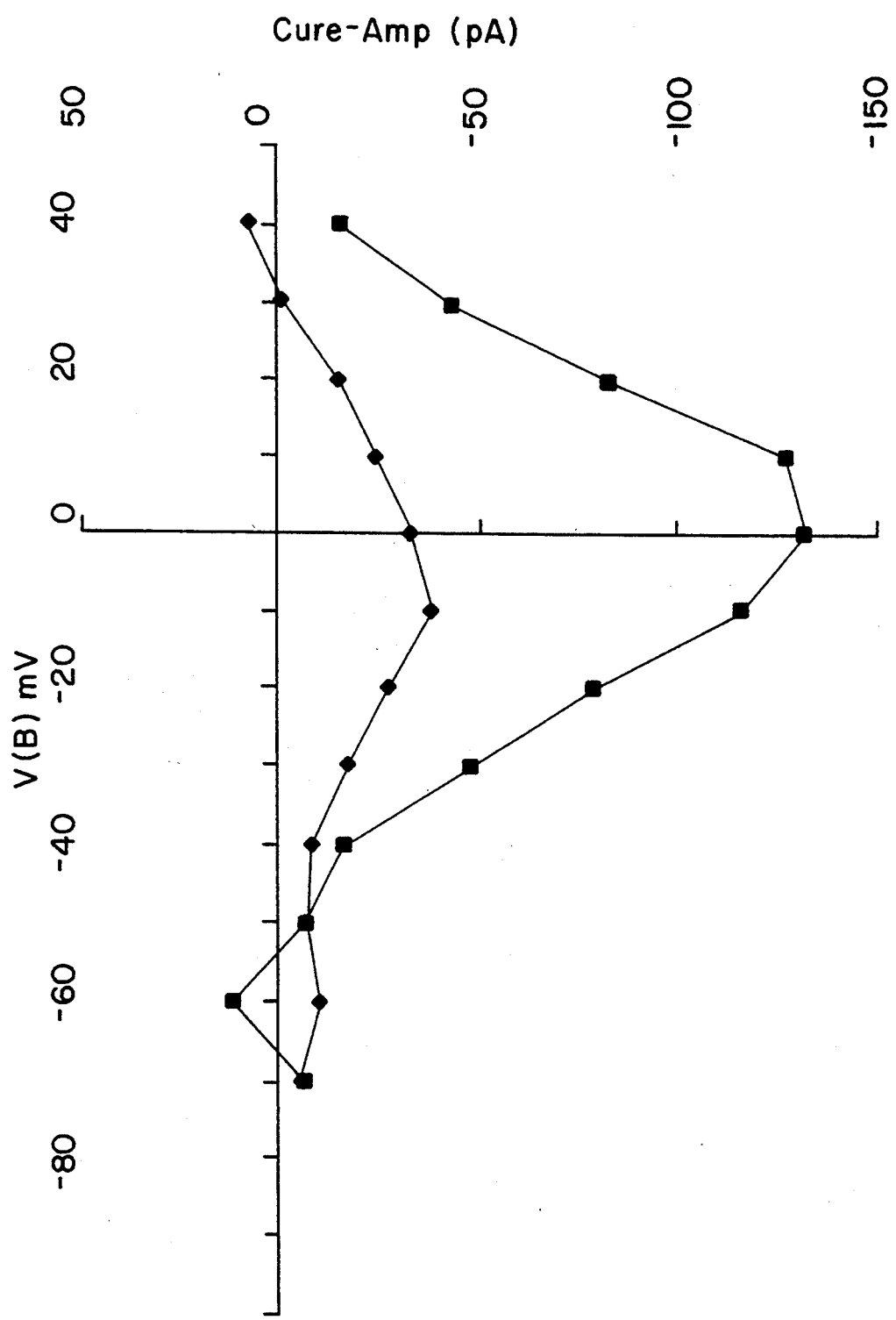

CNS β1 encodes nt 69 to 1546(Sequence ID #18). CNS β1 represents a partially spliced $\beta_2$ transcript that encodes a 448 bp intron (Sequence ID #21) inserted between nucleotides 1146 and 1147 of Sequence ID #18 and shown schematically in FIG. 5. This 448 bp intron was deleted via site-directed mutagenesis as described by J. Sambrook et al. (see Example I.A. for complete reference). The mutagenic oligonucleotide used to accomplish this mutagenesis encoded nt 1128 to 1165 (Sequence ID #18) and this construct was designated pβ1(−) encoding nucleotides 69 to 1546(Sequence ID #18).

b. CNS β4

DNA sequence characterization of CNS β4 showed that the first 1086 nt of β4 (Sequence ID #22) are identical to nt 246 to 1332 of β1 (Sequence ID #18). β4 then diverges at nt 1087 to 1515 (Sequence ID #22). CNS β4 represents an alternative splice form of the β transcript (⊖3) expressed in the CNS. The translation termination codon has not been identified.

2. CNS β1.18

Approximately $2 \times 10^6$ recombinants of the human hippocampus cDNA library (Example III.B.1.) were screened with a 5' PstI fragment of CNS β1 (nucleotide 69 to 511 Sequence ID #18). The hybridization was performed using standard hybridization conditions (Example I.C.) and the filters were washed under high stringency (Example I.C.). Twenty-six positive plaques were purified and characterized as described in Example III.B.1. One clone was identified as CNS β1.18 and shown to represent ~800 bp of 5' untranslated sequence that contains nt 1 to 65 (Sequence ID #20) followed by nt 1 to 325 (Sequence ID #18) followed by additional, seemingly unrelated sequence.

3. Construction of a Full-Length β2-Subunit cDNA a. pβ1-1.18

A full-length β2-subunit cDNA containing the CNS β1 intron was constructed. Plasmid CNS β1.18 was digested with EcoRI and XhoI and the approximately 1100 bp fragment (approximately 800 bp of 5' untranslated sequence plus nt 1 to 282 Sequence ID #18) was isolated from an agarose gel. Plasmid CNS β1 was digested with XhoI and EcoRI and the approximately 1730 bp fragment (beginning at nucleotide 277 of the coding sequence; see Sequence ID #18) was isolated from an agarose gel. The approximately 1100 bp EcoRI-XhoI fragment of CNS β1.18 was ligated to the approximately 1730 bp XhoI-EcoRI fragment of CNS β1 and cloned into the EcoRI site of pGEM7Z (Promega, Madison, Wisc.). The resulting plasmid was designated pβ1-1.18. The 5' end of the full-length $\beta_2$-subunit cDNA was proximal to the T7 promoter in pGEM7Z.

b. pβ1-1.18RBS pβ1-1.18 contains ~800 bp of 5' untranslated sequence. This sequence was replaced with an efficient ribosome binding site as follows.

A double-stranded adapter was synthesized that consists of an EcoRI site, sequence encoding a ribosome binding site, and nucleotides 1 to 25 (5' half of SmaI site) of the $\beta_2$ coding sequence (see Sequence ID #18):

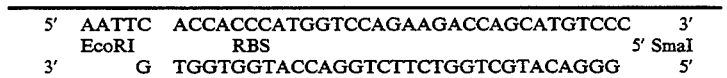

| 5' | AATTC | ACCACCCATGGTCCAGAAGACCAGCATGTCCC | 3' |
|---|---|---|---|
| | EcoRI | RBS | 5' SmaI |
| 3' | G | TGGTGGTACCAGGTCTTCTGGTCGTACAGGG | 5' |

This adapter was ligated to SmaI digested pβ1-1.18. The products of the ligation were then digested with EcoRI and the ~2000 bp EcoRI fragment containing the EcoRI adapter, the efficient ribosomal binding site (RBS) and nt 1 to 1546 of $\beta_2$ sequence (Sequence ID #18) plus the intron (Sequence ID #21) was cloned into a plasmid vector and designated pβ1-1.18RBS.

c. pHBCaCHβ1bA

The 5' EcoRI-XhoI fragment of pβ1-1.18RBS (Example III. B.3.b.) was ligated to the 3' XhoI-EcoRI fragment of pβ1(−), nt 282 to 1547 (Sequence ID #18) (Example III.B.1.a.), and subcloned into the pcDNA1 expression vector (Invitrogen, San Diego, Calif.) with the initiation of translation proximal to the CMV promoter.

EXAMPLE IV: Isolation of cDNAs Encoding the Human Neuronal Calcium Channel β2-Subunit

A. Isolation of cDNAs

Shown in FIG. 6 is a schematic of human neuronal calcium channel $\alpha_2$-subunit cDNAs that overlap to encode the complete coding sequence. The complete human neuronal $\alpha_2$ coding sequence plus a portion of the 3' untranslated sequence is shown as Sequence ID #24 (nt 1 to 3566). A portion of the 5' untranslated sequence, nt 1 to 34 is shown as Sequence ID #26.

To isolate human neuronal $\alpha_2$ cDNAs, human $\alpha_2$ genomic clones first were isolated by probing human genomic Southern blots using a rabbit skeletal muscle calcium channel $\alpha_2$-subunit cDNA fragment (nt 43 to 272, Ellis et al., (1988) *Science* 240:1661). Human genomic DNA was digested with EcoRI, electrophoresed, blotted, and probed with the rabbit skeletal muscle probe using standard hybridization conditions (Example I.C.) and low stringency washing conditions (Example I.C.). Two restriction fragments were identified, 3.5 kb and 3.0 kb. These EcoRI restriction fragments were cloned by preparing a λgt11 library containing human genomic EcoRI fragments ranging from 2.2 kb to 4.3 kb. The library was screened as described above using the rabbit $\alpha_2$ probe, the clones were isolated and characterized by DNA sequencing. HGCaCHα2.20 contained the 3.5 kb fragment and HGCaCHα2.9 contained the 3.0 kb fragment.

Restriction mapping and DNA sequencing revealed that HGCaCHα2.20 contains an 82 bp exon (nt 96 to 177 of the human $\alpha_2$ coding sequence, Sequence ID #24) on a 650 bp PstI-XbaI restriction fragment and that HGCaCHα2.9 contains 105 bp of an exon (nt 178 to 282 of the coding sequence, Sequence ID #24) on a 750 bp XbaI-BglII restriction fragment. These restriction fragments were used to screen the human basal banglia cDNA library (Example II.C.2.a.). HBCaCHα2.1 was isolated (nt 1 to 6, Sequence ID #26 and nt 1 to 1129, Sequence ID #24) and used to screen a human brain stem cDNA library obtained from the American Type Culture Collection (ATCC #37432). Two clones were isolated, HBCaCHα2.5 (nt 1 to 34, Sequence ID #26 and nt 1 to 1128, Sequence ID #24) and HBCaCHα2.8 (nt 680 to 1528, Sequence ID #24, followed by 1600 nt of intervening sequence). A 2400 bp fragment of HBCaCHα2.8 (beginning at nt 725 of Sequence ID #24 and ending at a SmaI site in the intron) was used to rescreen the brain stem library and to isolate HBCaCHα2.11 (nt 845 to 3566, Sequence ID #24). Clones HBCaCHα2.5 and HBCaCHα2.11 overlap to encode the entire human brain $\alpha_2$ protein.

B. Construction of pHBCaCHα2A

To construct pHBCaCHα2A containing a full-length human calcium channel $\alpha_2$ cDNA, an (EcoRI)-PvuII fragment of HBCaCHα2.5 (nt 1 to 34, Sequence ID #26 and nt 1 to 1027, Sequence ID #24 EcoRI adapter, PvuII partial digest) and a PvuII-PstI fragment of HBCaCHα2.11 (nt 1027 to 2390 Sequence ID #24; PvuII partial digest) were ligated together into EcoRI-PstI digested pIBI24 (Stratagene, La Jolla, Calif.). Subsequently, an (EcoRI)-PstI fragment (nt 1 to 34 Sequence ID #26 and 1 to 2390 Sequence ID #24) was isolated and ligated to a PstI-(EcoRI) fragment (nt 2390 to 3566 Sequence ID #24) of HBCaCHα2.11 in EcoRI digested pIBI24 to create a full-length human brain $\alpha_2$ cDNA, HBCaCHα2. The 3600 bp EcoRI insert of HBCaCHα2 (nt 1 to 34, Sequence ID #26 and nt 1 to 3566, Sequence ID #24) was subcloned into pcDNA1 (pHBCaCHα2A) with the methionine initiating codon proximal to the CMV promoter. The 3600 bp EcoRI insert of HBCaCHα2 was also subcloned into pSV2dHFR [Subramani, et al. (1981). *Mol. Cell. Biol.* 1:854–864] which contains the SV40 early promoter, mouse dihydrofolate reductase (dhfr) gene, SV40 polyadenylation and splice sites and sequences required for maintenance of the vector in bacteria.

EXAMPLE V. Differential Processing of the Human Transcript and the Human $\alpha_2$ Transcript

A. β

A comparison of the amino acid sequences encoded by the human neuronal and rabbit skeletal muscle calcium channel β-subunit cDNAs revealed a deletion of 45 amino acids in the human sequence (corresponding to nucleotides 628–782 of the rabbit skeletal muscle calcium channel β-subunit cDNA) relative to the rabbit sequence. This deletion is confirmed by the sequence of β4.

To determine if this difference between the rabbit and human sequences is a result of differential processing, human skeletal muscle and aorta poly(A+) RNAs were characterized by PCR analysis and DNA sequencing.

PCR products of human skeletal muscle and human aorta poly(A+) RNAs were synthesized by standard methods (*PCR Protocols, A Guide to Methods and Applications,* Ginnis, M., Gelfand, D., Sniasky, J. and White, T., eds. Acadamic Press, San Diego, Calif.) using $\beta_2$ oligonucleotide primers, nt 541 to 560 and the complement of nt 953 to 972 (Sequence ID #18). The PCR products were purified on an agarose gel and cloned in pcr1000 (Invitrogen, San Diego, Calif.).

Figure 7A:
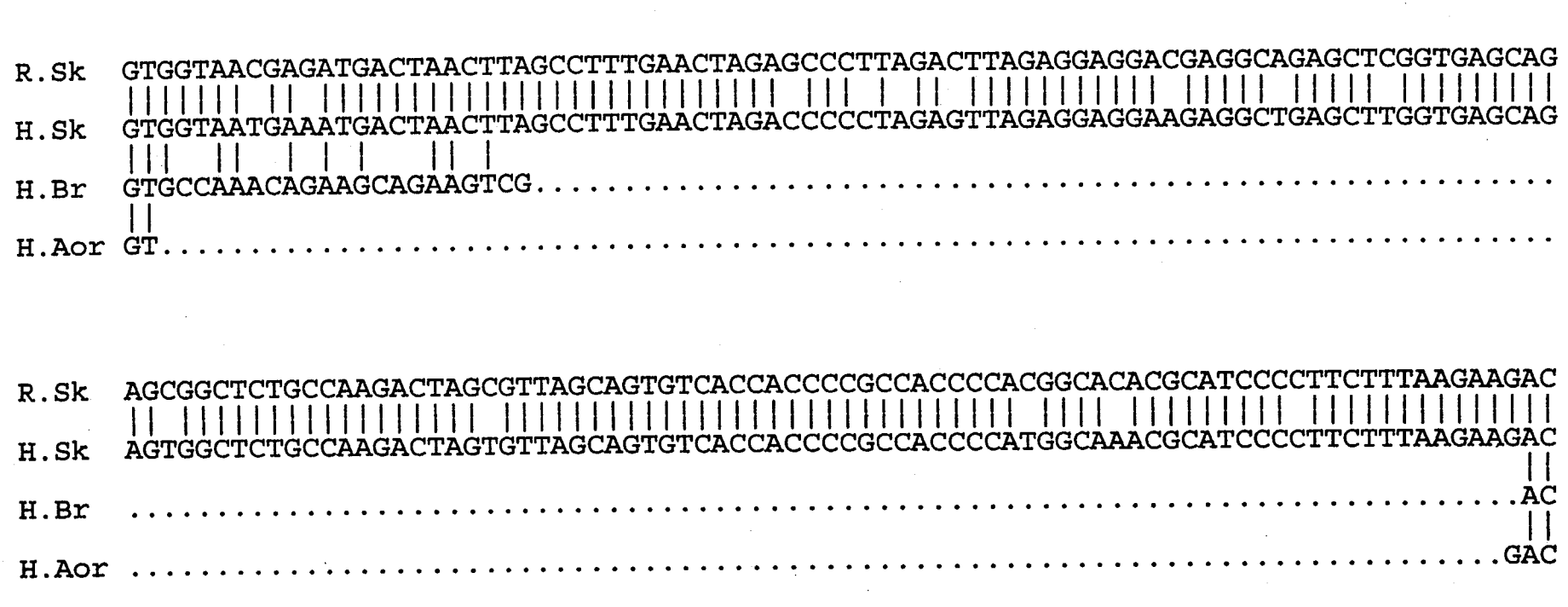

Shown in FIG. 7 are the comparisons of the nucleotide sequence and deduced amino acid sequence through a 156 nt (52 amino acid) region of the rabbit skeletal muscle $\beta$-subunit transcript, designated R.SK($\beta_1$), that is deleted from the human aorta and CNS $\beta$ transcripts. The human skeletal muscle sequence (Sequence ID #27), designated H.SK($\beta_1$), is very similar to the rabbit skeletal muscle sequence (Ruth et al (1988) *Science* 245:1115) through the analyzed region. In contrast, the human brain $\beta_2$ sequence (Sequence ID #18), designated H.BR($\beta_2$), lacks 156 nt of the human skeletal muscle sequence, nt 1 to 156 (Sequence ID #27) and, furthermore, has an insertion relative to the skeletal muscle sequence, nt 628 to 648 (Sequence ID #18). The human aorta transcript (designated H.AO($\beta_4$)), lacks the entire 156 nt region, nt 1 to 156 (Sequence ID #27). These results indicate that this 156 nt region is comprised of at least three exons that are differentially processed between the CNS, skeletal muscle, and aorta transcripts.

B. $\alpha_2$

A comparison of the amino acid sequences encoded by the human neuronal and rabbit skeletal muscle calcium channel $\alpha_2$-subunit cDNAs revealed a 19 amino acid deletion in the human sequence compared to the rabbit sequence (rabbit residues Pro 507 to Gln 525) which corresponds to a deletion between nt 1590 and 1591 of the human sequence (Sequence ID #24). Furthermore, a seven amino insertion was identified in the human sequence compared to the rabbit sequence (human residue Lys$^{626}$ to Asp$^{632}$) encoded by nt 1876 to 1896 (Sequence ID #24).

PCR analysis of this region using human neuronal $\alpha_2$ oligonucleotides, nt 1455 to 1479 and the complement of nt 1931 to 1955 (Sequence ID #24) to prime PCR assays of human skeletal muscle, aorta, and CNS poly(A+) RNAs showed that this region is alternatively spliced. The predicted size of the PCR products was 539 bp for the skeletal muscle reaction and 501 bp for the CNS reaction. An approximate 539 bp band was observed in the skeletal muscle reaction and an approximate 500 bp band was observed in the CNS reaction. An approximate 460 bp band also was observed in the aorta reaction plus at least two additional, larger bands, approximately 470 and 480 bp, suggesting additional alternative splicing.

EXAMPLE VI: Isolation of a Calcium Channel $\gamma$-Subunit cDNA from a Human Brain cDNA Library A human hippocampus cDNA library was screened as described in this example to determine if human brain tissue expresses a transcript that encodes a protein homologous to a calcium channel $\gamma$-subunit.

A. Isolation of cDNAs

Apporoximately $1\times10^6$ recombinants from a $\lambda$gt11-based human hippocampus cDNA library (Clontech catalog #HL1088b, Palo Alto, Calif.) were screened by hybridization to a 484 bp sequence of the rabbit skeletal muscle calcium channel $\gamma$-subunit cDNA (nucleotides 621–626 of the coding sequence plus 438 nucleotides of 3'-untranslated sequence) contained in vector $\gamma$J10 [Jay, S., et al. (1990). *Science* 248:490–492]. Hybridization was performed using moderate stringency conditions (20% deionized formamide, 5×Denhardt's; 6×SSPE, 0.2% SDS, 20 $\mu$g/ml herring sperm DNA, 42° C.) and the filters were washed under low stringency (see Example I.C.). A plaque that hybridized to this probe was purified and insert DNA was subcloned into pGEM7Z. This cDNA was designated $\gamma$1.4.

B. Characterization of $\gamma$1.4

$\gamma$1.4 was confirmed by DNA hybridization and characterized by DNA sequencing. The 1500 bp SstI fragment of $\gamma$1.4 hybridized to the rabbit skeletal muscle calcium channel $\gamma$-subunit cDNA $\gamma$J10 on a Southern blot. Sequence analysis of this fragment revealed that it consists of approximately 500 nt of human DNA sequence and ~1000 nt of $\lambda$gt11 sequence (included due to apparent destruction of one of the EcoRI cloning sites in $\lambda$gt11). The human DNA sequence consists of 129 nt of coding sequence followed immediately by a translational STOP codon and 3' untranslated sequence (Sequence ID #29).

To isolate the remaining 5' sequence of the human $\gamma$-subunit cDNA, human CNS cDNA libraries and/or preparations of mRNA from human CNS tissues can first be assayed by PCR methods using oligonucleotide primers based on the $\gamma$ cDNA-specific sequence of $\gamma$1.4. Additional human neuronal $\gamma$-subunit cDNAs could be isolated from cDNA libraries that, based on the results of the PCR assay, contain $\gamma$-specific amplifiable cDNA or, alternatively, cDNA libraries could be constructed from mRNA preparations that, based on the results of PCR assays, contain $\gamma$-specific amplifiable transcripts. cDNA libraries could be constructed by standard methods using oligo dT to prime first-strand cDNA synthesis from poly A+ RNA (see Example I.B.). Alternatively, first-strand cDNA could be specified by priming first-strand cDNA synthesis with a $\gamma$ cDNA-specific olionucleotide based on the human DNA sequence in $\gamma$1.4. A cDNA library would then be constructed based on this first-strand synthesis. The libraries would be screened with the $\gamma$-specific portion of $\gamma$1.4.

EXAMPLE VII: Recombinant Expression of Human Neuronal Calcium Channel Subunit cDNAs and Transcripts Prepared in vitro from the cDNAs in Mammalian Cells

A. Recombinant Expression of the Human Neuronal Calcium Channel $\alpha_2$-subunit cDNA in DG44 Cells

1. Stable transfection of DG44 cells

DG44 cells [dhf$^-$ Chinese hamster ovary cells; see Urlaub, G. et al. (1986). *Som. Cell Molec Genet.* 12:555–566] obtained from Lawrence Chasin at Columbia University were stably transfected by CaPO$_4$ precipitation methods [Wigler et al. (1979) *Proc. Natl. Acad.*

Sci. U.S.A. 76:1373-1376] with pSV2dhfr vector containing the human neuronal calcium channel $\alpha_2$-subunit cDNA (see Example IV) for polycistronic expression/selection in transfected cells. Transfectants were grown on 10% DMEM medium without hypoxanthine or thymidine in order to select cells that had incorporated the expression vector. Twelve transfectant cell lines were established as indicated by their ability to survive on this medium.

2. Analysis of $\alpha_2$-Subunit cDNA Expression in Transfected DG44 Cells

Total RNA was extracted according to the method of Birnboim [*Nuc. Acids Res.* 16:1487-1497 (1988)] from four of the DG44 cell lines that had been stably transfected with pSV2dhfr containing the human neuronal calcium channel $\alpha_2$-subunit cDNA. RNA (~15 µg per lane) was separated on a 1% agarose formaldehyde gel, transferred to nitrocellulose and hybridized to the random-primed human neuronal calcium channel $\alpha_2$ cDNA (hybridization: 50% formamide, 5×SSPE, 5×Denhardt's, 42° C.; wash :0.2×SSPE, 0.1% SDS, 65° C.). Northern blot analysis of total RNA from four of the DG44 cell lines that had been stably transfected with pSV2dhfr containing the human neuronal calcium channel $\alpha_2$-subunit cDNA revealed that one of the four cell lines contained hybridizing mRNA the size expected for the transcript of the $\alpha_2$-subunit cDNA (5000 nt based on the size of the cDNA) when grown in the presence of 10 mN sodium butyrate for two days. Butyrate nonspecifically induces transcription and is often used for inducing the SV40 early promoter [Gorman, C. and Howard, B. (1983). *Nuc. Acids Res.* 11:1631]. This cell line, 44$\alpha_2$-9, also produced mRNA species smaller (several species) and larger (6800 nt) than the size expected for the transcript of the $\alpha_2$ cDNA (5000 nt) that hybridized to the $\alpha_2$ cDNA-based probe. The 5000- and 6800-nt transcripts produced by this transfectant should contain the entire $\alpha_2$-subunit coding sequence and therefore should yield a full-length $\alpha_2$-subunit protein. A weakly hybridizing 8000-nucleotide transcript was present in both untransfected and transfected DG44 cells. Apparently, DG44 cells transcribe a calcium channel $\alpha_2$-subunit or similar gene at low levels. The level of expression of this endogenous $\alpha_2$-subunit transcript did not appear to be affected by exposing the cells to butyrate before isolation of RNA for northern analysis.

Total protein was extracted from three of the DG44 cell lines that had been stably transfected with pSV2dhfr containing the human neuronal calcium channel $\alpha_2$-subunit cDNA. Approximately $10^7$ cells were sonicated in 300 µl×50 mM HEPES, 1 mM EDTA, 1 mM PMSF. An equal volume of 2×loading dye [Laemmli, U,K. (1970). *Nature* 227:680] was added to the samples and the protein was subjected to electrophoresis on an 8% polyacrylamide gel and then electrotransferred to nitrocellulose. The nitrocellulose was incubated with polyclonal guinea pig antisera (1:200 dilution) directed against the rabbit skeletal muscle calcium channel $\alpha$-subunit (obtained from K. Campbell, University of Iowa) followed by incubation with [$^{125}$I]-protein A. The blot was exposed to X-ray film at $-70°$ C. Reduced samples of protein from the transfected cells as well as from untransfected DG44 cells contained immunoreactive protein of the size expected for the $\alpha_2$-subunit of the human neuronal calcium channel (130–150 kDa). However, the level of this immunoreactive protein was higher in 44$\alpha_2$-9 cells that had been grown in the presence of 10 mM sodium butyrate than in 44$\alpha_2$-9 cells that were grown in the absence of sodium butyrate. These data correlate well with those obtained in northern analyses of total RNA from 44$\alpha_2$-9 and untransfected DG44 cells. Cell line 44$\alpha_2$-9 also produced a 110-kDa immunoreactive protein which may be either a product or a proteolytic degradaton of the full-length $\alpha_2$-subunit or a product of translation of one of the shorter (<5000 nt) mRNAs produced in this cell line that hybridized to the $\alpha_2$-subunit cDNA probe.

B. Recombinant Expression of Human Neuronal Calcium Channel $\alpha_1$, $\alpha_2$ and $\beta$-subunit cDNAs in HEK 293 Cells Human embryonic kidney cells (HEK 293 cells) were transiently and stably transfected with human neuronal calcium channel subunit cDNAs. Individual transfectants were analyzed electrophysiologically for the presence of voltage-activated barium currents indicative of the presence of functional recombinant voltage-dependent calcium channels.

1. Transfection of HEK 293 Cells

Separate expression vectors containing cDNAs encoding human neuronal calcium channel $\alpha_1$ (VDCC III), $\alpha_2$ and $\beta$-subunits, vectors pVDCCIII(A), pHBCaCH$\alpha_2$A, and pB1-1.18, respectively, were constructed as described in Examples II.A.3, IV.B. and III.B.3., respectively. These three vectors were used to transiently co-transfect HEK 293 cells. For stable transfection of HEK 293 cells, vector PHBCaCH$\beta_1$bA (Example III.B.3.) was used in place of pB1-1.18 to introduce the $\beta$-subunit cDNA into the cells along with pVDCCIII(A) and pHBCaCH$\alpha_2$A.

a. Transient Transfection

Expression vectors pVDCCIII(A), pHBCaCH$\alpha_2$A and pB1-1.18 were used in two sets of transient transfections of HEK 293 cells (ATCC #CRL1573). In one transfection procedure, HEK 293 cells were transiently cotransfected with the $\alpha_1$-subunit cDNA expression vector, the $\alpha_2$-subunit cDNA expression vector, the $\beta$-subunit cDNA expression vector and vector pCMV$\beta$gal (Clontech Laboratories, Palo Alto, Calif.). Vector pCMV$\beta$gal contains the lacZ gene (encoding *E. coli* $\beta$-galactosidase) fused to the cytomegalovirus (CMV) promoter and was included in this transfection as a marker gene for monitoring the efficiency of transfection. In the other transfection procedure, HEK 293 cells were transiently co-transfected with the $\alpha_1$-subunit cDNA expression vector pVDCCIII(A) and pCMV$\beta$gal. In both transfections, 2–4×10$^6$ HEK 293 cells contained in a 10-cm tissue culture plate were transiently cotransfected with 5 µg of each of the vectors included in the experiment according to standard CaPO$_4$ precipitation transfection procedures (Wigler et al., supra). The transfectants were analyzed for $\beta$-galactosidase expression by direct staining of the product of a reaction involving $\beta$-galactosidase and the X-gal substrate [Jones, J. R. (1986). *EMBO* 5:3133–3142] and by measurement of $\beta$-galactosidase activity [Miller, J. H. (1972). Experiments in Molecular Genetics, pp. 352–355, Cold Spring Harbor Press]. To evaluate subunit cDNA expression in these transfectants, the cells were analyzed for subunit transcript production (northern analysis), subunit protein production (immunoblot analysis of cell lysates) and functional calcium channel expression (electrophysiological analysis).

b. Stable Transfection

HEK 293 cells were transfected using the calcium phosphate transfection procedure [*Current Protocols in Molecular Biology*, Vol. 1, Wiley Inter-Science, Supplement 14, Unit 9.1.1–9.1.9 (1990)]. Ten-cm plates, each containing one-to-two million HEK 293 cells, were transfected with 1 ml of DNA/calcium phosphate precipitate containing 5 μg pVDCCIII(A), 5 μg pHBCaCHα₂A, 5 μg pHBCaCHβ₁bA, 5 μg pCMVβgal and 1 μg pSV2neo (as a selectable marker). After 10–20 days of growth in media containing 500 μg G418, colonies had formed and were isolated using cloning cylinders.

2. Analysis of HEK 293 Cells Transiently Transfected with cDNAs Encoding Human Neuronal Calcium Channel Subunits a. Analysis of β-galactosidase Expression

Transient transfectants were assayed for galactosidase expression by β-galactosidase activity assays (Miller, J. H., supra) of cell lysates (prepared as described in Example V.A. 2) and staining of fixed cells (Jones, J. R. supra). The results of these assays indicated that approximately 30% of the HEK 293 cells had been transfected.

b. Northern Analysis

PolyA+ RNA was isolated using the Invitrogen Fast Trak Kit (InVitrogen, San Diego, Calif.) from HEK 293 cells transiently transfected with $\alpha_1$, $\alpha_2$ and β-subunit cDNAs and the lacZ gene or the $\alpha_1$-subunit cDNA and the lacZ gene. The RNA was subjected to electrophoresis on an agarose gel and transferred to nitrocellulose. The nitrocellulose was then hybridized with one or more of the following radiolabeled probes: lacZ gene, human neuronal calcium channel $\alpha_1$ (VDCC III) subunit cDNA, human neuronal calcium channel $\alpha_2$-subunit cDNA or human neuronal calcium channel β-subunit cDNA. Two transcripts that hybridized with the $\alpha_1$-subunit cDNA were detected in HEK 293 cells transfected with the $\alpha_1$, $\alpha_2$, and β-subunit cDNAs and the lacZ gene as well as in HEK 293 cells transfected with the β-subunit cDNA and the lacZ gene. One mRNA species was the size expected for the transcript of the $\alpha_1$-subunit cDNA (8000 nucleotides). The second RNA species was smaller (4000 nucleotides) than the size expected for this transcript. RNA the size expected for the transcript of the lacZ gene was detected in cells transfected with the $\alpha_1$, $\alpha_2$ and β-subunit cDNAs and the lacZ gene and in cells transfected with the $\alpha_1$-subunit cDNA and the lacZ gene by hybridization to the lacZ gene sequence.

RNA from cells transfected with the $\alpha_1$, $\alpha_2$ and β-subunit cDNAs and the lacZ gene was also hybridized with the $\alpha_2$ and β-subunit cDNA probes. Two mRNA species hybridized to the $\alpha_2$-subunit cDNA probe. One species was the size expected for the transcript of the $\alpha_2$-subunit cDNA (4000 nucleotides). The other species was larger (6000 nucleotides) than the expected size of this transcript. Multiple RNA species in the cells cotransfected with $\alpha_1$, $\alpha_2$ and β-subunit cDNAs and the lacZ gene hybridized to the β-subunit cDNA probe. Multiple β-subunit transcripts of varying sizes were not unexpected since the β-subunit cDNA expression vector contains two potential polyA+ addition sites. Differential processing of the 3' end of the β-subunit transcript at these multiple polyA+ addition sites could result in multiple β-subunit transcripts of varying sizes. It is unlikely that any of these multiple β-subunit transcripts contained the intron sequence that was present in the β-subunit cDNA used to transfect these HEK 293 cells since HEK 293 cells should be capable of recognizing the splice donor and acceptor sites on the 5' and 3' ends of the intron, respectively, and removing the intron from the primary transcript.

c. Electrophysiological Analysis

Individual transiently transfected HEK 293 cells were assayed for the presence of voltage-dependent barium currents using the whole-cell variant of the patch clamp technique [Hamill, O. P., Marty, A., Neher, E., Sakmann, B. and Sigworth, F. J. (1981). *Pflugers Arch.* 391:85–100]. HEK 293 cells transiently transfected with pCMVβgal only were assayed for barium currents as a negative control in these experiments. The cells were placed in a bathing solution that contained barium ions to serve as the current carrier. Choline chloride, instead of NaCl or KCl, was used as the major salt component of the bath solution to eliminate currents through sodium and potassium channels. The bathing solution contained in 1 mM $MgCl_2$ and was buffered at pH 7.3 with 10 mM HEPES (pH adjusted with sodium or tetraethylammonium hydroxide). Patch pipettes were filled with a solution containing 135 mM CsCl, 1 mM $MgCl_2$, 10 mM glucose, 10 mM EGTA, 4 mM ATP and 10 mM HEPES (pH adjusted to 7.3 with tetraethylammonium hydroxide). Cesium and tetraethylammonium ions block most types of potassium channels. Pipettes were coated with Sylgard (Dow-Corning, Midland, Mich.) and had resistances of 1–4 megohm. Currents were measured through a 500 megohm headstage resistor with the Axopatch IC (Axon Instruments, Foster City, Calif.) amplifier, interfaced with a Labmaster (Scientific Solutions, Solon, Ohio) data acquisition board in an IBM-compatible PC. PClamp (Axon Instruments) was used to generate voltage commands and acquire data. Data were analyzed with pClamp or Quattro Professional (Borland International, Scotts Valley, Calif.) programs.

To apply drugs, "puffer" pipettes positioned within several micrometers of the cell under study were used to apply solutions by pressure application. The drugs were used to apply solutions by pressure application. The drugs used for pharmacological characterization were dissolved in a solution identical to the bathing solution. Samples of a 10 mM stock solution of Bay K 8644 (RBI, Natick, Mass.), which was prepared in DMSO, were diluted to a final concentration of 1 μM in 15 mM $Ba^{2+}$-containing bath solution before they were applied.

Twenty-one negative control HEK 293 cells (transiently transfected with the lacZ gene expression vector pCMVβgal only) were analyzed by the whole-cell variant of the patch clamp method for recording currents. Only one cell diplayed a discernable inward barium current which was not affected by the presence of 1 μM Bay K 8644. In addition, application of Bay K 8644 to four cells that did not display $Ba^{2+}$ currents did not result in the appearance of any currents.

Two days after transient transfection of HEK 293 cells with $\alpha_1$, $\beta_2$ and β-subunit cDNAs and the lacZ gene, individual transfectants were assayed for voltage-dependent barium currents. The currents in nine transfectants were recorded. Because the efficiency of transfection of one cell can vary from the efficiency of transfection of another cell, the degree of expression of heterologous proteins in individual transfectants varies and some cells do not incorporate or express the foreign DNA. Therefore, it was not unexpected that seven of these nine transfectants did not display a voltage-dependent inward barium current. However, inward barium currents were detected in two of these nine transfectants. In these assays, the holding potential of the membrane was −90 mV. The membrane was depolarized in a series of voltage steps to different test potentials and the current in the presence and absence of 1 µM Bay K 8644 was recorded. The current tracings for one of the two cells are shown in FIG. 8. The inset in each tracing panel indicates the test potential to which the membrane was depolarized. The inward barium current in this cell was significantly enhanced in magnitude by the addition of Bay K 8644. The largest inward barium current (~160 pA) was recorded when the membrane was depolarized to 0 mV in the presence of 1 µM Bay K 8644. The data shown in the current tracings are also presented in FIG. 8 as an I–V curve generated by plotting the largest current recorded after each depolarization versus the depolarization voltage. A comparison of the I–V curves corresponding to recordings conducted in the absence and presence of Bay K 8644 illustrates the enhancement of the voltage-activated current in the presence of Bay K 8644.

It has been reported [Hess, J. B., et al. (1984), *Nature* 311: 538–544] that the dihydropyridine Bay K 8644 specifically enhances L-type calcium channel function by increasing the duration of the open state of the channels. Prolonged opening of the channels results in calcium currents of increased magnitude and duration. The generation of prolonged calcium currents and Bay K "tails" in whole-cell patch claim recordings of L cells transfected with the rabbit skeletal muscle calcium channel $\alpha_1$-subunit cDNA that were treated with Bay K 8644 has also been described [Perez-Reyes, E., et al. (1989). *Nature* 340:233–236]. Tail currents can be observed upon repolarization of the cell membrane after activation of ion channels by a depolarizing voltage command. The opened channels require a finite time to close or "deactivate" upon repolarization, and the current that flows through the channels during this period is referred to as a tail current. Because Bay K 8644 prolongs opening events in calcium channels, it tends to prolong these tail currents and make them more pronounced. As shown in FIG. 8, pronounced tail currents were detected in the tracings of currents generated in the presence of Bay K 8644 in this HEK 293 cell transfected with $\alpha_1$, $\alpha_2$ and $\beta$-subunit cDNAs and the lacZ gene. Therefore, the recombinant calcium channels responsible for the voltage-activated barium currents recorded in this transfected appear to be DHP sensitive.

The second of the two transfected cells that displayed inward barium currents expressed a ~50 pA current when the membrane was depolarized from −90 mV. This current was nearly completely blocked by 200 µM cadmium, an established calcium channel blocker.

Ten cells that were transiently transfected with the $\alpha_1$-subunit cDNA and the lacZ gene were analyzed by whole-cell patch clamp methods two days after transfection. One of these cells displayed a 30 pA inward barium current. This current amplified 2-fold in the presence of 1 µM Bay K 8644. Furthermore, small tail currents were detected in the presence of Bay K 8644.

These data indicate that expression of the human neuronal calcium channel VDCC III $\alpha_1$-subunit cDNA in HEK 293 yields a functional DHP-sensitive calcium channel.

3. Analysis of HEK 293 Cells Stably Transfected with cDNAs Encoding Human Neuronal Calcium Channel Subunits Individual stably transfected HEK 293 cells were assayed electrophysiologically for the presence of voltage-dependent barium currents as described for electrophysiological analysis of transiently transfected HEK 293 cells (see Example VII.B.2.c). In an effort to maximize calcium channel activity via cyclic-AMP-dependent kinase-mediated phosphorylation [Pelzer, et al. (1990) *Rev. Physiol. Biochem. Pharmacol.* 114:107–207], cAMP (Na salt, 250 µM) was added to the pipet solution and forskolin (10 µM) was added to the bath solution in some of the recordings. Qualitatively similar results were obtained whether these compounds were present or not.

Figure 9A:
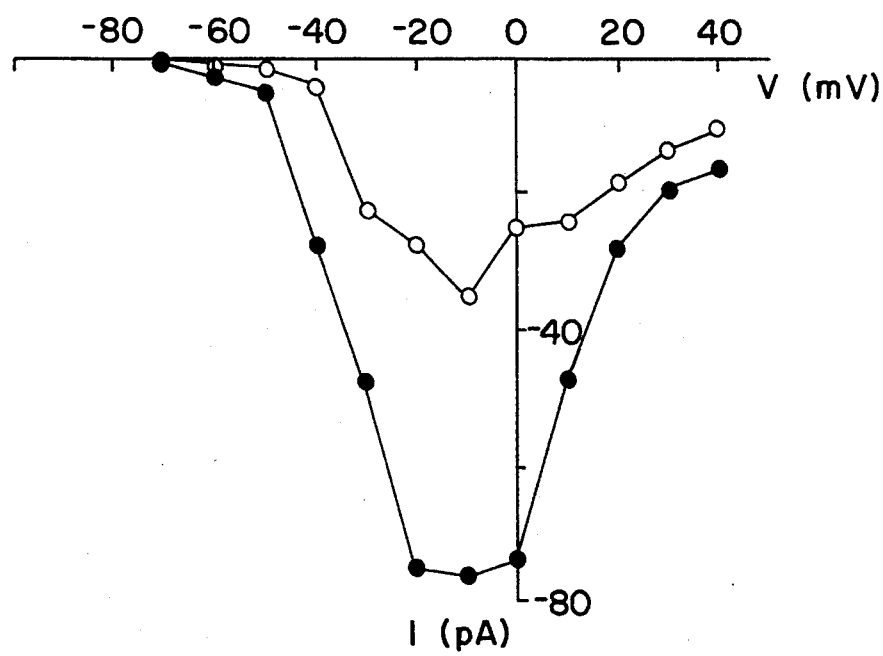
FIG. 9 shows recordings and IV curve depicting currents measured in an HEK cell stably transfected with $\alpha 1$-, $\alpha 2$-, and $\beta$-subunit-encoding cDNAs.
Figure 9B:
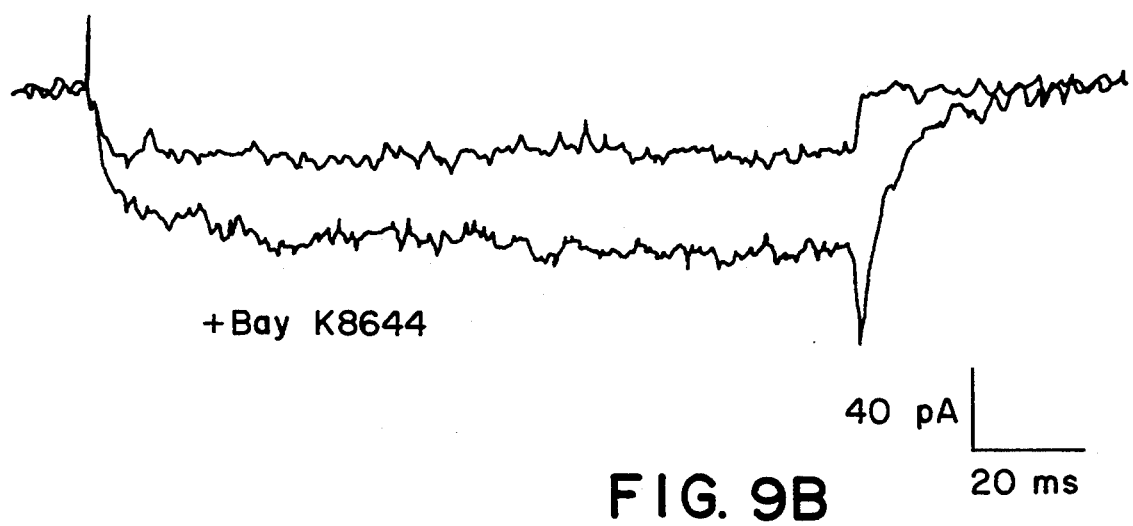
Figure 10A:
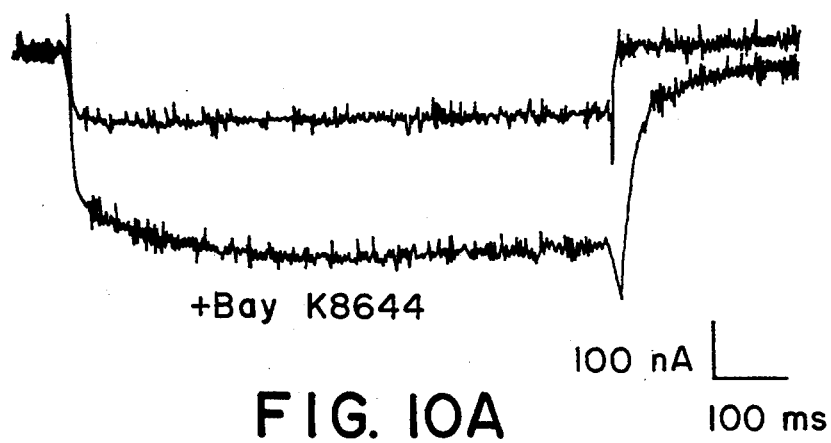
FIG. 10 shows recordings and IV curve depicting currents measured in oocytes injected with combinations of in vitro transcripts of the $\alpha 1$-, $\alpha 2$-, and $\beta$-subunit-encoding cDNAs.

Barium currents recorded from stably transfected cell in the absence and presence of Bay K 8644 (1 µM) are shown in FIG. 9. When the cell was depolarized to −10 mV from a holding potential of −90 mV in the absence of Bay K 8644, a current of approximately 35 pA with a rapidly deactivating tail current was recorded. During application of Bay K 8644, an identical depolarizing protocol elicited a current of approximately 75 pA, accompanied by an augmented and prolonged tail current. The current-voltage relations also shown in FIG. 10 summarize the peak magnitude of currents recorded from this same cell at a series of depolarizing voltages. The responses in the presence of Bay K 8644 (closed circles) are not only increased, but the entire current-voltage relation is shifted about −10 mV. Thus, three typical hallmarks of Bay K 8644 action, namely increased current magnitude, prolonged tail currents, and negatively shifted activation voltage, were observed, clearly indicating the expression of a DHP-sensitive calcium channel in these stably transfected cells. No such effects of Bay K 8644 were observed in untransfected HEK 293 cells, either with or without cAMP or forskolin.

C. Use of pCMV - vs. pcDNA1-Based Vectors for Recombinant Expression of Human Neuronal Calcium Channel Subunit cDNAs 1. Preparation of Constructs To determine if the levels of recombinant expression of human calcium channel subunit cDNAs in host cells could be enhanced by using pCMV-based instead of pcDNA1-based expression vectors, additional expression vectors were constructed. The full-length VDCC III cDNA from pVDCCIII(A) (see Example II.A.3.d), the full-length $\alpha_2$ cDNA, contained on a 3600 bp EcoRI fragment from HBCaCH$\alpha_2$ (see Example IV.B) and a full-length $\beta$-subunit cDNA from pHBCaCH$\beta_1$bA (see Example III.B.3) were separately subcloned into plasmid pCMV$\beta$gal. Plasmid pCMV$\beta$gal was digested with NotI to remove the lacZ gene. The remaining vector portion of the plasmid, referred to as pCMV, was blunt-ended at the NotI sites. The full-length $\alpha_2$ and $\beta$ cDNAs, contained on separate EcoRI fragments, were isolated, blunt-ended and separately ligated to the blunt-ended vector fragment of pCMV locating the cDNAs between the CMV promoter and SV40 polyadenylation sites in pCMV. To ligate the VDCC III cDNA with pCMV, the restriction sites in the polylinkers immediately 5' of the CMV promoter and immediately 3' of the SV40 polyadenylation site were removed from pCMV. A polylinker was added at the NotI site. The polylinker had the following sequence:

| GGCCGC | GAATTC | GTCGAC | AAGCTT | AGATCT | GT |
| CG | CTTAAG | CAGCTG | TTCGAA | TCTAGA | CACCGG |
| NotI | EcoRI | SalI | HindIII | BglII | ↑ |
| | | | | | Destroys Not |

The VCCCIII cDNA, isolated as a BamHI/XhoI fragment from pVDCCIII(A), was then ligated to BglII/SalI-digested pCMV to place it between the CMV promoter and SV40 polyadenylation site.

Plasmid pCMV contains the CMV promoter as does pcDNA1, but differs from pcDNA1 in the location of splice donor/splice acceptor sites relative to the inserted subunit cDNA. After inserting the subunit cDNA into pCMV, the splice donor/splice acceptor sites are located 3' of the CMV promoter and 5' of the subunit cDNA start codon. After inserting the subunit cDNA into pcDNA1, the splice donor/splice acceptor sites are located 3' of the subunit cDNA stop codon.

2. Transfection of HEK 293 Cells

HEK 293 cells were transiently co-transfected with the VDCC III, $\alpha_2$ and $\beta$-subunit cDNAs contained in pCMV or with the VDCC III, $\alpha_2$ and $\beta$-subunit cDNAs contained in pcDNA2, (i.e., vectors pVDCCIII(A), pHBCaCH$\alpha_2$A and PHBCaCH$\beta_1$bA) as described in Example VII.B.1.a. Plasmid pCMV$\beta$gal was included in each transfection to enable determination of transfection efficiency. Based on the results of $\beta$-galactosidase assays of the transfectants (see Example VII.B.2.a), HEK 293 cells were transfected equally efficiently with pCMV- and pcDNA1- based plasmids.

3. Northern Analysis

Total and polyA+ RNA was isolated from the transiently transfected cells as described in Examples VII.A.2 and VII.B.2.b. Northern blots of the RNA were hybridized with the following radiolabeled probes: VDCC III cDNA, human neuronal calcium channel $\alpha_2$-subunit cDNA and a human neuronal calcium channel $\beta$-subunit cDNA. Messenger RNAs of the size expected for VDCC III, $\alpha_2$ and $\beta$-subunit transcripts were detected in all transfectants. However, a greater amount of the VDCC III transcript was present in cells that were co-transfected with pCMV-based plasmids then in cells that were co-transfected with pcDNA1-based plasmids. Equivalent amounts of $\alpha_2$ and $\beta$-subunit transcripts were detected in all transfectants.

D. Recombinant Expression of Transcripts Prepared In Vitro from Human Neuronal Calcium Channel Subunit cDNAs in *Xenopus laevis* Oocytes Various combinations of the transcripts of cDNAs encoding the human neuronal $\alpha_1$ (VDCC III), $\alpha_2$ and $\beta$-subunits prepared in vitro were injected into *Xenopus laevis* oocytes which were then analyzed by two-electrode voltage clamp recording techniques for the presence of voltage-activated barium currents.

1. Preparation of Transcripts

In vitro transcripts of human neuronal calcium channel $\alpha_1$, $\alpha_2$ and $\beta$-subunit cDNAs were synthesized according to the instructions of the mCAP mRNA CAPPING KIT (Strategene, La Jolla, Calif. catalog #200350). Plasmids containing these cDNAs [i.e., plasmid pVDCC III.RBS(A), consisting of pcDNA1 and the VDCC III cDNA that begins with a ribosome binding site and the eighth ATG codon of the coding sequence (see Example III.A.3.d), plasmid pHBCaCH$\alpha_1$A consisting of pcDNA1 and an $\alpha_2$-subunit cDNA (see Example IV), and plasmid pHBCaCH$\beta_1$bA consisting of pcDNA1 and the $\beta$ cDNA lacking intron sequence and containing a ribosome binding site (see Example III)], where linearized by restriction digestion. The VDCC III cDNA- and $\alpha_2$-subunit cDNA-containing plasmids were digested with XhoI, whereas the $\beta$-subunit cDNA-containing plasmid was digested with EcoRV. T7 RNA polymerase was used to transcribe the cDNA in each case.

2. Injection of Oocytes

*Xenopus laevis* oocytes were isolated and defolliculated by collagenase treatment and maintained in 100 mM NaCl, 2 mM KCl, 1.8 mM CaCl$_2$, 1 mM MgCl$_2$, 5 mM HEPES,, pH 7.6, 20 $\mu$g/ml ampicillin and 25 $\mu$g/ml streptomycin at 19°-25° C. for 2 to 5 days after injection and prior to recording. For each transcript that was injected into the oocyte, 6 ng of the specific mRNA was injected per cell in a total volume of 50 nl.

3. Intracellular Voltage Recordings

Injected oocytes were examined for voltage-dependent barium currents using two-electrode voltage clamp methods [Dascal, N. (1987) *CRC Crit. Rev. Biochem.* 22:317]. The pClamp (Axon Instruments) software package was used in conjunction with a Labmaster 125 kHz data acquisition interface to generate voltage commands and to acquire and analyze data. Quattro Professional was also used in this analysis. Current signals were digitized at 1–5 kHz, and filtered appropriately. The bath solution consisted of the following: 40 mM BaCl$_2$, 36 mM tetraethylammonium chloride (TEA-Cl), 2 mM KCl, 5 mM 4-amnopyridine, 0.15 mM niflumic acid, 5 mM HEPES, pH 7.6.

a. Electrophysiological Analysis of Oocytes Injected with Transcripts of Human Neuronal Calcium Channel $\alpha_1$, $\alpha_2$ and $\beta$-Subunit cDNAs It has been reported that *Xenopus laevis* oocytes express endogenous voltage-dependent calcium channels [Dascal, N. (1987). *CRC Crit. Rev. Biochem.* 22:317]. Therefore, negative control uninjected oocytes were examined by two-electrode voltage clamp methods to determine if these cells express voltage-activated barium currents that are detectable in these recordings. A very small (25 nA) endogenous inward Ba$^{2+}$ current was detected in only one of seven analyzed cells.

Figure 10B:
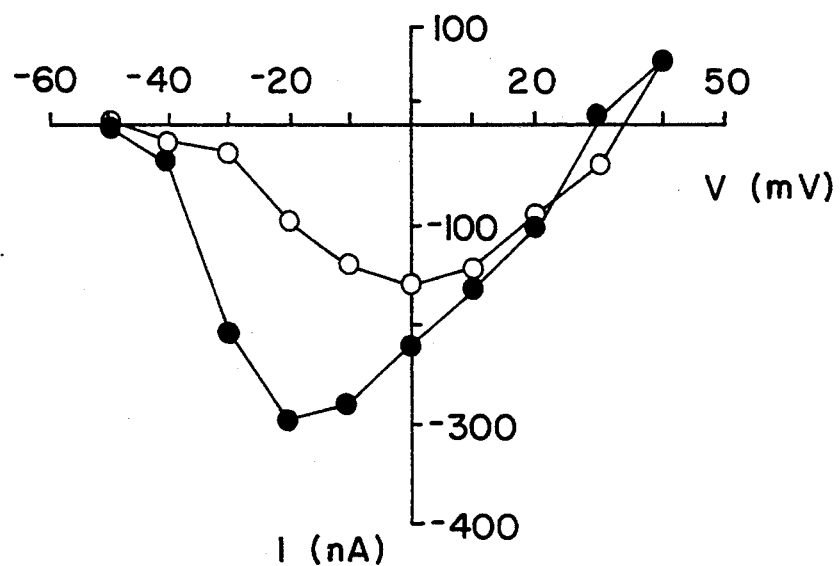
Figure 10C:
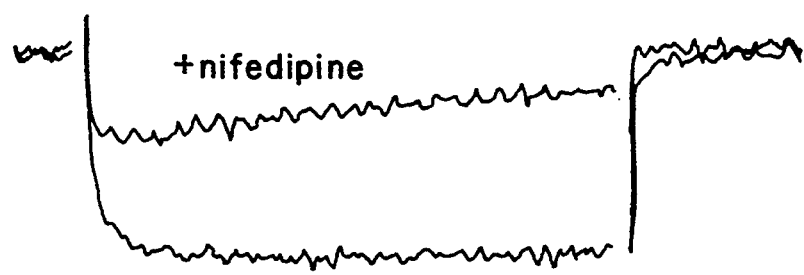

Oocytes coinjected with VDCC III, $\alpha_2$ and $\beta$-subunit transcripts expressed sustained inward barium currents upon depolarization of the membrane from a holding potential of $-90$ mV or $-50$ mV (154$\pm$129 nA, n=21). These currents typically showed little inactivation when test pulses ranging from 140 to 700 msec. were administered (FIG. 10B). Depolarization to a series of voltages revealed currents that first appeared at approximately −30 mV and peaked at approximately 0 mV (see I-V curve in FIG. 10B represented by open circles). Application of the dihydrophyridine Bay K 8644 increased the magnitude of the currents, prolonged the tail currents present upon repolarization of the cell and induced a hyperpolarizing shift in current activation (FIG. 10A and 10B, I-V curve represented by solid circles). (Bay K 8644 was prepared fresh from a stock solution in DMSO and diluted into the bath solution. Thus, Bay K 8644 was applied as a 10× concentrate directly into the 60 μl bath while the perfusion pump was turned off. The DMSO concentration of the final diluted drug solutions in contact with the cell never exceeded 0.1%. Control experiments showed that 0.1% DMSO had no effect on membrane currents.) Application of the dihydropyridine antagonist nifedipine (stock solution prepared in DMSO and applied to the cell as described for application of Bay K 8644) blocked a substantial fraction (91±6%, n=7) of the inward barium current in oocytes coinjected with transcripts of the VDCC III, $\alpha_2$ and $\beta$-subunits (FIG. 10C). A residual inactivating component of the inward barium current typically remained after nifedipine application (see FIG. 10C). The inward barium current was blocked completely by 50 μM $Cd^{2+}$, but only approximately 15% by 100 μM $Ni^{2+}$.

The effect of ωCgTX on the inward barium currents in oocytes co-injected with transcripts of the VDCC III, $\alpha_2$, and $\beta$-subunits was investigated. ωCgTX (Bachem, Inc., Torrance Calif.) was prepared in the 15 mM $BaCl_2$ bath solution plus 0.1% cytochrome C (Sigma) to serve as a carrier protein. Control experiments showed that cytochrome C had no effect on currents. A series of voltage pulses from a −90 mV holding potential to 0 mV were recorded at 20 msec. intervals. To reduce the inhibition of ωCgTX binding by divalent cations, recordings were made in 15 mM $BaCl_2$, 73.5 mM tetraethylammonium chloride, and the remaining ingredients identical to the 40 mM $Ba^{2+}$ recording solution. Bay K 8644 was applied to the cell prior to addition to ωCgTX in order to determine the effect of ωCgTX on the DHP-sensitive current component that was distinguished by the prolonged tail currents. The inward barium current was blocked weakly (54±29%, n=7) and reversibly by relatively high concentrations (10-15 μM) of ωCgTX (FIG. 10D). Both the test currents and the accompanying tail currents were blocked progressively within two to three minutes after application of ωCgTX, but both recovered partially as the ωCgTX was flushed from the bath.

b. Analysis of Oocytes Injected with Transcripts of a Human Neuronal Calcium Channel $\alpha_1$ (VDCC III) subunit cDNA only or Transcripts of an $\alpha_1$ and Other Subunit cDNAs The contribution of the $\alpha_2$ and $\beta$-subunits to the inward barium current in oocytes injected with transcripts of VDCC III, $\alpha_2$ and $\beta$ cDNAs was assessed by expression of the VDCC III subunit alone or in combination with either the $\beta$-subunit or the $\alpha_2$-subunit. In oocytes injected with only the transcript of a VDCC III cDNA, no $Ba^{2+}$ currents were detected (n=3). In oocytes injected with transcripts of VDCC III $\alpha_1$ and $\beta$ cDNAs, small (108±39 nA) $Ba^{2+}$ currents were detected upon depolarization of the membrane from a holding potential of −90 mV that resembled the currents observed in cells injected with transcripts of VDCC III, $\alpha_2$ and $\beta$ cDNAs, although the magnitude of the current was less. In two of the four oocytes injected with transcripts of the VDCC III and $\beta$ cDNAs, the $Ba^{2+}$ currents exhibited a sensitivity to Bay K 8644 that was similar to the Bay K 8644 sensitivity of $Ba^{2+}$ currents expressed in oocytes injected with transcripts of VDCC III $\alpha_1$-, $\alpha_2$- and $\beta$-subunits cDNAs.

Three of five oocytes injected with transcripts of VDCC III and $\alpha_2$ cDNAs exhibited very small $Ba^{2+}$ currents (15-30 nA) upon depolarization of the membrane from a holding potential of −90 mV. These barium currents showed little or no response to Bay K 8644.

c. Analysis of Oocytes Injected with Transcripts of Human Neuronal Calcium Channel $\alpha_2$ and/or $\beta$-subunit cDNAs To evaluate the contribution of the VDCC III $\alpha_1$-subunit to the inward barium currents detected in oocytes The inward barium currents detected in oocytes injected with transcripts of the $\alpha_2$ and $\beta$ cDNAs were pharmacologically distinct from those observed in oocytes co-injected with transcripts of the VDCC III, $\alpha_2$ and $\beta$ cDNAs. Oocytes injected with transcripts of the $\alpha_2$ and $\beta$ cDNAs displayed inward barium currents that were insensitive to Bay K 8644 (n=11) (FIG. 10E). Nifedipine sensitivity was difficult to measure because of the holding potential sensitivity of both nifedipine and the current observed in oocytes injected with transcripts of the $\alpha_2$ and $\beta$ cDNAs. Nevertheless, two oocytes that were co-injected with transcripts of the $\alpha_2$ and $\beta$ cDNAs displayed measurable (25 to 45 nA) inward barium currents when depolarized from a holding potential of −50 mV. These currents were insensitive to nifedipine (5 to 10 μM). The inward barium currents in oocytes injected with transcripts of the $\alpha_2$ and $\beta$ cDNAs showed the same sensitivity to heavy metals as the currents detected in oocytes injected with transcripts of VDCC III, $\alpha_2$ and $\beta$ cDNAs.

The inward barium current detected in oocytes injected with transcripts of human neuronal $\alpha_2$ and $\beta$-subunit cDNAs has pharmacological and biophysical properties that resemble calcium currents in uninjected Xenopus oocytes. Because the amino acid sequence encoded by this human neuronal calcium channel $\beta$-subunit cDNA lacks hydrophobic segments capable of forming transmembrane domains, it is unlikely that recombinant $\beta$-subunits alone can form an ion channel. It is more probable that a homologous $\alpha_1$-subunit exists in oocytes comprising an endogenous calcium channel and that the activity mediated by such an $\alpha_1$-subunit is enhanced by expression of a human neuronal $\beta$-subunit.

d. Summary of Data

Data presented in Example VII.C. demonstrates that a VDCC III $\alpha_1$-subunit mediates DHP-sensitive, high-voltage-activated, long-lasting calcium channel activity. This calcium channel activity detected when oocytes were co-co-injected with transcripts of VDCC III, $\alpha_2$ and $\beta$ cDNAs, oocytes injected with transcripts of human neuronal calcium channel $\alpha_2$ and/or $\beta$ cDNAs were assayed for barium currents. Oocytes injected with transcripts of the $\alpha_2$ cDNA displayed no detectable inward barium currents (n=5). Surprisingly, oocytes injected with transcripts of a $\beta$ cDNA displayed measurable (54±23 nA, n=5) inward barium currents upon depolarization. Oocytes injected with transcripts of the $\alpha_2$ and $\beta$ cDNAs displayed inward barium currents that were approximately 50% larger (80±61 nA, n=18) than those detected in oocytes injected with transcripts of the $\beta$ cDNA only.

The inward barium currents in oocytes injected with transcripts of a $\beta$ cDNA or of $\alpha_2$ and $\beta$ cDNAs typically were first observed when the membrane was depolarized to −30 mV from a holding potential of −90 mV and peaked when the membrane was depolarized to 10 to 20 mV (FIG. 10F). Macroscopically, the currents in oocytes injected with transcripts of the $\alpha_2$ and $\beta$ cDNAs or with transcripts of the $\beta$ cDNA were indistinguishable. In contrast to the currents in oocytes co-injected with transcripts of VDCC III, $\alpha_2$ and $\beta$-subunit cDNAs, these currents showed both a significant inactivation during the test pulse and a strong sensitivity to the holding potential. The inward barium currents in oocytes co-injected with transcripts of the $\alpha_2$ and $\beta$ cDNAs usually inactivated to 10–60% of the peak magnitude during a 140-msec pulse (FIG. 10E) and were significantly more sensitive to holding potential than those in oocytes coinjected with transcripts of VDCC III, $\alpha_2$ and $\beta$ cDNAs. Changing the holding potential of the membranes of oocytes co-injected with transcripts of the $\alpha_2$ and $\beta$ cDNAs from −90 to −50 mV resulted in an approximately 81% (n=11) reduction in the magnitude of the inward barium current of these cells. In contrast, the inward barium current measured in oocytes co-injected with transcripts of the VDCC III, $\alpha_2$ and $\beta$ cDNAs were reduced approximately 24% (n=11) when the holding potential was changed from −90 to −50 mV. injected with transcripts of VDCC III and $\beta$ or VDCC III, $\alpha_2$ and $\beta$-subunit cDNAs was distinguished from $Ba^{2+}$ currents detected when oocytes were injected with transcripts of $\beta \pm \alpha_2$-subunit cDNAs (which resembled $Ca^{2+}$ currents reported for uninjected oocytes) both pharmacologically and biophysically.

While the invention has been described with some specificity, modifications apparent to those with ordinary skill in the art may be made without departing from the scope of the invention.

Various features of the invention are set forth in the claims which follow the nucleotide sequence ID listing.

---

What is claimed is:

1. A method for testing a compound for activity as an agonist or antagonist of a calcium channel, comprising the steps of:
suspending a eukaryotic cell expressing functional, heterologous calcium channels in a solution which contains the compound and an ion or molecule capable of entering the cell through a functional calcium channel;
depolarizing the cell membrane of the cell;
detecting the current flowing into the cell; and
comparing the current thus detected to a current produced by cells in a control experiment; wherein:
the only heterologous ion channels expressed by the cells are calcium channels which comprise one or more subunits;
each heterologously expressed calcium channel subunit has the amino acid sequence of a naturally occurring human calcium channel subunit; and
the heterologous calcium channels comprise at least a heterologous $\alpha_1$ subunit that is selected from the group consisting of
a VDCC type II ($\alpha_{1C}$) subunit having an amino acid sequence comprising the sequence of amino acids set forth in SEQ ID NO: 7,
a VDCC type III ($\alpha_{1D}$) subunit having an amino acid sequence comprising the sequence shown as amino acids 11-2161 of SEQ ID NO: 2, and
a calcium channel $\alpha_1$ subunit encoded by DNA capable of hybridizing under conditions of high stringency with DNA that is complementary to an mRNA transcript present in a human cell and that encodes one of the aforesaid VDCC type II or type III subunits.

2. The method of claim 1, wherein:
the heterologous calcium channels further comprise one or more subunits selected from the group consisting of
an $\alpha_2$ subunit which is
a protein having the sequence of amino acids set forth as the translation of the DNA shown in SEQ ID NO: 24, or
a calcium channel $\alpha_2$ subunit encoded by DNA capable of hybridizing under conditions of high stringency with DNA which is complementary to an mRNA transcript present in a human cell and which comprises the sequence of nucleotides shown as nucleotides 1-3273 of SEQ ID NO: 24;
a $\beta$ subunit which is
a protein having the sequence of amino acids set forth as the translation of the DNA shown in SEQ ID NO: 18,
a protein having an amino acid sequence comprising the sequence of amino acids shown in SEQ ID NO: 23, or
a calcium channel $\beta$ subunit encoded by DNA capable of hybridizing under conditions of high stringency with DNA which is complementary to an mRNA transcript present in a human cell and which comprises the sequence of nucleotides shown as nucleotides 1-1434 of SEQ ID NO: 18 or encodes the sequence of amino acids shown in SEQ ID NO: 23; and
a $\gamma$ subunit which is
a protein having an amino acid sequence comprising the sequence of amino acids set forth as the translation of the DNA shown in SEQ ID NO: 29, or
a calcium channel $\gamma$ subunit encoded by DNA capable of hybridizing under conditions of high stringency with DNA which is complementary to an mRNA transcript present in a human cell and which comprises the sequence of nucleotides shown as nucleotides 1-129 of SEQ ID NO: 29.

3. The method of claim 1, wherein the heterologous $\alpha 1$ subunit is a VDCC type III ($\alpha_{1D}$) subunit.

4. The method of claim 2, wherein the heterologous $\alpha_1$ subunit is a VDCC type III ($\alpha_{1D}$) subunit.

5. The method of claim 1, wherein the heterologous $\alpha_1$ subunit is a VDCC type II ($\alpha_{1C}$) subunit.

6. The method of claim 2, wherein the heterologous subunit is a VDCC type II ($\alpha_{1C}$) subunit.

7. The method of claim 1, further comprising, prior to or simultaneously with the step of suspending the cell in solution with the test compound, contacting the cell with a calcium channel agonist, wherein the compound is tested for activity as an antagonist.

8. The method of claim 2, further comprising, prior to or simultaneously with the step of suspending the cell in solution with the test compound, contacting the cell with a calcium channel agonist, wherein the compound is tested for activity as an antagonist.

9. The method of claim 2, wherein the cell is a mammalian cell and the heterologous calcium channels comprise an $\alpha_1$ subunit and $\beta$ subunit.

10. The method of claim 9, wherein the heterologous calcium channels further comprise an $\alpha_2$ subunit.

11. The method of claim 10, wherein the heterologous calcium channels further comprise a γ subunit.

12. The method of claim 1, wherein the eukaryotic cell is selected from the group consisting of a COS cell, a mouse L cell, a Chinese hamster ovary (CHO) cell, a human embryonic kidney (HEK) cell, and an African green monkey cell.

13. The method of claim 2, wherein the eukaryotic cell is selected from the group consisting of a COS cell, a mouse L cell, a Chinese hamster ovary (CHO) cell, a human embryonic kidney (HEK) cell, and an African green monkey cell.

14. The method of claim 1, wherein the eukaryotic cell is prepared by microinjecting into an amphibian oöcyte RNA that is translatable therein into the one or more calcium channel subunits.

15. The method of claim 2, wherein the eukaryotic cell is prepared by microinjecting into an amphibian oöcyte RNA that is translatable therein into the one or more calcium channel subunits.

16. The method of claim 14, further comprising, prior to or simultaneously with the step of suspending the cell in solution with the test compound, contacting the cell with a calcium channel agonist, wherein the compound is tested for activity as an antagonist.

17. The method of claim 15, further comprising, prior to or simultaneously with the step of suspending the cell in solution with the test compound, contacting the cell with a calcium channel agonist, wherein the compound is tested for activity as an antagonist.

18. The method of claim 15, wherein the heterologous calcium channels comprise an $\alpha_1$ subunit and a $\beta$ subunit.

19. The method of claim 18, wherein the heterologous calcium channels further comprise an $\alpha_2$ subunit.

20. The method of claim 19, wherein the heterologous calcium channels further comprise a γ subunit.

21. The method of claim 15, wherein the heterologous calcium channels comprise an $\alpha_1$ subunit and an $\alpha_2$ subunit.

22. The method of any of claims 1, 2, or 14, wherein, prior to the depolarization step, the cell is maintained at a holding potential that substantially inactivates calcium channels that are endogenous to the cell.

23. The method of claim 15, wherein, prior to the depolarization step, the cell is maintained at a holding potential that substantially inactivates calcium channels that are endogenous to the cell.

24. The method of claim 22, wherein the holding potential is −50 mV.

25. The method of claim 23, wherein the holding potential is −50 mV.

26. The method of claim 1, wherein the control experiment uses the same or a substantially identical cell but is performed in the absence of the test compound.

27. The method of claim 1, wherein the control experiment (i) uses a cell that is substantially identical to the suspended cell but that does not express the heterologous channels, and (ii) is performed in the presence of the test compound.

28. The method of claim 2, wherein the control experiment uses the same or a substantially identical cell but is performed in the absence of the test compound.

29. The method of claim 2, wherein the control experiment (i) uses a cell that is substantially identical to the suspended cell but that does not express the heterologous channels, and (ii) is performed in the presence of the test compound.

* * * * *

SEQUENCE LISTING ( 1 ) GENERAL INFORMATION:

( i i i ) NUMBER OF SEQUENCES: 32

( 2 ) INFORMATION FOR SEQ ID NO:1:

( i ) SEQUENCE CHARACTERISTICS:
        ( A ) LENGTH: 7125 base pairs
        ( B ) TYPE: nucleic acid
        ( C ) STRANDEDNESS: unknown
        ( D ) TOPOLOGY: unknown ( i i ) MOLECULE TYPE: DNA (genomic)

( i x ) FEATURE:
        ( A ) NAME/KEY: CDS
        ( B ) LOCATION: 1..6483

( x i ) SEQUENCE DESCRIPTION: SEQ ID NO:1:

```
ATG ATG ATG ATG ATG ATG ATG AAA AAA ATG CAG CAT CAA CGG CAG CAG         48
Met Met Met Met Met Met Met Lys Lys Met Gln His Gln Arg Gln Gln
 1               5                  10                  15

CAA GCG GAC CAC GCG AAC GAG GCA AAC TAT GCA AGA GGC ACC AGA CTT         96
Gln Ala Asp His Ala Asn Glu Ala Asn Tyr Ala Arg Gly Thr Arg Leu
                20                  25                  30

CCT CTT TCT GGT GAA GGA CCA ACT TCT CAG CCG AAT AGC TCC AAG CAA        144
Pro Leu Ser Gly Glu Gly Pro Thr Ser Gln Pro Asn Ser Ser Lys Gln
             35                  40                  45

ACT GTC CTG TCT TGG CAA GCT GCA ATC GAT GCT GCT AGA CAG GCC AAG        192
Thr Val Leu Ser Trp Gln Ala Ala Ile Asp Ala Ala Arg Gln Ala Lys
         50                  55                  60

GCT GCC CAA ACT ATG AGC ACC TCT GCA CCC CCA CCT GTA GGA TCT CTC        240
Ala Ala Gln Thr Met Ser Thr Ser Ala Pro Pro Pro Val Gly Ser Leu
 65                  70                  75                  80

TCC CAA AGA AAA CGT CAG CAA TAC GCC AAG AGC AAA AAA CAG GGT AAC        288
Ser Gln Arg Lys Arg Gln Gln Tyr Ala Lys Ser Lys Lys Gln Gly Asn
                 85                  90                  95

TCG TCC AAC AGC CGA CCT GCC CGC GCC CTT TTC TGT TTA TCA CTC AAT        336
Ser Ser Asn Ser Arg Pro Ala Arg Ala Leu Phe Cys Leu Ser Leu Asn
                100                 105                 110

AAC CCC ATC CGA AGA GCC TGC ATT AGT ATA GTG GAA TGG AAA CCA TTT        384
```

| | | | | | | | | | | | | | | | | |
|---|---|---|---|---|---|---|---|---|---|---|---|---|---|---|---|---|
| Asn | Pro | Ile | Arg | Arg | Ala | Cys | Ile | Ser | Ile | Val | Glu | Trp | Lys | Pro | Phe | |
| | | 115 | | | | 120 | | | | 125 | | | | | | |
| GAC | ATA | TTT | ATA | TTA | TTG | GCT | ATT | TTT | GCC | AAT | TGT | GTG | GCC | TTA | GCT | 432 |
| Asp | Ile | Phe | Ile | Leu | Leu | Ala | Ile | Phe | Ala | Asn | Cys | Val | Ala | Leu | Ala | |
| 130 | | | | | 135 | | | | | 140 | | | | | | |
| ATT | TAC | ATC | CCA | TTC | CCT | GAA | GAT | GAT | TCT | AAT | TCA | ACA | AAT | CAT | AAC | 480 |
| Ile | Tyr | Ile | Pro | Phe | Pro | Glu | Asp | Asp | Ser | Asn | Ser | Thr | Asn | His | Asn | |
| 145 | | | | | 150 | | | | | 155 | | | | | 160 | |
| TTG | GAA | AAA | GTA | GAA | TAT | GCC | TTC | CTG | ATT | ATT | TTT | ACA | GTC | GAG | ACA | 528 |
| Leu | Glu | Lys | Val | Glu | Tyr | Ala | Phe | Leu | Ile | Ile | Phe | Thr | Val | Glu | Thr | |
| | | | | 165 | | | | | 170 | | | | | 175 | | |
| TTT | TTG | AAG | ATT | ATA | GCG | TAT | GGA | TTA | TTG | CTA | CAT | CCT | AAT | GCT | TAT | 576 |
| Phe | Leu | Lys | Ile | Ile | Ala | Tyr | Gly | Leu | Leu | Leu | His | Pro | Asn | Ala | Tyr | |
| | | | 180 | | | | | 185 | | | | | 190 | | | |
| GTT | AGG | AAT | GGA | TGG | AAT | TTA | CTG | GAT | TTT | GTT | ATA | GTA | ATA | GTA | GGA | 624 |
| Val | Arg | Asn | Gly | Trp | Asn | Leu | Leu | Asp | Phe | Val | Ile | Val | Ile | Val | Gly | |
| | | 195 | | | | | 200 | | | | | 205 | | | | |
| TTG | TTT | AGT | GTA | ATT | TTG | GAA | CAA | TTA | ACC | AAA | GAA | ACA | GAA | GGC | GGG | 672 |
| Leu | Phe | Ser | Val | Ile | Leu | Glu | Gln | Leu | Thr | Lys | Glu | Thr | Glu | Gly | Gly | |
| | 210 | | | | | 215 | | | | | 220 | | | | | |
| AAC | CAC | TCA | AGC | GGC | AAA | TCT | GGA | GGC | TTT | GAT | GTC | AAA | GCC | CTC | CGT | 720 |
| Asn | His | Ser | Ser | Gly | Lys | Ser | Gly | Gly | Phe | Asp | Val | Lys | Ala | Leu | Arg | |
| 225 | | | | | 230 | | | | | 235 | | | | | 240 | |
| GCC | TTT | CGA | GTG | TTG | CGA | CCA | CTT | CGA | CTA | GTG | TCA | GGA | GTG | CCC | AGT | 768 |
| Ala | Phe | Arg | Val | Leu | Arg | Pro | Leu | Arg | Leu | Val | Ser | Gly | Val | Pro | Ser | |
| | | | | 245 | | | | | 250 | | | | | 255 | | |
| TTA | CAA | GTT | GTC | CTG | AAC | TCC | ATT | ATA | AAA | GCC | ATG | GTT | CCC | CTC | CTT | 816 |
| Leu | Gln | Val | Val | Leu | Asn | Ser | Ile | Ile | Lys | Ala | Met | Val | Pro | Leu | Leu | |
| | | | 260 | | | | | 265 | | | | | 270 | | | |
| CAC | ATA | GCC | CTT | TTG | GTA | TTA | TTT | GTA | ATC | ATA | ATC | TAT | GCT | ATT | ATA | 864 |
| His | Ile | Ala | Leu | Leu | Val | Leu | Phe | Val | Ile | Ile | Ile | Tyr | Ala | Ile | Ile | |
| | | 275 | | | | | 280 | | | | | 285 | | | | |
| GGA | TTG | GAA | CTT | TTT | ATT | GGA | AAA | ATG | CAC | AAA | ACA | TGT | TTT | TTT | GCT | 912 |
| Gly | Leu | Glu | Leu | Phe | Ile | Gly | Lys | Met | His | Lys | Thr | Cys | Phe | Phe | Ala | |
| | 290 | | | | | 295 | | | | | 300 | | | | | |
| GAC | TCA | GAT | ATC | GTA | GCT | GAA | GAG | GAC | CCA | GCT | CCA | TGT | GCG | TTC | TCA | 960 |
| Asp | Ser | Asp | Ile | Val | Ala | Glu | Glu | Asp | Pro | Ala | Pro | Cys | Ala | Phe | Ser | |
| 305 | | | | | 310 | | | | | 315 | | | | | 320 | |
| GGG | AAT | GGA | CGC | CAG | TGT | ACT | GCC | AAT | GGC | ACG | GAA | TGT | AGG | AGT | GGC | 1008 |
| Gly | Asn | Gly | Arg | Gln | Cys | Thr | Ala | Asn | Gly | Thr | Glu | Cys | Arg | Ser | Gly | |
| | | | | 325 | | | | | 330 | | | | | 335 | | |
| TGG | GTT | GGC | CCG | AAC | GGA | GGC | ATC | ACC | AAC | TTT | GAT | AAC | TTT | GCC | TTT | 1056 |
| Trp | Val | Gly | Pro | Asn | Gly | Gly | Ile | Thr | Asn | Phe | Asp | Asn | Phe | Ala | Phe | |
| | | | 340 | | | | | 345 | | | | | 350 | | | |
| GCC | ATG | CTT | ACT | GTG | TTT | CAG | TGC | ATC | ACC | ATG | GAG | GGC | TGG | ACA | GAC | 1104 |
| Ala | Met | Leu | Thr | Val | Phe | Gln | Cys | Ile | Thr | Met | Glu | Gly | Trp | Thr | Asp | |
| | | 355 | | | | | 360 | | | | | 365 | | | | |
| GTG | CTC | TAC | TGG | ATG | AAT | GAT | GCT | ATG | GGA | TTT | GAA | TTG | CCC | TGG | GTG | 1152 |
| Val | Leu | Tyr | Trp | Met | Asn | Asp | Ala | Met | Gly | Phe | Glu | Leu | Pro | Trp | Val | |
| | 370 | | | | | 375 | | | | | 380 | | | | | |
| TAT | TTT | GTC | AGT | CTC | GTC | ATC | TTT | GGG | TCA | TTT | TTC | GTA | CTA | AAT | CTT | 1200 |
| Tyr | Phe | Val | Ser | Leu | Val | Ile | Phe | Gly | Ser | Phe | Phe | Val | Leu | Asn | Leu | |
| 385 | | | | | 390 | | | | | 395 | | | | | 400 | |
| GTA | CTT | GGT | GTA | TTG | AGC | GGA | GAA | TTC | TCA | AAG | GAA | AGA | GAG | AAG | GCA | 1248 |
| Val | Leu | Gly | Val | Leu | Ser | Gly | Glu | Phe | Ser | Lys | Glu | Arg | Glu | Lys | Ala | |
| | | | | 405 | | | | | 410 | | | | | 415 | | |
| AAA | GCA | CGG | GGA | GAT | TTC | CAG | AAG | CTC | CGG | GAG | AAG | CAG | CAG | CTG | GAG | 1296 |
| Lys | Ala | Arg | Gly | Asp | Phe | Gln | Lys | Leu | Arg | Glu | Lys | Gln | Gln | Leu | Glu | |
| | | | 420 | | | | | 425 | | | | | 430 | | | |
| GAG | GAT | CTA | AAG | GGC | TAC | TTG | GAT | TGG | ATC | ACC | CAA | GCT | GAG | GAC | ATC | 1344 |
| Glu | Asp | Leu | Lys | Gly | Tyr | Leu | Asp | Trp | Ile | Thr | Gln | Ala | Glu | Asp | Ile | |
| | | 435 | | | | | 440 | | | | | 445 | | | | |

| | | | | | | | | | | | | | | | | |
|---|---|---|---|---|---|---|---|---|---|---|---|---|---|---|---|---|
|GAT|CCG|GAG|AAT|GAG|GAA|GAA|GGA|GGA|GAG|GAA|GGC|AAA|CGA|AAT|ACT|1392|
|Asp|Pro|Glu|Asn|Glu|Glu|Glu|Gly|Gly|Glu|Glu|Gly|Lys|Arg|Asn|Thr| |
| |450| | | |455| | | | |460| | | | | | |

| | | | | | | | | | | | | | | | | |
|---|---|---|---|---|---|---|---|---|---|---|---|---|---|---|---|---|
|AGC|ATG|CCC|ACC|AGC|GAG|ACT|GAG|TCT|GTG|AAC|ACA|GAG|AAC|GTC|AGC|1440|
|Ser|Met|Pro|Thr|Ser|Glu|Thr|Glu|Ser|Val|Asn|Thr|Glu|Asn|Val|Ser| |
|465| | | | |470| | | | |475| | | | |480| |

| | | | | | | | | | | | | | | | | |
|---|---|---|---|---|---|---|---|---|---|---|---|---|---|---|---|---|
|GGT|GAA|GGC|GAG|AAC|CGA|GGC|TGC|TGT|GGA|AGT|CTC|TGT|CAA|GCC|ATC|1488|
|Gly|Glu|Gly|Glu|Asn|Arg|Gly|Cys|Cys|Gly|Ser|Leu|Cys|Gln|Ala|Ile| |
| | | | |485| | | | |490| | | | |495| | |

| | | | | | | | | | | | | | | | | |
|---|---|---|---|---|---|---|---|---|---|---|---|---|---|---|---|---|
|TCA|AAA|TCC|AAA|CTC|AGC|CGA|CGC|TGG|CGT|CGC|TGG|AAC|CGA|TTC|AAT|1536|
|Ser|Lys|Ser|Lys|Leu|Ser|Arg|Arg|Trp|Arg|Arg|Trp|Asn|Arg|Phe|Asn| |
| | | |500| | | | |505| | | | |510| | | |

| | | | | | | | | | | | | | | | | |
|---|---|---|---|---|---|---|---|---|---|---|---|---|---|---|---|---|
|CGC|AGA|AGA|TGT|AGG|GCC|GCC|GTG|AAG|TCT|GTC|ACG|TTT|TAC|TGG|CTG|1584|
|Arg|Arg|Arg|Cys|Arg|Ala|Ala|Val|Lys|Ser|Val|Thr|Phe|Tyr|Trp|Leu| |
| | |515| | | | |520| | | | |525| | | | |

| | | | | | | | | | | | | | | | | |
|---|---|---|---|---|---|---|---|---|---|---|---|---|---|---|---|---|
|GTT|ATC|GTC|CTG|GTG|TTT|CTG|AAC|ACC|TTA|ACC|ATT|TCC|TCT|GAG|CAC|1632|
|Val|Ile|Val|Leu|Val|Phe|Leu|Asn|Thr|Leu|Thr|Ile|Ser|Ser|Glu|His| |
| |530| | | | |535| | | | |540| | | | | |

| | | | | | | | | | | | | | | | | |
|---|---|---|---|---|---|---|---|---|---|---|---|---|---|---|---|---|
|TAC|AAT|CAG|CCA|GAT|TGG|TTG|ACA|CAG|ATT|CAA|GAT|ATT|GCC|AAC|AAA|1680|
|Tyr|Asn|Gln|Pro|Asp|Trp|Leu|Thr|Gln|Ile|Gln|Asp|Ile|Ala|Asn|Lys| |
|545| | | | |550| | | | |555| | | | |560| |

| | | | | | | | | | | | | | | | | |
|---|---|---|---|---|---|---|---|---|---|---|---|---|---|---|---|---|
|GTC|CTC|TTG|GCT|CTG|TTC|ACC|TGC|GAG|ATG|CTG|GTA|AAA|ATG|TAC|AGC|1728|
|Val|Leu|Leu|Ala|Leu|Phe|Thr|Cys|Glu|Met|Leu|Val|Lys|Met|Tyr|Ser| |
| | | | |565| | | | |570| | | | |575| | |

| | | | | | | | | | | | | | | | | |
|---|---|---|---|---|---|---|---|---|---|---|---|---|---|---|---|---|
|TTG|GGC|CTC|CAA|GCA|TAT|TTC|GTC|TCT|CTT|TTC|AAC|CGG|TTT|GAT|TGC|1776|
|Leu|Gly|Leu|Gln|Ala|Tyr|Phe|Val|Ser|Leu|Phe|Asn|Arg|Phe|Asp|Cys| |
| | | |580| | | | |585| | | | |590| | | |

| | | | | | | | | | | | | | | | | |
|---|---|---|---|---|---|---|---|---|---|---|---|---|---|---|---|---|
|TTC|GTG|GTG|TGT|GGT|GGA|ATC|ACT|GAG|ACG|ATC|TTG|GTG|GAA|CTG|GAA|1824|
|Phe|Val|Val|Cys|Gly|Gly|Ile|Thr|Glu|Thr|Ile|Leu|Val|Glu|Leu|Glu| |
| | |595| | | | |600| | | | |605| | | | |

| | | | | | | | | | | | | | | | | |
|---|---|---|---|---|---|---|---|---|---|---|---|---|---|---|---|---|
|ATC|ATG|TCT|CCC|CTG|GGG|ATC|TCT|GTG|TTT|CGG|TGT|GTG|CGC|CTC|TTA|1872|
|Ile|Met|Ser|Pro|Leu|Gly|Ile|Ser|Val|Phe|Arg|Cys|Val|Arg|Leu|Leu| |
| |610| | | | |615| | | | |620| | | | | |

| | | | | | | | | | | | | | | | | |
|---|---|---|---|---|---|---|---|---|---|---|---|---|---|---|---|---|
|AGA|ATC|TTC|AAA|GTG|ACC|AGG|CAC|TGG|ACT|TCC|CTG|AGC|AAC|TTA|GTG|1920|
|Arg|Ile|Phe|Lys|Val|Thr|Arg|His|Trp|Thr|Ser|Leu|Ser|Asn|Leu|Val| |
|625| | | | |630| | | | |635| | | | |640| |

| | | | | | | | | | | | | | | | | |
|---|---|---|---|---|---|---|---|---|---|---|---|---|---|---|---|---|
|GCA|TCC|TTA|TTA|AAC|TCC|ATG|AAG|TCC|ATC|GCT|TCG|CTG|TTG|CTT|CTG|1968|
|Ala|Ser|Leu|Leu|Asn|Ser|Met|Lys|Ser|Ile|Ala|Ser|Leu|Leu|Leu|Leu| |
| | | | |645| | | | |650| | | | |655| | |

| | | | | | | | | | | | | | | | | |
|---|---|---|---|---|---|---|---|---|---|---|---|---|---|---|---|---|
|CTT|TTT|CTC|TTC|ATT|ATC|ATC|TTT|TCC|TTG|CTT|GGG|ATG|CAG|CTG|TTT|2016|
|Leu|Phe|Leu|Phe|Ile|Ile|Ile|Phe|Ser|Leu|Leu|Gly|Met|Gln|Leu|Phe| |
| | | |660| | | | |665| | | | |670| | | |

| | | | | | | | | | | | | | | | | |
|---|---|---|---|---|---|---|---|---|---|---|---|---|---|---|---|---|
|GGC|GGC|AAG|TTT|AAT|TTT|GAT|GAA|ACG|CAA|ACC|AAG|CGG|AGC|ACC|TTT|2064|
|Gly|Gly|Lys|Phe|Asn|Phe|Asp|Glu|Thr|Gln|Thr|Lys|Arg|Ser|Thr|Phe| |
| | |675| | | | |680| | | | |685| | | | |

| | | | | | | | | | | | | | | | | |
|---|---|---|---|---|---|---|---|---|---|---|---|---|---|---|---|---|
|GAC|AAT|TTC|CCT|CAA|GCA|CTT|CTC|ACA|GTG|TTC|CAG|ATC|CTG|ACA|GGC|2112|
|Asp|Asn|Phe|Pro|Gln|Ala|Leu|Leu|Thr|Val|Phe|Gln|Ile|Leu|Thr|Gly| |
| |690| | | | |695| | | | |700| | | | | |

| | | | | | | | | | | | | | | | | |
|---|---|---|---|---|---|---|---|---|---|---|---|---|---|---|---|---|
|GAA|GAC|TGG|AAT|GCT|GTG|ATG|TAC|GAT|GGC|ATC|ATG|GCT|TAC|GGG|GGC|2160|
|Glu|Asp|Trp|Asn|Ala|Val|Met|Tyr|Asp|Gly|Ile|Met|Ala|Tyr|Gly|Gly| |
|705| | | | |710| | | | |715| | | | |720| |

| | | | | | | | | | | | | | | | | |
|---|---|---|---|---|---|---|---|---|---|---|---|---|---|---|---|---|
|CCA|TCC|TCT|TCA|GGA|ATG|ATC|GTC|TGC|ATC|TAC|TTC|ATC|ATC|CTC|TTC|2208|
|Pro|Ser|Ser|Ser|Gly|Met|Ile|Val|Cys|Ile|Tyr|Phe|Ile|Ile|Leu|Phe| |
| | | | |725| | | | |730| | | | |735| | |

| | | | | | | | | | | | | | | | | |
|---|---|---|---|---|---|---|---|---|---|---|---|---|---|---|---|---|
|ATT|TGT|GGT|AAC|TAT|ATT|CTA|CTG|AAT|GTC|TTC|TTG|GCC|ATC|GCT|GTA|2256|
|Ile|Cys|Gly|Asn|Tyr|Ile|Leu|Leu|Asn|Val|Phe|Leu|Ala|Ile|Ala|Val| |
| | | |740| | | | |745| | | | |750| | | |

| | | | | | | | | | | | | | | | | |
|---|---|---|---|---|---|---|---|---|---|---|---|---|---|---|---|---|
|GAC|AAT|TTG|GCT|GAT|GCT|GAA|AGT|CTG|AAC|ACT|GCT|CAG|AAA|GAA|GAA|2304|
|Asp|Asn|Leu|Ala|Asp|Ala|Glu|Ser|Leu|Asn|Thr|Ala|Gln|Lys|Glu|Glu| |
| | |755| | | | |760| | | | |765| | | | |

| | | | | | | | | | | | | | | | | |
|---|---|---|---|---|---|---|---|---|---|---|---|---|---|---|---|---|
|GCG|GAA|GAA|AAG|GAG|AGG|AAA|AAG|ATT|GCC|AGA|AAA|GAG|AGC|CTA|GAA|2352|

|       |       |       |       |       |       |       |       |       |       |       |       |       |       |       |       |      |
|-------|-------|-------|-------|-------|-------|-------|-------|-------|-------|-------|-------|-------|-------|-------|-------|------|
| Ala   | Glu   | Glu   | Lys   | Glu   | Arg   | Lys   | Lys   | Ile   | Ala   | Arg   | Lys   | Glu   | Ser   | Leu   | Glu   |      |
|       | 770   |       |       |       | 775   |       |       |       |       | 780   |       |       |       |       |       |      |
| AAT   | AAA   | AAG   | AAC   | AAC   | AAA   | CCA   | GAA   | GTC   | AAC   | CAG   | ATA   | GCC   | AAC   | AGT   | GAC   | 2400 |
| Asn   | Lys   | Lys   | Asn   | Asn   | Lys   | Pro   | Glu   | Val   | Asn   | Gln   | Ile   | Ala   | Asn   | Ser   | Asp   |      |
| 785   |       |       |       | 790   |       |       |       |       | 795   |       |       |       |       |       | 800   |      |
| AAC   | AAG   | GTT   | ACA   | ATT   | GAT   | GAC   | TAT   | AGA   | GAA   | GAG   | GAT   | GAA   | GAC   | AAG   | GAC   | 2448 |
| Asn   | Lys   | Val   | Thr   | Ile   | Asp   | Asp   | Tyr   | Arg   | Glu   | Glu   | Asp   | Glu   | Asp   | Lys   | Asp   |      |
|       |       |       |       | 805   |       |       |       |       | 810   |       |       |       |       | 815   |       |      |
| CCC   | TAT   | CCG   | CCT   | TGC   | GAT   | GTG   | CCA   | GTA   | GGG   | GAA   | GAG   | GAA   | GAG   | GAA   | GAG   | 2496 |
| Pro   | Tyr   | Pro   | Pro   | Cys   | Asp   | Val   | Pro   | Val   | Gly   | Glu   | Glu   | Glu   | Glu   | Glu   | Glu   |      |
|       |       |       | 820   |       |       |       |       | 825   |       |       |       |       | 830   |       |       |      |
| GAG   | GAG   | GAT   | GAA   | CCT   | GAG   | GTT   | CCT   | GCC   | GGA   | CCC   | CGT   | CCT   | CGA   | AGG   | ATC   | 2544 |
| Glu   | Glu   | Asp   | Glu   | Pro   | Glu   | Val   | Pro   | Ala   | Gly   | Pro   | Arg   | Pro   | Arg   | Arg   | Ile   |      |
|       |       | 835   |       |       |       | 840   |       |       |       |       | 845   |       |       |       |       |      |
| TCG   | GAG   | TTG   | AAC   | ATG   | AAG   | GAA   | AAA   | ATT   | GCC   | CCC   | ATC   | CCT   | GAA   | GGG   | AGC   | 2592 |
| Ser   | Glu   | Leu   | Asn   | Met   | Lys   | Glu   | Lys   | Ile   | Ala   | Pro   | Ile   | Pro   | Glu   | Gly   | Ser   |      |
| 850   |       |       |       |       | 855   |       |       |       |       | 860   |       |       |       |       |       |      |
| GCT   | TTC   | TTC   | ATT   | CTT   | AGC   | AAG   | ACC   | AAC   | CCG   | ATC   | CGC   | GTA   | GGC   | TGC   | CAC   | 2640 |
| Ala   | Phe   | Phe   | Ile   | Leu   | Ser   | Lys   | Thr   | Asn   | Pro   | Ile   | Arg   | Val   | Gly   | Cys   | His   |      |
| 865   |       |       |       |       | 870   |       |       |       |       | 875   |       |       |       |       | 880   |      |
| AAG   | CTC   | ATC   | AAC   | CAC   | CAC   | ATC   | TTC   | ACC   | AAC   | CTC   | ATC   | CTT   | GTC   | TTC   | ATC   | 2688 |
| Lys   | Leu   | Ile   | Asn   | His   | His   | Ile   | Phe   | Thr   | Asn   | Leu   | Ile   | Leu   | Val   | Phe   | Ile   |      |
|       |       |       |       | 885   |       |       |       |       | 890   |       |       |       |       | 895   |       |      |
| ATG   | CTG   | AGC   | AGT   | GCT   | GCC   | CTG   | GCC   | GCA   | GAG   | GAC   | CCC   | ATC   | CGC   | AGC   | CAC   | 2736 |
| Met   | Leu   | Ser   | Ser   | Ala   | Ala   | Leu   | Ala   | Ala   | Glu   | Asp   | Pro   | Ile   | Arg   | Ser   | His   |      |
|       |       |       | 900   |       |       |       |       | 905   |       |       |       |       | 910   |       |       |      |
| TCC   | TTC   | CGG   | AAC   | ACG   | ATA   | CTG   | GGT   | TAC   | TTT   | GAC   | TAT   | GCC   | TTC   | ACA   | GCC   | 2784 |
| Ser   | Phe   | Arg   | Asn   | Thr   | Ile   | Leu   | Gly   | Tyr   | Phe   | Asp   | Tyr   | Ala   | Phe   | Thr   | Ala   |      |
|       |       | 915   |       |       |       |       | 920   |       |       |       |       | 925   |       |       |       |      |
| ATC   | TTT   | ACT   | GTT   | GAG   | ATC   | CTG   | TTG   | AAG   | ATG   | ACA   | ACT   | TTT   | GGA   | GCT   | TTC   | 2832 |
| Ile   | Phe   | Thr   | Val   | Glu   | Ile   | Leu   | Leu   | Lys   | Met   | Thr   | Thr   | Phe   | Gly   | Ala   | Phe   |      |
|       |       | 930   |       |       |       |       | 935   |       |       |       |       | 940   |       |       |       |      |
| CTC   | CAC   | AAA   | GGG   | GCC   | TTC   | TGC   | AGG   | AAC   | TAC   | TTC   | AAT   | TTG   | CTG   | GAT   | ATG   | 2880 |
| Leu   | His   | Lys   | Gly   | Ala   | Phe   | Cys   | Arg   | Asn   | Tyr   | Phe   | Asn   | Leu   | Leu   | Asp   | Met   |      |
| 945   |       |       |       |       | 950   |       |       |       |       | 955   |       |       |       |       | 960   |      |
| CTG   | GTG   | GTT   | GGG   | GTG   | TCT   | CTG   | GTG   | TCA   | TTT   | GGG   | ATT   | CAA   | TCC   | AGT   | GCC   | 2928 |
| Leu   | Val   | Val   | Gly   | Val   | Ser   | Leu   | Val   | Ser   | Phe   | Gly   | Ile   | Gln   | Ser   | Ser   | Ala   |      |
|       |       |       |       | 965   |       |       |       |       | 970   |       |       |       |       | 975   |       |      |
| ATC   | TCC   | GTT   | GTG   | AAG   | ATT   | CTG   | AGG   | GTC   | TTA   | AGG   | GTC   | CTG   | CGT   | CCC   | CTC   | 2976 |
| Ile   | Ser   | Val   | Val   | Lys   | Ile   | Leu   | Arg   | Val   | Leu   | Arg   | Val   | Leu   | Arg   | Pro   | Leu   |      |
|       |       |       | 980   |       |       |       |       | 985   |       |       |       |       | 990   |       |       |      |
| AGG   | GCC   | ATC   | AAC   | AGA   | GCA   | AAA   | GGA   | CTT   | AAG   | CAC   | GTG   | GTC   | CAG   | TGC   | GTC   | 3024 |
| Arg   | Ala   | Ile   | Asn   | Arg   | Ala   | Lys   | Gly   | Leu   | Lys   | His   | Val   | Val   | Gln   | Cys   | Val   |      |
|       |       | 995   |       |       |       | 1000  |       |       |       |       | 1005  |       |       |       |       |      |
| TTC   | GTG   | GCC   | ATC   | CGG   | ACC   | ATC   | GGC   | AAC   | ATC   | ATG   | ATC   | GTC   | ACC   | ACC   | CTC   | 3072 |
| Phe   | Val   | Ala   | Ile   | Arg   | Thr   | Ile   | Gly   | Asn   | Ile   | Met   | Ile   | Val   | Thr   | Thr   | Leu   |      |
|       |       |       | 1010  |       |       |       | 1015  |       |       |       |       | 1020  |       |       |       |      |
| CTG   | CAG   | TTC   | ATG   | TTT   | GCC   | TGT   | ATC   | GGG   | GTC   | CAG   | TTG   | TTC   | AAG   | GGG   | AAG   | 3120 |
| Leu   | Gln   | Phe   | Met   | Phe   | Ala   | Cys   | Ile   | Gly   | Val   | Gln   | Leu   | Phe   | Lys   | Gly   | Lys   |      |
| 1025  |       |       |       |       | 1030  |       |       |       |       | 1035  |       |       |       |       | 1040  |      |
| TTC   | TAT   | CGC   | TGT   | ACG   | GAT   | GAA   | GCC   | AAA   | AGT   | AAC   | CCT   | GAA   | GAA   | TGC   | AGG   | 3168 |
| Phe   | Tyr   | Arg   | Cys   | Thr   | Asp   | Glu   | Ala   | Lys   | Ser   | Asn   | Pro   | Glu   | Glu   | Cys   | Arg   |      |
|       |       |       |       | 1045  |       |       |       |       | 1050  |       |       |       |       | 1055  |       |      |
| GGA   | CTT   | TTC   | ATC   | CTC   | TAC   | AAG   | GAT   | GGG   | GAT   | GTT   | GAC   | AGT   | CCT   | GTG   | GTC   | 3216 |
| Gly   | Leu   | Phe   | Ile   | Leu   | Tyr   | Lys   | Asp   | Gly   | Asp   | Val   | Asp   | Ser   | Pro   | Val   | Val   |      |
|       |       |       | 1060  |       |       |       | 1065  |       |       |       |       | 1070  |       |       |       |      |
| CGT   | GAA   | CGG   | ATC   | TGG   | CAA   | AAC   | AGT   | GAT   | TTC   | AAC   | TTC   | GAC   | AAC   | GTC   | CTC   | 3264 |
| Arg   | Glu   | Arg   | Ile   | Trp   | Gln   | Asn   | Ser   | Asp   | Phe   | Asn   | Phe   | Asp   | Asn   | Val   | Leu   |      |
|       |       | 1075  |       |       |       |       | 1080  |       |       |       |       | 1085  |       |       |       |      |
| TCT   | GCT   | ATG   | ATG   | GCG   | CTC   | TTC   | ACA   | GTC   | TCC   | ACG   | TTT   | GAG   | GGC   | TGG   | CCT   | 3312 |
| Ser   | Ala   | Met   | Met   | Ala   | Leu   | Phe   | Thr   | Val   | Ser   | Thr   | Phe   | Glu   | Gly   | Trp   | Pro   |      |
|       |       | 1090  |       |       |       |       | 1095  |       |       |       |       | 1100  |       |       |       |      |

| | | | | | | | | | | | | | | | | |
|---|---|---|---|---|---|---|---|---|---|---|---|---|---|---|---|---|
| GCG | TTG | CTG | TAT | AAA | GCC | ATC | GAC | TCG | AAT | GGA | GAG | AAC | ATC | GGC | CCA | 3360 |
| Ala | Leu | Leu | Tyr | Lys | Ala | Ile | Asp | Ser | Asn | Gly | Glu | Asn | Ile | Gly | Pro | |
| 1105 | | | | 1110 | | | | 1115 | | | | | | 1120 | | |
| ATC | TAC | AAC | CAC | CGC | GTG | GAG | ATC | TCC | ATC | TTC | TTC | ATC | ATC | TAC | ATC | 3408 |
| Ile | Tyr | Asn | His | Arg | Val | Glu | Ile | Ser | Ile | Phe | Phe | Ile | Ile | Tyr | Ile | |
| | | | | 1125 | | | | | 1130 | | | | | | 1135 | |
| ATC | ATT | GTA | GCT | TTC | TTC | ATG | ATG | AAC | ATC | TTT | GTG | GGC | TTT | GTC | ATC | 3456 |
| Ile | Ile | Val | Ala | Phe | Phe | Met | Met | Asn | Ile | Phe | Val | Gly | Phe | Val | Ile | |
| | | | 1140 | | | | | 1145 | | | | | 1150 | | | |
| GTT | ACA | TTT | CAG | GAA | CAA | GGA | GAA | AAA | GAG | TAT | AAG | AAC | TGT | GAG | CTG | 3504 |
| Val | Thr | Phe | Gln | Glu | Gln | Gly | Glu | Lys | Glu | Tyr | Lys | Asn | Cys | Glu | Leu | |
| | | | | 1155 | | | | | 1160 | | | | | 1165 | | |
| GAC | AAA | AAT | CAG | CGT | CAG | TGT | GTT | GAA | TAC | GCC | TTG | AAA | GCA | CGT | CCC | 3552 |
| Asp | Lys | Asn | Gln | Arg | Gln | Cys | Val | Glu | Tyr | Ala | Leu | Lys | Ala | Arg | Pro | |
| | | 1170 | | | | | 1175 | | | | | 1180 | | | | |
| TTG | CGG | AGA | TAC | ATC | CCC | AAA | AAC | CCC | TAC | CAG | TAC | AAG | TTC | TGG | TAC | 3600 |
| Leu | Arg | Arg | Tyr | Ile | Pro | Lys | Asn | Pro | Tyr | Gln | Tyr | Lys | Phe | Trp | Tyr | |
| 1185 | | | | | 1190 | | | | | 1195 | | | | | 1200 | |
| GTG | GTG | AAC | TCT | TCG | CCT | TTC | GAA | TAC | ATG | ATG | TTT | GTC | CTC | ATC | ATG | 3648 |
| Val | Val | Asn | Ser | Ser | Pro | Phe | Glu | Tyr | Met | Met | Phe | Val | Leu | Ile | Met | |
| | | | | 1205 | | | | | 1210 | | | | | 1215 | | |
| CTC | AAC | ACA | CTC | TGC | TTG | GCC | ATG | CAG | CAC | TAC | GAG | CAG | TCC | AAG | ATG | 3696 |
| Leu | Asn | Thr | Leu | Cys | Leu | Ala | Met | Gln | His | Tyr | Glu | Gln | Ser | Lys | Met | |
| | | 1220 | | | | | 1225 | | | | | 1230 | | | | |
| TTC | AAT | GAT | GCC | ATG | GAC | ATT | CTG | AAC | ATG | GTC | TTC | ACC | GGG | GTG | TTC | 3744 |
| Phe | Asn | Asp | Ala | Met | Asp | Ile | Leu | Asn | Met | Val | Phe | Thr | Gly | Val | Phe | |
| | | | 1235 | | | | | 1240 | | | | | 1245 | | | |
| ACC | GTC | GAG | ATG | GTT | TTG | AAA | GTC | ATC | GCA | TTT | AAG | CCT | AAG | GGG | TAT | 3792 |
| Thr | Val | Glu | Met | Val | Leu | Lys | Val | Ile | Ala | Phe | Lys | Pro | Lys | Gly | Tyr | |
| | | | 1250 | | | | | 1255 | | | | | 1260 | | | |
| TTT | AGT | GAC | GCC | TGG | AAC | ACG | TTT | GAC | TCC | CTC | ATC | GTA | ATC | GGC | AGC | 3840 |
| Phe | Ser | Asp | Ala | Trp | Asn | Thr | Phe | Asp | Ser | Leu | Ile | Val | Ile | Gly | Ser | |
| 1265 | | | | | 1270 | | | | | 1275 | | | | | 1280 | |
| ATT | ATA | GAC | GTG | GCC | CTC | AGC | GAA | GCA | GAC | CCA | ACT | GAA | AGT | GAA | AAT | 3888 |
| Ile | Ile | Asp | Val | Ala | Leu | Ser | Glu | Ala | Asp | Pro | Thr | Glu | Ser | Glu | Asn | |
| | | | | 1285 | | | | | 1290 | | | | | 1295 | | |
| GTC | CCT | GTC | CCA | ACT | GCT | ACA | CCT | GGG | AAC | TCT | GAA | GAG | AGC | AAT | AGA | 3936 |
| Val | Pro | Val | Pro | Thr | Ala | Thr | Pro | Gly | Asn | Ser | Glu | Glu | Ser | Asn | Arg | |
| | | | 1300 | | | | | 1305 | | | | | 1310 | | | |
| ATC | TCC | ATC | ACC | TTT | TTC | CGT | CTT | TTC | CGA | GTG | ATG | CGA | TTG | GTG | AAG | 3984 |
| Ile | Ser | Ile | Thr | Phe | Phe | Arg | Leu | Phe | Arg | Val | Met | Arg | Leu | Val | Lys | |
| | | | 1315 | | | | | 1320 | | | | | 1325 | | | |
| CTT | CTC | AGC | AGG | GGG | GAA | GGC | ATC | CGG | ACA | TTG | CTG | TGG | ACT | TTT | ATT | 4032 |
| Leu | Leu | Ser | Arg | Gly | Glu | Gly | Ile | Arg | Thr | Leu | Leu | Trp | Thr | Phe | Ile | |
| | 1330 | | | | | 1335 | | | | | 1340 | | | | | |
| AAG | TTC | TTT | CAG | GCG | CTC | CCG | TAT | GTG | GCC | CTC | CTC | ATA | GCC | ATG | CTG | 4080 |
| Lys | Phe | Phe | Gln | Ala | Leu | Pro | Tyr | Val | Ala | Leu | Leu | Ile | Ala | Met | Leu | |
| 1345 | | | | | 1350 | | | | | 1355 | | | | | 1360 | |
| TTC | TTC | ATC | TAT | GCG | GTC | ATT | GGC | ATG | CAG | ATG | TTT | GGG | AAA | GTT | GCC | 4128 |
| Phe | Phe | Ile | Tyr | Ala | Val | Ile | Gly | Met | Gln | Met | Phe | Gly | Lys | Val | Ala | |
| | | | | 1365 | | | | | 1370 | | | | | 1375 | | |
| ATG | AGA | GAT | AAC | AAC | CAG | ATC | AAT | AGG | AAC | AAT | AAC | TTC | CAG | ACG | TTT | 4176 |
| Met | Arg | Asp | Asn | Asn | Gln | Ile | Asn | Arg | Asn | Asn | Asn | Phe | Gln | Thr | Phe | |
| | | | 1380 | | | | | 1385 | | | | | 1390 | | | |
| CCC | CAG | GCG | GTG | CTG | CTG | CTC | TTC | AGG | TGT | GCA | ACA | GGT | GAG | GCC | TGG | 4224 |
| Pro | Gln | Ala | Val | Leu | Leu | Leu | Phe | Arg | Cys | Ala | Thr | Gly | Glu | Ala | Trp | |
| | | | 1395 | | | | | 1400 | | | | | 1405 | | | |
| CAG | GAG | ATC | ATG | CTG | GCC | TGT | CTC | CCA | GGG | AAG | CTC | TGT | GAC | CCT | GAG | 4272 |
| Gln | Glu | Ile | Met | Leu | Ala | Cys | Leu | Pro | Gly | Lys | Leu | Cys | Asp | Pro | Glu | |
| | 1410 | | | | | 1415 | | | | | 1420 | | | | | |
| TCA | GAT | TAC | AAC | CCC | GGG | GAG | GAG | CAT | ACA | TGT | GGG | AGC | AAC | TTT | GCC | 4320 |

| | | |
|---|---|---|
| Ser Asp Tyr Asn Pro Gly Glu Glu His Thr Cys Gly Ser Asn Phe Ala | | |
| 1425            1430            1435            1440 | | |

| | |
|---|---|
| ATT GTC TAT TTC ATC AGT TTT TAC ATG CTC TGT GCA TTT CTG ATC ATC | 4368 |
| Ile Val Tyr Phe Ile Ser Phe Tyr Met Leu Cys Ala Phe Leu Ile Ile | |
|               1445            1450            1455 | |

| | |
|---|---|
| AAT CTG TTT GTG GCT GTC ATC ATG GAT AAT TTC GAC TAT CTG ACC CGG | 4416 |
| Asn Leu Phe Val Ala Val Ile Met Asp Asn Phe Asp Tyr Leu Thr Arg | |
|           1460            1465            1470 | |

| | |
|---|---|
| GAC TGG TCT ATT TTG GGG CCT CAC CAT TTA GAT GAA TTC AAA AGA ATA | 4464 |
| Asp Trp Ser Ile Leu Gly Pro His His Leu Asp Glu Phe Lys Arg Ile | |
|       1475            1480            1485 | |

| | |
|---|---|
| TGG TCA GAA TAT GAC CCT GAG GCA AAG GGA AGG ATA AAA CAC CTT GAT | 4512 |
| Trp Ser Glu Tyr Asp Pro Glu Ala Lys Gly Arg Ile Lys His Leu Asp | |
|       1490            1495            1500 | |

| | |
|---|---|
| GTG GTC ACT CTG CTT CGA CGC ATC CAG CCT CCC CTG GGG TTT GGG AAG | 4560 |
| Val Val Thr Leu Leu Arg Arg Ile Gln Pro Pro Leu Gly Phe Gly Lys | |
| 1505            1510            1515            1520 | |

| | |
|---|---|
| TTA TGT CCA CAC AGG GTA GCG TGC AAG AGA TTA GTT GCC ATG AAC ATG | 4608 |
| Leu Cys Pro His Arg Val Ala Cys Lys Arg Leu Val Ala Met Asn Met | |
|           1525            1530            1535 | |

| | |
|---|---|
| CCT CTC AAC AGT GAC GGG ACA GTC ATG TTT AAT GCA ACC CTG TTT GCT | 4656 |
| Pro Leu Asn Ser Asp Gly Thr Val Met Phe Asn Ala Thr Leu Phe Ala | |
|       1540            1545            1550 | |

| | |
|---|---|
| TTG GTT CGA ACG GCT CTT AAG ATC AAG ACC GAA GGG AAC CTG GAG CAA | 4704 |
| Leu Val Arg Thr Ala Leu Lys Ile Lys Thr Glu Gly Asn Leu Glu Gln | |
|       1555            1560            1565 | |

| | |
|---|---|
| GCT AAT GAA GAA CTT CGG GCT GTG ATA AAG AAA ATT TGG AAG AAA ACC | 4752 |
| Ala Asn Glu Glu Leu Arg Ala Val Ile Lys Lys Ile Trp Lys Lys Thr | |
| 1570            1575            1580 | |

| | |
|---|---|
| AGC ATG AAA TTA CTT GAC CAA GTT GTC CCT CCA GCT GGT GAT GAT GAG | 4800 |
| Ser Met Lys Leu Leu Asp Gln Val Val Pro Pro Ala Gly Asp Asp Glu | |
| 1585            1590            1595            1600 | |

| | |
|---|---|
| GTA ACC GTG GGG AAG TTC TAT GCC ACT TTC CTG ATA CAG GAC TAC TTT | 4848 |
| Val Thr Val Gly Lys Phe Tyr Ala Thr Phe Leu Ile Gln Asp Tyr Phe | |
|           1605            1610            1615 | |

| | |
|---|---|
| AGG AAA TTC AAG AAA CGG AAA GAA CAA GGA CTG GTG GGA AAG TAC CCT | 4896 |
| Arg Lys Phe Lys Lys Arg Lys Glu Gln Gly Leu Val Gly Lys Tyr Pro | |
|       1620            1625            1630 | |

| | |
|---|---|
| GCG AAG AAC ACC ACA ATT GCC CTA CAG GCG GGA TTA AGG ACA CTG CAT | 4944 |
| Ala Lys Asn Thr Thr Ile Ala Leu Gln Ala Gly Leu Arg Thr Leu His | |
| 1635            1640            1645 | |

| | |
|---|---|
| GAC ATT GGG CCA GAA ATC CGG CGT GCT ATA TCG TGT GAT TTG CAA GAT | 4992 |
| Asp Ile Gly Pro Glu Ile Arg Arg Ala Ile Ser Cys Asp Leu Gln Asp | |
|       1650            1655            1660 | |

| | |
|---|---|
| GAC GAG CCT GAG GAA ACA AAA CGA GAA GAA GAA GAT GAT GTG TTC AAA | 5040 |
| Asp Glu Pro Glu Glu Thr Lys Arg Glu Glu Glu Asp Asp Val Phe Lys | |
| 1665            1670            1675            1680 | |

| | |
|---|---|
| AGA AAT GGT GCC CTG CTT GGA AAC CAT GTC AAT CAT GTT AAT AGT GAT | 5088 |
| Arg Asn Gly Ala Leu Leu Gly Asn His Val Asn His Val Asn Ser Asp | |
|           1685            1690            1695 | |

| | |
|---|---|
| AGG AGA GAT TCC CTT CAG CAG ACC AAT ACC ACC CAC CGT CCC CTG CAT | 5136 |
| Arg Arg Asp Ser Leu Gln Gln Thr Asn Thr Thr His Arg Pro Leu His | |
|       1700            1705            1710 | |

| | |
|---|---|
| GTC CAA AGG CCT TCA ATT CCA CCT GCA AGT GAT ACT GAG AAA CCG CTG | 5184 |
| Val Gln Arg Pro Ser Ile Pro Pro Ala Ser Asp Thr Glu Lys Pro Leu | |
|       1715            1720            1725 | |

| | |
|---|---|
| TTT CCT CCA GCA GGA AAT TCG GTG TGT CAT AAC CAT CAT AAC CAT AAT | 5232 |
| Phe Pro Pro Ala Gly Asn Ser Val Cys His Asn His His Asn His Asn | |
| 1730            1735            1740 | |

| | |
|---|---|
| TCC ATA GGA AAG CAA GTT CCC ACC TCA ACA AAT GCC AAT CTC AAT AAT | 5280 |
| Ser Ile Gly Lys Gln Val Pro Thr Ser Thr Asn Ala Asn Leu Asn Asn | |
| 1745            1750            1755            1760 | |

| | | | | | | | | | | | | | | | | |
|---|---|---|---|---|---|---|---|---|---|---|---|---|---|---|---|---|
| GCC | AAT | ATG | TCC | AAA | GCT | GCC | CAT | GGA | AAG | CGG | CCC | AGC | ATT | GGG | AAC | 5328 |
| Ala | Asn | Met | Ser | Lys | Ala | Ala | His | Gly | Lys | Arg | Pro | Ser | Ile | Gly | Asn | |
| | | | | 1765 | | | | 1770 | | | | | 1775 | | | |
| CTT | GAG | CAT | GTG | TCT | GAA | AAT | GGG | CAT | CAT | TCT | TCC | CAC | AAG | CAT | GAC | 5376 |
| Leu | Glu | His | Val | Ser | Glu | Asn | Gly | His | His | Ser | Ser | His | Lys | His | Asp | |
| | | | 1780 | | | | | 1785 | | | | | 1790 | | | |
| CGG | GAG | CCT | CAG | AGA | AGG | TCC | AGT | GTG | AAA | AGA | ACC | CGC | TAT | TAT | GAA | 5424 |
| Arg | Glu | Pro | Gln | Arg | Arg | Ser | Ser | Val | Lys | Arg | Thr | Arg | Tyr | Tyr | Glu | |
| | | | 1795 | | | | | 1800 | | | | | 1805 | | | |
| ACT | TAC | ATT | AGG | TCC | GAC | TCA | GGA | GAT | GAA | CAG | CTC | CCA | ACT | ATT | TGC | 5472 |
| Thr | Tyr | Ile | Arg | Ser | Asp | Ser | Gly | Asp | Glu | Gln | Leu | Pro | Thr | Ile | Cys | |
| | | | 1810 | | | | | 1815 | | | | | 1820 | | | |
| CGG | GAA | GAC | CCA | GAG | ATA | CAT | GGC | TAT | TTC | AGG | GAC | CCC | CAC | TGC | TTG | 5520 |
| Arg | Glu | Asp | Pro | Glu | Ile | His | Gly | Tyr | Phe | Arg | Asp | Pro | His | Cys | Leu | |
| 1825 | | | | | 1830 | | | | | 1835 | | | | | 1840 | |
| GGG | GAG | CAG | GAG | TAT | TTC | AGT | AGT | GAG | GAA | TGC | TAC | GAG | GAT | GAC | AGC | 5568 |
| Gly | Glu | Gln | Glu | Tyr | Phe | Ser | Ser | Glu | Glu | Cys | Tyr | Glu | Asp | Asp | Ser | |
| | | | | 1845 | | | | | 1850 | | | | | 1855 | | |
| TCG | CCC | ACC | TGG | AGC | AGG | CAA | AAC | TAT | GGC | TAC | TAC | AGC | AGA | TAC | CCA | 5616 |
| Ser | Pro | Thr | Trp | Ser | Arg | Gln | Asn | Tyr | Gly | Tyr | Tyr | Ser | Arg | Tyr | Pro | |
| | | | 1860 | | | | | 1865 | | | | | 1870 | | | |
| GGC | AGA | AAC | ATC | GAC | TCT | GAG | AGG | CCC | CGA | GGC | TAC | CAT | CAT | CCC | CAA | 5664 |
| Gly | Arg | Asn | Ile | Asp | Ser | Glu | Arg | Pro | Arg | Gly | Tyr | His | His | Pro | Gln | |
| | | | 1875 | | | | | 1880 | | | | | 1885 | | | |
| GGA | TTC | TTG | GAG | GAC | GAT | GAC | TCG | CCC | GTT | TGC | TAT | GAT | TCA | CGG | AGA | 5712 |
| Gly | Phe | Leu | Glu | Asp | Asp | Asp | Ser | Pro | Val | Cys | Tyr | Asp | Ser | Arg | Arg | |
| | | | 1890 | | | | | 1895 | | | | | 1900 | | | |
| TCT | CCA | AGG | AGA | CGC | CTA | CTA | CCT | CCC | ACC | CCA | GCA | TCC | CAC | CGG | AGA | 5760 |
| Ser | Pro | Arg | Arg | Arg | Leu | Leu | Pro | Pro | Thr | Pro | Ala | Ser | His | Arg | Arg | |
| 1905 | | | | | 1910 | | | | | 1915 | | | | | 1920 | |
| TCC | TCC | TTC | AAC | TTT | GAG | TGC | CTG | CGC | CGG | CAG | AGC | AGC | CAG | GAA | GAG | 5808 |
| Ser | Ser | Phe | Asn | Phe | Glu | Cys | Leu | Arg | Arg | Gln | Ser | Ser | Gln | Glu | Glu | |
| | | | | 1925 | | | | | 1930 | | | | | 1935 | | |
| GTC | CCG | TCG | TCT | CCC | ATC | TTC | CCC | CAT | CGC | ACG | GCC | CTG | CCT | CTG | CAT | 5856 |
| Val | Pro | Ser | Ser | Pro | Ile | Phe | Pro | His | Arg | Thr | Ala | Leu | Pro | Leu | His | |
| | | | | 1940 | | | | | 1945 | | | | | 1950 | | |
| CTA | ATG | CAG | CAA | CAG | ATC | ATG | GCA | GTT | GCC | GGC | CTA | GAT | TCA | AGT | AAA | 5904 |
| Leu | Met | Gln | Gln | Gln | Ile | Met | Ala | Val | Ala | Gly | Leu | Asp | Ser | Ser | Lys | |
| | | | | 1955 | | | | | 1960 | | | | | 1965 | | |
| GCC | CAG | AAG | TAC | TCA | CCG | AGT | CAC | TCG | ACC | CGG | TCG | TGG | GCC | ACC | CCT | 5952 |
| Ala | Gln | Lys | Tyr | Ser | Pro | Ser | His | Ser | Thr | Arg | Ser | Trp | Ala | Thr | Pro | |
| 1970 | | | | | 1975 | | | | | 1980 | | | | | | |
| CCA | GCA | ACC | CCT | CCC | TAC | CGG | GAC | TGG | ACA | CCG | TGC | TAC | ACC | CCC | CTG | 6000 |
| Pro | Ala | Thr | Pro | Pro | Tyr | Arg | Asp | Trp | Thr | Pro | Cys | Tyr | Thr | Pro | Leu | |
| 1985 | | | | | 1990 | | | | | 1995 | | | | | 2000 | |
| ATC | CAA | GTG | GAG | CAG | TCA | GAG | GCC | CTG | GAC | CAG | GTG | AAC | GGC | AGC | CTG | 6048 |
| Ile | Gln | Val | Glu | Gln | Ser | Glu | Ala | Leu | Asp | Gln | Val | Asn | Gly | Ser | Leu | |
| | | | | 2005 | | | | | 2010 | | | | | 2015 | | |
| CCG | TCC | CTG | CAC | CGC | AGC | TCC | TGG | TAC | ACA | GAC | GAG | CCC | GAC | ATC | TCC | 6096 |
| Pro | Ser | Leu | His | Arg | Ser | Ser | Trp | Tyr | Thr | Asp | Glu | Pro | Asp | Ile | Ser | |
| | | | | 2020 | | | | | 2025 | | | | | 2030 | | |
| TAC | CGG | ACT | TTC | ACA | CCA | GCC | AGC | CTG | ACT | GTC | CCC | AGC | AGC | TTC | CGG | 6144 |
| Tyr | Arg | Thr | Phe | Thr | Pro | Ala | Ser | Leu | Thr | Val | Pro | Ser | Ser | Phe | Arg | |
| | | | 2035 | | | | | 2040 | | | | | 2045 | | | |
| AAC | AAA | AAC | AGC | GAC | AAG | CAG | AGG | AGT | GCG | GAC | AGC | TTG | GTG | GAG | GCA | 6192 |
| Asn | Lys | Asn | Ser | Asp | Lys | Gln | Arg | Ser | Ala | Asp | Ser | Leu | Val | Glu | Ala | |
| | | 2050 | | | | | 2055 | | | | | 2060 | | | | |
| GTC | CTG | ATA | TCC | GAA | GGC | TTG | GGA | CGC | TAT | GCA | AGG | GAC | CCA | AAA | TTT | 6240 |
| Val | Leu | Ile | Ser | Glu | Gly | Leu | Gly | Arg | Tyr | Ala | Arg | Asp | Pro | Lys | Phe | |
| 2065 | | | | | 2070 | | | | | 2075 | | | | | 2080 | |
| GTG | TCA | GCA | ACA | AAA | CAC | GAA | ATC | GCT | GAT | GCC | TGT | GAC | CTC | ACC | ATC | 6288 |

| | | | | | | | | | | | | | | | |
|---|---|---|---|---|---|---|---|---|---|---|---|---|---|---|---|
| Val | Ser | Ala | Thr | Lys<br>2085 | His | Glu | Ile | Ala | Asp<br>2090 | Ala | Cys | Asp | Leu | Thr<br>2095 | Ile |

| | | | | | | | | | | | | | | | | |
|---|---|---|---|---|---|---|---|---|---|---|---|---|---|---|---|---|
| GAC | GAG | ATG | GAG | AGT | GCA | GCC | AGC | ACC | CTG | CTT | AAT | GGG | AAC | GTG | CGT | 6336 |
| Asp | Glu | Met | Glu<br>2100 | Ser | Ala | Ala | Ser | Thr<br>2105 | Leu | Leu | Asn | Gly | Asn<br>2110 | Val | Arg | |
| CCC | CGA | GCC | AAC | GGG | GAT | GTG | GGC | CCC | CTC | TCA | CAC | CGG | CAG | GAC | TAT | 6384 |
| Pro | Arg | Ala | Asn<br>2115 | Gly | Asp | Val | Gly | Pro<br>2120 | Leu | Ser | His | Arg | Gln<br>2125 | Asp | Tyr | |
| GAG | CTA | CAG | GAC | TTT | GGT | CCT | GGC | TAC | AGC | GAC | GAA | GAG | CCA | GAC | CCT | 6432 |
| Glu | Leu | Gln<br>2130 | Asp | Phe | Gly | Pro | Gly<br>2135 | Tyr | Ser | Asp | Glu | Glu<br>2140 | Pro | Asp | Pro | |
| GGG | AGG | GAT | GAG | GAG | GAC | CTG | GCG | GAT | GAA | ATG | ATA | TGC | ATC | ACC | ACC | 6480 |
| Gly | Arg<br>2145 | Asp | Glu | Glu | Asp | Leu<br>2150 | Ala | Asp | Glu | Met | Ile<br>2155 | Cys | Ile | Thr | Thr<br>2160 | |
| TTG | | | | | | | | | | | | | | | | 6533 |
| Leu | TAGCCCCCAG | | CGAGGGGCAG | | ACTGGCTCTG | | GCCTCAGGTG | | GGGCGCAGGA | | | | | | | |

| | | | | |
|---|---|---|---|---|
| GAGCCAGGGG | AAAAGTGCCT | CATAGTTAGG | AAAGTTTAGG | CACTAGTTGG | GAGTAATATT | 6593 |
| CAATTAATTA | GACTTTTGTA | TAAGAGATGT | CATGCCTCAA | GAAAGCCATA | AACCTGGTAG | 6653 |
| GAACAGGTCC | CAAGCGGTTG | AGCCTGGCAG | AGTACCATGC | GCTCGGCCCC | AGCTGCAGGA | 6713 |
| AACAGCAGGC | CCCGCCCTCT | CACAGAGGAT | GGGTGAGGAG | CCAGACCTG | CCCTGCCCCA | 6773 |
| TTGTCCAGAT | GGGCACTGCT | GTGGAGTCTG | CTTCTCCCAT | GTACCAGGGC | ACCAGGCCCA | 6833 |
| CCCAACTGAA | GGCATGGCGG | CGGGGTGCAG | GGGAAAGTTA | AAGGTGATGA | CGATCATCAC | 6893 |
| ACCTGTGTCG | TTACCTCAGC | CATCGGTCTA | GCATATCAGT | CACTGGGCCC | AACATATCCA | 6953 |
| TTTTTAAACC | CTTTCCCCCA | AATACACTGC | GTCCTGGTTC | CTGTTTAGCT | GTTCTGAAAT | 7013 |
| ACGGTGTGTA | AGTAAGTCAG | AACCCAGCTA | CCAGTGATTA | TTGCGAGGGC | AATGGGACCT | 7073 |
| CATAAATAAG | GTTTTCTGTG | ATGTGACGCC | AGTTTACATA | AGAGAATATC | AC | 7125 |

( 2 ) INFORMATION FOR SEQ ID NO:2:

( i ) SEQUENCE CHARACTERISTICS:
        ( A ) LENGTH: 2161 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| | | | | | | | | | | | | | | |
|---|---|---|---|---|---|---|---|---|---|---|---|---|---|---|
| Met<br>1 | Met | Met | Met | Met<br>5 | Met | Met | Lys | Lys | Met<br>10 | Gln | His | Gln | Arg | Gln<br>15 | Gln |
| Gln | Ala | Asp | His<br>20 | Ala | Asn | Glu | Ala | Asn<br>25 | Tyr | Ala | Arg | Gly | Thr<br>30 | Arg | Leu |
| Pro | Leu | Ser<br>35 | Gly | Glu | Gly | Pro | Thr<br>40 | Ser | Gln | Pro | Asn | Ser<br>45 | Ser | Lys | Gln |
| Thr | Val<br>50 | Leu | Ser | Trp | Gln | Ala<br>55 | Ala | Ile | Asp | Ala | Ala<br>60 | Arg | Gln | Ala | Lys |
| Ala<br>65 | Ala | Gln | Thr | Met | Ser<br>70 | Thr | Ser | Ala | Pro | Pro<br>75 | Pro | Val | Gly | Ser | Leu<br>80 |
| Ser | Gln | Arg | Lys | Arg<br>85 | Gln | Gln | Tyr | Ala | Lys<br>90 | Ser | Lys | Lys | Gln | Gly<br>95 | Asn |
| Ser | Ser | Asn | Ser<br>100 | Arg | Pro | Ala | Arg | Ala<br>105 | Leu | Phe | Cys | Leu | Ser<br>110 | Leu | Asn |
| Asn | Pro | Ile<br>115 | Arg | Arg | Ala | Cys | Ile<br>120 | Ser | Ile | Val | Glu | Trp<br>125 | Lys | Pro | Phe |
| Asp | Ile<br>130 | Phe | Ile | Leu | Leu | Ala<br>135 | Ile | Phe | Ala | Asn | Cys<br>140 | Val | Ala | Leu | Ala |
| Ile | Tyr | Ile | Pro | Phe | Pro | Glu | Asp | Asp | Ser | Asn | Ser | Thr | Asn | His | Asn |

|     |     |     | 145 |     |     |     | 150 |     |     |     | 155 |     |     |     | 160 |
| --- | --- | --- | --- | --- | --- | --- | --- | --- | --- | --- | --- | --- | --- | --- | --- |

Leu Glu Lys Val Glu Tyr Ala Phe Leu Ile Ile Phe Thr Val Glu Thr
                        165                   170               175

Phe Leu Lys Ile Ile Ala Tyr Gly Leu Leu Leu His Pro Asn Ala Tyr
              180                   185                   190

Val Arg Asn Gly Trp Asn Leu Leu Asp Phe Val Ile Val Ile Val Gly
        195                   200                   205

Leu Phe Ser Val Ile Leu Glu Gln Leu Thr Lys Glu Thr Glu Gly Gly
    210                       215                   220

Asn His Ser Ser Gly Lys Ser Gly Gly Phe Asp Val Lys Ala Leu Arg
225                   230                   235                240

Ala Phe Arg Val Leu Arg Pro Leu Arg Leu Val Ser Gly Val Pro Ser
             245                   250                   255

Leu Gln Val Val Leu Asn Ser Ile Ile Lys Ala Met Val Pro Leu Leu
             260                   265                   270

His Ile Ala Leu Leu Val Leu Phe Val Ile Ile Ile Tyr Ala Ile Ile
         275                   280                   285

Gly Leu Glu Leu Phe Ile Gly Lys Met His Lys Thr Cys Phe Phe Ala
    290                       295                   300

Asp Ser Asp Ile Val Ala Glu Glu Asp Pro Ala Pro Cys Ala Phe Ser
305                   310                   315                320

Gly Asn Gly Arg Gln Cys Thr Ala Asn Gly Thr Glu Cys Arg Ser Gly
             325                   330                   335

Trp Val Gly Pro Asn Gly Gly Ile Thr Asn Phe Asp Asn Phe Ala Phe
         340                   345                   350

Ala Met Leu Thr Val Phe Gln Cys Ile Thr Met Glu Gly Trp Thr Asp
        355                   360                   365

Val Leu Tyr Trp Met Asn Asp Ala Met Gly Phe Glu Leu Pro Trp Val
370                   375                   380

Tyr Phe Val Ser Leu Val Ile Phe Gly Ser Phe Phe Val Leu Asn Leu
385                   390                   395                400

Val Leu Gly Val Leu Ser Gly Glu Phe Ser Lys Glu Arg Glu Lys Ala
             405                   410                   415

Lys Ala Arg Gly Asp Phe Gln Lys Leu Arg Glu Lys Gln Gln Leu Glu
            420                 425                 430

Glu Asp Leu Lys Gly Tyr Leu Asp Trp Ile Thr Gln Ala Glu Asp Ile
         435                  440                 445

Asp Pro Glu Asn Glu Glu Glu Gly Gly Glu Glu Gly Lys Arg Asn Thr
450                   455                   460

Ser Met Pro Thr Ser Glu Thr Glu Ser Val Asn Thr Glu Asn Val Ser
465                   470                   475                480

Gly Glu Gly Glu Asn Arg Gly Cys Cys Gly Ser Leu Cys Gln Ala Ile
             485                   490                   495

Ser Lys Ser Lys Leu Ser Arg Arg Trp Arg Arg Trp Asn Arg Phe Asn
         500                   505                   510

Arg Arg Arg Cys Arg Ala Ala Val Lys Ser Val Thr Phe Tyr Trp Leu
        515                   520                   525

Val Ile Val Leu Val Phe Leu Asn Thr Leu Thr Ile Ser Ser Glu His
    530                       535                   540

Tyr Asn Gln Pro Asp Trp Leu Thr Gln Ile Gln Asp Ile Ala Asn Lys
545                   550                   555                560

Val Leu Leu Ala Leu Phe Thr Cys Glu Met Leu Val Lys Met Tyr Ser
             565                   570                   575

Leu Gly Leu Gln Ala Tyr Phe Val Ser Leu Phe Asn Arg Phe Asp Cys
        580                   585                   590

-continued

| | | | | | | | | | | | | | | |
|---|---|---|---|---|---|---|---|---|---|---|---|---|---|---|
| Phe | Val | Val 595 | Cys | Gly | Gly | Ile | Thr 600 | Glu | Thr | Ile | Leu | Val 605 | Glu | Leu | Glu |
| Ile | Met 610 | Ser | Pro | Leu | Gly | Ile 615 | Ser | Val | Phe | Arg | Cys 620 | Val | Arg | Leu | Leu |
| Arg 625 | Ile | Phe | Lys | Val | Thr 630 | Arg | His | Trp | Thr | Ser 635 | Leu | Ser | Asn | Leu | Val 640 |
| Ala | Ser | Leu | Leu | Asn 645 | Ser | Met | Lys | Ser | Ile 650 | Ala | Ser | Leu | Leu | Leu 655 | Leu |
| Leu | Phe | Leu | Phe 660 | Ile | Ile | Ile | Phe | Ser 665 | Leu | Leu | Gly | Met | Gln 670 | Leu | Phe |
| Gly | Gly | Lys 675 | Phe | Asn | Phe | Asp | Glu 680 | Thr | Gln | Thr | Lys | Arg 685 | Ser | Thr | Phe |
| Asp | Asn 690 | Phe | Pro | Gln | Ala | Leu 695 | Leu | Thr | Val | Phe | Gln 700 | Ile | Leu | Thr | Gly |
| Glu 705 | Asp | Trp | Asn | Ala | Val 710 | Met | Tyr | Asp | Gly | Ile 715 | Met | Ala | Tyr | Gly | Gly 720 |
| Pro | Ser | Ser | Ser | Gly 725 | Met | Ile | Val | Cys | Ile 730 | Tyr | Phe | Ile | Ile | Leu 735 | Phe |
| Ile | Cys | Gly | Asn 740 | Tyr | Ile | Leu | Leu | Asn 745 | Val | Phe | Leu | Ala | Ile 750 | Ala | Val |
| Asp | Asn | Leu 755 | Ala | Asp | Ala | Glu | Ser 760 | Leu | Asn | Thr | Ala | Gln 765 | Lys | Glu | Glu |
| Ala | Glu | Glu 770 | Lys | Glu | Arg | Lys | Lys 775 | Ile | Ala | Arg | Lys 780 | Glu | Ser | Leu | Glu |
| Asn 785 | Lys | Lys | Asn | Asn | Lys 790 | Pro | Glu | Val | Asn | Gln 795 | Ile | Ala | Asn | Ser | Asp 800 |
| Asn | Lys | Val | Thr | Ile 805 | Asp | Asp | Tyr | Arg | Glu 810 | Glu | Asp | Glu | Asp | Lys 815 | Asp |
| Pro | Tyr | Pro | Pro 820 | Cys | Asp | Val | Pro | Val 825 | Gly | Glu | Glu | Glu | Glu 830 | Glu | Glu |
| Glu | Glu | Asp 835 | Glu | Pro | Glu | Val | Pro 840 | Ala | Gly | Pro | Arg | Pro 845 | Arg | Arg | Ile |
| Ser | Glu 850 | Leu | Asn | Met | Lys | Glu 855 | Lys | Ile | Ala | Pro | Ile 860 | Pro | Glu | Gly | Ser |
| Ala 865 | Phe | Phe | Ile | Leu | Ser 870 | Lys | Thr | Asn | Pro | Ile 875 | Arg | Val | Gly | Cys 880 | His |
| Lys | Leu | Ile | Asn | His 885 | His | Ile | Phe | Thr | Asn 890 | Leu | Ile | Leu | Val | Phe 895 | Ile |
| Met | Leu | Ser | Ser 900 | Ala | Ala | Leu | Ala | Ala 905 | Glu | Asp | Pro | Ile | Arg 910 | Ser | His |
| Ser | Phe | Arg 915 | Asn | Thr | Ile | Leu | Gly 920 | Tyr | Phe | Asp | Tyr | Ala 925 | Phe | Thr | Ala |
| Ile | Phe | Thr 930 | Val | Glu | Ile | Leu 935 | Leu | Lys | Met | Thr | Thr 940 | Phe | Gly | Ala | Phe |
| Leu 945 | His | Lys | Gly | Ala | Phe 950 | Cys | Arg | Asn | Tyr | Phe 955 | Asn | Leu | Leu | Asp | Met 960 |
| Leu | Val | Val | Gly | Val 965 | Ser | Leu | Val | Ser | Phe 970 | Gly | Ile | Gln | Ser | Ser 975 | Ala |
| Ile | Ser | Val | Val 980 | Lys | Ile | Leu | Arg | Val 985 | Leu | Arg | Val | Leu | Arg 990 | Pro | Leu |
| Arg | Ala | Ile 995 | Asn | Arg | Ala | Lys | Gly 1000 | Leu | Lys | His | Val | Val 1005 | Gln | Cys | Val |
| Phe | Val | Ala 1010 | Ile | Arg | Thr | Ile | Gly 1015 | Asn | Ile | Met | Ile | Val 1020 | Thr | Thr | Leu |

-continued

| Leu | Gln | Phe | Met | Phe | Ala | Cys | Ile | Gly | Val | Gln | Leu | Phe | Lys | Gly | Lys |
|---|---|---|---|---|---|---|---|---|---|---|---|---|---|---|---|
| 1025 | | | | 1030 | | | | | 1035 | | | | | | 1040 |

Phe Tyr Arg Cys Thr Asp Glu Ala Lys Ser Asn Pro Glu Glu Cys Arg
            1045                1050                1055

Gly Leu Phe Ile Leu Tyr Lys Asp Gly Asp Val Asp Ser Pro Val Val
            1060                1065                1070

Arg Glu Arg Ile Trp Gln Asn Ser Asp Phe Asn Phe Asp Asn Val Leu
        1075                1080                1085

Ser Ala Met Met Ala Leu Phe Thr Val Ser Thr Phe Glu Gly Trp Pro
1090                1095                1100

Ala Leu Leu Tyr Lys Ala Ile Asp Ser Asn Gly Glu Asn Ile Gly Pro
1105                1110                1115                1120

Ile Tyr Asn His Arg Val Glu Ile Ser Ile Phe Phe Ile Ile Tyr Ile
            1125                1130                1135

Ile Ile Val Ala Phe Phe Met Met Asn Ile Phe Val Gly Phe Val Ile
            1140                1145                1150

Val Thr Phe Gln Glu Gln Gly Glu Lys Glu Tyr Lys Asn Cys Glu Leu
            1155                1160                1165

Asp Lys Asn Gln Arg Gln Cys Val Glu Tyr Ala Leu Lys Ala Arg Pro
        1170                1175                1180

Leu Arg Arg Tyr Ile Pro Lys Asn Pro Tyr Gln Tyr Lys Phe Trp Tyr
1185                1190                1195                1200

Val Val Asn Ser Ser Pro Phe Glu Tyr Met Met Phe Val Leu Ile Met
            1205                1210                1215

Leu Asn Thr Leu Cys Leu Ala Met Gln His Tyr Glu Gln Ser Lys Met
            1220                1225                1230

Phe Asn Asp Ala Met Asp Ile Leu Asn Met Val Phe Thr Gly Val Phe
            1235                1240                1245

Thr Val Glu Met Val Leu Lys Val Ile Ala Phe Lys Pro Lys Gly Tyr
            1250                1255                1260

Phe Ser Asp Ala Trp Asn Thr Phe Asp Ser Leu Ile Val Ile Gly Ser
1265                1270                1275                1280

Ile Ile Asp Val Ala Leu Ser Glu Ala Asp Pro Thr Glu Ser Glu Asn
            1285                1290                1295

Val Pro Val Pro Thr Ala Thr Pro Gly Asn Ser Glu Glu Ser Asn Arg
            1300                1305                1310

Ile Ser Ile Thr Phe Phe Arg Leu Phe Arg Val Met Arg Leu Val Lys
        1315                1320                1325

Leu Leu Ser Arg Gly Glu Gly Ile Arg Thr Leu Leu Trp Thr Phe Ile
            1330                1335                1340

Lys Phe Phe Gln Ala Leu Pro Tyr Val Ala Leu Leu Ile Ala Met Leu
1345                1350                1355                1360

Phe Phe Ile Tyr Ala Val Ile Gly Met Gln Met Phe Gly Lys Val Ala
            1365                1370                1375

Met Arg Asp Asn Asn Gln Ile Asn Arg Asn Asn Asn Phe Gln Thr Phe
            1380                1385                1390

Pro Gln Ala Val Leu Leu Leu Phe Arg Cys Ala Thr Gly Glu Ala Trp
        1395                1400                1405

Gln Glu Ile Met Leu Ala Cys Leu Pro Gly Lys Leu Cys Asp Pro Glu
    1410                1415                1420

Ser Asp Tyr Asn Pro Gly Glu Glu His Thr Cys Gly Ser Asn Phe Ala
1425                1430                1435                1440

Ile Val Tyr Phe Ile Ser Phe Tyr Met Leu Cys Ala Phe Leu Ile Ile
            1445                1450                1455

Asn Leu Phe Val Ala Val Ile Met Asp Asn Phe Asp Tyr Leu Thr Arg

-continued

```
                    1460                     1465                      1470
Asp  Trp  Ser  Ile  Leu  Gly  Pro  His  His  Leu  Asp  Glu  Phe  Lys  Arg  Ile
                    1475                     1480                      1485
Trp  Ser  Glu  Tyr  Asp  Pro  Glu  Ala  Lys  Gly  Arg  Ile  Lys  His  Leu  Asp
                    1490                     1495                      1500
Val  Val  Thr  Leu  Leu  Arg  Arg  Ile  Gln  Pro  Pro  Leu  Gly  Phe  Gly  Lys
1505                     1510                     1515                      1520
Leu  Cys  Pro  His  Arg  Val  Ala  Cys  Lys  Arg  Leu  Val  Ala  Met  Asn  Met
                    1525                     1530                      1535
Pro  Leu  Asn  Ser  Asp  Gly  Thr  Val  Met  Phe  Asn  Ala  Thr  Leu  Phe  Ala
                    1540                     1545                      1550
Leu  Val  Arg  Thr  Ala  Leu  Lys  Ile  Lys  Thr  Glu  Gly  Asn  Leu  Glu  Gln
                    1555                     1560                      1565
Ala  Asn  Glu  Glu  Leu  Arg  Ala  Val  Ile  Lys  Lys  Ile  Trp  Lys  Lys  Thr
                    1570                     1575                      1580
Ser  Met  Lys  Leu  Leu  Asp  Gln  Val  Val  Pro  Pro  Ala  Gly  Asp  Asp  Glu
1585                     1590                     1595                      1600
Val  Thr  Val  Gly  Lys  Phe  Tyr  Ala  Thr  Phe  Leu  Ile  Gln  Asp  Tyr  Phe
                    1605                     1610                      1615
Arg  Lys  Phe  Lys  Lys  Arg  Lys  Glu  Gln  Gly  Leu  Val  Gly  Lys  Tyr  Pro
                    1620                     1625                      1630
Ala  Lys  Asn  Thr  Thr  Ile  Ala  Leu  Gln  Ala  Gly  Leu  Arg  Thr  Leu  His
                    1635                     1640                      1645
Asp  Ile  Gly  Pro  Glu  Ile  Arg  Arg  Ala  Ile  Ser  Cys  Asp  Leu  Gln  Asp
                    1650                     1655                      1660
Asp  Glu  Pro  Glu  Glu  Thr  Lys  Arg  Glu  Glu  Asp  Asp  Val  Phe  Lys
1665                     1670                     1675                      1680
Arg  Asn  Gly  Ala  Leu  Leu  Gly  Asn  His  Val  Asn  His  Val  Asn  Ser  Asp
                    1685                     1690                      1695
Arg  Arg  Asp  Ser  Leu  Gln  Gln  Thr  Asn  Thr  Thr  His  Arg  Pro  Leu  His
                    1700                     1705                      1710
Val  Gln  Arg  Pro  Ser  Ile  Pro  Pro  Ala  Ser  Asp  Thr  Glu  Lys  Pro  Leu
                    1715                     1720                      1725
Phe  Pro  Pro  Ala  Gly  Asn  Ser  Val  Cys  His  Asn  His  His  Asn  His  Asn
                    1730                     1735                      1740
Ser  Ile  Gly  Lys  Gln  Val  Pro  Thr  Ser  Thr  Asn  Ala  Asn  Leu  Asn  Asn
1745                     1750                     1755                      1760
Ala  Asn  Met  Ser  Lys  Ala  Ala  His  Gly  Lys  Arg  Pro  Ser  Ile  Gly  Asn
                    1765                     1770                      1775
Leu  Glu  His  Val  Ser  Glu  Asn  Gly  His  His  Ser  Ser  His  Lys  His  Asp
                    1780                     1785                      1790
Arg  Glu  Pro  Gln  Arg  Arg  Ser  Ser  Val  Lys  Arg  Thr  Arg  Tyr  Tyr  Glu
                    1795                     1800                      1805
Thr  Tyr  Ile  Arg  Ser  Asp  Ser  Gly  Asp  Glu  Gln  Leu  Pro  Thr  Ile  Cys
                    1810                     1815                      1820
Arg  Glu  Asp  Pro  Glu  Ile  His  Gly  Tyr  Phe  Arg  Asp  Pro  His  Cys  Leu
1825                     1830                     1835                      1840
Gly  Glu  Gln  Glu  Tyr  Phe  Ser  Ser  Glu  Glu  Cys  Tyr  Glu  Asp  Asp  Ser
                    1845                     1850                      1855
Ser  Pro  Thr  Trp  Ser  Arg  Gln  Asn  Tyr  Gly  Tyr  Tyr  Ser  Arg  Tyr  Pro
                    1860                     1865                      1870
Gly  Arg  Asn  Ile  Asp  Ser  Glu  Arg  Pro  Arg  Gly  Tyr  His  His  Pro  Gln
                    1875                     1880                      1885
Gly  Phe  Leu  Glu  Asp  Asp  Asp  Ser  Pro  Val  Cys  Tyr  Asp  Ser  Arg  Arg
                    1890                     1895                      1900
```

```
Ser  Pro  Arg  Arg  Arg  Leu  Leu  Pro  Pro  Thr  Pro  Ala  Ser  His  Arg  Arg
1905                1910                1915                1920

Ser  Ser  Phe  Asn  Phe  Glu  Cys  Leu  Arg  Arg  Gln  Ser  Ser  Gln  Glu  Glu
               1925                1930                1935

Val  Pro  Ser  Ser  Pro  Ile  Phe  Pro  His  Arg  Thr  Ala  Leu  Pro  Leu  His
               1940                1945                1950

Leu  Met  Gln  Gln  Gln  Ile  Met  Ala  Val  Ala  Gly  Leu  Asp  Ser  Ser  Lys
               1955                1960                1965

Ala  Gln  Lys  Tyr  Ser  Pro  Ser  His  Ser  Thr  Arg  Ser  Trp  Ala  Thr  Pro
     1970                1975                1980

Pro  Ala  Thr  Pro  Pro  Tyr  Arg  Asp  Trp  Thr  Pro  Cys  Tyr  Thr  Pro  Leu
1985                1990                1995                2000

Ile  Gln  Val  Glu  Gln  Ser  Glu  Ala  Leu  Asp  Gln  Val  Asn  Gly  Ser  Leu
               2005                2010                2015

Pro  Ser  Leu  His  Arg  Ser  Ser  Trp  Tyr  Thr  Asp  Glu  Pro  Asp  Ile  Ser
               2020                2025                2030

Tyr  Arg  Thr  Phe  Thr  Pro  Ala  Ser  Leu  Thr  Val  Pro  Ser  Ser  Phe  Arg
          2035                2040                2045

Asn  Lys  Asn  Ser  Asp  Lys  Gln  Arg  Ser  Ala  Asp  Ser  Leu  Val  Glu  Ala
     2050                2055                2060

Val  Leu  Ile  Ser  Glu  Gly  Leu  Gly  Arg  Tyr  Ala  Arg  Asp  Pro  Lys  Phe
2065                2070                2075                2080

Val  Ser  Ala  Thr  Lys  His  Glu  Ile  Ala  Asp  Ala  Cys  Asp  Leu  Thr  Ile
               2085                2090                2095

Asp  Glu  Met  Glu  Ser  Ala  Ala  Ser  Thr  Leu  Leu  Asn  Gly  Asn  Val  Arg
               2100                2105                2110

Pro  Arg  Ala  Asn  Gly  Asp  Val  Gly  Pro  Leu  Ser  His  Arg  Gln  Asp  Tyr
     2115                2120                2125

Glu  Leu  Gln  Asp  Phe  Gly  Pro  Gly  Tyr  Ser  Asp  Glu  Glu  Pro  Asp  Pro
     2130                2135                2140

Gly  Arg  Asp  Glu  Glu  Asp  Leu  Ala  Asp  Glu  Met  Ile  Cys  Ile  Thr  Thr
2145                2150                2155                2160

Leu
```

( 2 ) INFORMATION FOR SEQ ID NO:3:

( i ) SEQUENCE CHARACTERISTICS:
        ( A ) LENGTH: 510 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:3:

```
GGGCGAGCGC  CTCCGTCCCC  GGATGTGAGC  TCCGGCTGCC  CGCGGTCCCG  AGCCAGCGGC     60

GCGCGGGCGG  CGGCGGCGGG  CACCGGGCAC  CGCGGCGGGC  GGGCAGACGG  GCGGGCATGG    120

GGGGAGCGCC  GAGCGGCCCC  GGCGGCCGGG  CCGGCATCAC  CGCGGCGTCT  CTCCGCTAGA    180

GGAGGGGACA  AGCCAGTTCT  CCTTTGCAGC  AAAAAATTAC  ATGTATATAT  TATTAAGATA    240

ATATATACAT  TGGATTTTAT  TTTTTAAAA   AGTTTATTTT  GCTCCATTTT  TGAAAAAGAG    300

AGAGCTTGGG  TGGCGAGCGG  TTTTTTTTA   AAATCAATTA  TCCTTATTTT  CTGTTATTTG    360

TCCCCGTCCC  TCCCCACCCC  CCTGCTGAAG  CGAGAATAAG  GGCAGGGACC  GCGGCTCCTA    420

CCTCTTGGTG  ATCCCCTTCC  CCATTCCGCC  CCCGCCCCAA  CGCCCAGCAC  AGTGCCCTGC    480

ACACAGTAGT  CGCTCAATAA  ATGTTCGTGG                                       510
```

( 2 ) INFORMATION FOR SEQ ID NO:4:

( i ) SEQUENCE CHARACTERISTICS:
        ( A ) LENGTH: 104 base pairs
        ( B ) TYPE: nucleic acid
        ( C ) STRANDEDNESS: unknown
        ( D ) TOPOLOGY: unknown ( i i ) MOLECULE TYPE: DNA (genomic)

( i x ) FEATURE:
        ( A ) NAME/KEY: CDS
        ( B ) LOCATION: 1..102

( x i ) SEQUENCE DESCRIPTION: SEQ ID NO:4:

```
GTA AAT GAT GCG ATA GGA TGG GAA TGG CCA TGG GTG TAT TTT GTT AGT        48
Val Asn Asp Ala Ile Gly Trp Glu Trp Pro Trp Val Tyr Phe Val Ser
 1               5                  10                  15

CTG ATC ATC CTT GGC TCA TTT TTC GTC CTT AAC CTG GTT CTT GGT GTC        96
Leu Ile Ile Leu Gly Ser Phe Phe Val Leu Asn Leu Val Leu Gly Val
             20                  25                  30

CTT AGT GG                                                            104
Leu Ser
```

( 2 ) INFORMATION FOR SEQ ID NO:5:

( i ) SEQUENCE CHARACTERISTICS:
        ( A ) LENGTH: 34 amino acids
        ( B ) TYPE: amino acid
        ( D ) TOPOLOGY: linear ( i i ) MOLECULE TYPE: protein ( x i ) SEQUENCE DESCRIPTION: SEQ ID NO:5:

```
Val Asn Asp Ala Ile Gly Trp Glu Trp Pro Trp Val Tyr Phe Val Ser
 1               5                  10                  15

Leu Ile Ile Leu Gly Ser Phe Phe Val Leu Asn Leu Val Leu Gly Val
             20                  25                  30

Leu Ser
```

( 2 ) INFORMATION FOR SEQ ID NO:6:

( i ) SEQUENCE CHARACTERISTICS:
        ( A ) LENGTH: 5904 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:6:

```
ATGGTCAATG AGAATACGAG GATGTACATT CCAGAGGAAA ACCACCAAGG TTCCAACTAT       60
GGGAGCCCAC GCCCCGCCCA TGCCAACATG AATGCCAATG CGGCAGCGGG GCTGGCCCCT      120
GAGCACATCC CCACCCCGGG GGCTGCCCTG TCGTGGCAGG CGGCCATCGA CGCAGCCCGG      180
CAGGCTAAGC TGATGGGCAG CGCTGGCAAT GCGACCATCT CCACAGTCAG CTCCACGCAG      240
CGGAAGCGCC AGCAATATGG GAAACCCAAG AAGCAGGGCA GCACCACGGC CACACGCCCG      300
CCCCGAGCCC TGCTCTGCCT GACCCTGAAG AACCCCATCC GGAGGGCCTG CATCAGCATT      360
GTCGAATGGA AACCATTTGA ATAATTATT TTACTGACTA TTTTTGCCAA TTGTGTGGCC       420
TTAGCGATCT ATATTCCCTT TCCAGAAGAT GATTCCAACG CCACCAATTC CAACCTGGAA      480
CGAGTGGAAT ATCTCTTTCT CATAATTTTT ACGGTGGAAG CGTTTTTAAA AGTAATCGCC      540
TATGGACTCC TCTTTCACCC CAATGCCTAC CTCCGCAACG GCTGGAACCT ACTAGATTTT      600
ATAATTGTGG TTGTGGGGCT TTTTAGTGCA ATTTTAGAAC AAGCAACCAA AGCAGATGGG      660
```

```
GCAAACGCTC TCGGAGGGAA AGGGGCCGGA TTTGATGTGA AGGCGCTGAG GGCCTTCCGC      720
GTGCTGCGCC CCCTGCGGCT GGTGTCCGGA GTCCCAAGTC TCCAGGTGGT CCTGAATTCC      780
ATCATCAAGG CCATGGTCCC CCTGCTGCAC ATCGCCCTGC TTGTGCTGTT TGTCATCATC      840
ATCTACGCCA TCATCGGCTT GGAGCTCTTC ATGGGGAAGA TGCACAAGAC CTGCTACAAC      900
CAGGAGGGCA TAGCAGATGT TCCAGCAGAA GATGACCCTT CCCCTTGTGC GCTGGAAACG      960
GGCCACGGGC GGCAGTGCCA GAACGGCACG GTGTGCAAGC CCGGCTGGGA TGGTCCCAAG     1020
CACGGCATCA CCAACTTTGA CAACTTTGCC TTCGCCATGC TCACGGTGTT CCAGTGCATC     1080
ACCATGGAGG CTGGACGGA CGTGCTGTAC TGGGTCAATG ATGCCGTAGG AAGGGACTGG     1140
CCCTGGATCT ATTTTGTTAC ACTAATCATC ATAGGGTCAT TTTTTGTACT TAACTTGGTT     1200
CTCGGTGTGC TTAGCGGAGA GTTTTCCAAA GAGAGGGAGA AGGCCAAGGC CCGGGGAGAT     1260
TTCCAGAAGC TGCGGGAGAA GCAGCAGCTA GAAGAGGATC TCAAAGGCTA CCTGGATTGG     1320
ATCACTCAGG CCGAAGACAT CGNTCCTGAG AATGAGGACG AAGGCATGGA TGAGGAGAAG     1380
CCCCGAAACA GAGGCACTCC GGCGGGCATG CTTGATCAGA AGAAAGGGAA GTTTGCTTGG     1440
TTTAGTCACT CCACAGAAAC CCATGTGAGC ATGCCCACCA GTGAGACCGA GTCCGTCAAC     1500
ACCGAAAACG TGGCTGGAGG TGACATCGAG GGAGAAAACT GCGGGGCCAG GCTGGCCCAC     1560
CGGATCTCCA AGTCAAAGTT CAGCCGCTAC TGGCGCCGGT GGAATCGGTT CTGCAGAAGG     1620
AAGTGCCGCG CCGCAGTCAA GTCTAATGTC TTCTACTGGC TGGTGATTTT CCTGGTGTTC     1680
CTCAACACGC TCACCATTGC CTCTGAGCAC TACAACCAGC CCAACTGGCT CACAGAAGTC     1740
CAAGACACGG CAAACAAGGC CCTGCTGGCC CTGTTCACGG CAGAGATGCT CCTGAAGATG     1800
TACAGCCTGG GCCTGCAGGC CTACTTCGTG TCCCTCTTCA ACCGCTTTGA CTGCTTCGTC     1860
GTGTGTGGCG GCATCCTGGA GACCATCCTG GTGGAGACCA AGATCATGTC CCCACTGGGC     1920
ATCTCCGTGC TCAGATGCGT CCGGCTGCTG AGGATTTTCA AGATCACGAG GTACTGGAAC     1980
TCCTTGAGCA ACCTGGTGGC ATCCTTGCTG AACTCTGTGC GCTCCATCGC CTCCCTGCTC     2040
CTTCTCCTCT TCCTCTTCAT CATCATCTTC TCCCTCCTGG GGATGCAGCT CTTTGGAGGA     2100
AAGTTCAACT TTGATGAGAT GCAGACCCGG AGGAGCACAT TCGATAACTT CCCCCAGTCC     2160
CTCCTCACTG TGTTTNNNNN NNNNNNNNNN NNNNNNNNNN NNNNGGTGAT GTATGATGGG     2220
ATCATGGCTT ATGGGGGCCC CTCTTTTCCA GGGATGTTAG TCTGTATTTA CTTCATCATC     2280
CTCTTCATCT CTGGAAACTA TATCCTACTG AATGTGTTCT TGGCCATTGC TGTGGACAAC     2340
CTGGCTGATG CTGAGAGCCT CACATCTGCC CTAAAGGAGG AGGAAGAGGA GAAGGAGAGA     2400
AAGAAGCTGG CCAGGACTGC CAGCCCAGAG AAGAAACAAG AGTTGGTGGA GAAGCCGGCA     2460
GTGGGGGAAT CCAAGGAGGA GAAGATTGAG CTGAAATCCA TCACGGCTGA CGGAGAGTCT     2520
CCACCCGCCA CCAAGATCAA CATGGATGAC CTCCAGCCCA ATGAAAATGA GGATAAGAGC     2580
CCCTACCCCA ACCCAGAAAC TACAGGAGAA GAGGATGAGG AGGAGCCAGA GATGCCTGTC     2640
GGCCCTCGCC CACGACCACT CTCTGAGCTT CACCTTAAGG AAAAGGCAGT GCCCATGCCA     2700
GAAGCCAGCG CGTTTTTCAT CTTCAGCTCT AACAACAGGT TTCGCCTCCA GTGCCACCGC     2760
ATTGTCAATG ACACGATCTT CACCAACCTG ATCCTCTTCT TCATTCTGCT CAGCAGCATT     2820
TCCCTGGCTG CTGAGGACCC GGTCCAGCAC ACCTCCTTCA GGAACCATAT TCTGTTTTAT     2880
TTTGATATTG TTTTTACCAC CATTTTCACC ATTGAAATTG CTCTGAAGAT GACTGCTTAT     2940
GGGGCTTTCT TGCACAAGGG TTCTTTCTGC CGGAACTACT TCAACATCCT GGACCTGCTG     3000
GTGGTCAGCG TGTCCCTCAT CTCCTTTGGC ATCCAGTCCA GTGCAATCAA TGTCGTGAAG     3060
ATCTTGCGAG TCCTGCGAGT ACTCAGGCCC CTGAGGGCCA TCAACAGGGC CAAGGGGCTA    3120
```

```
AAGCATGTGG TTCAGTGTGT GTTTGTCGCC ATCCGGACCA TCGGGAACAT CGTGATTGTC    3180
ACCACCCTGC TGCAGTTCAT GTTTGCCTGC ATCGGGGTCC AGCTCTTCAA GGGAAAGCTG    3240
TACACCTGTT CAGACAGTTC CAAGCAGACA GAGGCGGAAT GCAAGGGCAA CTACATCACG    3300
TACAAAGACG GGGAGGTTGA CCACCCCATC ATCCAACCCC GCAGCTGGGA GAACAGCAAG    3360
TTTGACTTTG ACAATGTTCT GGCAGCCATG ATGGCCCTCT TCACCGTCTC CACCTTCGAA    3420
GGGTGGCCAG AGCTGCTGTA CCGCTCCATC GACTCCACA CGGAAGACAA GGGCCCCATC     3480
TACAACTACC GTGTGGAGAT CTCCATCTTC TTCATCATCT ACATCATCAT CATCGCCTTC    3540
TTCATGATGA ACATCTTCGT GGGCTTCGTC ATCGTCACCT TCAGGAGCA GGGGGAGCAG     3600
GAGTACAAGA ACTGTGAGCT GGACAAGAAC CAGCGACAGT GCGTGGAATA CGCCCTCAAG    3660
GCCCGGCCCC TGCGGAGGTA CATCCCCAAG AACCAGCACC AGTACAAAGT GTGGTACGTG    3720
GTCAACTCCA CCTACTTCGA GTACCTGATG TTCGTCCTCA TCCTGCTCAA CACCATCTGC    3780
CTGGCCATGC AGCACTACGG CCAGAGCTGC CTGTTCAAAA TCGCCATGAA CATCCTCAAC    3840
ATGCTCTTCA CTGGCCTCTT CACCGTGGAG ATGATCCTGA AGCTCATTGC CTTCAAACCC    3900
AAGGGTTACT TTAGTGATCC CTGGAATGTT TTTGACTTCC TCATCGTAAT GGCAGCATA     3960
ATTGACGTCA TTCTCAGTGA GACTAATCCA GCTGAACATA CCCAATGCTC TCCCTCTATG    4020
AACGCAGAGG AAAACTCCCG CATCTCCATC ACCTTCTTCC GCCTGTTCCG GGTCATGCGT    4080
CTGGTGAAGC TGCTGAGCCG TGGGGAGGGC ATCCGGACGC TGCTGTGGAC CTTCATCAAG    4140
TCCTTCCAGG CCCTGCCCTA TGTGGCCCTC TGATCGTGA TGCTGTTCTT CATCTACGCG     4200
GTGATCGGGA TGCAGGTGTT TGGGAAAATT GCCCTGAATG ATACCACAGA GATCAACCGG    4260
AACAACAACT TCAGACCTT CCCCCAGGCC GTGCTGCTCC TCTTCAGGTG TGCCACCGGG     4320
GAGGCCTGGC AGGACATCAT GCTGGCCTGC ATGCCAGGCA AGAAGTGTGC CCCAGAGTCC    4380
GAGCCCAGCA ACAGCACGGA GGGTGAAACA CCCTGTGGTA GCAGCTTTGC TGTCTTCTAC    4440
TTCATCAGCT TCTACATGCG CTGTGCCTTC CTGATCATCA ACCTCTTTGT AGCTGTCATC    4500
ATGGACAACT TTGACTACCT GACAAGGGAC TGGTCCATCC TTGGTCCCCA CCACCTGGAT    4560
GAGTTTAAAA GAATCTGGGC AGAGTATGAC CCTGAAGCCA AGGGTCGTAT CAAACACCTG    4620
GATGTGGTGA CCCTCCTCCG GCGGATTCAG CCGCCACTAG GTTTTGGGAA GCTGTGCCCT    4680
CACCGCGTGG CTTGCAAACG CCTGGTCTCC ATGAACATGC CTCTGAACAG CGACGGGACA    4740
GTCATGTTCA ATGCCACCCT GTTTGCCCTG GTCAGGACGG CCCTGAGGAT CAAAACAGAA    4800
GGGAACCTAG AACAAGCCAA TGAGGAGCTG CGGGCGATCA TCAAGAAGAT CTGGAAGCGG    4860
ACCAGCATGA AGCTGCTGGA CCAGGTGGTG CCCCCTGCAG GTGATGATGA GGTCACCGTT    4920
GGCAAGTTCT ACGCCACGTT CCTGATCCAG GAGTACTTCC GGAAGTTCAA GAAGCGCAAA    4980
GAGCAGGGCC TTGTGGGCAA GCCCTCCCAG AGGAACGCGC TGTCTCTGCA GGCTGGCTTG    5040
CGCACACTGC ATGACATCGG GCCTGAGATC CGACGGGCCA TCTCTGGAGA TCTCACCGCT    5100
GAGGAGGAGC TGGACAAGGC CATGAAGGAG GCTGTGTCCG CTGCTTCTGA AGATGACATC    5160
TTCAGGAGGG CCGGTGGCCT GTTCGGCAAC CACGTCAGCT ACTACCAAAG CGACGGCCGG    5220
AGCGCCTTCC CCCAGACCTT CACCACTCAG CGCCCGCTGC ACATCAACAA GGCGGGCAGC    5280
AGCCAGGGCG ACACTGAGTC GCCATCCCAC GAGAAGCTGG TGGACTCCAC CTTCACCCCG    5340
AGCAGCTACT CGTCCACCGG CTCCAACGCC AACATCAACA ACGCCAACAA CACCGCCCTG    5400
GGTCGCCTCC CTCGCCCCGC CGGCTACCCC AGCACAGTCA GCACTGTGGA GGGCCACGGG    5460
CCCCCCTTGT CCCCTGCCAT CCGGGTGCAG GAGGTGGCGT GGAAGCTCAG CTCCAACAGG    5520
TGCCACTCCC GGGAGAGCCA GGCAGCCATG GCGCGTCAGG AGGAGACGTC TCAGGATGAG    5580
```

```
ACCTATGAAG TGAAGATGAA CCATGACACG GAGGCCTGCA GTGAGCCCAG CCTGCTCTCC    5640

ACAGAGATGC TCTCCTACCA GGATGACGAA AATCGGCAAC TGACGCTCCC AGAGGAGGAC    5700

AAGAGGGACA TCCGGCAATC TCCGAAGAGG GGTTTCCTCC GCTCTTCCTC ACTAGGTCGA    5760

AGGGCCTCCT TCCACCTGGA ATGTCTGAAG CGACAGAAGG ACCGAGGGGG AGACATCTCT    5820

CAGAAGACAG TCCTGCCCTT GCATCTGGTT CATCATCAGG CATTGGCAGT GGCAGGCCTG    5880

AGCCCCCTCC TCCAGAGAAG CCAT                                          5904
```

( 2 ) INFORMATION FOR SEQ ID NO:7:

( i ) SEQUENCE CHARACTERISTICS:
        ( A ) LENGTH: 1968 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:7:

```
Met Val Asn Glu Asn Thr Arg Met Tyr Ile Pro Glu Glu Asn His Gln
 1               5                  10                  15

Gly Ser Asn Tyr Gly Ser Pro Arg Pro Ala His Ala Asn Met Asn Ala
                20                  25                  30

Asn Ala Ala Ala Gly Leu Ala Pro Glu His Ile Pro Thr Pro Gly Ala
            35                  40                  45

Ala Leu Ser Trp Gln Ala Ala Ile Asp Ala Ala Arg Gln Ala Lys Leu
    50                  55                  60

Met Gly Ser Ala Gly Asn Ala Thr Ile Ser Thr Val Ser Ser Thr Gln
65                  70                  75                  80

Arg Lys Arg Gln Gln Tyr Gly Lys Pro Lys Lys Gln Gly Ser Thr Thr
                85                  90                  95

Ala Thr Arg Pro Pro Arg Ala Leu Leu Cys Leu Thr Leu Lys Asn Pro
            100                 105                 110

Ile Arg Arg Ala Cys Ile Ser Ile Val Glu Trp Lys Pro Phe Glu Ile
        115                 120                 125

Ile Ile Leu Leu Thr Ile Phe Ala Asn Cys Val Ala Leu Ala Ile Tyr
130                 135                 140

Ile Pro Phe Pro Glu Asp Asp Ser Asn Ala Thr Asn Ser Asn Leu Glu
145                 150                 155                 160

Arg Val Glu Tyr Leu Phe Leu Ile Ile Phe Thr Val Glu Ala Phe Leu
                165                 170                 175

Lys Val Ile Ala Tyr Gly Leu Leu Phe His Pro Asn Ala Tyr Leu Arg
            180                 185                 190

Asn Gly Trp Asn Leu Leu Asp Phe Ile Ile Val Val Gly Leu Phe
        195                 200                 205

Ser Ala Ile Leu Glu Gln Ala Thr Lys Ala Asp Gly Ala Asn Ala Leu
210                 215                 220

Gly Gly Lys Gly Ala Gly Phe Asp Val Lys Ala Leu Arg Ala Phe Arg
225                 230                 235                 240

Val Leu Arg Pro Leu Arg Leu Val Ser Gly Val Pro Ser Leu Gln Val
                245                 250                 255

Val Leu Asn Ser Ile Ile Lys Ala Met Val Pro Leu Leu His Ile Ala
            260                 265                 270

Leu Leu Val Leu Phe Val Ile Ile Ile Tyr Ala Ile Ile Gly Leu Glu
        275                 280                 285

Leu Phe Met Gly Lys Met His Lys Thr Cys Tyr Asn Gln Glu Gly Ile
290                 295                 300
```

```
Ala Asp Val Pro Ala Glu Asp Pro Ser Pro Cys Ala Leu Glu Thr
305                 310                 315                 320

Gly His Gly Arg Gln Cys Gln Asn Gly Thr Val Cys Lys Pro Gly Trp
            325                 330                 335

Asp Gly Pro Lys His Gly Ile Thr Asn Phe Asp Asn Phe Ala Phe Ala
            340                 345                 350

Met Leu Thr Val Phe Gln Cys Ile Thr Met Glu Gly Trp Thr Asp Val
            355                 360                 365

Leu Tyr Trp Val Asn Asp Ala Val Gly Arg Asp Trp Pro Trp Ile Tyr
    370                 375                 380

Phe Val Thr Leu Ile Ile Ile Gly Ser Phe Phe Val Leu Asn Leu Val
385                 390                 395                 400

Leu Gly Val Leu Ser Gly Glu Phe Ser Lys Glu Arg Glu Lys Ala Lys
                405                 410                 415

Ala Arg Gly Asp Phe Gln Lys Leu Arg Glu Lys Gln Gln Leu Glu Glu
            420                 425                 430

Asp Leu Lys Gly Tyr Leu Asp Trp Ile Thr Gln Ala Glu Asp Ile Xaa
        435                 440                 445

Pro Glu Asn Glu Asp Glu Gly Met Asp Glu Glu Lys Pro Arg Asn Arg
450                 455                 460

Gly Thr Pro Ala Gly Met Leu Asp Gln Lys Lys Gly Lys Phe Ala Trp
465                 470                 475                 480

Phe Ser His Ser Thr Glu Thr His Val Ser Met Pro Thr Ser Glu Thr
                485                 490                 495

Glu Ser Val Asn Thr Glu Asn Val Ala Gly Gly Asp Ile Glu Gly Glu
                500                 505                 510

Asn Cys Gly Ala Arg Leu Ala His Arg Ile Ser Lys Ser Lys Phe Ser
            515                 520                 525

Arg Tyr Trp Arg Arg Trp Asn Arg Phe Cys Arg Arg Lys Cys Arg Ala
    530                 535                 540

Ala Val Lys Ser Asn Val Phe Tyr Trp Leu Val Ile Phe Leu Val Phe
545                 550                 555                 560

Leu Asn Thr Leu Thr Ile Ala Ser Glu His Tyr Asn Gln Pro Asn Trp
                565                 570                 575

Leu Thr Glu Val Gln Asp Thr Ala Asn Lys Ala Leu Leu Ala Leu Phe
                580                 585                 590

Thr Ala Glu Met Leu Leu Lys Met Tyr Ser Leu Gly Leu Gln Ala Tyr
            595                 600                 605

Phe Val Ser Leu Phe Asn Arg Phe Asp Cys Phe Val Val Cys Gly Gly
    610                 615                 620

Ile Leu Glu Thr Ile Leu Val Glu Thr Lys Ile Met Ser Pro Leu Gly
625                 630                 635                 640

Ile Ser Val Leu Arg Cys Val Arg Leu Leu Arg Ile Phe Lys Ile Thr
                645                 650                 655

Arg Tyr Trp Asn Ser Leu Ser Asn Leu Val Ala Ser Leu Leu Asn Ser
            660                 665                 670

Val Arg Ser Ile Ala Ser Leu Leu Leu Leu Phe Leu Phe Ile Ile
    675                 680                 685

Ile Phe Ser Leu Leu Gly Met Gln Leu Phe Gly Gly Lys Phe Asn Phe
    690                 695                 700

Asp Glu Met Gln Thr Arg Arg Ser Thr Phe Asp Asn Phe Pro Gln Ser
705                 710                 715                 720

Leu Leu Thr Val Phe Xaa Xaa Xaa Xaa Xaa Xaa Xaa Xaa Xaa Xaa Val
                725                 730                 735
```

```
Met Tyr Asp Gly Ile Met Ala Tyr Gly Gly Pro Ser Phe Pro Gly Met
        740                 745                 750
Leu Val Cys Ile Tyr Phe Ile Ile Leu Phe Ile Ser Gly Asn Tyr Ile
        755                 760                 765
Leu Leu Asn Val Phe Leu Ala Ile Ala Val Asp Asn Leu Ala Asp Ala
        770                 775                 780
Glu Ser Leu Thr Ser Ala Leu Lys Glu Glu Glu Glu Glu Lys Glu Arg
785             790                 795                     800
Lys Lys Leu Ala Arg Thr Ala Ser Pro Lys Lys Gln Glu Leu Val
                805                 810                 815
Glu Lys Pro Ala Val Gly Glu Ser Lys Glu Glu Lys Ile Glu Leu Lys
            820                 825                 830
Ser Ile Thr Ala Asp Gly Glu Ser Pro Pro Ala Thr Lys Ile Asn Met
        835                 840                 845
Asp Asp Leu Gln Pro Asn Glu Asn Glu Asp Lys Ser Pro Tyr Pro Asn
850                 855                     860
Pro Glu Thr Thr Gly Glu Glu Asp Glu Glu Glu Pro Glu Met Pro Val
865             870                 875                     880
Gly Pro Arg Pro Arg Pro Leu Ser Glu Leu His Leu Lys Glu Lys Ala
            885                 890                 895
Val Pro Met Pro Glu Ala Ser Ala Phe Phe Ile Phe Ser Ser Asn Asn
            900                 905                 910
Arg Phe Arg Leu Gln Cys His Arg Ile Val Asn Asp Thr Ile Phe Thr
            915                 920                 925
Asn Leu Ile Leu Phe Phe Ile Leu Leu Ser Ser Ile Ser Leu Ala Ala
930                 935                 940
Glu Asp Pro Val Gln His Thr Ser Phe Arg Asn His Ile Leu Phe Tyr
945             950                 955                     960
Phe Asp Ile Val Phe Thr Thr Ile Phe Thr Ile Glu Ile Ala Leu Lys
                965                 970                 975
Met Thr Ala Tyr Gly Ala Phe Leu His Lys Gly Ser Phe Cys Arg Asn
            980                 985                 990
Tyr Phe Asn Ile Leu Asp Leu Leu Val Val Ser Val Ser Leu Ile Ser
        995                 1000                1005
Phe Gly Ile Gln Ser Ser Ala Ile Asn Val Val Lys Ile Leu Arg Val
    1010                1015                1020
Leu Arg Val Leu Arg Pro Leu Arg Ala Ile Asn Arg Ala Lys Gly Leu
1025                1030                1035                1040
Lys His Val Val Gln Cys Val Phe Val Ala Ile Arg Thr Ile Gly Asn
                1045                1050                1055
Ile Val Ile Val Thr Thr Leu Leu Gln Phe Met Phe Ala Cys Ile Gly
            1060                1065                1070
Val Gln Leu Phe Lys Gly Lys Leu Tyr Thr Cys Ser Asp Ser Ser Lys
        1075                1080                1085
Gln Thr Glu Ala Glu Cys Lys Gly Asn Tyr Ile Thr Tyr Lys Asp Gly
    1090                1095                1100
Glu Val Asp His Pro Ile Ile Gln Pro Arg Ser Trp Glu Asn Ser Lys
1105                1110                1115                1120
Phe Asp Phe Asp Asn Val Leu Ala Ala Met Met Ala Leu Phe Thr Val
                1125                1130                1135
Ser Thr Phe Glu Gly Trp Pro Glu Leu Leu Tyr Arg Ser Ile Asp Ser
            1140                1145                1150
His Thr Glu Asp Lys Gly Pro Ile Tyr Asn Tyr Arg Val Glu Ile Ser
        1155                1160                1165
Ile Phe Phe Ile Ile Tyr Ile Ile Ile Ile Ala Phe Phe Met Met Asn
```

```
            1170                    1175                    1180
Ile Phe Val Gly Phe Val Ile Val Thr Phe Gln Glu Gln Gly Glu Gln
1185                    1190                    1195                    1200
Glu Tyr Lys Asn Cys Glu Leu Asp Lys Asn Gln Arg Gln Cys Val Glu
                        1205                    1210                    1215
Tyr Ala Leu Lys Ala Arg Pro Leu Arg Arg Tyr Ile Pro Lys Asn Gln
                1220                    1225                    1230
His Gln Tyr Lys Val Trp Tyr Val Val Asn Ser Thr Tyr Phe Glu Tyr
            1235                    1240                    1245
Leu Met Phe Val Leu Ile Leu Leu Asn Thr Ile Cys Leu Ala Met Gln
                1250                    1255                    1260
His Tyr Gly Gln Ser Cys Leu Phe Lys Ile Ala Met Asn Ile Leu Asn
1265                    1270                    1275                    1280
Met Leu Phe Thr Gly Leu Phe Thr Val Glu Met Ile Leu Lys Leu Ile
                    1285                    1290                    1295
Ala Phe Lys Pro Lys Gly Tyr Phe Ser Asp Pro Trp Asn Val Phe Asp
                1300                    1305                    1310
Phe Leu Ile Val Ile Gly Ser Ile Ile Asp Val Ile Leu Ser Glu Thr
            1315                    1320                    1325
Asn Pro Ala Glu His Thr Gln Cys Ser Pro Ser Met Asn Ala Glu Glu
            1330                    1335                    1340
Asn Ser Arg Ile Ser Ile Thr Phe Phe Arg Leu Phe Arg Val Met Arg
1345                    1350                    1355                    1360
Leu Val Lys Leu Leu Ser Arg Gly Glu Gly Ile Arg Thr Leu Leu Trp
                    1365                    1370                    1375
Thr Phe Ile Lys Ser Phe Gln Ala Leu Pro Tyr Val Ala Leu Leu Ile
            1380                    1385                    1390
Val Met Leu Phe Phe Ile Tyr Ala Val Ile Gly Met Gln Val Phe Gly
            1395                    1400                    1405
Lys Ile Ala Leu Asn Asp Thr Thr Glu Ile Asn Arg Asn Asn Asn Phe
        1410                    1415                    1420
Gln Thr Phe Pro Gln Ala Val Leu Leu Leu Phe Arg Cys Ala Thr Gly
1425                    1430                    1435                    1440
Glu Ala Trp Gln Asp Ile Met Leu Ala Cys Met Pro Gly Lys Lys Cys
                    1445                    1450                    1455
Ala Pro Glu Ser Glu Pro Ser Asn Ser Thr Glu Gly Glu Thr Pro Cys
            1460                    1465                    1470
Gly Ser Ser Phe Ala Val Phe Tyr Phe Ile Ser Phe Tyr Met Arg Cys
                1475                    1480                    1485
Ala Phe Leu Ile Ile Asn Leu Phe Val Ala Val Ile Met Asp Asn Phe
        1490                    1495                    1500
Asp Tyr Leu Thr Arg Asp Trp Ser Ile Leu Gly Pro His His Leu Asp
1505                    1510                    1515                    1520
Glu Phe Lys Arg Ile Trp Ala Glu Tyr Asp Pro Glu Ala Lys Gly Arg
                    1525                    1530                    1535
Ile Lys His Leu Asp Val Val Thr Leu Leu Arg Arg Ile Gln Pro Pro
                1540                    1545                    1550
Leu Gly Phe Gly Lys Leu Cys Pro His Arg Val Ala Cys Lys Arg Leu
            1555                    1560                    1565
Val Ser Met Asn Met Pro Leu Asn Ser Asp Gly Thr Val Met Phe Asn
            1570                    1575                    1580
Ala Thr Leu Phe Ala Leu Val Arg Thr Ala Leu Arg Ile Lys Thr Glu
1585                    1590                    1595                    1600
Gly Asn Leu Glu Gln Ala Asn Glu Glu Leu Arg Ala Ile Ile Lys Lys
                    1605                    1610                    1615
```

| | | | | | | | | | | | | | |
|---|---|---|---|---|---|---|---|---|---|---|---|---|---|
|Ile|Trp|Lys|Arg|Thr|Ser|Met|Lys|Leu|Leu|Asp|Gln|Val|Val Pro Pro|
| | |  |1620| | | |1625| | | |1630| | |
|Ala|Gly|Asp|Asp|Glu|Val|Thr|Val|Gly|Lys|Phe|Tyr|Ala|Thr Phe Leu|
| | | |1635| | | |1640| | | |1645| | |
|Ile|Gln|Glu|Tyr|Phe|Arg|Lys|Phe|Lys|Lys|Arg|Lys|Glu|Gln Gly Leu|
| | | |1650| | | |1655| | | |1660| | |
|Val|Gly|Lys|Pro|Ser|Gln|Arg|Asn|Ala|Leu|Ser|Leu|Gln|Ala Gly Leu|
|1665| | | |1670| | | |1675| | | | |1680|
|Arg|Thr|Leu|His|Asp|Ile|Gly|Pro|Glu|Ile|Arg|Arg|Ala|Ile Ser Gly|
| | | | |1685| | | |1690| | | | |1695|
|Asp|Leu|Thr|Ala|Glu|Glu|Glu|Leu|Asp|Lys|Ala|Met|Lys|Glu Ala Val|
| | | |1700| | | |1705| | | |1710| | |
|Ser|Ala|Ala|Ser|Glu|Asp|Asp|Ile|Phe|Arg|Arg|Ala|Gly|Gly Leu Phe|
| | | |1715| | | |1720| | | |1725| | |
|Gly|Asn|His|Val|Ser|Tyr|Tyr|Gln|Ser|Asp|Gly|Arg|Ser|Ala Phe Pro|
| | | |1730| | | |1735| | | |1740| | |
|Gln|Thr|Phe|Thr|Thr|Gln|Arg|Pro|Leu|His|Ile|Asn|Lys|Ala Gly Ser|
|1745| | | |1750| | | |1755| | | | |1760|
|Ser|Gln|Gly|Asp|Thr|Glu|Ser|Pro|Ser|His|Glu|Lys|Leu|Val Asp Ser|
| | | |1765| | | |1770| | | |1775| | |
|Thr|Phe|Thr|Pro|Ser|Ser|Tyr|Ser|Ser|Thr|Gly|Ser|Asn|Ala Asn Ile|
| | | |1780| | | |1785| | | |1790| | |
|Asn|Asn|Ala|Asn|Asn|Thr|Ala|Leu|Gly|Arg|Leu|Pro|Arg|Pro Ala Gly|
| | | |1795| | | |1800| | | |1805| | |
|Tyr|Pro|Ser|Thr|Val|Ser|Thr|Val|Glu|Gly|His|Gly|Pro|Pro Leu Ser|
| | | |1810| | | |1815| | | |1820| | |
|Pro|Ala|Ile|Arg|Val|Gln|Glu|Val|Ala|Trp|Lys|Leu|Ser|Ser Asn Arg|
|1825| | | |1830| | | |1835| | | | |1840|
|Cys|His|Ser|Arg|Glu|Ser|Gln|Ala|Ala|Met|Ala|Arg|Gln|Glu Glu Thr|
| | | |1845| | | |1850| | | |1855| | |
|Ser|Gln|Asp|Glu|Thr|Tyr|Glu|Val|Lys|Met|Asn|His|Asp|Thr Glu Ala|
| | | |1860| | | |1865| | | |1870| | |
|Cys|Ser|Glu|Pro|Ser|Leu|Leu|Ser|Thr|Glu|Met|Leu|Ser|Tyr Gln Asp|
| | | |1875| | | |1880| | | |1885| | |
|Asp|Glu|Asn|Arg|Gln|Leu|Thr|Leu|Pro|Glu|Glu|Asp|Lys|Arg Asp Ile|
| | | |1890| | | |1895| | | |1900| | |
|Arg|Gln|Ser|Pro|Lys|Arg|Gly|Phe|Leu|Arg|Ser|Ser|Ser|Leu Gly Arg|
|1905| | | |1910| | | |1915| | | | |1920|
|Arg|Ala|Ser|Phe|His|Leu|Glu|Cys|Leu|Lys|Arg|Gln|Lys|Asp Arg Gly|
| | | |1925| | | |1930| | | |1935| | |
|Gly|Asp|Ile|Ser|Gln|Lys|Thr|Val|Leu|Pro|Leu|His|Leu|Val His His|
| | | |1940| | | |1945| | | |1950| | |
|Gln|Ala|Leu|Ala|Val|Ala|Gly|Leu|Ser|Pro|Leu|Leu|Gln|Arg Ser His|
| | | |1955| | | |1960| | | |1965| | |

( 2 ) INFORMATION FOR SEQ ID NO:8:

( i ) SEQUENCE CHARACTERISTICS:
        ( A ) LENGTH: 132 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:8:

```
AGACCACGGC TTCCTCGAAT CTTGCGCGAA GCCGCCGGCC TCGGAGGAGG GATTAATCCA      60
```

```
GACCCGCCGG GGGGTGTTTT CACATTTCTT CCTCTTCGTG GCTGCTCCTC CTATTAAAAC        120

CATTTTTGGT CC                                                            132
```

( 2 ) INFORMATION FOR SEQ ID NO:9:

( i ) SEQUENCE CHARACTERISTICS:
        ( A ) LENGTH: 89 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:9:

```
CGCTGAGGGC CTTCCGCGTG CTGCGCCCCC TGCGGCTGGT GTCCGGAGTC CCAAGTCTCC         60

AGGTGGTCCT GAATTCCATC ATCAAGGCC                                          89
```

( 2 ) INFORMATION FOR SEQ ID NO:10:

( i ) SEQUENCE CHARACTERISTICS:
        ( A ) LENGTH: 84 base pairs
        ( B ) TYPE: nucleic acid
        ( C ) STRANDEDNESS: unknown
        ( D ) TOPOLOGY: unknown ( i i ) MOLECULE TYPE: DNA (genomic)

( i x ) FEATURE:
        ( A ) NAME/KEY: CDS
        ( B ) LOCATION: 1..84

( x i ) SEQUENCE DESCRIPTION: SEQ ID NO:10:

```
CAC TAT TTC TGT GAT GCA TGG AAT ACA TTT GAC GCC TTG ATT GTT GTG          48
His Tyr Phe Cys Asp Ala Trp Asn Thr Phe Asp Ala Leu Ile Val Val
 1               5                  10                  15

GGT AGC ATT GTT GAT ATA GCA ATC ACC GAG GTA AAC                          84
Gly Ser Ile Val Asp Ile Ala Ile Thr Glu Val Asn
             20                  25
```

( 2 ) INFORMATION FOR SEQ ID NO:11:

( i ) SEQUENCE CHARACTERISTICS:
        ( A ) LENGTH: 28 amino acids
        ( B ) TYPE: amino acid
        ( D ) TOPOLOGY: linear ( i i ) MOLECULE TYPE: protein ( x i ) SEQUENCE DESCRIPTION: SEQ ID NO:11:

```
His Tyr Phe Cys Asp Ala Trp Asn Thr Phe Asp Ala Leu Ile Val Val
 1               5                  10                  15

Gly Ser Ile Val Asp Ile Ala Ile Thr Glu Val Asn
             20                  25
```

( 2 ) INFORMATION FOR SEQ ID NO:12:

( i ) SEQUENCE CHARACTERISTICS:
        ( A ) LENGTH: 5467 base pairs
        ( B ) TYPE: nucleic acid
        ( C ) STRANDEDNESS: unknown
        ( D ) TOPOLOGY: unknown ( i i ) MOLECULE TYPE: DNA (genomic)

( i x ) FEATURE:
        ( A ) NAME/KEY: CDS
        ( B ) LOCATION: join(144..3164, 3168..3245, 3249..3386, 3390
            . . 3392, 3396..3488, 3495..3539, 3543..3581, 3585
            . . 3587, 3591..3626, 3630..3689, 3693..3737, 3744
            . . 3746, 3750..4823, 4827..4841, 4845..5006, 5010
            . . 5096, 5100..5306, 5310..5366, 5370..5465)

( x i ) SEQUENCE DESCRIPTION: SEQ ID NO:12:

```
GCGGCGGCGG CTGCGGCGGT GGGGCCGGGC GAGGTCCGTG CGGTCCCGGC GGCTCCGTGG        60

CTGCTCCGCT CTGAGCGCCT GCGCGCCCCG CGCCCTCCCT GCCGGGGCCG CTGGGCCGGG       120

GATGCACGCG GGGCCCGGGA GCC ATG GTC CGC TTC GGG GAC GAG CTG GGC          170
                         Met Val Arg Phe Gly Asp Glu Leu Gly
                          1                   5

GGC CGC TAT GGA GGC CCC GGC GGC GGA GAG CGG GCC CGG GGC GGC GGG        218
Gly Arg Tyr Gly Gly Pro Gly Gly Gly Glu Arg Ala Arg Gly Gly Gly
 10              15                  20                  25

GCC GGC GGG GCG GGG GGC CCG GGT CCC GGG GGG CTG CAG CCC GGC CAG        266
Ala Gly Gly Ala Gly Gly Pro Gly Pro Gly Gly Leu Gln Pro Gly Gln
             30                  35                  40

CGG GTC CTC TAC AAG CAA TCG ATG GCC CAG CGC GCG CGG ACC ATG GCG        314
Arg Val Leu Tyr Lys Gln Ser Met Ala Gln Arg Ala Arg Thr Met Ala
         45                  50                  55

CTG TAC AAC CCC ATC CCG GTC AAG CAG AAC TGC TTC ACC GTC AAC CGC        362
Leu Tyr Asn Pro Ile Pro Val Lys Gln Asn Cys Phe Thr Val Asn Arg
             60                  65                  70

TCG CTC TTC GTC TTC AGC GAG GAC AAC GTC GTC CGC AAA TAC GCG AAG        410
Ser Leu Phe Val Phe Ser Glu Asp Asn Val Val Arg Lys Tyr Ala Lys
 75                  80                  85

CGC ATC ACC GAG TGG CCT CCA TTC GAG AAT ATG ATC CTG GCC ACC ATC        458
Arg Ile Thr Glu Trp Pro Pro Phe Glu Asn Met Ile Leu Ala Thr Ile
 90                  95                 100                 105

ATC GCC AAC TGC ATC GTG CTG GCC CTG GAG CAG CAC CTC CCT GAT GGG        506
Ile Ala Asn Cys Ile Val Leu Ala Leu Glu Gln His Leu Pro Asp Gly
                 110                 115                 120

GAC AAA ACG CCC ATG TCC GAG CGG CTG GAC GAC ACG GAG CCC TAT TTC        554
Asp Lys Thr Pro Met Ser Glu Arg Leu Asp Asp Thr Glu Pro Tyr Phe
             125                 130                 135

ATC GGG ATC TTT TGC TTC GAG GCA GGG ATC AAA ATC ATC GCT CTG GGC        602
Ile Gly Ile Phe Cys Phe Glu Ala Gly Ile Lys Ile Ile Ala Leu Gly
             140                 145                 150

TTT GTC TTC CAC AAG GGC TCT TAC CTG CGG AAC GGC TGG AAC GTC ATG        650
Phe Val Phe His Lys Gly Ser Tyr Leu Arg Asn Gly Trp Asn Val Met
 155                 160                 165

GAC TTC GTG GTC GTC CTC ACA GGG ATC CTT GCC ACG GCT GGA ACT GAC        698
Asp Phe Val Val Val Leu Thr Gly Ile Leu Ala Thr Ala Gly Thr Asp
170                  175                 180                 185

TTC GAC CTG CGA ACA CTG AGG GCT GTG CGT GTG CTG AGG CCC CTG AAG        746
Phe Asp Leu Arg Thr Leu Arg Ala Val Arg Val Leu Arg Pro Leu Lys
                 190                 195                 200

CTG GTG TCT GGG ATT CCA AGT TTG CAG GTG GTG CTC AAG TCC ATC ATG        794
Leu Val Ser Gly Ile Pro Ser Leu Gln Val Val Leu Lys Ser Ile Met
             205                 210                 215

AAG GCC ATG GTT CCA CTC CTG CAG ATT GGG CTG CTT CTC TTC TTT GCC        842
Lys Ala Met Val Pro Leu Leu Gln Ile Gly Leu Leu Leu Phe Phe Ala
             220                 225                 230

ATC CTC ATG TTT GCC ATC ATT GGC CTG GAG TTC TAC ATG GGC AAG TTC        890
Ile Leu Met Phe Ala Ile Ile Gly Leu Glu Phe Tyr Met Gly Lys Phe
 235                 240                 245

CAC AAG GCC TGT TTC CCC AAC AGC ACA GAT GCG GAG CCC GTG GGT GAC        938
His Lys Ala Cys Phe Pro Asn Ser Thr Asp Ala Glu Pro Val Gly Asp
250                  255                 260                 265

TTC CCC TGT GGC AAG GAG GCC CCA GCC CGG CTG TGC GAG GGC GAC ACT        986
Phe Pro Cys Gly Lys Glu Ala Pro Ala Arg Leu Cys Glu Gly Asp Thr
                 270                 275                 280

GAG TGC CGG GAG TAC TGG CCA GGA CCC AAC TTT GGC ATC ACC AAC TTT       1034
Glu Cys Arg Glu Tyr Trp Pro Gly Pro Asn Phe Gly Ile Thr Asn Phe
             285                 290                 295
```

-continued

| | | | | | | | | | | | | | | | | |
|---|---|---|---|---|---|---|---|---|---|---|---|---|---|---|---|---|
| GAC | AAT | ATC | CTG | TTT | GCC | ATC | TTG | ACG | GTG | TTC | CAG | TGC | ATC | ACC | ATG | 1082 |
| Asp | Asn | Ile | Leu | Phe | Ala | Ile | Leu | Thr | Val | Phe | Gln | Cys | Ile | Thr | Met | |
| | | 300 | | | | | 305 | | | | | 310 | | | | |
| GAG | GGC | TGG | ACT | GAC | ATC | CTC | TAT | AAT | ACA | AAC | GAT | GCG | GCC | GGC | AAC | 1130 |
| Glu | Gly | Trp | Thr | Asp | Ile | Leu | Tyr | Asn | Thr | Asn | Asp | Ala | Ala | Gly | Asn | |
| | 315 | | | | | 320 | | | | | 325 | | | | | |
| ACC | TGG | AAC | TGG | CTC | TAC | TTC | ATC | CCT | CTC | ATC | ATC | ATC | GGC | TCC | TTC | 1178 |
| Thr | Trp | Asn | Trp | Leu | Tyr | Phe | Ile | Pro | Leu | Ile | Ile | Ile | Gly | Ser | Phe | |
| 330 | | | | | 335 | | | | | 340 | | | | | 345 | |
| TTC | ATG | CTC | AAC | CTG | GTG | CTG | GGC | GTG | CTC | TCG | GGG | GAG | TTT | GCC | AAG | 1226 |
| Phe | Met | Leu | Asn | Leu | Val | Leu | Gly | Val | Leu | Ser | Gly | Glu | Phe | Ala | Lys | |
| | | | | 350 | | | | | 355 | | | | | 360 | | |
| GAG | CGA | GAG | AGG | GTG | GAG | AAC | CGC | CGC | GCC | TTC | CTG | AAC | GTG | CGC | CGG | 1274 |
| Glu | Arg | Glu | Arg | Val | Glu | Asn | Arg | Arg | Ala | Phe | Leu | Asn | Val | Arg | Arg | |
| | | 365 | | | | | 370 | | | | | 375 | | | | |
| CAG | CAG | CAG | ATC | GAG | CGA | GAG | CTC | AAC | GGG | TAC | CTG | GAG | TGG | ATC | TTC | 1322 |
| Gln | Gln | Gln | Ile | Glu | Arg | Glu | Leu | Asn | Gly | Tyr | Leu | Glu | Trp | Ile | Phe | |
| | 380 | | | | | 385 | | | | | 390 | | | | | |
| AAG | GCG | GAG | GAA | GTC | ATG | CTG | GCC | GAG | GAG | GAC | AGG | AAT | GCA | GAG | GAG | 1370 |
| Lys | Ala | Glu | Glu | Val | Met | Leu | Ala | Glu | Glu | Asp | Arg | Asn | Ala | Glu | Glu | |
| 395 | | | | | 400 | | | | | 405 | | | | | | |
| AAG | TCC | CCT | TTG | GAC | GTG | CTG | AAG | AGA | GCG | GCC | ACC | AAG | AAG | AGC | AGA | 1418 |
| Lys | Ser | Pro | Leu | Asp | Val | Leu | Lys | Arg | Ala | Ala | Thr | Lys | Lys | Ser | Arg | |
| 410 | | | | | 415 | | | | | 420 | | | | | 425 | |
| AAT | GAC | CTG | ATC | CAC | GCA | GAG | GAG | GGA | GAG | GAC | CGG | TTT | GCA | GAT | CTC | 1466 |
| Asn | Asp | Leu | Ile | His | Ala | Glu | Glu | Gly | Glu | Asp | Arg | Phe | Ala | Asp | Leu | |
| | | | | 430 | | | | | 435 | | | | | 440 | | |
| TGT | GCT | GTT | GGA | TCC | CCC | TTC | GCC | CGC | GCC | AGC | CTC | AAG | AGC | GGG | AAG | 1514 |
| Cys | Ala | Val | Gly | Ser | Pro | Phe | Ala | Arg | Ala | Ser | Leu | Lys | Ser | Gly | Lys | |
| | | | 445 | | | | | 450 | | | | | 455 | | | |
| ACA | GAG | AGC | TCG | TCA | TAC | TTC | CGG | AGG | AAG | GAG | AAG | ATG | TTC | CGG | TTT | 1562 |
| Thr | Glu | Ser | Ser | Ser | Tyr | Phe | Arg | Arg | Lys | Glu | Lys | Met | Phe | Arg | Phe | |
| | | 460 | | | | | 465 | | | | | 470 | | | | |
| TTT | ATC | CGG | CGC | ATG | GTG | AAG | GCT | CAG | AGC | TTC | TAC | TGG | GTG | GTG | CTG | 1610 |
| Phe | Ile | Arg | Arg | Met | Val | Lys | Ala | Gln | Ser | Phe | Tyr | Trp | Val | Val | Leu | |
| | 475 | | | | | 480 | | | | | 485 | | | | | |
| TGC | GTG | GTG | GCC | CTG | AAC | ACA | CTG | TGT | GTG | GCC | ATG | GTG | CAT | TAC | AAC | 1658 |
| Cys | Val | Val | Ala | Leu | Asn | Thr | Leu | Cys | Val | Ala | Met | Val | His | Tyr | Asn | |
| 490 | | | | | 495 | | | | | 500 | | | | | 505 | |
| CAG | CCG | CGG | CGG | CTT | ACC | ACG | ACC | CTG | TAT | TTT | GCA | GAG | TTT | GTT | TTC | 1706 |
| Gln | Pro | Arg | Arg | Leu | Thr | Thr | Thr | Leu | Tyr | Phe | Ala | Glu | Phe | Val | Phe | |
| | | | | 510 | | | | | 515 | | | | | 520 | | |
| CTG | GGT | CTC | TTC | CTC | ACA | GAG | ATG | TCC | CTG | AAG | ATG | TAT | GGC | CTG | GGG | 1754 |
| Leu | Gly | Leu | Phe | Leu | Thr | Glu | Met | Ser | Leu | Lys | Met | Tyr | Gly | Leu | Gly | |
| | | | 525 | | | | | 530 | | | | | 535 | | | |
| CCC | AGA | AGC | TAC | TTC | CGG | TCC | TCC | TTC | AAC | TGC | TTC | GAC | TTT | GGG | GTC | 1802 |
| Pro | Arg | Ser | Tyr | Phe | Arg | Ser | Ser | Phe | Asn | Cys | Phe | Asp | Phe | Gly | Val | |
| | | 540 | | | | | 545 | | | | | 550 | | | | |
| ATC | GTG | GGG | AGC | GTC | TTT | GAA | GTG | GTC | TGG | GCG | GCC | ATC | AAG | CCG | GGA | 1850 |
| Ile | Val | Gly | Ser | Val | Phe | Glu | Val | Val | Trp | Ala | Ala | Ile | Lys | Pro | Gly | |
| | 555 | | | | | 560 | | | | | 565 | | | | | |
| AGC | TCC | TTT | GGG | ATC | AGT | GTG | CTG | CGG | GCC | CTC | CGC | CTG | CTG | AGG | ATC | 1898 |
| Ser | Ser | Phe | Gly | Ile | Ser | Val | Leu | Arg | Ala | Leu | Arg | Leu | Leu | Arg | Ile | |
| 570 | | | | | 575 | | | | | 580 | | | | | 585 | |
| TTC | AAA | GTC | ACG | AAG | TAC | TGG | AGC | TCC | CTG | CGG | AAC | CTG | GTG | GTG | TCC | 1946 |
| Phe | Lys | Val | Thr | Lys | Tyr | Trp | Ser | Ser | Leu | Arg | Asn | Leu | Val | Val | Ser | |
| | | | | 590 | | | | | 595 | | | | | 600 | | |
| CTG | CTG | AAC | TCC | ATG | AAG | TCC | ATC | ATC | AGC | CTG | CTC | TTC | TTG | CTC | TTC | 1994 |
| Leu | Leu | Asn | Ser | Met | Lys | Ser | Ile | Ile | Ser | Leu | Leu | Phe | Leu | Leu | Phe | |
| | | | 605 | | | | | 610 | | | | | 615 | | | |
| CTG | TTC | ATT | GTG | GTC | TTC | GCC | CTG | CTG | GGG | ATG | CAG | CTG | TTT | GGG | GGA | 2042 |

```
          Leu  Phe  Ile  Val  Val  Phe  Ala  Leu  Leu  Gly  Met  Gln  Leu  Phe  Gly  Gly
                    620                      625                      630

CAG  TTC  AAC  TTC  CAG  GAT  GAG  ACT  CCC  ACA  ACC  AAC  TTC  GAC  ACC  TTC            2090
Gln  Phe  Asn  Phe  Gln  Asp  Glu  Thr  Pro  Thr  Thr  Asn  Phe  Asp  Thr  Phe
          635                      640                      645

CCT  GCC  GCC  ATC  CTC  ACT  GTC  TTC  CAG  ATC  CTG  ACG  GGA  GAG  GAC  TGG            2138
Pro  Ala  Ala  Ile  Leu  Thr  Val  Phe  Gln  Ile  Leu  Thr  Gly  Glu  Asp  Trp
650                      655                      660                      665

AAT  GCA  GTG  ATG  TAT  CAC  GGG  ATC  GAA  TCG  CAA  GGC  GGC  GTC  AGC  AAA            2186
Asn  Ala  Val  Met  Tyr  His  Gly  Ile  Glu  Ser  Gln  Gly  Gly  Val  Ser  Lys
                    670                      675                      680

GGC  ATG  TTC  TCG  TCC  TTT  TAC  TTC  ATT  GTC  CTG  ACA  CTG  TTC  GGA  AAC            2234
Gly  Met  Phe  Ser  Ser  Phe  Tyr  Phe  Ile  Val  Leu  Thr  Leu  Phe  Gly  Asn
               685                      690                      695

TAC  ACT  CTG  CTG  AAT  GTC  TTT  CTG  GCC  ATC  GCT  GTG  GAC  AAC  CTG  GCC            2282
Tyr  Thr  Leu  Leu  Asn  Val  Phe  Leu  Ala  Ile  Ala  Val  Asp  Asn  Leu  Ala
          700                      705                      710

AAC  GCC  CAA  GAG  CTG  ACC  AAG  GAT  GAA  GAG  GAG  ATG  GAA  GAA  GCA  GCC            2330
Asn  Ala  Gln  Glu  Leu  Thr  Lys  Asp  Glu  Glu  Glu  Met  Glu  Glu  Ala  Ala
     715                      720                      725

AAT  CAG  AAG  CTT  GCT  CTG  CAA  AAG  GCC  AAA  GAA  GTG  GCT  GAA  GTC  AGC            2378
Asn  Gln  Lys  Leu  Ala  Leu  Gln  Lys  Ala  Lys  Glu  Val  Ala  Glu  Val  Ser
730                      735                      740                      745

CCC  ATG  TCT  GCC  GCG  AAC  ATC  TCC  ATC  GCC  GCC  AGC  GAG  CAG  AAC  TCG            2426
Pro  Met  Ser  Ala  Ala  Asn  Ile  Ser  Ile  Ala  Ala  Ser  Glu  Gln  Asn  Ser
                    750                      755                      760

GCC  AAG  GCG  CGC  TCG  GTG  TGG  GAG  CAG  CGG  GCC  AGC  CAG  CTA  CGG  CTG            2474
Ala  Lys  Ala  Arg  Ser  Val  Trp  Glu  Gln  Arg  Ala  Ser  Gln  Leu  Arg  Leu
               765                      770                      775

CAG  AAC  CTG  CGG  GCC  AGC  TGC  GAG  GCG  CTG  TAC  AGC  GAG  ATG  GAC  CCC            2522
Gln  Asn  Leu  Arg  Ala  Ser  Cys  Glu  Ala  Leu  Tyr  Ser  Glu  Met  Asp  Pro
          780                      785                      790

GAG  GAG  CGG  CTG  CGC  TTC  GCC  ACT  ACG  CGC  CAC  CTG  CGG  CCC  GAC  ATG            2570
Glu  Glu  Arg  Leu  Arg  Phe  Ala  Thr  Thr  Arg  His  Leu  Arg  Pro  Asp  Met
     795                      800                      805

AAG  ACG  CAC  CTG  GAC  CGG  CCG  CTG  GTG  GTG  GAG  CTG  GGC  CGC  GAC  GGC            2618
Lys  Thr  His  Leu  Asp  Arg  Pro  Leu  Val  Val  Glu  Leu  Gly  Arg  Asp  Gly
810                      815                      820                      825

GCG  CGG  GGG  CCC  GTG  GGA  GGC  AAA  GCC  CGA  CCT  GAG  GCT  GCG  GAG  GCC            2666
Ala  Arg  Gly  Pro  Val  Gly  Gly  Lys  Ala  Arg  Pro  Glu  Ala  Ala  Glu  Ala
                    830                      835                      840

CCC  GAG  GGC  GTC  GAC  CCT  CCG  CGC  AGG  CAC  CAC  CGG  CAC  CGC  GAC  AAG            2714
Pro  Glu  Gly  Val  Asp  Pro  Pro  Arg  Arg  His  His  Arg  His  Arg  Asp  Lys
               845                      850                      855

GAC  AAG  ACC  CCC  GCG  GCG  GGG  GAC  CAG  GAC  CGA  GCA  GAG  GCC  CCG  AAG            2762
Asp  Lys  Thr  Pro  Ala  Ala  Gly  Asp  Gln  Asp  Arg  Ala  Glu  Ala  Pro  Lys
          860                      865                      870

GCG  GAG  AGC  GGG  GAG  CCC  GGT  GCC  CGG  GAG  GAG  CGG  CCG  CGC  GCC  GAC            2810
Ala  Glu  Ser  Gly  Glu  Pro  Gly  Ala  Arg  Glu  Glu  Arg  Pro  Arg  Ala  Asp
     875                      880                      885

CGC  AGC  CAC  AGC  AAG  GAG  GCC  GCG  GGG  CCC  CCG  GAG  GCG  CGG  ACG  AGC            2858
Arg  Ser  His  Ser  Lys  Glu  Ala  Ala  Gly  Pro  Pro  Glu  Ala  Arg  Thr  Ser
890                      895                      900                      905

GCG  GCC  GAG  GCC  CAG  GCC  CCG  AGG  GCG  GCC  GGC  GGC  ACC  ACC  GGC  GCG            2906
Ala  Ala  Glu  Ala  Gln  Ala  Pro  Arg  Ala  Ala  Gly  Gly  Thr  Thr  Gly  Ala
                    910                      915                      920

GCT  CCC  CGG  AGG  AGG  CGG  CCG  AGC  GGG  AGC  CCC  GAC  GCC  ACC  GCG  CGC            2954
Ala  Pro  Arg  Arg  Arg  Arg  Pro  Ser  Gly  Ser  Pro  Asp  Ala  Thr  Ala  Arg
               925                      930                      935

ACC  GGC  ACC  AGG  ATC  CGA  GCA  AGG  AGT  GCG  CCG  GCG  CCA  AGG  GCG  AGC            3002
Thr  Gly  Thr  Arg  Ile  Arg  Ala  Arg  Ser  Ala  Pro  Ala  Pro  Arg  Ala  Ser
          940                      945                      950
```

| | |
|---|---|
| GGC GCG CGC GGC ACC GCG GCG GCC CCC GAG CGG GGC CCC GGG AGG CGG<br>Gly Ala Arg Gly Thr Ala Ala Ala Pro Glu Arg Gly Pro Gly Arg Arg<br>955                                  960                          965 | 3050 |
| AGA GCG GGG AGG AGC CGG CGC GGC GGC ACC GGG CCC GGC ACA AGG CGC<br>Arg Ala Gly Arg Ser Arg Arg Gly Gly Thr Gly Pro Gly Thr Arg Arg<br>970                         975                       980                  985 | 3098 |
| AGC CTG CTC ACG AGG CTG TGG AGA AGG AGA CCA CGG AGA AGG AGG CCA<br>Ser Leu Leu Thr Arg Leu Trp Arg Arg Arg Pro Arg Arg Arg Arg Pro<br>               990                         995                          1000 | 3146 |
| CGG AGA AGG AGG CTG AGA TAG TGG AAG CCG ACA AGG AAA AGG AGC TCC<br>Arg Arg Arg Arg Leu Arg       Trp Lys Pro Thr Arg Lys Arg Ser Ser<br>             1005                      1010                       1015 | 3194 |
| GGA ACC ACC AGC CCC GGG AGC CAC ACT GTG ACC TGG AGA CCA GTG GGA<br>Gly Thr Thr Ser Pro Gly Ser His Thr Val Thr Trp Arg Pro Val Gly<br>1020                              1025                        1030 | 3242 |
| CTG TGA CTG TGG GTC CAT GCA CAC ACT GCC CAG CAA CCT GTC TCC AGA<br>Leu       Leu Trp Val His Ala His Thr Ala Gln Gln Pro Val Ser Arg<br>              1035                         1040                        1045 | 3290 |
| AGG TGG AGG AAC AGC CAG AGG ATG CAG ACA ATC AGC GGA ACG TCA CTC<br>Arg Trp Arg Asn Ser Gln Arg Met Gln Thr Ile Ser Gly Thr Ser Leu<br>       1050                           1055                       1060 | 3338 |
| GCA TGG GCA GTC AGC CCC CAG ACC CGA ACA CTA TTG TAC ATA TCC CAG<br>Ala Trp Ala Val Ser Pro Gln Thr Arg Thr Leu Leu Tyr Ile Ser Gln<br>1065                              1070                        1075 | 3386 |
| TGA TGC TGA CGG GCC CTC TTG GGG AAG CCA CGG TCG TTC CCA GTG GTA<br>Cys       Arg Ala Leu Leu Gly Lys Pro Arg Ser Phe Pro Val Val<br>1080                              1085                        1090 | 3434 |
| ACG TGG ACC TGG AAA GCC AAG CAG AGG GGA AGA AGG AGG TGG AAG CGG<br>Thr Trp Thr Trp Lys Ala Lys Gln Arg Gly Arg Arg Arg Trp Lys Arg<br>1095                              1100                        1105 | 3482 |
| ATG ACG TGATGA GGA GCG GCC CCC GGC CTA TCG TCC CAT ACA GCT CCA<br>Met Thr              Gly Ala Ala Pro Gly Leu Ser Ser His Thr Ala Pro<br>1110                              1115                        1120 | 3530 |
| TGT TCT GTT TAA GCC CCA CCA ACC TGC TCC GCC GCT TCT GCC ACT ACA<br>Cys Ser Val       Ala Pro Pro Thr Cys Ser Ala Ala Ser Ala Thr Thr<br>1125                              1130                        1135 | 3578 |
| TCG TGA CCA TGA GGT ACT TCG AGG TGG TCA TTC TCG TGG TCA TCG CCT<br>Ser       Pro       Gly Thr Ser Arg Trp Ser Phe Ser Trp Ser Ser Pro<br>              1140                         1145                        1150 | 3626 |
| TGA GCA GCA TCG CCC TGG CTG CTG AGG ACC CAG TGC GCA CAG ACT CGC<br>       Ala Ala Ser Pro Trp Leu Leu Arg Thr Gln Cys Ala Gln Thr Arg<br>              1155                         1160                        1165 | 3674 |
| CCA GGA ACA ACG CTC TGA AAT ACC TGG ATT ACA TTT TCA CTG GTG TCT<br>Pro Gly Thr Thr Leu       Asn Thr Trp Ile Thr Phe Ser Leu Val Ser<br>             1170                          1175                       1180 | 3722 |
| TTA CCT TTG AGA TGG TGATAA AGA TGA TCG ACT TGG GAC TGC TGC TTC<br>Leu Pro Leu Arg Trp           Arg       Ser Thr Trp Asp Cys Cys Phe<br>              1185                                        1190                       1195 | 3770 |
| ACC CTG GAG CCT ATT TCC GGG ACT TGT GGA ACA TTC TGG ACT TCA TTG<br>Thr Leu Glu Pro Ile Ser Gly Thr Cys Gly Thr Phe Trp Thr Ser Leu<br>                             1200                        1205                        1210 | 3818 |
| TGG TCA GTG GCG CCC TGG TGG CGT TTG CTT TCT CGA TCC AAA GGG AAA<br>Trp Ser Val Ala Pro Trp Trp Arg Leu Leu Ser Arg Ser Lys Gly Lys<br>                     1215                                1220                        1225 | 3866 |
| GAC ATC AAT ACC ATC AAG TCT CTG AGA GTC CTT CGT GTC CTG CGG CCC<br>Asp Ile Asn Thr Ile Lys Ser Leu Arg Val Leu Arg Val Leu Arg Pro<br>       1230                           1235                       1240 | 3914 |
| CTC AAG ACC ATC AAA CGG CTG CCC AAG CTC AAG GCT GTG TTT GAC TGT<br>Leu Lys Thr Ile Lys Arg Leu Pro Lys Leu Lys Ala Val Phe Asp Cys<br>1245                              1250                        1255 | 3962 |
| GTG GTG AAC TCC CTG AAG AAT GTC CTC AAC ATC TTG ATT GTC TAC ATG | 4010 |

|  |  |
|---|---|
| Val Val Asn Ser Leu Lys Asn Val Leu Asn Ile Leu Ile Val Tyr Met<br>1260                    1265                      1270                     1275 |  |
| CTC TTC ATG TTC ATA TTT GCC GTC ATT GCG GTG CAG CTC TTC AAA GGG<br>Leu Phe Met Phe Ile Phe Ala Val Ile Ala Val Gln Leu Phe Lys Gly<br>                      1280                     1285                     1290 | 4058 |
| AAG TTT TTC TAC TGC ACA GAT GAA TCC AAG GAG CTG GAG AGG GAC TGC<br>Lys Phe Phe Tyr Cys Thr Asp Glu Ser Lys Glu Leu Glu Arg Asp Cys<br>               1295                     1300                     1305 | 4106 |
| AGG GGT CAG TAT TTG GAT TAT GAG AAG GAG GAA GTG GAA GCT CAG CCC<br>Arg Gly Gln Tyr Leu Asp Tyr Glu Lys Glu Glu Val Glu Ala Gln Pro<br>                   1310                    1315                    1320 | 4154 |
| AGG CAG TGG AAG AAA TAC GAC TTT CAC TAC GAC AAT GTG CTC TGG GCT<br>Arg Gln Trp Lys Lys Tyr Asp Phe His Tyr Asp Asn Val Leu Trp Ala<br>       1325                     1330                    1335 | 4202 |
| CTG CTG ACG CTG TTC ACA GTG TCC ACG GGA GAA GGC TGG CCC ATG GTG<br>Leu Leu Thr Leu Phe Thr Val Ser Thr Gly Glu Gly Trp Pro Met Val<br>1340                    1345                    1350                    1355 | 4250 |
| CTG AAA CAC TCC GTG GAT GCC ACC TAT GAG GAG CAG GGT CCA AGC CCT<br>Leu Lys His Ser Val Asp Ala Thr Tyr Glu Glu Gln Gly Pro Ser Pro<br>                 1360                    1365                    1370 | 4298 |
| GGG TAC CGC ATG GAG CTG TCC ATC TTC TAC GTG GTC TAC TTT GTG GTC<br>Gly Tyr Arg Met Glu Leu Ser Ile Phe Tyr Val Val Tyr Phe Val Val<br>             1375                     1380                    1385 | 4346 |
| TTT CCC TTC TTC TTC GTC AAC ATC TTT GTG GCT TTG ATC ATC ATC ACC<br>Phe Pro Phe Phe Phe Val Asn Ile Phe Val Ala Leu Ile Ile Ile Thr<br>                 1390                    1395                    1400 | 4394 |
| TTC CAG GAG CAG GGG GAC AAG GTG ATG TCT GAA TGC AGC CTG GAG AAG<br>Phe Gln Glu Gln Gly Asp Lys Val Met Ser Glu Cys Ser Leu Glu Lys<br>       1405                     1410                    1415 | 4442 |
| AAC GAG AGG GCT TGC ATT GAC TTC GCC ATC AGC GCC AAA CCC CTG ACA<br>Asn Glu Arg Ala Cys Ile Asp Phe Ala Ile Ser Ala Lys Pro Leu Thr<br>1420                    1425                    1430                    1435 | 4490 |
| CGG TAC ATG CCC CAA AAC CGG CAG TCG TTC CAG TAT AAG ACG TGG ACA<br>Arg Tyr Met Pro Gln Asn Arg Gln Ser Phe Gln Tyr Lys Thr Trp Thr<br>                 1440                    1445                    1450 | 4538 |
| TTT GTG GTC TCC CCG CCC TTT GAA TAC TTC ATC ATG GCC ATG ATA GCC<br>Phe Val Val Ser Pro Pro Phe Glu Tyr Phe Ile Met Ala Met Ile Ala<br>             1455                     1460                    1465 | 4586 |
| CTC AAC ACT GTG GTG CTG ATG ATG AAG TTC TAT GAT GCA CCC TAT GAG<br>Leu Asn Thr Val Val Leu Met Met Lys Phe Tyr Asp Ala Pro Tyr Glu<br>               1470                    1475                    1480 | 4634 |
| TAC GAG CTG ATG CTG AAA TGC CTG AAC ATC GTG TTC ACA TCC ATG TTC<br>Tyr Glu Leu Met Leu Lys Cys Leu Asn Ile Val Phe Thr Ser Met Phe<br>1485                    1490                    1495 | 4682 |
| TCC ATG GAA TGC GTG CTG AAG ATC ATC GCC TTT GGG GTG CTG AAC TAT<br>Ser Met Glu Cys Val Leu Lys Ile Ile Ala Phe Gly Val Leu Asn Tyr<br>1500                    1505                    1510                    1515 | 4730 |
| TTC AGA GAT GCC TGG AAT TTT GTC TTT GAC TTT GTC ACT GTG TTG GGA<br>Phe Arg Asp Ala Trp Asn Phe Val Phe Asp Phe Val Thr Val Leu Gly<br>             1520                     1525                    1530 | 4778 |
| AGT ATT ACT GAT ATT TTA GTA ACA GAG ATT GCG ATT TGC CCA AGA<br>Ser Ile Thr Asp Ile Leu Val Thr Glu Ile Ala Ile Cys Pro Arg<br>             1535                     1540                    1545 | 4823 |
| TGA AGG TTT CAG CAG TTT TAA TGC TAC AGC ACA CCA GGA GTT ACC GTC<br>    Arg Phe Gln Gln Phe     Cys Tyr Ser Thr Pro Gly Val Thr Val<br>                   1550                           1555                    1560 | 4871 |
| ACC TCA CTT ACC ACC CAC CAA CAG AGG AGA ATC TGT CCA GTG AGC CAC<br>Thr Ser Leu Thr Thr His Gln Gln Arg Arg Ile Cys Pro Val Ser His<br>                 1565                     1570                    1575 | 4919 |
| TCC CCA AGG TCT CCA TCC TTA GAG TCG GCT TCC AAG GAA CCA CCC CTG<br>Ser Pro Arg Ser Pro Ser Leu Glu Ser Ala Ser Lys Glu Pro Pro Leu<br>             1580                     1585                    1590 | 4967 |

```
GTG TCA CCT GTC TTT GGA TCA GAA CGT GTG ATC CAA ATG TGA TTT ACT        5015
Val Ser Pro Val Phe Gly Ser Glu Arg Val Ile Gln Met     Phe Thr
        1595                1600                1605

GGA ATC ACA GTT TCC AGG AAT AGT TGG AAA CGA ACA ATT TCA TCA ACC        5063
Gly Ile Thr Val Ser Arg Asn Ser Trp Lys Arg Thr Ile Ser Ser Thr
        1610                1615                1620

TCA GCT TCC TCC GCC TCT TTC GAG CTG CGC GGC TGA TCA AGC TGC TCC        5111
Ser Ala Ser Ser Ala Ser Phe Glu Leu Arg Gly     Ser Ser Cys Ser
        1625                1630                1635

GCC AGG GCT ACA CCA TCC GCA TCC TGC TGT GGA CCT TTG TCC AGT CCT        5159
Ala Arg Ala Thr Pro Ser Ala Ser Cys Cys Gly Pro Leu Ser Ser Pro
        1640                1645                1650

TCA AGG CCC TGC CCT ACG TGT GTC TGC TCA TTG CCA TGC TGT TCT TCA        5207
Ser Arg Pro Cys Pro Thr Cys Val Cys Ser Leu Pro Cys Cys Ser Ser
1655                1660                1665                1670

TCT ACG CCA TCA TCG GCA TGC AGG TGT TTG GGA ATA TTG CCC TGG ATG        5255
Ser Thr Pro Ser Ser Ala Cys Arg Cys Leu Gly Ile Leu Pro Trp Met
        1675                1680                1685

ATG ACA CCA GCA TCA ACC GCC ACA ACA ACT TCC GGA CGT TTT TGC AAG        5303
Met Thr Pro Ala Ser Thr Ala Thr Thr Thr Ser Gly Arg Phe Cys Lys
        1690                1695                1700

CCC TGA TGC TGC TGT TCA GGA GCG CCA CGG GGG AGG CCT GGC ACG AGA        5351
Pro     Cys Cys Cys Ser Gly Ala Pro Arg Gly Arg Pro Gly Thr Arg
        1705                1710                1715

TCA TGC TGT CCT GCC TGA GCA ACC AGG CCT GTG ATG AGC AGG CCA ATG        5399
Ser Cys Cys Pro Ala     Ala Thr Arg Pro Val Met Ser Arg Pro Met
        1720                1725                1730

CCA CCG AGT GTG GAA GTG ACT TTG CCT ACT TCT ACT TCG TCT CCT TCA        5447
Pro Pro Ser Val Glu Val Thr Leu Pro Thr Ser Thr Ser Ser Pro Ser
        1735                1740                1745

TCG CTC GAG TGT ACG TAC CG                                             5467
Ser Leu Glu Cys Thr Tyr
        1750
```

( 2 ) INFORMATION FOR SEQ ID NO:13:

( i ) SEQUENCE CHARACTERISTICS:
        ( A ) LENGTH: 1754 amino acids
        ( B ) TYPE: amino acid
        ( D ) TOPOLOGY: linear ( i i ) MOLECULE TYPE: protein ( x i ) SEQUENCE DESCRIPTION: SEQ ID NO:13:

```
Met Val Arg Phe Gly Asp Glu Leu Gly Gly Arg Tyr Gly Gly Pro Gly
 1           5              10              15

Gly Gly Glu Arg Ala Arg Gly Gly Ala Gly Gly Ala Gly Gly Pro
        20              25              30

Gly Pro Gly Gly Leu Gln Pro Gly Gln Arg Val Leu Tyr Lys Gln Ser
        35              40              45

Met Ala Gln Arg Ala Arg Thr Met Ala Leu Tyr Asn Pro Ile Pro Val
        50              55              60

Lys Gln Asn Cys Phe Thr Val Asn Arg Ser Leu Phe Val Phe Ser Glu
 65              70              75              80

Asp Asn Val Val Arg Lys Tyr Ala Lys Arg Ile Thr Glu Trp Pro Pro
                85              90              95

Phe Glu Asn Met Ile Leu Ala Thr Ile Ile Ala Asn Cys Ile Val Leu
                100             105             110

Ala Leu Glu Gln His Leu Pro Asp Gly Asp Lys Thr Pro Met Ser Glu
        115             120             125

Arg Leu Asp Asp Thr Glu Pro Tyr Phe Ile Gly Ile Phe Cys Phe Glu
```

-continued

```
             130                      135                      140
Ala  Gly  Ile  Lys  Ile  Ile  Ala  Leu  Gly  Phe  Val  Phe  His  Lys  Gly  Ser
145                      150                      155                      160

Tyr  Leu  Arg  Asn  Gly  Trp  Asn  Val  Met  Asp  Phe  Val  Val  Val  Leu  Thr
                    165                      170                      175

Gly  Ile  Leu  Ala  Thr  Ala  Gly  Thr  Asp  Phe  Asp  Leu  Arg  Thr  Leu  Arg
                    180                      185                      190

Ala  Val  Arg  Val  Leu  Arg  Pro  Leu  Lys  Leu  Val  Ser  Gly  Ile  Pro  Ser
               195                      200                      205

Leu  Gln  Val  Val  Leu  Lys  Ser  Ile  Met  Lys  Ala  Met  Val  Pro  Leu  Leu
          210                      215                      220

Gln  Ile  Gly  Leu  Leu  Leu  Phe  Phe  Ala  Ile  Leu  Met  Phe  Ala  Ile  Ile
225                      230                      235                      240

Gly  Leu  Glu  Phe  Tyr  Met  Gly  Lys  Phe  His  Lys  Ala  Cys  Phe  Pro  Asn
                    245                      250                      255

Ser  Thr  Asp  Ala  Glu  Pro  Val  Gly  Asp  Phe  Pro  Cys  Gly  Lys  Glu  Ala
                    260                      265                      270

Pro  Ala  Arg  Leu  Cys  Glu  Gly  Asp  Thr  Glu  Cys  Arg  Glu  Tyr  Trp  Pro
               275                      280                      285

Gly  Pro  Asn  Phe  Gly  Ile  Thr  Asn  Phe  Asp  Asn  Ile  Leu  Phe  Ala  Ile
          290                      295                      300

Leu  Thr  Val  Phe  Gln  Cys  Ile  Thr  Met  Glu  Gly  Trp  Thr  Asp  Ile  Leu
305                      310                      315                      320

Tyr  Asn  Thr  Asn  Asp  Ala  Ala  Gly  Asn  Thr  Trp  Asn  Trp  Leu  Tyr  Phe
                    325                      330                      335

Ile  Pro  Leu  Ile  Ile  Ile  Gly  Ser  Phe  Phe  Met  Leu  Asn  Leu  Val  Leu
                    340                      345                      350

Gly  Val  Leu  Ser  Gly  Glu  Phe  Ala  Lys  Glu  Arg  Glu  Arg  Val  Glu  Asn
               355                      360                      365

Arg  Arg  Ala  Phe  Leu  Asn  Val  Arg  Arg  Gln  Gln  Gln  Ile  Glu  Arg  Glu
          370                      375                      380

Leu  Asn  Gly  Tyr  Leu  Glu  Trp  Ile  Phe  Lys  Ala  Glu  Glu  Val  Met  Leu
385                      390                      395                      400

Ala  Glu  Glu  Asp  Arg  Asn  Ala  Glu  Glu  Lys  Ser  Pro  Leu  Asp  Val  Leu
                    405                      410                      415

Lys  Arg  Ala  Ala  Thr  Lys  Lys  Ser  Arg  Asn  Asp  Leu  Ile  His  Ala  Glu
                    420                      425                      430

Glu  Gly  Glu  Asp  Arg  Phe  Ala  Asp  Leu  Cys  Ala  Val  Gly  Ser  Pro  Phe
               435                      440                      445

Ala  Arg  Ala  Ser  Leu  Lys  Ser  Gly  Lys  Thr  Glu  Ser  Ser  Ser  Tyr  Phe
          450                      455                      460

Arg  Arg  Lys  Glu  Lys  Met  Phe  Arg  Phe  Phe  Ile  Arg  Arg  Met  Val  Lys
465                      470                      475                      480

Ala  Gln  Ser  Phe  Tyr  Trp  Val  Val  Leu  Cys  Val  Val  Ala  Leu  Asn  Thr
                    485                      490                      495

Leu  Cys  Val  Ala  Met  Val  His  Tyr  Asn  Gln  Pro  Arg  Arg  Leu  Thr  Thr
                    500                      505                      510

Thr  Leu  Tyr  Phe  Ala  Glu  Phe  Val  Phe  Leu  Gly  Leu  Phe  Leu  Thr  Glu
               515                      520                      525

Met  Ser  Leu  Lys  Met  Tyr  Gly  Leu  Gly  Pro  Arg  Ser  Tyr  Phe  Arg  Ser
          530                      535                      540

Ser  Phe  Asn  Cys  Phe  Asp  Phe  Gly  Val  Ile  Val  Gly  Ser  Val  Phe  Glu
545                      550                      555                      560

Val  Val  Trp  Ala  Ala  Ile  Lys  Pro  Gly  Ser  Ser  Phe  Gly  Ile  Ser  Val
                    565                      570                      575
```

-continued

| Leu | Arg | Ala | Leu | Arg | Leu | Leu | Arg | Ile | Phe | Lys | Val | Thr | Lys | Tyr | Trp |
|  |  | 580 |  |  |  |  | 585 |  |  |  |  | 590 |  |  |  |

| Ser | Ser | Leu | Arg | Asn | Leu | Val | Val | Ser | Leu | Leu | Asn | Ser | Met | Lys | Ser |
|  |  | 595 |  |  |  |  | 600 |  |  |  |  | 605 |  |  |  |

| Ile | Ile | Ser | Leu | Leu | Phe | Leu | Leu | Phe | Leu | Phe | Ile | Val | Val | Phe | Ala |
| 610 |  |  |  |  |  | 615 |  |  |  |  | 620 |  |  |  |  |

| Leu | Leu | Gly | Met | Gln | Leu | Phe | Gly | Gly | Gln | Phe | Asn | Phe | Gln | Asp | Glu |
| 625 |  |  |  |  | 630 |  |  |  |  | 635 |  |  |  |  | 640 |

| Thr | Pro | Thr | Thr | Asn | Phe | Asp | Thr | Phe | Pro | Ala | Ala | Ile | Leu | Thr | Val |
|  |  |  |  | 645 |  |  |  |  | 650 |  |  |  |  | 655 |  |

| Phe | Gln | Ile | Leu | Thr | Gly | Glu | Asp | Trp | Asn | Ala | Val | Met | Tyr | His | Gly |
|  |  |  | 660 |  |  |  |  | 665 |  |  |  |  | 670 |  |  |

| Ile | Glu | Ser | Gln | Gly | Gly | Val | Ser | Lys | Gly | Met | Phe | Ser | Ser | Phe | Tyr |
|  |  | 675 |  |  |  |  | 680 |  |  |  |  | 685 |  |  |  |

| Phe | Ile | Val | Leu | Thr | Leu | Phe | Gly | Asn | Tyr | Thr | Leu | Leu | Asn | Val | Phe |
|  | 690 |  |  |  |  | 695 |  |  |  |  | 700 |  |  |  |  |

| Leu | Ala | Ile | Ala | Val | Asp | Asn | Leu | Ala | Asn | Ala | Gln | Glu | Leu | Thr | Lys |
| 705 |  |  |  |  | 710 |  |  |  |  | 715 |  |  |  |  | 720 |

| Asp | Glu | Glu | Glu | Met | Glu | Glu | Ala | Ala | Asn | Gln | Lys | Leu | Ala | Leu | Gln |
|  |  |  |  | 725 |  |  |  |  | 730 |  |  |  |  | 735 |  |

| Lys | Ala | Lys | Glu | Val | Ala | Glu | Val | Ser | Pro | Met | Ser | Ala | Ala | Asn | Ile |
|  |  |  | 740 |  |  |  |  | 745 |  |  |  |  | 750 |  |  |

| Ser | Ile | Ala | Ala | Ser | Glu | Gln | Asn | Ser | Ala | Lys | Ala | Arg | Ser | Val | Trp |
|  |  | 755 |  |  |  |  | 760 |  |  |  |  | 765 |  |  |  |

| Glu | Gln | Arg | Ala | Ser | Gln | Leu | Arg | Leu | Gln | Asn | Leu | Arg | Ala | Ser | Cys |
|  | 770 |  |  |  |  | 775 |  |  |  |  | 780 |  |  |  |  |

| Glu | Ala | Leu | Tyr | Ser | Glu | Met | Asp | Pro | Glu | Glu | Arg | Leu | Arg | Phe | Ala |
| 785 |  |  |  |  | 790 |  |  |  |  | 795 |  |  |  |  | 800 |

| Thr | Thr | Arg | His | Leu | Arg | Pro | Asp | Met | Lys | Thr | His | Leu | Asp | Arg | Pro |
|  |  |  |  | 805 |  |  |  |  | 810 |  |  |  |  | 815 |  |

| Leu | Val | Val | Glu | Leu | Gly | Arg | Asp | Gly | Ala | Arg | Gly | Pro | Val | Gly | Gly |
|  |  |  | 820 |  |  |  |  | 825 |  |  |  |  | 830 |  |  |

| Lys | Ala | Arg | Pro | Glu | Ala | Ala | Glu | Ala | Pro | Glu | Gly | Val | Asp | Pro | Pro |
|  |  | 835 |  |  |  |  | 840 |  |  |  |  | 845 |  |  |  |

| Arg | Arg | His | His | Arg | His | Arg | Asp | Lys | Asp | Lys | Thr | Pro | Ala | Ala | Gly |
|  | 850 |  |  |  |  | 855 |  |  |  |  | 860 |  |  |  |  |

| Asp | Gln | Asp | Arg | Ala | Glu | Ala | Pro | Lys | Ala | Glu | Ser | Gly | Glu | Pro | Gly |
| 865 |  |  |  |  | 870 |  |  |  |  | 875 |  |  |  |  | 880 |

| Ala | Arg | Glu | Glu | Arg | Pro | Arg | Ala | Asp | Arg | Ser | His | Ser | Lys | Glu | Ala |
|  |  |  |  | 885 |  |  |  |  | 890 |  |  |  |  | 895 |  |

| Ala | Gly | Pro | Pro | Glu | Ala | Arg | Thr | Ser | Ala | Ala | Glu | Ala | Gln | Ala | Pro |
|  |  |  | 900 |  |  |  |  | 905 |  |  |  |  | 910 |  |  |

| Arg | Ala | Ala | Gly | Gly | Thr | Thr | Gly | Ala | Ala | Pro | Arg | Arg | Arg | Arg | Pro |
|  |  | 915 |  |  |  |  | 920 |  |  |  |  | 925 |  |  |  |

| Ser | Gly | Ser | Pro | Asp | Ala | Thr | Ala | Arg | Thr | Gly | Thr | Arg | Ile | Arg | Ala |
|  | 930 |  |  |  |  | 935 |  |  |  |  | 940 |  |  |  |  |

| Arg | Ser | Ala | Pro | Ala | Pro | Arg | Ala | Ser | Gly | Ala | Arg | Gly | Thr | Ala | Ala |
| 945 |  |  |  |  | 950 |  |  |  |  | 955 |  |  |  |  | 960 |

| Ala | Pro | Glu | Arg | Gly | Pro | Gly | Arg | Arg | Arg | Ala | Gly | Arg | Ser | Arg | Arg |
|  |  |  |  | 965 |  |  |  |  | 970 |  |  |  |  | 975 |  |

| Gly | Gly | Thr | Gly | Pro | Gly | Thr | Arg | Arg | Ser | Leu | Leu | Thr | Arg | Leu | Trp |
|  |  |  | 980 |  |  |  |  | 985 |  |  |  |  | 990 |  |  |

| Arg | Arg | Arg | Pro | Arg | Arg | Arg | Arg | Pro | Arg | Arg | Arg | Arg | Leu | Arg | Trp |
|  |  | 995 |  |  |  |  | 1000 |  |  |  |  | 1005 |  |  |  |

| | | | | | | | | | | | | | | |
|---|---|---|---|---|---|---|---|---|---|---|---|---|---|---|
| Lys | Pro | Thr | Arg | Lys | Arg | Ser | Ser | Gly | Thr | Thr | Ser | Pro | Gly | Ser | His |
| | | 1010 | | | | 1015 | | | | 1020 | | | | |
| Thr | Val | Thr | Trp | Arg | Pro | Val | Gly | Leu | Leu | Trp | Val | His | Ala | His | Thr |
| 1025 | | | | | 1030 | | | | | 1035 | | | | | 1040 |
| Ala | Gln | Gln | Pro | Val | Ser | Arg | Arg | Trp | Arg | Asn | Ser | Gln | Arg | Met | Gln |
| | | | | 1045 | | | | | 1050 | | | | | 1055 | |
| Thr | Ile | Ser | Gly | Thr | Ser | Leu | Ala | Trp | Ala | Val | Ser | Pro | Gln | Thr | Arg |
| | | | 1060 | | | | | 1065 | | | | | 1070 | | |
| Thr | Leu | Leu | Tyr | Ile | Ser | Gln | Cys | Arg | Ala | Leu | Leu | Gly | Lys | Pro | Arg |
| | | 1075 | | | | | 1080 | | | | | 1085 | | | |
| Ser | Phe | Pro | Val | Val | Thr | Trp | Thr | Trp | Lys | Ala | Lys | Gln | Arg | Gly | Arg |
| | | 1090 | | | | | 1095 | | | | | 1100 | | | |
| Arg | Arg | Trp | Lys | Arg | Met | Thr | Gly | Ala | Ala | Pro | Gly | Leu | Ser | Ser | His |
| 1105 | | | | | 1110 | | | | | 1115 | | | | | 1120 |
| Thr | Ala | Pro | Cys | Ser | Val | Ala | Pro | Pro | Thr | Cys | Ser | Ala | Ala | Ser | Ala |
| | | | | 1125 | | | | | 1130 | | | | | 1135 | |
| Thr | Thr | Ser | Pro | Gly | Thr | Ser | Arg | Trp | Ser | Phe | Ser | Trp | Ser | Ser | Pro |
| | | | | 1140 | | | | | 1145 | | | | | 1150 | |
| Ala | Ala | Ser | Pro | Trp | Leu | Leu | Arg | Thr | Gln | Cys | Ala | Gln | Thr | Arg | Pro |
| | | | 1155 | | | | | 1160 | | | | | 1165 | | |
| Gly | Thr | Thr | Leu | Asn | Thr | Trp | Ile | Thr | Phe | Ser | Leu | Val | Ser | Leu | Pro |
| | | 1170 | | | | | 1175 | | | | | 1180 | | | |
| Leu | Arg | Trp | Arg | Ser | Thr | Trp | Asp | Cys | Cys | Phe | Thr | Leu | Glu | Pro | Ile |
| 1185 | | | | | 1190 | | | | | 1195 | | | | | 1200 |
| Ser | Gly | Thr | Cys | Gly | Thr | Phe | Trp | Thr | Ser | Leu | Trp | Ser | Val | Ala | Pro |
| | | | | 1205 | | | | | 1210 | | | | | 1215 | |
| Trp | Trp | Arg | Leu | Leu | Ser | Arg | Ser | Lys | Gly | Lys | Asp | Ile | Asn | Thr | Ile |
| | | | 1220 | | | | | 1225 | | | | | 1230 | | |
| Lys | Ser | Leu | Arg | Val | Leu | Arg | Val | Leu | Arg | Pro | Leu | Lys | Thr | Ile | Lys |
| | | | 1235 | | | | | 1240 | | | | | 1245 | | |
| Arg | Leu | Pro | Lys | Leu | Lys | Ala | Val | Phe | Asp | Cys | Val | Val | Asn | Ser | Leu |
| | | 1250 | | | | | 1255 | | | | | 1260 | | | |
| Lys | Asn | Val | Leu | Asn | Ile | Leu | Ile | Val | Tyr | Met | Leu | Phe | Met | Phe | Ile |
| 1265 | | | | | 1270 | | | | | 1275 | | | | | 1280 |
| Phe | Ala | Val | Ile | Ala | Val | Gln | Leu | Phe | Lys | Gly | Lys | Phe | Phe | Tyr | Cys |
| | | | | 1285 | | | | | 1290 | | | | | 1295 | |
| Thr | Asp | Glu | Ser | Lys | Glu | Leu | Glu | Arg | Asp | Cys | Arg | Gly | Gln | Tyr | Leu |
| | | | 1300 | | | | | 1305 | | | | | 1310 | | |
| Asp | Tyr | Glu | Lys | Glu | Glu | Val | Glu | Ala | Gln | Pro | Arg | Gln | Trp | Lys | Lys |
| | | | 1315 | | | | | 1320 | | | | | 1325 | | |
| Tyr | Asp | Phe | His | Tyr | Asp | Asn | Val | Leu | Trp | Ala | Leu | Leu | Thr | Leu | Phe |
| | | | 1330 | | | | | 1335 | | | | | 1340 | | |
| Thr | Val | Ser | Thr | Gly | Glu | Gly | Trp | Pro | Met | Val | Leu | Lys | His | Ser | Val |
| 1345 | | | | | 1350 | | | | | 1355 | | | | | 1360 |
| Asp | Ala | Thr | Tyr | Glu | Glu | Gln | Gly | Pro | Ser | Pro | Gly | Tyr | Arg | Met | Glu |
| | | | | 1365 | | | | | 1370 | | | | | 1375 | |
| Leu | Ser | Ile | Phe | Tyr | Val | Val | Tyr | Phe | Val | Val | Phe | Pro | Phe | Phe | Phe |
| | | | | 1380 | | | | | 1385 | | | | | 1390 | |
| Val | Asn | Ile | Phe | Val | Ala | Leu | Ile | Ile | Ile | Thr | Phe | Gln | Glu | Gln | Gly |
| | | | 1395 | | | | | 1400 | | | | | 1405 | | |
| Asp | Lys | Val | Met | Ser | Glu | Cys | Ser | Leu | Glu | Lys | Asn | Glu | Arg | Ala | Cys |
| | | | 1410 | | | | | 1415 | | | | | 1420 | | |
| Ile | Asp | Phe | Ala | Ile | Ser | Ala | Lys | Pro | Leu | Thr | Arg | Tyr | Met | Pro | Gln |
| 1425 | | | | | 1430 | | | | | 1435 | | | | | 1440 |
| Asn | Arg | Gln | Ser | Phe | Gln | Tyr | Lys | Thr | Trp | Thr | Phe | Val | Val | Ser | Pro |

|     |     |     | 1445 |     |     |     | 1450 |     |     |     | 1455 |     |
|-----|-----|-----|------|-----|-----|-----|------|-----|-----|-----|------|-----|

Pro Phe Glu Tyr Phe Ile Met Ala Met Ile Ala Leu Asn Thr Val Val
            1460                1465            1470

Leu Met Met Lys Phe Tyr Asp Ala Pro Tyr Glu Tyr Glu Leu Met Leu
            1475                1480            1485

Lys Cys Leu Asn Ile Val Phe Thr Ser Met Phe Ser Met Glu Cys Val
    1490                1495            1500

Leu Lys Ile Ile Ala Phe Gly Val Leu Asn Tyr Phe Arg Asp Ala Trp
1505            1510                1515            1520

Asn Phe Val Phe Asp Phe Val Thr Val Leu Gly Ser Ile Thr Asp Ile
            1525                1530            1535

Leu Val Thr Glu Ile Ala Ile Cys Pro Arg Arg Phe Gln Gln Phe Cys
            1540                1545            1550

Tyr Ser Thr Pro Gly Val Thr Val Thr Ser Leu Thr Thr His Gln Gln
        1555                1560            1565

Arg Arg Ile Cys Pro Val Ser His Ser Pro Arg Ser Pro Ser Leu Glu
        1570                1575            1580

Ser Ala Ser Lys Glu Pro Pro Leu Val Ser Pro Val Phe Gly Ser Glu
1585            1590                1595            1600

Arg Val Ile Gln Met Phe Thr Gly Ile Thr Val Ser Arg Asn Ser Trp
                1605                1610            1615

Lys Arg Thr Ile Ser Ser Thr Ser Ala Ser Ser Ala Ser Phe Glu Leu
            1620                1625            1630

Arg Gly Ser Ser Cys Ser Ala Arg Ala Thr Pro Ser Ala Ser Cys Cys
            1635                1640            1645

Gly Pro Leu Ser Ser Pro Ser Arg Pro Cys Pro Thr Cys Val Cys Ser
        1650                1655            1660

Leu Pro Cys Cys Ser Ser Ser Thr Pro Ser Ser Ala Cys Arg Cys Leu
1665            1670                1675            1680

Gly Ile Leu Pro Trp Met Met Thr Pro Ala Ser Thr Ala Thr Thr Thr
                1685                1690            1695

Ser Gly Arg Phe Cys Lys Pro Cys Cys Cys Ser Gly Ala Pro Arg Gly
            1700                1705            1710

Arg Pro Gly Thr Arg Ser Cys Cys Pro Ala Ala Thr Arg Pro Val Met
        1715                1720            1725

Ser Arg Pro Met Pro Pro Ser Val Glu Val Thr Leu Pro Thr Ser Thr
    1730                1735            1740

Ser Ser Pro Ser Ser Leu Glu Cys Thr Tyr
1745            1750

( 2 ) INFORMATION FOR SEQ ID NO:14:

( i ) SEQUENCE CHARACTERISTICS:
        ( A ) LENGTH: 2470 base pairs
        ( B ) TYPE: nucleic acid
        ( C ) STRANDEDNESS: unknown
        ( D ) TOPOLOGY: unknown ( i i ) MOLECULE TYPE: DNA (genomic)

( i x ) FEATURE:
        ( A ) NAME/KEY: CDS
        ( B ) LOCATION: 1..2469

( x i ) SEQUENCE DESCRIPTION: SEQ ID NO:14:

ATG GTC CGC TTC GGG GAC GAG CTG GGC GGC CGC TAT GGA GGC CCC GGC    48
Met Val Arg Phe Gly Asp Glu Leu Gly Gly Arg Tyr Gly Gly Pro Gly
1               5                   10                  15

GGC GGA GAG CGG GCC CGG GGC GGC GGG GCC GGC GGG GCG GGG GGC CCG    96
Gly Gly Glu Arg Ala Arg Gly Gly Gly Ala Gly Gly Ala Gly Gly Pro

|  |  |  |  |  |  |  |  |  |  |  |  |  |  |  |  |  |
|---|---|---|---|---|---|---|---|---|---|---|---|---|---|---|---|---|
|  |  | 20 |  |  |  |  | 25 |  |  |  |  | 30 |  |  |  |  |
| GGT | CCC | GGG | GGG | CTG | CAG | CCC | GGC | CAG | CGG | GTC | CTC | TAC | AAG | CAA | TCG | 144 |
| Gly | Pro | Gly | Gly | Leu | Gln | Pro | Gly | Gln | Arg | Val | Leu | Tyr | Lys | Gln | Ser |  |
|  |  | 35 |  |  |  | 40 |  |  |  |  | 45 |  |  |  |  |  |
| ATG | GCC | CAG | CGC | GCG | CGG | ACC | ATG | GCG | CTG | TAC | AAC | CCC | ATC | CCG | GTC | 192 |
| Met | Ala | Gln | Arg | Ala | Arg | Thr | Met | Ala | Leu | Tyr | Asn | Pro | Ile | Pro | Val |  |
|  | 50 |  |  |  | 55 |  |  |  |  | 60 |  |  |  |  |  |  |
| AAG | CAG | AAC | TGC | TTC | ACC | GTC | AAC | CGC | TCG | CTC | TTC | GTC | TTC | AGC | GAG | 240 |
| Lys | Gln | Asn | Cys | Phe | Thr | Val | Asn | Arg | Ser | Leu | Phe | Val | Phe | Ser | Glu |  |
| 65 |  |  |  | 70 |  |  |  |  | 75 |  |  |  |  | 80 |  |  |
| GAC | AAC | GTC | GTC | CGC | AAA | TAC | GCG | AAG | CGC | ATC | ACC | GAG | TGG | CCT | CCA | 288 |
| Asp | Asn | Val | Val | Arg | Lys | Tyr | Ala | Lys | Arg | Ile | Thr | Glu | Trp | Pro | Pro |  |
|  |  |  |  | 85 |  |  |  |  | 90 |  |  |  |  | 95 |  |  |
| TTC | GAG | AAT | ATG | ATC | CTG | GCC | ACC | ATC | ATC | GCC | AAC | TGC | ATC | GTG | CTG | 336 |
| Phe | Glu | Asn | Met | Ile | Leu | Ala | Thr | Ile | Ile | Ala | Asn | Cys | Ile | Val | Leu |  |
|  |  |  | 100 |  |  |  |  | 105 |  |  |  |  | 110 |  |  |  |
| GCC | CTG | GAG | CAG | CAC | CTC | CCT | GAT | GGG | GAC | AAA | ACG | CCC | ATG | TCC | GAG | 384 |
| Ala | Leu | Glu | Gln | His | Leu | Pro | Asp | Gly | Asp | Lys | Thr | Pro | Met | Ser | Glu |  |
|  |  | 115 |  |  |  |  | 120 |  |  |  |  | 125 |  |  |  |  |
| CGG | CTG | GAC | GAC | ACG | GAG | CCC | TAT | TTC | ATC | GGG | ATC | TTT | TGC | TTC | GAG | 432 |
| Arg | Leu | Asp | Asp | Thr | Glu | Pro | Tyr | Phe | Ile | Gly | Ile | Phe | Cys | Phe | Glu |  |
|  | 130 |  |  |  |  | 135 |  |  |  |  | 140 |  |  |  |  |  |
| GCA | GGG | ATC | AAA | ATC | ATC | GCT | CTG | GGC | TTT | GTC | TTC | CAC | AAG | GGC | TCT | 480 |
| Ala | Gly | Ile | Lys | Ile | Ile | Ala | Leu | Gly | Phe | Val | Phe | His | Lys | Gly | Ser |  |
| 145 |  |  |  | 150 |  |  |  |  | 155 |  |  |  |  | 160 |  |  |
| TAC | CTG | CGG | AAC | GGC | TGG | AAC | GTC | ATG | GAC | TTC | GTG | GTC | GTC | CTC | ACA | 528 |
| Tyr | Leu | Arg | Asn | Gly | Trp | Asn | Val | Met | Asp | Phe | Val | Val | Val | Leu | Thr |  |
|  |  |  |  | 165 |  |  |  |  | 170 |  |  |  |  | 175 |  |  |
| GGG | ATC | CTT | GCC | ACG | GCT | GGA | ACT | GAC | TTC | GAC | CTG | CGA | ACA | CTG | AGG | 576 |
| Gly | Ile | Leu | Ala | Thr | Ala | Gly | Thr | Asp | Phe | Asp | Leu | Arg | Thr | Leu | Arg |  |
|  |  |  | 180 |  |  |  |  | 185 |  |  |  |  | 190 |  |  |  |
| GCT | GTG | CGT | GTG | CTG | AGG | CCC | CTG | AAG | CTG | GTG | TCT | GGG | ATT | CCA | AGT | 624 |
| Ala | Val | Arg | Val | Leu | Arg | Pro | Leu | Lys | Leu | Val | Ser | Gly | Ile | Pro | Ser |  |
|  | 195 |  |  |  |  | 200 |  |  |  |  | 205 |  |  |  |  |  |
| TTG | CAG | GTG | GTG | CTC | AAG | TCC | ATC | ATG | AAG | GCC | ATG | GTT | CCA | CTC | CTG | 672 |
| Leu | Gln | Val | Val | Leu | Lys | Ser | Ile | Met | Lys | Ala | Met | Val | Pro | Leu | Leu |  |
| 210 |  |  |  |  | 215 |  |  |  |  | 220 |  |  |  |  |  |  |
| CAG | ATT | GGG | CTG | CTT | CTC | TTC | TTT | GCC | ATC | CTC | ATG | TTT | GCC | ATC | ATT | 720 |
| Gln | Ile | Gly | Leu | Leu | Leu | Phe | Phe | Ala | Ile | Leu | Met | Phe | Ala | Ile | Ile |  |
| 225 |  |  |  | 230 |  |  |  |  | 235 |  |  |  |  | 240 |  |  |
| GGC | CTG | GAG | TTC | TAC | ATG | GGC | AAG | TTC | CAC | AAG | GCC | TGT | TTC | CCC | AAC | 768 |
| Gly | Leu | Glu | Phe | Tyr | Met | Gly | Lys | Phe | His | Lys | Ala | Cys | Phe | Pro | Asn |  |
|  |  |  |  | 245 |  |  |  |  | 250 |  |  |  |  | 255 |  |  |
| AGC | ACA | GAT | GCG | GAG | CCC | GTG | GGT | GAC | TTC | CCC | TGT | GGC | AAG | GAG | GCC | 816 |
| Ser | Thr | Asp | Ala | Glu | Pro | Val | Gly | Asp | Phe | Pro | Cys | Gly | Lys | Glu | Ala |  |
|  |  | 260 |  |  |  |  | 265 |  |  |  |  | 270 |  |  |  |  |
| CCA | GCC | CGG | CTG | TGC | GAG | GGC | GAC | ACT | GAG | TGC | CGG | GAG | TAC | TGG | CCA | 864 |
| Pro | Ala | Arg | Leu | Cys | Glu | Gly | Asp | Thr | Glu | Cys | Arg | Glu | Tyr | Trp | Pro |  |
|  |  | 275 |  |  |  |  | 280 |  |  |  |  | 285 |  |  |  |  |
| GGA | CCC | AAC | TTT | GGC | ATC | ACC | AAC | TTT | GAC | AAT | ATC | CTG | TTT | GCC | ATC | 912 |
| Gly | Pro | Asn | Phe | Gly | Ile | Thr | Asn | Phe | Asp | Asn | Ile | Leu | Phe | Ala | Ile |  |
|  | 290 |  |  |  | 295 |  |  |  |  | 300 |  |  |  |  |  |  |
| TTG | ACG | GTG | TTC | CAG | TGC | ATC | ACC | ATG | GAG | GGC | TGG | ACT | GAC | ATC | CTC | 960 |
| Leu | Thr | Val | Phe | Gln | Cys | Ile | Thr | Met | Glu | Gly | Trp | Thr | Asp | Ile | Leu |  |
| 305 |  |  |  | 310 |  |  |  |  | 315 |  |  |  |  | 320 |  |  |
| TAT | AAT | ACA | AAC | GAT | GCG | GCC | GGC | AAC | ACC | TGG | AAC | TGG | CTC | TAC | TTC | 1008 |
| Tyr | Asn | Thr | Asn | Asp | Ala | Ala | Gly | Asn | Thr | Trp | Asn | Trp | Leu | Tyr | Phe |  |
|  |  |  |  | 325 |  |  |  |  | 330 |  |  |  |  | 335 |  |  |
| ATC | CCT | CTC | ATC | ATC | ATC | GGC | TCC | TTC | TTC | ATG | CTC | AAC | CTG | GTG | CTG | 1056 |
| Ile | Pro | Leu | Ile | Ile | Ile | Gly | Ser | Phe | Phe | Met | Leu | Asn | Leu | Val | Leu |  |
|  |  |  | 340 |  |  |  |  | 345 |  |  |  |  | 350 |  |  |  |

-continued

| | | | | | | | | | | | | | | | | |
|---|---|---|---|---|---|---|---|---|---|---|---|---|---|---|---|---|
| GGC | GTG | CTC | TCG | GGG | GAG | TTT | GCC | AAG | GAG | CGA | GAG | AGG | GTG | GAG | AAC | 1104 |
| Gly | Val | Leu | Ser | Gly | Glu | Phe | Ala | Lys | Glu | Arg | Glu | Arg | Val | Glu | Asn | |
| | | 355 | | | | 360 | | | | | | 365 | | | | |
| CGC | CGC | GCC | TTC | CTG | AAC | GTG | CGC | CGG | CAG | CAG | CAG | ATC | GAG | CGA | GAG | 1152 |
| Arg | Arg | Ala | Phe | Leu | Asn | Val | Arg | Arg | Gln | Gln | Gln | Ile | Glu | Arg | Glu | |
| | 370 | | | | 375 | | | | | 380 | | | | | | |
| CTC | AAC | GGG | TAC | CTG | GAG | TGG | ATC | TTC | AAG | GCG | GAG | GAA | GTC | ATG | CTG | 1200 |
| Leu | Asn | Gly | Tyr | Leu | Glu | Trp | Ile | Phe | Lys | Ala | Glu | Glu | Val | Met | Leu | |
| 385 | | | | | 390 | | | | | 395 | | | | | 400 | |
| GCC | GAG | GAG | GAC | AGG | AAT | GCA | GAG | GAG | AAG | TCC | CCT | TTG | GAC | GTG | CTG | 1248 |
| Ala | Glu | Glu | Asp | Arg | Asn | Ala | Glu | Glu | Lys | Ser | Pro | Leu | Asp | Val | Leu | |
| | | | | 405 | | | | | 410 | | | | | 415 | | |
| AAG | AGA | GCG | GCC | ACC | AAG | AAG | AGC | AGA | AAT | GAC | CTG | ATC | CAC | GCA | GAG | 1296 |
| Lys | Arg | Ala | Ala | Thr | Lys | Lys | Ser | Arg | Asn | Asp | Leu | Ile | His | Ala | Glu | |
| | | | 420 | | | | | 425 | | | | | 430 | | | |
| GAG | GGA | GAG | GAC | CGG | TTT | GCA | GAT | CTC | TGT | GCT | GTT | GGA | TCC | CCC | TTC | 1344 |
| Glu | Gly | Glu | Asp | Arg | Phe | Ala | Asp | Leu | Cys | Ala | Val | Gly | Ser | Pro | Phe | |
| | | 435 | | | | | 440 | | | | | 445 | | | | |
| GCC | CGC | GCC | AGC | CTC | AAG | AGC | GGG | AAG | ACA | GAG | AGC | TCG | TCA | TAC | TTC | 1392 |
| Ala | Arg | Ala | Ser | Leu | Lys | Ser | Gly | Lys | Thr | Glu | Ser | Ser | Ser | Tyr | Phe | |
| | 450 | | | | | 455 | | | | | 460 | | | | | |
| CGG | AGG | AAG | GAG | AAG | ATG | TTC | CGG | TTT | TTT | ATC | CGG | CGC | ATG | GTG | AAG | 1440 |
| Arg | Arg | Lys | Glu | Lys | Met | Phe | Arg | Phe | Phe | Ile | Arg | Arg | Met | Val | Lys | |
| 465 | | | | | 470 | | | | | 475 | | | | | 480 | |
| GCT | CAG | AGC | TTC | TAC | TGG | GTG | GTG | CTG | TGC | GTG | GTG | GCC | CTG | AAC | ACA | 1488 |
| Ala | Gln | Ser | Phe | Tyr | Trp | Val | Val | Leu | Cys | Val | Val | Ala | Leu | Asn | Thr | |
| | | | | 485 | | | | | 490 | | | | | 495 | | |
| CTG | TGT | GTG | GCC | ATG | GTG | CAT | TAC | AAC | CAG | CCG | CGG | CGG | CTT | ACC | ACG | 1536 |
| Leu | Cys | Val | Ala | Met | Val | His | Tyr | Asn | Gln | Pro | Arg | Arg | Leu | Thr | Thr | |
| | | | 500 | | | | | 505 | | | | | 510 | | | |
| ACC | CTG | TAT | TTT | GCA | GAG | TTT | GTT | TTC | CTG | GGT | CTC | TTC | CTC | ACA | GAG | 1584 |
| Thr | Leu | Tyr | Phe | Ala | Glu | Phe | Val | Phe | Leu | Gly | Leu | Phe | Leu | Thr | Glu | |
| | | 515 | | | | | 520 | | | | | 525 | | | | |
| ATG | TCC | CTG | AAG | ATG | TAT | GGC | CTG | GGG | CCC | AGA | AGC | TAC | TTC | CGG | TCC | 1632 |
| Met | Ser | Leu | Lys | Met | Tyr | Gly | Leu | Gly | Pro | Arg | Ser | Tyr | Phe | Arg | Ser | |
| | | 530 | | | | | 535 | | | | | 540 | | | | |
| TCC | TTC | AAC | TGC | TTC | GAC | TTT | GGG | GTC | ATC | GTG | GGG | AGC | GTC | TTT | GAA | 1680 |
| Ser | Phe | Asn | Cys | Phe | Asp | Phe | Gly | Val | Ile | Val | Gly | Ser | Val | Phe | Glu | |
| 545 | | | | | 550 | | | | | 555 | | | | | 560 | |
| GTG | GTC | TGG | GCG | GCC | ATC | AAG | CCG | GGA | AGC | TCC | TTT | GGG | ATC | AGT | GTG | 1728 |
| Val | Val | Trp | Ala | Ala | Ile | Lys | Pro | Gly | Ser | Ser | Phe | Gly | Ile | Ser | Val | |
| | | | | 565 | | | | | 570 | | | | | 575 | | |
| CTG | CGG | GCC | CTC | CGC | CTG | CTG | AGG | ATC | TTC | AAA | GTC | ACG | AAG | TAC | TGG | 1776 |
| Leu | Arg | Ala | Leu | Arg | Leu | Leu | Arg | Ile | Phe | Lys | Val | Thr | Lys | Tyr | Trp | |
| | | | 580 | | | | | 585 | | | | | 590 | | | |
| AGC | TCC | CTG | CGG | AAC | CTG | GTG | GTG | TCC | CTG | CTG | AAC | TCC | ATG | AAG | TCC | 1824 |
| Ser | Ser | Leu | Arg | Asn | Leu | Val | Val | Ser | Leu | Leu | Asn | Ser | Met | Lys | Ser | |
| | | 595 | | | | | 600 | | | | | 605 | | | | |
| ATC | ATC | AGC | CTG | CTC | TTC | TTG | CTC | TTC | CTG | TTC | ATT | GTG | GTC | TTC | GCC | 1872 |
| Ile | Ile | Ser | Leu | Leu | Phe | Leu | Leu | Phe | Leu | Phe | Ile | Val | Val | Phe | Ala | |
| | | 610 | | | | | 615 | | | | | 620 | | | | |
| CTG | CTG | GGG | ATG | CAG | CTG | TTT | GGG | GGA | CAG | TTC | AAC | TTC | CAG | GAT | GAG | 1920 |
| Leu | Leu | Gly | Met | Gln | Leu | Phe | Gly | Gly | Gln | Phe | Asn | Phe | Gln | Asp | Glu | |
| 625 | | | | | 630 | | | | | 635 | | | | | 640 | |
| ACT | CCC | ACA | ACC | AAC | TTC | GAC | ACC | TTC | CCT | GCC | GCC | ATC | CTC | ACT | GTC | 1968 |
| Thr | Pro | Thr | Thr | Asn | Phe | Asp | Thr | Phe | Pro | Ala | Ala | Ile | Leu | Thr | Val | |
| | | | | 645 | | | | | 650 | | | | | 655 | | |
| TTC | CAG | ATC | CTG | ACG | GGA | GAG | GAC | TGG | AAT | GCA | GTG | ATG | TAT | CAC | GGG | 2016 |
| Phe | Gln | Ile | Leu | Thr | Gly | Glu | Asp | Trp | Asn | Ala | Val | Met | Tyr | His | Gly | |
| | | | 660 | | | | | 665 | | | | | 670 | | | |
| ATC | GAA | TCG | CAA | GGC | GGC | GTC | AGC | AAA | GGC | ATG | TTC | TCG | TCC | TTT | TAC | 2064 |
| Ile | Glu | Ser | Gln | Gly | Gly | Val | Ser | Lys | Gly | Met | Phe | Ser | Ser | Phe | Tyr | |

| | | | | | | | | | | | | | | | | |
|---|---|---|---|---|---|---|---|---|---|---|---|---|---|---|---|---|
| | | 675 | | | | | 680 | | | | | 685 | | | | |
| TTC | ATT | GTC | CTG | ACA | CTG | TTC | GGA | AAC | TAC | ACT | CTG | CTG | AAT | GTC | TTT | 2112 |
| Phe | Ile | Val | Leu | Thr | Leu | Phe | Gly | Asn | Tyr | Thr | Leu | Leu | Asn | Val | Phe | |
| | 690 | | | | | 695 | | | | | 700 | | | | | |
| CTG | GCC | ATC | GCT | GTG | GAC | AAC | CTG | GCC | AAC | GCC | CAA | GAG | CTG | ACC | AAG | 2160 |
| Leu | Ala | Ile | Ala | Val | Asp | Asn | Leu | Ala | Asn | Ala | Gln | Glu | Leu | Thr | Lys | |
| 705 | | | | | 710 | | | | | 715 | | | | | 720 | |
| GAT | GAA | GAG | GAG | ATG | GAA | GAA | GCA | GCC | AAT | CAG | AAG | CTT | GCT | CTG | CAA | 2208 |
| Asp | Glu | Glu | Glu | Met | Glu | Glu | Ala | Ala | Asn | Gln | Lys | Leu | Ala | Leu | Gln | |
| | | | | 725 | | | | | 730 | | | | | 735 | | |
| AAG | GCC | AAA | GAA | GTG | GCT | GAA | GTC | AGC | CCC | ATG | TCT | GCC | GCG | AAC | ATC | 2256 |
| Lys | Ala | Lys | Glu | Val | Ala | Glu | Val | Ser | Pro | Met | Ser | Ala | Ala | Asn | Ile | |
| | | | 740 | | | | | 745 | | | | | 750 | | | |
| TCC | ATC | GCC | GCC | AGC | GAG | CAG | AAC | TCG | GCC | AAG | GCG | CGC | TCG | GTG | TGG | 2304 |
| Ser | Ile | Ala | Ala | Ser | Glu | Gln | Asn | Ser | Ala | Lys | Ala | Arg | Ser | Val | Trp | |
| | | 755 | | | | | 760 | | | | | 765 | | | | |
| GAG | CAG | CGG | GCC | AGC | CAG | CTA | CGG | CTG | CAG | AAC | CTG | CGG | GCC | AGC | TGC | 2352 |
| Glu | Gln | Arg | Ala | Ser | Gln | Leu | Arg | Leu | Gln | Asn | Leu | Arg | Ala | Ser | Cys | |
| | 770 | | | | | 775 | | | | | 780 | | | | | |
| GAG | GCG | CTG | TAC | AGC | GAG | ATG | GAC | CCC | GAG | GAG | CGG | CTG | CGC | TTC | GCC | 2400 |
| Glu | Ala | Leu | Tyr | Ser | Glu | Met | Asp | Pro | Glu | Glu | Arg | Leu | Arg | Phe | Ala | |
| 785 | | | | | 790 | | | | | 795 | | | | | 800 | |
| ACT | ACG | CGC | CAC | CTG | CGG | CCC | GAC | ATG | AAG | ACG | CAC | CTG | GAC | CGG | CCG | 2448 |
| Thr | Thr | Arg | His | Leu | Arg | Pro | Asp | Met | Lys | Thr | His | Leu | Asp | Arg | Pro | |
| | | | | 805 | | | | | 810 | | | | | 815 | | |
| CTG | GTG | GTG | GAG | CTG | GGC | CGC | G | | | | | | | | | 2470 |
| Leu | Val | Val | Glu | Leu | Gly | Arg | | | | | | | | | | |
| | | | 820 | | | | | | | | | | | | | |

( 2 ) INFORMATION FOR SEQ ID NO:15:

( i ) SEQUENCE CHARACTERISTICS:
( A ) LENGTH: 823 amino acids
( B ) TYPE: amino acid
( D ) TOPOLOGY: linear ( i i ) MOLECULE TYPE: protein ( x i ) SEQUENCE DESCRIPTION: SEQ ID NO:15:

| | | | | | | | | | | | | | | |
|---|---|---|---|---|---|---|---|---|---|---|---|---|---|---|
| Met | Val | Arg | Phe | Gly | Asp | Glu | Leu | Gly | Gly | Arg | Tyr | Gly | Gly | Pro | Gly |
| 1 | | | | 5 | | | | | 10 | | | | | 15 | |
| Gly | Gly | Glu | Arg | Ala | Arg | Gly | Gly | Ala | Gly | Gly | Ala | Gly | Gly | Pro | |
| | | | 20 | | | | | 25 | | | | | 30 | | |
| Gly | Pro | Gly | Gly | Leu | Gln | Pro | Gly | Gln | Arg | Val | Leu | Tyr | Lys | Gln | Ser |
| | | 35 | | | | | 40 | | | | | 45 | | | |
| Met | Ala | Gln | Arg | Ala | Arg | Thr | Met | Ala | Leu | Tyr | Asn | Pro | Ile | Pro | Val |
| | 50 | | | | | 55 | | | | | 60 | | | | |
| Lys | Gln | Asn | Cys | Phe | Thr | Val | Asn | Arg | Ser | Leu | Phe | Val | Phe | Ser | Glu |
| 65 | | | | | 70 | | | | | 75 | | | | | 80 |
| Asp | Asn | Val | Val | Arg | Lys | Tyr | Ala | Lys | Arg | Ile | Thr | Glu | Trp | Pro | Pro |
| | | | | 85 | | | | | 90 | | | | | 95 | |
| Phe | Glu | Asn | Met | Ile | Leu | Ala | Thr | Ile | Ile | Ala | Asn | Cys | Ile | Val | Leu |
| | | | 100 | | | | | 105 | | | | | 110 | | |
| Ala | Leu | Glu | Gln | His | Leu | Pro | Asp | Gly | Asp | Lys | Thr | Pro | Met | Ser | Glu |
| | | 115 | | | | | 120 | | | | | 125 | | | |
| Arg | Leu | Asp | Asp | Thr | Glu | Pro | Tyr | Phe | Ile | Gly | Ile | Phe | Cys | Phe | Glu |
| | 130 | | | | | 135 | | | | | 140 | | | | |
| Ala | Gly | Ile | Lys | Ile | Ile | Ala | Leu | Gly | Phe | Val | Phe | His | Lys | Gly | Ser |
| 145 | | | | | 150 | | | | | 155 | | | | | 160 |
| Tyr | Leu | Arg | Asn | Gly | Trp | Asn | Val | Met | Asp | Phe | Val | Val | Val | Leu | Thr |
| | | | | 165 | | | | | 170 | | | | | 175 | |

```
Gly Ile Leu Ala Thr Ala Gly Thr Asp Phe Asp Leu Arg Thr Leu Arg
            180                 185                 190

Ala Val Arg Val Leu Arg Pro Leu Lys Leu Val Ser Gly Ile Pro Ser
        195                 200                 205

Leu Gln Val Val Leu Lys Ser Ile Met Lys Ala Met Val Pro Leu Leu
    210                 215                 220

Gln Ile Gly Leu Leu Phe Phe Ala Ile Leu Met Phe Ala Ile Ile
225                 230                 235                 240

Gly Leu Glu Phe Tyr Met Gly Lys Phe His Lys Ala Cys Phe Pro Asn
            245                 250                 255

Ser Thr Asp Ala Glu Pro Val Gly Asp Phe Pro Cys Gly Lys Glu Ala
            260                 265                 270

Pro Ala Arg Leu Cys Glu Gly Asp Thr Glu Cys Arg Glu Tyr Trp Pro
        275                 280                 285

Gly Pro Asn Phe Gly Ile Thr Asn Phe Asp Asn Ile Leu Phe Ala Ile
    290                 295                 300

Leu Thr Val Phe Gln Cys Ile Thr Met Glu Gly Trp Thr Asp Ile Leu
305                 310                 315                 320

Tyr Asn Thr Asn Asp Ala Ala Gly Asn Thr Trp Asn Trp Leu Tyr Phe
            325                 330                 335

Ile Pro Leu Ile Ile Ile Gly Ser Phe Phe Met Leu Asn Leu Val Leu
            340                 345                 350

Gly Val Leu Ser Gly Glu Phe Ala Lys Glu Arg Glu Arg Val Glu Asn
        355                 360                 365

Arg Arg Ala Phe Leu Asn Val Arg Arg Gln Gln Gln Ile Glu Arg Glu
    370                 375                 380

Leu Asn Gly Tyr Leu Glu Trp Ile Phe Lys Ala Glu Glu Val Met Leu
385                 390                 395                 400

Ala Glu Glu Asp Arg Asn Ala Glu Glu Lys Ser Pro Leu Asp Val Leu
            405                 410                 415

Lys Arg Ala Ala Thr Lys Lys Ser Arg Asn Asp Leu Ile His Ala Glu
            420                 425                 430

Glu Gly Glu Asp Arg Phe Ala Asp Leu Cys Ala Val Gly Ser Pro Phe
        435                 440                 445

Ala Arg Ala Ser Leu Lys Ser Gly Lys Thr Glu Ser Ser Ser Tyr Phe
    450                 455                 460

Arg Arg Lys Glu Lys Met Phe Arg Phe Phe Ile Arg Arg Met Val Lys
465                 470                 475                 480

Ala Gln Ser Phe Tyr Trp Val Val Leu Cys Val Val Ala Leu Asn Thr
            485                 490                 495

Leu Cys Val Ala Met Val His Tyr Asn Gln Pro Arg Arg Leu Thr Thr
            500                 505                 510

Thr Leu Tyr Phe Ala Glu Phe Val Phe Leu Gly Leu Phe Leu Thr Glu
        515                 520                 525

Met Ser Leu Lys Met Tyr Gly Leu Gly Pro Arg Ser Tyr Phe Arg Ser
    530                 535                 540

Ser Phe Asn Cys Phe Asp Phe Gly Val Ile Val Gly Ser Val Phe Glu
545                 550                 555                 560

Val Val Trp Ala Ala Ile Lys Pro Gly Ser Ser Phe Gly Ile Ser Val
            565                 570                 575

Leu Arg Ala Leu Arg Leu Leu Arg Ile Phe Lys Val Thr Lys Tyr Trp
            580                 585                 590

Ser Ser Leu Arg Asn Leu Val Val Ser Leu Leu Asn Ser Met Lys Ser
        595                 600                 605
```

| | | | | | | | | | | | | | | | |
|---|---|---|---|---|---|---|---|---|---|---|---|---|---|---|---|
| Ile | Ile | Ser | Leu | Leu | Phe | Leu | Leu | Phe | Leu | Phe | Ile | Val | Val | Phe | Ala |
| 610 | | | | | 615 | | | | | | 620 | | | | |
| Leu | Leu | Gly | Met | Gln | Leu | Phe | Gly | Gly | Gln | Phe | Asn | Phe | Gln | Asp | Glu |
| 625 | | | | | 630 | | | | | 635 | | | | | 640 |
| Thr | Pro | Thr | Thr | Asn | Phe | Asp | Thr | Phe | Pro | Ala | Ala | Ile | Leu | Thr | Val |
| | | | | 645 | | | | | 650 | | | | | 655 | |
| Phe | Gln | Ile | Leu | Thr | Gly | Glu | Asp | Trp | Asn | Ala | Val | Met | Tyr | His | Gly |
| | | | 660 | | | | | 665 | | | | | 670 | | |
| Ile | Glu | Ser | Gln | Gly | Gly | Val | Ser | Lys | Gly | Met | Phe | Ser | Ser | Phe | Tyr |
| | | 675 | | | | | 680 | | | | | 685 | | | |
| Phe | Ile | Val | Leu | Thr | Leu | Phe | Gly | Asn | Tyr | Thr | Leu | Leu | Asn | Val | Phe |
| | | 690 | | | | 695 | | | | | 700 | | | | |
| Leu | Ala | Ile | Ala | Val | Asp | Asn | Leu | Ala | Asn | Ala | Gln | Glu | Leu | Thr | Lys |
| 705 | | | | | 710 | | | | | 715 | | | | | 720 |
| Asp | Glu | Glu | Glu | Met | Glu | Glu | Ala | Ala | Asn | Gln | Lys | Leu | Ala | Leu | Gln |
| | | | | 725 | | | | | 730 | | | | | 735 | |
| Lys | Ala | Lys | Glu | Val | Ala | Glu | Val | Ser | Pro | Met | Ser | Ala | Ala | Asn | Ile |
| | | | 740 | | | | | 745 | | | | | 750 | | |
| Ser | Ile | Ala | Ala | Ser | Glu | Gln | Asn | Ser | Ala | Lys | Ala | Arg | Ser | Val | Trp |
| | | 755 | | | | | 760 | | | | | 765 | | | |
| Glu | Gln | Arg | Ala | Ser | Gln | Leu | Arg | Leu | Gln | Asn | Leu | Arg | Ala | Ser | Cys |
| 770 | | | | | 775 | | | | | 780 | | | | | |
| Glu | Ala | Leu | Tyr | Ser | Glu | Met | Asp | Pro | Glu | Glu | Arg | Leu | Arg | Phe | Ala |
| 785 | | | | | 790 | | | | | 795 | | | | | 800 |
| Thr | Thr | Arg | His | Leu | Arg | Pro | Asp | Met | Lys | Thr | His | Leu | Asp | Arg | Pro |
| | | | | 805 | | | | | 810 | | | | | 815 | |
| Leu | Val | Val | Glu | Leu | Gly | Arg | | | | | | | | | |
| | | | 820 | | | | | | | | | | | | |

( 2 ) INFORMATION FOR SEQ ID NO:16:

( i ) SEQUENCE CHARACTERISTICS:
        ( A ) LENGTH: 957 base pairs
        ( B ) TYPE: nucleic acid
        ( C ) STRANDEDNESS: unknown
        ( D ) TOPOLOGY: unknown ( i i ) MOLECULE TYPE: DNA (genomic)

( i x ) FEATURE:
        ( A ) NAME/KEY: CDS
        ( B ) LOCATION: 1..957

( x i ) SEQUENCE DESCRIPTION: SEQ ID NO:16:

| | | | | | | | | | | | | | | | | |
|---|---|---|---|---|---|---|---|---|---|---|---|---|---|---|---|---|
| TCC | AAA | GGG | AAA | GAC | ATC | AAT | ACC | ATC | AAG | TCT | CTG | AGA | GTC | CTT | CGT | 48 |
| Ser | Lys | Gly | Lys | Asp | Ile | Asn | Thr | Ile | Lys | Ser | Leu | Arg | Val | Leu | Arg | |
| 1 | | | | 5 | | | | | 10 | | | | | 15 | | |
| GTC | CTG | CGG | CCC | CTC | AAG | ACC | ATC | AAA | CGG | CTG | CCC | AAG | CTC | AAG | GCT | 96 |
| Val | Leu | Arg | Pro | Leu | Lys | Thr | Ile | Lys | Arg | Leu | Pro | Lys | Leu | Lys | Ala | |
| | | | 20 | | | | | 25 | | | | | 30 | | | |
| GTG | TTT | GAC | TGT | GTG | GTG | AAC | TCC | CTG | AAG | AAT | GTC | CTC | AAC | ATC | TTG | 144 |
| Val | Phe | Asp | Cys | Val | Val | Asn | Ser | Leu | Lys | Asn | Val | Leu | Asn | Ile | Leu | |
| | | | 35 | | | | | 40 | | | | | 45 | | | |
| ATT | GTC | TAC | ATG | CTC | TTC | ATG | TTC | ATA | TTT | GCC | GTC | ATT | GCG | GTG | CAG | 192 |
| Ile | Val | Tyr | Met | Leu | Phe | Met | Phe | Ile | Phe | Ala | Val | Ile | Ala | Val | Gln | |
| | | 50 | | | | | 55 | | | | | 60 | | | | |
| CTC | TTC | AAA | GGG | AAG | TTT | TTC | TAC | TGC | ACA | GAT | GAA | TCC | AAG | GAG | CTG | 240 |
| Leu | Phe | Lys | Gly | Lys | Phe | Phe | Tyr | Cys | Thr | Asp | Glu | Ser | Lys | Glu | Leu | |
| 65 | | | | | 70 | | | | | 75 | | | | | 80 | |
| GAG | AGG | GAC | TGC | AGG | GGT | CAG | TAT | TTG | GAT | TAT | GAG | AAG | GAG | GAA | GTG | 288 |
| Glu | Arg | Asp | Cys | Arg | Gly | Gln | Tyr | Leu | Asp | Tyr | Glu | Lys | Glu | Glu | Val | |
| | | | | 85 | | | | | 90 | | | | | 95 | | |

-continued

| | | | | | | | | | | | | | | | | |
|---|---|---|---|---|---|---|---|---|---|---|---|---|---|---|---|---|
| GAA | GCT | CAG | CCC | AGG | CAG | TGG | AAG | AAA | TAC | GAC | TTT | CAC | TAC | GAC | AAT | 336 |
| Glu | Ala | Gln | Pro | Arg | Gln | Trp | Lys | Lys | Tyr | Asp | Phe | His | Tyr | Asp | Asn | |
| | | | 100 | | | | 105 | | | | | 110 | | | | |
| GTG | CTC | TGG | GCT | CTG | CTG | ACG | CTG | TTC | ACA | GTG | TCC | ACG | GGA | GAA | GGC | 384 |
| Val | Leu | Trp | Ala | Leu | Leu | Thr | Leu | Phe | Thr | Val | Ser | Thr | Gly | Glu | Gly | |
| | | 115 | | | | | 120 | | | | | 125 | | | | |
| TGG | CCC | ATG | GTG | CTG | AAA | CAC | TCC | GTG | GAT | GCC | ACC | TAT | GAG | GAG | CAG | 432 |
| Trp | Pro | Met | Val | Leu | Lys | His | Ser | Val | Asp | Ala | Thr | Tyr | Glu | Glu | Gln | |
| | 130 | | | | | 135 | | | | | 140 | | | | | |
| GGT | CCA | AGC | CCT | GGG | TAC | CGC | ATG | GAG | CTG | TCC | ATC | TTC | TAC | GTG | GTC | 480 |
| Gly | Pro | Ser | Pro | Gly | Tyr | Arg | Met | Glu | Leu | Ser | Ile | Phe | Tyr | Val | Val | |
| 145 | | | | | 150 | | | | | 155 | | | | | 160 | |
| TAC | TTT | GTG | GTC | TTT | CCC | TTC | TTC | TTC | GTC | AAC | ATC | TTT | GTG | GCT | TTG | 528 |
| Tyr | Phe | Val | Val | Phe | Pro | Phe | Phe | Phe | Val | Asn | Ile | Phe | Val | Ala | Leu | |
| | | | | 165 | | | | | 170 | | | | | 175 | | |
| ATC | ATC | ATC | ACC | TTC | CAG | GAG | CAG | GGG | GAC | AAG | GTG | ATG | TCT | GAA | TGC | 576 |
| Ile | Ile | Ile | Thr | Phe | Gln | Glu | Gln | Gly | Asp | Lys | Val | Met | Ser | Glu | Cys | |
| | | | 180 | | | | | 185 | | | | | 190 | | | |
| AGC | CTG | GAG | AAG | AAC | GAG | AGG | GCT | TGC | ATT | GAC | TTC | GCC | ATC | AGC | GCC | 624 |
| Ser | Leu | Glu | Lys | Asn | Glu | Arg | Ala | Cys | Ile | Asp | Phe | Ala | Ile | Ser | Ala | |
| | | 195 | | | | | 200 | | | | | 205 | | | | |
| AAA | CCC | CTG | ACA | CGG | TAC | ATG | CCC | CAA | AAC | CGG | CAG | TCG | TTC | CAG | TAT | 672 |
| Lys | Pro | Leu | Thr | Arg | Tyr | Met | Pro | Gln | Asn | Arg | Gln | Ser | Phe | Gln | Tyr | |
| | 210 | | | | | 215 | | | | | 220 | | | | | |
| AAG | ACG | TGG | ACA | TTT | GTG | GTC | TCC | CCG | CCC | TTT | GAA | TAC | TTC | ATC | ATG | 720 |
| Lys | Thr | Trp | Thr | Phe | Val | Val | Ser | Pro | Pro | Phe | Glu | Tyr | Phe | Ile | Met | |
| 225 | | | | | 230 | | | | | 235 | | | | | 240 | |
| GCC | ATG | ATA | GCC | CTC | AAC | ACT | GTG | GTG | CTG | ATG | ATG | AAG | TTC | TAT | GAT | 768 |
| Ala | Met | Ile | Ala | Leu | Asn | Thr | Val | Val | Leu | Met | Met | Lys | Phe | Tyr | Asp | |
| | | | | 245 | | | | | 250 | | | | | 255 | | |
| GCA | CCC | TAT | GAG | TAC | GAG | CTG | ATG | CTG | AAA | TGC | CTG | AAC | ATC | GTG | TTC | 816 |
| Ala | Pro | Tyr | Glu | Tyr | Glu | Leu | Met | Leu | Lys | Cys | Leu | Asn | Ile | Val | Phe | |
| | | | 260 | | | | | 265 | | | | | 270 | | | |
| ACA | TCC | ATG | TTC | TCC | ATG | GAA | TGC | GTG | CTG | AAG | ATC | ATC | GCC | TTT | GGG | 864 |
| Thr | Ser | Met | Phe | Ser | Met | Glu | Cys | Val | Leu | Lys | Ile | Ile | Ala | Phe | Gly | |
| | | 275 | | | | | 280 | | | | | 285 | | | | |
| GTG | CTG | AAC | TAT | TTC | AGA | GAT | GCC | TGG | AAT | TTT | GTC | TTT | GAC | TTT | GTC | 912 |
| Val | Leu | Asn | Tyr | Phe | Arg | Asp | Ala | Trp | Asn | Phe | Val | Phe | Asp | Phe | Val | |
| | 290 | | | | | 295 | | | | | 300 | | | | | |
| ACT | GTG | TTG | GGA | AGT | ATT | ACT | GAT | ATT | TTA | GTA | ACA | GAG | ATT | GCG | | 957 |
| Thr | Val | Leu | Gly | Ser | Ile | Thr | Asp | Ile | Leu | Val | Thr | Glu | Ile | Ala | | |
| 305 | | | | | 310 | | | | | 315 | | | | | | |

( 2 ) INFORMATION FOR SEQ ID NO:17:

( i ) SEQUENCE CHARACTERISTICS:
        ( A ) LENGTH: 319 amino acids
        ( B ) TYPE: amino acid
        ( D ) TOPOLOGY: linear ( i i ) MOLECULE TYPE: protein ( x i ) SEQUENCE DESCRIPTION: SEQ ID NO:17:

| | | | | | | | | | | | | | | |
|---|---|---|---|---|---|---|---|---|---|---|---|---|---|---|
| Ser | Lys | Gly | Lys | Asp | Ile | Asn | Thr | Ile | Lys | Ser | Leu | Arg | Val | Leu | Arg |
| 1 | | | | 5 | | | | | 10 | | | | | 15 | |
| Val | Leu | Arg | Pro | Leu | Lys | Thr | Ile | Lys | Arg | Leu | Pro | Lys | Leu | Lys | Ala |
| | | | 20 | | | | | 25 | | | | | 30 | | |
| Val | Phe | Asp | Cys | Val | Val | Asn | Ser | Leu | Lys | Asn | Val | Leu | Asn | Ile | Leu |
| | | | 35 | | | | | 40 | | | | | 45 | | |
| Ile | Val | Tyr | Met | Leu | Phe | Met | Phe | Ile | Phe | Ala | Val | Ile | Ala | Val | Gln |
| | | 50 | | | | | 55 | | | | | 60 | | | |
| Leu | Phe | Lys | Gly | Lys | Phe | Phe | Tyr | Cys | Thr | Asp | Glu | Ser | Lys | Glu | Leu |

|  | 65 |  |  |  |  | 70 |  |  |  |  | 75 |  |  |  |  | 80 |
|---|---|---|---|---|---|---|---|---|---|---|---|---|---|---|---|---|
| Glu | Arg | Asp | Cys | Arg | Gly | Gln | Tyr | Leu | Asp | Tyr | Glu | Lys | Glu | Glu | Val |
|  |  |  |  | 85 |  |  |  |  | 90 |  |  |  |  | 95 |  |
| Glu | Ala | Gln | Pro | Arg | Gln | Trp | Lys | Lys | Tyr | Asp | Phe | His | Tyr | Asp | Asn |
|  |  |  | 100 |  |  |  |  | 105 |  |  |  |  | 110 |  |  |
| Val | Leu | Trp | Ala | Leu | Leu | Thr | Leu | Phe | Thr | Val | Ser | Thr | Gly | Glu | Gly |
|  |  | 115 |  |  |  |  | 120 |  |  |  |  | 125 |  |  |  |
| Trp | Pro | Met | Val | Leu | Lys | His | Ser | Val | Asp | Ala | Thr | Tyr | Glu | Glu | Gln |
| 130 |  |  |  |  | 135 |  |  |  |  | 140 |  |  |  |  |  |
| Gly | Pro | Ser | Pro | Gly | Tyr | Arg | Met | Glu | Leu | Ser | Ile | Phe | Tyr | Val | Val |
| 145 |  |  |  | 150 |  |  |  |  | 155 |  |  |  |  | 160 |  |
| Tyr | Phe | Val | Val | Phe | Pro | Phe | Phe | Phe | Val | Asn | Ile | Phe | Val | Ala | Leu |
|  |  |  |  | 165 |  |  |  |  | 170 |  |  |  |  | 175 |  |
| Ile | Ile | Ile | Thr | Phe | Gln | Glu | Gln | Gly | Asp | Lys | Val | Met | Ser | Glu | Cys |
|  |  |  | 180 |  |  |  |  | 185 |  |  |  |  | 190 |  |  |
| Ser | Leu | Glu | Lys | Asn | Glu | Arg | Ala | Cys | Ile | Asp | Phe | Ala | Ile | Ser | Ala |
|  |  | 195 |  |  |  |  | 200 |  |  |  |  | 205 |  |  |  |
| Lys | Pro | Leu | Thr | Arg | Tyr | Met | Pro | Gln | Asn | Arg | Gln | Ser | Phe | Gln | Tyr |
|  | 210 |  |  |  |  | 215 |  |  |  |  | 220 |  |  |  |  |
| Lys | Thr | Trp | Thr | Phe | Val | Val | Ser | Pro | Pro | Phe | Glu | Tyr | Phe | Ile | Met |
| 225 |  |  |  |  | 230 |  |  |  |  | 235 |  |  |  |  | 240 |
| Ala | Met | Ile | Ala | Leu | Asn | Thr | Val | Val | Leu | Met | Met | Lys | Phe | Tyr | Asp |
|  |  |  |  | 245 |  |  |  |  | 250 |  |  |  |  | 255 |  |
| Ala | Pro | Tyr | Glu | Tyr | Glu | Leu | Met | Leu | Lys | Cys | Leu | Asn | Ile | Val | Phe |
|  |  |  | 260 |  |  |  |  | 265 |  |  |  |  | 270 |  |  |
| Thr | Ser | Met | Phe | Ser | Met | Glu | Cys | Val | Leu | Lys | Ile | Ile | Ala | Phe | Gly |
|  |  | 275 |  |  |  |  | 280 |  |  |  |  | 285 |  |  |  |
| Val | Leu | Asn | Tyr | Phe | Arg | Asp | Ala | Trp | Asn | Phe | Val | Phe | Asp | Phe | Val |
|  | 290 |  |  |  |  | 295 |  |  |  |  | 300 |  |  |  |  |
| Thr | Val | Leu | Gly | Ser | Ile | Thr | Asp | Ile | Leu | Val | Thr | Glu | Ile | Ala |  |
| 305 |  |  |  |  | 310 |  |  |  |  | 315 |  |  |  |  |  |

( 2 ) INFORMATION FOR SEQ ID NO:18:

( i ) SEQUENCE CHARACTERISTICS:
        ( A ) LENGTH: 1546 base pairs
        ( B ) TYPE: nucleic acid
        ( C ) STRANDEDNESS: unknown
        ( D ) TOPOLOGY: unknown ( i i ) MOLECULE TYPE: DNA (genomic)

( i x ) FEATURE:
        ( A ) NAME/KEY: CDS
        ( B ) LOCATION: 1..1434

( x i ) SEQUENCE DESCRIPTION: SEQ ID NO:18:

| ATG | GTC | CAG | AAG | ACC | AGC | ATG | TCC | CGG | GGC | CCT | TAC | CCA | CCC | TCC | CAG | 48 |
|---|---|---|---|---|---|---|---|---|---|---|---|---|---|---|---|---|
| Met | Val | Gln | Lys | Thr | Ser | Met | Ser | Arg | Gly | Pro | Tyr | Pro | Pro | Ser | Gln |  |
| 1 |  |  |  | 5 |  |  |  |  | 10 |  |  |  |  | 15 |  |  |

| GAG | ATC | CCC | ATG | GGA | GTC | TTC | GAC | CCC | AGC | CCG | CAG | GGC | AAA | TAC | AGC | 96 |
|---|---|---|---|---|---|---|---|---|---|---|---|---|---|---|---|---|
| Glu | Ile | Pro | Met | Gly | Val | Phe | Asp | Pro | Ser | Pro | Gln | Gly | Lys | Tyr | Ser |  |
|  |  |  | 20 |  |  |  |  | 25 |  |  |  |  | 30 |  |  |  |

| AAG | AGG | AAA | GGG | CGA | TTC | AAA | CGG | TCA | GAT | GGG | AGC | ACG | TCC | TCG | GAT | 144 |
|---|---|---|---|---|---|---|---|---|---|---|---|---|---|---|---|---|
| Lys | Arg | Lys | Gly | Arg | Phe | Lys | Arg | Ser | Asp | Gly | Ser | Thr | Ser | Ser | Asp |  |
|  |  | 35 |  |  |  |  | 40 |  |  |  |  | 45 |  |  |  |  |

| ACC | ACA | TCC | AAC | AGC | TTT | GTC | CGC | CAG | GGC | TCA | GCG | GAG | TCC | TAC | ACC | 192 |
|---|---|---|---|---|---|---|---|---|---|---|---|---|---|---|---|---|
| Thr | Thr | Ser | Asn | Ser | Phe | Val | Arg | Gln | Gly | Ser | Ala | Glu | Ser | Tyr | Thr |  |
|  |  | 50 |  |  |  |  | 55 |  |  |  |  | 60 |  |  |  |  |

| AGC | CGT | CCA | TCA | GAC | TCT | GAT | GTA | TCT | CTG | GAG | GAG | GAC | CGG | GAA | GCC | 240 |
|---|---|---|---|---|---|---|---|---|---|---|---|---|---|---|---|---|
| Ser | Arg | Pro | Ser | Asp | Ser | Asp | Val | Ser | Leu | Glu | Glu | Asp | Arg | Glu | Ala |  |

-continued

| 65 | 70 | 75 | 80 |
|---|---|---|---|

| | | | | | | | | | | | | | | | | |
|---|---|---|---|---|---|---|---|---|---|---|---|---|---|---|---|---|
| TTA | AGG | AAG | GAA | GCA | GAG | CGC | CAG | GCA | TTA | GCG | CAG | CTC | GAG | AAG | GCC | 288 |
| Leu | Arg | Lys | Glu | Ala | Glu | Arg | Gln | Ala | Leu | Ala | Gln | Leu | Glu | Lys | Ala | |
| | | | | 85 | | | | | 90 | | | | | 95 | | |
| AAG | ACC | AAG | CCA | GTG | GCA | TTT | GCT | GTG | CGG | ACA | AAT | GTT | GGC | TAC | AAT | 336 |
| Lys | Thr | Lys | Pro | Val | Ala | Phe | Ala | Val | Arg | Thr | Asn | Val | Gly | Tyr | Asn | |
| | | | 100 | | | | | 105 | | | | | 110 | | | |
| CCG | TCT | CCA | GGG | GAT | GAG | GTG | CCT | GTG | CAG | GGA | GTG | GCC | ATC | ACC | TTC | 384 |
| Pro | Ser | Pro | Gly | Asp | Glu | Val | Pro | Val | Gln | Gly | Val | Ala | Ile | Thr | Phe | |
| | | 115 | | | | | 120 | | | | | 125 | | | | |
| GAG | CCC | AAA | GAC | TTC | CTG | CAC | ATC | AAG | GAG | AAA | TAC | AAT | AAT | GAC | TGG | 432 |
| Glu | Pro | Lys | Asp | Phe | Leu | His | Ile | Lys | Glu | Lys | Tyr | Asn | Asn | Asp | Trp | |
| | 130 | | | | 135 | | | | | 140 | | | | | | |
| TGG | ATC | GGG | CGG | CTG | GTG | AAG | GAG | GGC | TGT | GAG | GTT | GGC | TTC | ATT | CCC | 480 |
| Trp | Ile | Gly | Arg | Leu | Val | Lys | Glu | Gly | Cys | Glu | Val | Gly | Phe | Ile | Pro | |
| 145 | | | | | 150 | | | | | 155 | | | | | 160 | |
| AGC | CCC | GTC | AAA | CTG | GAC | AGC | CTT | CGC | CTG | CTG | CAG | GAA | CAG | AAG | CTG | 528 |
| Ser | Pro | Val | Lys | Leu | Asp | Ser | Leu | Arg | Leu | Leu | Gln | Glu | Gln | Lys | Leu | |
| | | | | 165 | | | | | 170 | | | | | 175 | | |
| CGC | CAG | AAC | CGC | CTC | GGC | TCC | AGC | AAA | TCA | GGC | GAT | AAC | TCC | AGT | TCC | 576 |
| Arg | Gln | Asn | Arg | Leu | Gly | Ser | Ser | Lys | Ser | Gly | Asp | Asn | Ser | Ser | Ser | |
| | | | 180 | | | | | 185 | | | | | 190 | | | |
| AGT | CTG | GGA | GAT | GTG | GTG | ACT | GGC | ACC | CGC | CGC | CCC | ACA | CCC | CCT | GCC | 624 |
| Ser | Leu | Gly | Asp | Val | Val | Thr | Gly | Thr | Arg | Arg | Pro | Thr | Pro | Pro | Ala | |
| | | 195 | | | | | 200 | | | | | 205 | | | | |
| AGT | GCC | AAA | CAG | AAG | CAG | AAG | TCG | ACA | GAG | CAT | GTG | CCC | CCC | TAT | GAC | 672 |
| Ser | Ala | Lys | Gln | Lys | Gln | Lys | Ser | Thr | Glu | His | Val | Pro | Pro | Tyr | Asp | |
| | 210 | | | | 215 | | | | | 220 | | | | | | |
| GTG | GTG | CCT | TCC | ATG | AGG | CCC | ATC | ATC | CTG | GTG | GGA | CCG | TCG | CTC | AAG | 720 |
| Val | Val | Pro | Ser | Met | Arg | Pro | Ile | Ile | Leu | Val | Gly | Pro | Ser | Leu | Lys | |
| 225 | | | | | 230 | | | | | 235 | | | | | 240 | |
| GGC | TAC | GAG | GTT | ACA | GAC | ATG | ATG | CAG | AAA | GCT | TTA | TTT | GAC | TTC | TTG | 768 |
| Gly | Tyr | Glu | Val | Thr | Asp | Met | Met | Gln | Lys | Ala | Leu | Phe | Asp | Phe | Leu | |
| | | | | 245 | | | | | 250 | | | | | 255 | | |
| AAG | CAT | CGG | TTT | GAT | GGC | AGG | ATC | TCC | ATC | ACT | CGT | GTG | ACG | GCA | GAT | 816 |
| Lys | His | Arg | Phe | Asp | Gly | Arg | Ile | Ser | Ile | Thr | Arg | Val | Thr | Ala | Asp | |
| | | | 260 | | | | | 265 | | | | | 270 | | | |
| ATT | TCC | CTG | GCT | AAG | CGC | TCA | GTT | CTC | AAC | AAC | CCC | AGC | AAA | CAC | ATC | 864 |
| Ile | Ser | Leu | Ala | Lys | Arg | Ser | Val | Leu | Asn | Asn | Pro | Ser | Lys | His | Ile | |
| | | 275 | | | | | 280 | | | | | 285 | | | | |
| ATC | ATT | GAG | CGC | TCC | AAC | ACA | CGC | TCC | AGC | CTG | GCT | GAG | GTG | CAG | AGT | 912 |
| Ile | Ile | Glu | Arg | Ser | Asn | Thr | Arg | Ser | Ser | Leu | Ala | Glu | Val | Gln | Ser | |
| | 290 | | | | 295 | | | | | 300 | | | | | | |
| GAA | ATC | GAG | CGA | ATC | TTC | GAG | CTG | GCC | CGG | ACC | CTT | CAG | TTG | GTC | GCT | 960 |
| Glu | Ile | Glu | Arg | Ile | Phe | Glu | Leu | Ala | Arg | Thr | Leu | Gln | Leu | Val | Ala | |
| 305 | | | | | 310 | | | | | 315 | | | | | 320 | |
| CTG | GAT | GCT | GAC | ACC | ATC | AAT | CAC | CCA | GCC | CAG | CTG | TCC | AAG | ACC | TCG | 1008 |
| Leu | Asp | Ala | Asp | Thr | Ile | Asn | His | Pro | Ala | Gln | Leu | Ser | Lys | Thr | Ser | |
| | | | | 325 | | | | | 330 | | | | | 335 | | |
| CTG | GCC | CCC | ATC | ATT | GTT | TAC | ATC | AAG | ATC | ACC | TCT | CCC | AAG | GTA | CTT | 1056 |
| Leu | Ala | Pro | Ile | Ile | Val | Tyr | Ile | Lys | Ile | Thr | Ser | Pro | Lys | Val | Leu | |
| | | | 340 | | | | | 345 | | | | | 350 | | | |
| CAA | AGG | CTC | ATC | AAG | TCC | CGA | GGA | AAG | TCT | CAG | TCC | AAA | CAC | CTC | AAT | 1104 |
| Gln | Arg | Leu | Ile | Lys | Ser | Arg | Gly | Lys | Ser | Gln | Ser | Lys | His | Leu | Asn | |
| | | 355 | | | | | 360 | | | | | 365 | | | | |
| GTC | CAA | ATA | GCG | GCC | TCG | GAA | AAG | CTG | GCA | CAG | TGC | CCC | CCT | GAA | ATG | 1152 |
| Val | Gln | Ile | Ala | Ala | Ser | Glu | Lys | Leu | Ala | Gln | Cys | Pro | Pro | Glu | Met | |
| | 370 | | | | 375 | | | | | 380 | | | | | | |
| TTT | GAC | ATC | ATC | CTG | GAT | GAG | AAC | CAA | TTG | GAG | GAT | GCC | TGC | GAG | CAT | 1200 |
| Phe | Asp | Ile | Ile | Leu | Asp | Glu | Asn | Gln | Leu | Glu | Asp | Ala | Cys | Glu | His | |
| 385 | | | | | 390 | | | | | 395 | | | | | 400 | |

| | | | | | | | | | | | | | | | |
|---|---|---|---|---|---|---|---|---|---|---|---|---|---|---|---|
|CTG|GCG|GAG|TAC|TTG|GAA|GCC|TAT|TGG|AAG|GCC|ACA|CAC|CCG|CCC|AGC|
|Leu|Ala|Glu|Tyr|Leu|Glu|Ala|Tyr|Trp|Lys|Ala|Thr|His|Pro|Pro|Ser|
| | | |405| | | |410| | | | |415| | |1248|

| | | | | | | | | | | | | | | | |
|---|---|---|---|---|---|---|---|---|---|---|---|---|---|---|---|
|AGC|ACG|CCA|CCC|AAT|CCG|CTG|CTG|AAC|CGC|ACC|ATG|GCT|ACC|GCA|GCC|
|Ser|Thr|Pro|Pro|Asn|Pro|Leu|Leu|Asn|Arg|Thr|Met|Ala|Thr|Ala|Ala|
| | |420| | | | |425| | | | |430| | |1296|

| | | | | | | | | | | | | | | | |
|---|---|---|---|---|---|---|---|---|---|---|---|---|---|---|---|
|CTG|GCT|GCC|AGC|CCT|GCC|CCT|GTC|TCC|AAC|CTC|CAG|GTA|CAG|GTG|CTC|
|Leu|Ala|Ala|Ser|Pro|Ala|Pro|Val|Ser|Asn|Leu|Gln|Val|Gln|Val|Leu|
| | |435| | | |440| | | | |445| | | |1344|

| | | | | | | | | | | | | | | | |
|---|---|---|---|---|---|---|---|---|---|---|---|---|---|---|---|
|ACC|TCG|CTC|AGG|AGA|AAC|CTC|GGC|TTC|TGG|GGC|GGG|CTG|GAG|TCC|TCA|
|Thr|Ser|Leu|Arg|Arg|Asn|Leu|Gly|Phe|Trp|Gly|Gly|Leu|Glu|Ser|Ser|
|450| | | | |455| | | | |460| | | | |1392|

| | | | | | | | | | | | | | |
|---|---|---|---|---|---|---|---|---|---|---|---|---|---|
|CAG|CGG|GGC|AGT|GTG|GTG|CCC|CAG|GAG|CAG|GAA|CAT|GCC|ATG|
|Gln|Arg|Gly|Ser|Val|Val|Pro|Gln|Glu|Gln|Glu|His|Ala|Met|
|465| | | | |470| | | | |475| | | |1434|

TAGTGGGCGC CCTGCCCGTC TTCCCTCCTG CTCTGGGGTC GGAACTGGAG TGCAGGGAAC 1494

ATGGAGGAGG AAGGGAAGAG CTTTATTTTG TAAAAAATA AGATGAGCGG CA 1546

( 2 ) INFORMATION FOR SEQ ID NO:19:

( i ) SEQUENCE CHARACTERISTICS:
        ( A ) LENGTH: 478 amino acids
        ( B ) TYPE: amino acid
        ( D ) TOPOLOGY: linear ( i i ) MOLECULE TYPE: protein ( x i ) SEQUENCE DESCRIPTION: SEQ ID NO:19:

| | | | | | | | | | | | | | | |
|---|---|---|---|---|---|---|---|---|---|---|---|---|---|---|
|Met|Val|Gln|Lys|Thr|Ser|Met|Ser|Arg|Gly|Pro|Tyr|Pro|Pro|Ser|Gln|
|1| | | |5| | | |10| | | | |15| |

| | | | | | | | | | | | | | | |
|---|---|---|---|---|---|---|---|---|---|---|---|---|---|---|
|Glu|Ile|Pro|Met|Gly|Val|Phe|Asp|Pro|Ser|Pro|Gln|Gly|Lys|Tyr|Ser|
| | | |20| | | |25| | | | |30| | |

| | | | | | | | | | | | | | | |
|---|---|---|---|---|---|---|---|---|---|---|---|---|---|---|
|Lys|Arg|Lys|Gly|Arg|Phe|Lys|Arg|Ser|Asp|Gly|Ser|Thr|Ser|Ser|Asp|
| | |35| | | | |40| | | | |45| | |

| | | | | | | | | | | | | | | |
|---|---|---|---|---|---|---|---|---|---|---|---|---|---|---|
|Thr|Thr|Ser|Asn|Ser|Phe|Val|Arg|Gln|Gly|Ser|Ala|Glu|Ser|Tyr|Thr|
| |50| | | | |55| | | | |60| | | |

| | | | | | | | | | | | | | | |
|---|---|---|---|---|---|---|---|---|---|---|---|---|---|---|
|Ser|Arg|Pro|Ser|Asp|Ser|Asp|Val|Ser|Leu|Glu|Glu|Asp|Arg|Glu|Ala|
|65| | | | |70| | | | |75| | | | |80|

| | | | | | | | | | | | | | | |
|---|---|---|---|---|---|---|---|---|---|---|---|---|---|---|
|Leu|Arg|Lys|Glu|Ala|Glu|Arg|Gln|Ala|Leu|Ala|Gln|Leu|Glu|Lys|Ala|
| | | | |85| | | | |90| | | | |95|

| | | | | | | | | | | | | | | |
|---|---|---|---|---|---|---|---|---|---|---|---|---|---|---|
|Lys|Thr|Lys|Pro|Val|Ala|Phe|Ala|Val|Arg|Thr|Asn|Val|Gly|Tyr|Asn|
| | | |100| | | | |105| | | | |110| | |

| | | | | | | | | | | | | | | |
|---|---|---|---|---|---|---|---|---|---|---|---|---|---|---|
|Pro|Ser|Pro|Gly|Asp|Glu|Val|Pro|Val|Gln|Gly|Val|Ala|Ile|Thr|Phe|
| | | |115| | | |120| | | | |125| | | |

| | | | | | | | | | | | | | | |
|---|---|---|---|---|---|---|---|---|---|---|---|---|---|---|
|Glu|Pro|Lys|Asp|Phe|Leu|His|Ile|Lys|Glu|Lys|Tyr|Asn|Asn|Asp|Trp|
| | |130| | | | |135| | | | |140| | | |

| | | | | | | | | | | | | | | |
|---|---|---|---|---|---|---|---|---|---|---|---|---|---|---|
|Trp|Ile|Gly|Arg|Leu|Val|Lys|Glu|Gly|Cys|Glu|Val|Gly|Phe|Ile|Pro|
|145| | | | |150| | | | |155| | | | |160|

| | | | | | | | | | | | | | | |
|---|---|---|---|---|---|---|---|---|---|---|---|---|---|---|
|Ser|Pro|Val|Lys|Leu|Asp|Ser|Leu|Arg|Leu|Leu|Gln|Glu|Gln|Lys|Leu|
| | | | |165| | | | |170| | | | |175|

| | | | | | | | | | | | | | | |
|---|---|---|---|---|---|---|---|---|---|---|---|---|---|---|
|Arg|Gln|Asn|Arg|Leu|Gly|Ser|Ser|Lys|Ser|Gly|Asp|Asn|Ser|Ser|Ser|
| | | |180| | | | |185| | | | |190| | |

| | | | | | | | | | | | | | | |
|---|---|---|---|---|---|---|---|---|---|---|---|---|---|---|
|Ser|Leu|Gly|Asp|Val|Val|Thr|Gly|Thr|Arg|Arg|Pro|Thr|Pro|Pro|Ala|
| | |195| | | | |200| | | | |205| | | |

| | | | | | | | | | | | | | | |
|---|---|---|---|---|---|---|---|---|---|---|---|---|---|---|
|Ser|Ala|Lys|Gln|Lys|Gln|Lys|Ser|Thr|Glu|His|Val|Pro|Pro|Tyr|Asp|
| | |210| | | | |215| | | | |220| | | |

| | | | | | | | | | | | | | | |
|---|---|---|---|---|---|---|---|---|---|---|---|---|---|---|
|Val|Val|Pro|Ser|Met|Arg|Pro|Ile|Ile|Leu|Val|Gly|Pro|Ser|Leu|Lys|
|225| | | | |230| | | | |235| | | | |240|

| | | | | | | | | | | | | | | |
|---|---|---|---|---|---|---|---|---|---|---|---|---|---|---|
|Gly|Tyr|Glu|Val|Thr|Asp|Met|Met|Gln|Lys|Ala|Leu|Phe|Asp|Phe|Leu|

|     | 245 |     |     |     |     | 250 |     |     |     |     | 255 |     |     |
| --- | --- | --- | --- | --- | --- | --- | --- | --- | --- | --- | --- | --- | --- |

Lys His Arg Phe Asp Gly Arg Ile Ser Ile Thr Arg Val Thr Ala Asp
            260                 265                 270

Ile Ser Leu Ala Lys Arg Ser Val Leu Asn Asn Pro Ser Lys His Ile
        275                 280                 285

Ile Ile Glu Arg Ser Asn Thr Arg Ser Ser Leu Ala Glu Val Gln Ser
290                         295                 300

Glu Ile Glu Arg Ile Phe Glu Leu Ala Arg Thr Leu Gln Leu Val Ala
305                 310                 315                 320

Leu Asp Ala Asp Thr Ile Asn His Pro Ala Gln Leu Ser Lys Thr Ser
                325                 330                 335

Leu Ala Pro Ile Ile Val Tyr Ile Lys Ile Thr Ser Pro Lys Val Leu
            340                 345                 350

Gln Arg Leu Ile Lys Ser Arg Gly Lys Ser Gln Ser Lys His Leu Asn
        355                 360                 365

Val Gln Ile Ala Ala Ser Glu Lys Leu Ala Gln Cys Pro Pro Glu Met
370                 375                 380

Phe Asp Ile Ile Leu Asp Glu Asn Gln Leu Glu Asp Ala Cys Glu His
385                 390                 395                 400

Leu Ala Glu Tyr Leu Glu Ala Tyr Trp Lys Ala Thr His Pro Pro Ser
            405                 410                 415

Ser Thr Pro Pro Asn Pro Leu Leu Asn Arg Thr Met Ala Thr Ala Ala
            420                 425                 430

Leu Ala Ala Ser Pro Ala Pro Val Ser Asn Leu Gln Val Gln Val Leu
        435                 440                 445

Thr Ser Leu Arg Arg Asn Leu Gly Phe Trp Gly Gly Leu Glu Ser Ser
    450                 455                 460

Gln Arg Gly Ser Val Val Pro Gln Glu Gln Glu His Ala Met
465                 470                 475

( 2 ) INFORMATION FOR SEQ ID NO:20:

( i ) SEQUENCE CHARACTERISTICS:
        ( A ) LENGTH: 65 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:20:

| | |
|---|---|
| TAAGTTGGGT GCTTTGTGTT AAGCAACACT CTGGTTCGTC CAAGTGCACT TTCCAGTCCC | 60 |
| TCTCC | 65 |

( 2 ) INFORMATION FOR SEQ ID NO:21:

( i ) SEQUENCE CHARACTERISTICS:
        ( A ) LENGTH: 448 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:21:

| | |
|---|---|
| GTGAGTGCCT AGATCCCAGA GAAGGGAATG GAGGGAGAAC ATTTGGGTTG TCCTGGTTTC | 60 |
| CTCTGGCCTA CATGAGAGAC AGGGTGACCA GGAACACCTG GGTCAGGCCT GTGGGTGCAG | 120 |
| ACTGGTCTTC TGGGAAGAGC GCAGGTCCCG TCAGTCAAAG ACTGGGTTCA AGCCCCAGAA | 180 |
| GCACCCTTCT GCGTGGAGAG TCAAGCCCTG TCTCCCAGCC TTGGTTGCCT TATCTCTAGA | 240 |

```
ATGAGGGAGT  TGGACTGAGT  GCCAAAACTT  CTTGCAGTTC  TGCCAATCTG  TAGATCTGAG     300

AGCTCTCCTT  CCCTTCTACA  TCCAGAGGCC  TCTTTTTAAC  CTTGTCCTTC  AATCCCTTGA     360

CTCTACCCAC  TGCACCCAGG  CCACACCCTC  AACCCCCTTG  GCCATGCCCC  ACTCATCCCA     420

GCCCTGCCCC  CTAACCCCGC  CTTCACAG                                           448
```

( 2 ) INFORMATION FOR SEQ ID NO:22:

( i ) SEQUENCE CHARACTERISTICS:
        ( A ) LENGTH: 1515 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:22:

```
AAGGAAGCAG  AGCGCCAGGC  ATTAGCGCAC  GTCGAGAAGG  CCAAGACCAA  GCCAGTGGCA      60

TTTGCTGTGC  GGACAAATGT  TGGCTACAAT  CCGTCTCCAG  GGGATGAGGT  GCCTGTGCAG     120

GGAGTGGCCA  TCACCTTCGA  GCCCAAAGAC  TTCCTGCACA  TCAAGGAGAA  ATACAATAAT     180

GACTGGTGGA  TCGGGCGGCT  GGTGAAGGAG  GGCTGTGAGG  TTGGCTTCAT  TCCCAGCCCC     240

GTCAAACTGG  ACAGCCTTCG  CCTGCTGCAG  GAACAGAAGC  TGCGCCAGAA  CCGCCTCGGC     300

TCCAGCAAAT  CAGGCGATAA  CTCCAGTTCC  AGTCTGGGAG  ATGTGGTGAC  TGGCACCCGC     360

CGCCCCACAC  CCCCTGCCAG  TGCCAAACAG  AAGCAGAAGT  CGACAGAGCA  TGTGCCCCCC     420

TATGACGTGG  TGCCTTCCAT  GAGGCCCATC  ATCCTGGTGG  ACCGTCGCT   CAAGGGCTAC     480

GAGGTTACAG  ACATGATGCA  GAAAGCTTTA  TTTGACTTCT  TGAAGCATCG  GTTTGATGGC     540

AGGATCTCCA  TCACTCGTGT  GACGGCAGAT  ATTTCCCTGG  CTAAGCGCTC  AGTTCTCAAC     600

AACCCCAGCA  AACACATCAT  CATTGAGCGC  TCCAACACAC  GCTCCAGCCT  GGCTGAGGTG     660

CAGAGTGAAA  TCGAGCGAAT  CTTCGAGCTG  GCCCGGACCC  TTCAGTTGGT  CGCTCTGGAT     720

GCTGACACCA  TCAATCACCC  AGCCCAGCTG  TCCAAGACCT  CGCTGGCCCC  CATCATTGTT     780

TACATCAAGA  TCACCTCTCC  CAAGGTACTT  CAAAGGCTCA  TCAAGTCCCG  AGGAAAGTCT     840

CAGTCCAAAC  ACCTCAATGT  CCAAATAGCG  GCCTCGGAAA  AGCTGGCACA  GTGCCCCCCT     900

GAAATGTTTG  ACATCATCCT  GGATGAGAAC  CAATTGGAGG  ATGCCTGCGA  GCATCTGGCG     960

GAGTACTTGG  AAGCCTATTG  GAAGGCCACA  CACCCGCCCA  GCAGCACGCC  ACCCAATCCG    1020

CTGCTGAACC  GCACCATGGC  TACCGCAGCC  CTGGCTGCCA  GCCCTGCCCC  TGTCTCCAAC    1080

CTCCAGCCAC  CCTACCTTCC  TTCCGGGACC  AGCCACTGGA  ACGGCCCACC  NNGGAGCACG    1140

CCAGCATGCA  CGAGTACTCA  GGGGAGCTGG  CCAGCCCCA   GGCCTTTACC  CCAGCAGCCA    1200

CCCACCAGGC  CGGGCAGGCA  CGCTAGGGCA  CTGTCCCGCC  AAGACACTTT  TGATGCCGAC    1260

ACCCCCGGCA  GCCGAAACTC  TGCCTACACG  GAGCTGGGAG  ACTCATGTGT  GGACATGGAG    1320

ACTGACCCCT  CAGAGGGGCC  AGGGCTTGGA  GACCCTGCAG  GGGGCGGCAC  GCCCCCAGCC    1380

CGACAGGGAT  CCTGGGAGGA  CGAGGAAGAA  GACTATGAGG  AAGAGCTGAC  CGACAACCGG    1440

AACCGGGGCC  GGAATAAGGC  CCGCTACTGC  GCTGAGGGTG  GGGGTCCAGT  TTTGGGGCGC    1500

AACAAGAATG  AGGGA                                                        1515
```

( 2 ) INFORMATION FOR SEQ ID NO:23:

( i ) SEQUENCE CHARACTERISTICS:
        ( A ) LENGTH: 505 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:23:

```
Lys Glu Ala Glu Arg Gln Ala Leu Ala His Val Glu Lys Ala Lys Thr
1               5                   10                  15
Lys Pro Val Ala Phe Ala Val Arg Thr Asn Val Gly Tyr Asn Pro Ser
                20                  25                  30
Pro Gly Asp Glu Val Pro Val Gln Gly Val Ala Ile Thr Phe Glu Pro
            35                  40                  45
Lys Asp Phe Leu His Ile Lys Glu Lys Tyr Asn Asn Asp Trp Trp Ile
    50                  55                  60
Gly Arg Leu Val Lys Glu Gly Cys Glu Val Gly Phe Ile Pro Ser Pro
65                  70                  75                  80
Val Lys Leu Asp Ser Leu Arg Leu Leu Gln Glu Gln Lys Leu Arg Gln
                85                  90                  95
Asn Arg Leu Gly Ser Ser Lys Ser Gly Asp Asn Ser Ser Ser Ser Leu
            100                 105                 110
Gly Asp Val Val Thr Gly Thr Arg Arg Pro Thr Pro Pro Ala Ser Ala
            115                 120                 125
Lys Gln Lys Gln Lys Ser Thr Glu His Val Pro Pro Tyr Asp Val Val
130                 135                 140
Pro Ser Met Arg Pro Ile Ile Leu Val Gly Pro Ser Leu Lys Gly Tyr
145                 150                 155                 160
Glu Val Thr Asp Met Met Gln Lys Ala Leu Phe Asp Phe Leu Lys His
                165                 170                 175
Arg Phe Asp Gly Arg Ile Ser Ile Thr Arg Val Thr Ala Asp Ile Ser
            180                 185                 190
Leu Ala Lys Arg Ser Val Leu Asn Asn Pro Ser Lys His Ile Ile Ile
            195                 200                 205
Glu Arg Ser Asn Thr Arg Ser Ser Leu Ala Glu Val Gln Ser Glu Ile
    210                 215                 220
Glu Arg Ile Phe Glu Leu Ala Arg Thr Leu Gln Leu Val Ala Leu Asp
225                 230                 235                 240
Ala Asp Thr Ile Asn His Pro Ala Gln Leu Ser Lys Thr Ser Leu Ala
            245                 250                 255
Pro Ile Ile Val Tyr Ile Lys Ile Thr Ser Pro Lys Val Leu Gln Arg
            260                 265                 270
Leu Ile Lys Ser Arg Gly Lys Ser Gln Ser Lys His Leu Asn Val Gln
    275                 280                 285
Ile Ala Ala Ser Glu Lys Leu Ala Gln Cys Pro Pro Glu Met Phe Asp
290                 295                 300
Ile Ile Leu Asp Glu Asn Gln Leu Glu Asp Ala Cys Glu His Leu Ala
305                 310                 315                 320
Glu Tyr Leu Glu Ala Tyr Trp Lys Ala Thr His Pro Pro Ser Ser Thr
            325                 330                 335
Pro Pro Asn Pro Leu Leu Asn Arg Thr Met Ala Thr Ala Ala Leu Ala
            340                 345                 350
Ala Ser Pro Ala Pro Val Ser Asn Leu Gln Pro Pro Tyr Leu Pro Ser
            355                 360                 365
Gly Thr Ser His Trp Asn Gly Pro Pro Xaa Ser Thr Pro Ala Cys Thr
            370                 375                 380
Ser Thr Gln Gly Ser Trp Ala Ser Pro Arg Pro Leu Pro Gln Gln Pro
385                 390                 395                 400
Pro Thr Arg Pro Gly Arg His Ala Arg Ala Leu Ser Arg Gln Asp Thr
            405                 410                 415
```

```
          Phe  Asp  Ala  Asp  Thr  Pro  Gly  Ser  Arg  Asn  Ser  Ala  Tyr  Thr  Glu  Leu
                         420                      425                      430

Gly  Asp  Ser  Cys  Val  Asp  Met  Glu  Thr  Asp  Pro  Ser  Glu  Gly  Pro  Gly
                         435                      440                      445

Leu  Gly  Asp  Pro  Ala  Gly  Gly  Thr  Pro  Pro  Ala  Arg  Gln  Gly  Ser
                    450                      455                      460

Trp  Glu  Asp  Glu  Glu  Glu  Asp  Tyr  Glu  Glu  Glu  Leu  Thr  Asp  Asn  Arg
          465                      470                      475                      480

Asn  Arg  Gly  Arg  Asn  Lys  Ala  Arg  Tyr  Cys  Ala  Glu  Gly  Gly  Gly  Pro
                              485                      490                      495

Val  Leu  Gly  Arg  Asn  Lys  Asn  Glu  Gly
                         500                      505
```

( 2 ) INFORMATION FOR SEQ ID NO:24:

( i ) SEQUENCE CHARACTERISTICS:
        ( A ) LENGTH: 3566 base pairs
        ( B ) TYPE: nucleic acid
        ( C ) STRANDEDNESS: unknown
        ( D ) TOPOLOGY: unknown ( i i ) MOLECULE TYPE: DNA (genomic)

( i x ) FEATURE:
        ( A ) NAME/KEY: CDS
        ( B ) LOCATION: 1..3273

( x i ) SEQUENCE DESCRIPTION: SEQ ID NO:24:

```
ATG  GCT  GCT  GGC  TGC  CTG  CTG  GCC  TTG  ACT  CTG  ACA  CTT  TTC  CAA  TCT        48
Met  Ala  Ala  Gly  Cys  Leu  Leu  Ala  Leu  Thr  Leu  Thr  Leu  Phe  Gln  Ser
 1                  5                        10                       15

TTG  CTC  ATC  GGC  CCC  TCG  TCG  GAG  GAG  CCG  TTC  CCT  TCG  GCC  GTC  ACT        96
Leu  Leu  Ile  Gly  Pro  Ser  Ser  Glu  Glu  Pro  Phe  Pro  Ser  Ala  Val  Thr
               20                       25                       30

ATC  AAA  TCA  TGG  GTG  GAT  AAG  ATG  CAA  GAA  GAC  CTT  GTC  ACA  CTG  GCA       144
Ile  Lys  Ser  Trp  Val  Asp  Lys  Met  Gln  Glu  Asp  Leu  Val  Thr  Leu  Ala
          35                       40                       45

AAA  ACA  GCA  AGT  GGA  GTC  AAT  CAG  CTT  GTT  GAT  ATT  TAT  GAG  AAA  TAT       192
Lys  Thr  Ala  Ser  Gly  Val  Asn  Gln  Leu  Val  Asp  Ile  Tyr  Glu  Lys  Tyr
     50                       55                       60

CAA  GAT  TTG  TAT  ACT  GTG  GAA  CCA  AAT  AAT  GCA  CGC  CAG  CTG  GTA  GAA       240
Gln  Asp  Leu  Tyr  Thr  Val  Glu  Pro  Asn  Asn  Ala  Arg  Gln  Leu  Val  Glu
 65                      70                       75                       80

ATT  GCA  GCC  AGG  GAT  ATT  GAG  AAA  CTT  CTG  AGC  AAC  AGA  TCT  AAA  GCC       288
Ile  Ala  Ala  Arg  Asp  Ile  Glu  Lys  Leu  Leu  Ser  Asn  Arg  Ser  Lys  Ala
                    85                       90                       95

CTG  GTG  AGC  CTG  GCA  TTG  GAA  GCG  GAG  AAA  GTT  CAA  GCA  GCT  CAC  CAG       336
Leu  Val  Ser  Leu  Ala  Leu  Glu  Ala  Glu  Lys  Val  Gln  Ala  Ala  His  Gln
                    100                      105                      110

TGG  AGA  GAA  GAT  TTT  GCA  AGC  AAT  GAA  GTT  GTC  TAC  TAC  AAT  GCA  AAG       384
Trp  Arg  Glu  Asp  Phe  Ala  Ser  Asn  Glu  Val  Val  Tyr  Tyr  Asn  Ala  Lys
               115                      120                      125

GAT  GAT  CTC  GAT  CCT  GAG  AAA  AAT  GAC  AGT  GAG  CCA  GGC  AGC  CAG  AGG       432
Asp  Asp  Leu  Asp  Pro  Glu  Lys  Asn  Asp  Ser  Glu  Pro  Gly  Ser  Gln  Arg
          130                      135                      140

ATA  AAA  CCT  GTT  TTC  ATT  GAA  GAT  GCT  AAT  TTT  GGA  CGA  CAA  ATA  TCT       480
Ile  Lys  Pro  Val  Phe  Ile  Glu  Asp  Ala  Asn  Phe  Gly  Arg  Gln  Ile  Ser
145                      150                      155                      160

TAT  CAG  CAC  GCA  GCA  GTC  CAT  ATT  CCT  ACT  GAC  ATC  TAT  GAG  GGC  TCA       528
Tyr  Gln  His  Ala  Ala  Val  His  Ile  Pro  Thr  Asp  Ile  Tyr  Glu  Gly  Ser
               165                      170                      175

ACA  ATT  GTG  TTA  AAT  GAA  CTC  AAC  TGG  ACA  AGT  GCC  TTA  GAT  GAA  GTT       576
Thr  Ile  Val  Leu  Asn  Glu  Leu  Asn  Trp  Thr  Ser  Ala  Leu  Asp  Glu  Val
               180                      185                      190
```

| | | | | | | | | | | | | | | | |
|---|---|---|---|---|---|---|---|---|---|---|---|---|---|---|---|
| TTC | AAA | AAG | AAT | CGC | GAG | GAA | GAC | CCT | TCA | TTA | TTG | TGG | CAG | GTT | TTT | 624
| Phe | Lys | Lys | Asn | Arg | Glu | Glu | Asp | Pro | Ser | Leu | Leu | Trp | Gln | Val | Phe |
| | 195 | | | | 200 | | | | | | 205 | | | | |
| GGC | AGT | GCC | ACT | GGC | CTA | GCT | CGA | TAT | TAT | CCA | GCT | TCA | CCA | TGG | GTT | 672
| Gly | Ser | Ala | Thr | Gly | Leu | Ala | Arg | Tyr | Tyr | Pro | Ala | Ser | Pro | Trp | Val |
| | 210 | | | | | 215 | | | | | 220 | | | | |
| GAT | AAT | AGT | AGA | ACT | CCA | AAT | AAG | ATT | GAC | CTT | TAT | GAT | GTA | CGC | AGA | 720
| Asp | Asn | Ser | Arg | Thr | Pro | Asn | Lys | Ile | Asp | Leu | Tyr | Asp | Val | Arg | Arg |
| 225 | | | | | 230 | | | | | 235 | | | | | 240 |
| AGA | CCA | TGG | TAC | ATC | CAA | GGA | GCT | GCA | TCT | CCT | AAA | GAC | ATG | CTT | ATT | 768
| Arg | Pro | Trp | Tyr | Ile | Gln | Gly | Ala | Ala | Ser | Pro | Lys | Asp | Met | Leu | Ile |
| | | | | 245 | | | | | 250 | | | | | 255 | |
| CTG | GTG | GAT | GTG | AGT | GGA | AGT | GTT | AGT | GGA | TTG | ACA | CTT | AAA | CTG | ATC | 816
| Leu | Val | Asp | Val | Ser | Gly | Ser | Val | Ser | Gly | Leu | Thr | Leu | Lys | Leu | Ile |
| | | | 260 | | | | | 265 | | | | | 270 | | |
| CGA | ACA | TCT | GTC | TCC | GAA | ATG | TTA | GAA | ACC | CTC | TCA | GAT | GAT | GAT | TTC | 864
| Arg | Thr | Ser | Val | Ser | Glu | Met | Leu | Glu | Thr | Leu | Ser | Asp | Asp | Asp | Phe |
| | | 275 | | | | | 280 | | | | | 285 | | | |
| GTG | AAT | GTA | GCT | TCA | TTT | AAC | AGC | AAT | GCT | CAG | GAT | GTA | AGC | TGT | TTT | 912
| Val | Asn | Val | Ala | Ser | Phe | Asn | Ser | Asn | Ala | Gln | Asp | Val | Ser | Cys | Phe |
| | 290 | | | | | 295 | | | | | 300 | | | | |
| CAG | CAC | CTT | GTC | CAA | GCA | AAT | GTA | AGA | AAT | AAA | AAA | GTG | TTG | AAA | GAC | 960
| Gln | His | Leu | Val | Gln | Ala | Asn | Val | Arg | Asn | Lys | Lys | Val | Leu | Lys | Asp |
| 305 | | | | | 310 | | | | | 315 | | | | | 320 |
| GCG | GTG | AAT | AAT | ATC | ACA | GCC | AAA | GGA | ATT | ACA | GAT | TAT | AAG | AAG | GGC | 1008
| Ala | Val | Asn | Asn | Ile | Thr | Ala | Lys | Gly | Ile | Thr | Asp | Tyr | Lys | Lys | Gly |
| | | | | 325 | | | | | 330 | | | | | 335 | |
| TTT | AGT | TTT | GCT | TTT | GAA | CAG | CTG | CTT | AAT | TAT | AAT | GTT | TCC | AGA | GCA | 1056
| Phe | Ser | Phe | Ala | Phe | Glu | Gln | Leu | Leu | Asn | Tyr | Asn | Val | Ser | Arg | Ala |
| | | | 340 | | | | | 345 | | | | | 350 | | |
| AAC | TGC | AAT | AAG | ATT | ATT | ATG | CTA | TTC | ACG | GAT | GGA | GGA | GAA | GAG | AGA | 1104
| Asn | Cys | Asn | Lys | Ile | Ile | Met | Leu | Phe | Thr | Asp | Gly | Gly | Glu | Glu | Arg |
| | | 355 | | | | | 360 | | | | | 365 | | | |
| GCC | CAG | GAG | ATA | TTT | AAC | AAA | TAC | AAT | AAA | GAT | AAA | AAA | GTA | CGT | GTA | 1152
| Ala | Gln | Glu | Ile | Phe | Asn | Lys | Tyr | Asn | Lys | Asp | Lys | Lys | Val | Arg | Val |
| | 370 | | | | | 375 | | | | | 380 | | | | |
| TTC | AGG | TTT | TCA | GTT | GGT | CAA | CAC | AAT | TAT | GAG | AGA | GGA | CCT | ATT | CAG | 1200
| Phe | Arg | Phe | Ser | Val | Gly | Gln | His | Asn | Tyr | Glu | Arg | Gly | Pro | Ile | Gln |
| 385 | | | | | 390 | | | | | 395 | | | | | 400 |
| TGG | ATG | GCC | TGT | GAA | AAC | AAA | GGT | TAT | TAT | TAT | GAA | ATT | CCT | TCC | ATT | 1248
| Trp | Met | Ala | Cys | Glu | Asn | Lys | Gly | Tyr | Tyr | Tyr | Glu | Ile | Pro | Ser | Ile |
| | | | 405 | | | | | 410 | | | | | 415 | | |
| GGT | GCA | ATA | AGA | ATC | AAT | ACT | CAG | GAA | TAT | TTG | GAT | GTT | TTG | GGA | AGA | 1296
| Gly | Ala | Ile | Arg | Ile | Asn | Thr | Gln | Glu | Tyr | Leu | Asp | Val | Leu | Gly | Arg |
| | | | 420 | | | | | 425 | | | | | 430 | | |
| CCA | ATG | GTT | TTA | GCA | GGA | GAC | AAA | GCT | AAG | CAA | GTC | CAA | TGG | ACA | AAT | 1344
| Pro | Met | Val | Leu | Ala | Gly | Asp | Lys | Ala | Lys | Gln | Val | Gln | Trp | Thr | Asn |
| | | 435 | | | | | 440 | | | | | 445 | | | |
| GTG | TAC | CTG | GAT | GCA | TTG | GAA | CTG | GGA | CTT | GTC | ATT | ACT | GGA | ACT | CTT | 1392
| Val | Tyr | Leu | Asp | Ala | Leu | Glu | Leu | Gly | Leu | Val | Ile | Thr | Gly | Thr | Leu |
| | 450 | | | | | 455 | | | | | 460 | | | | |
| CCG | GTC | TTC | AAC | ATA | ACC | GGC | CAA | TTT | GAA | AAT | AAG | ACA | AAC | TTA | AAG | 1440
| Pro | Val | Phe | Asn | Ile | Thr | Gly | Gln | Phe | Glu | Asn | Lys | Thr | Asn | Leu | Lys |
| 465 | | | | 470 | | | | | 475 | | | | | 480 | |
| AAC | CAG | CTG | ATT | CTT | GGT | GTG | ATG | GGA | GTA | GAT | GTG | TCT | TTG | GAA | GAT | 1488
| Asn | Gln | Leu | Ile | Leu | Gly | Val | Met | Gly | Val | Asp | Val | Ser | Leu | Glu | Asp |
| | | | | 485 | | | | | 490 | | | | | 495 | |
| ATT | AAA | AGA | CTG | ACA | CCA | CGT | TTT | ACA | CTG | TGC | CCC | AAT | GGG | TAT | TAC | 1536
| Ile | Lys | Arg | Leu | Thr | Pro | Arg | Phe | Thr | Leu | Cys | Pro | Asn | Gly | Tyr | Tyr |
| | | | 500 | | | | | 505 | | | | | 510 | | |
| TTT | GCA | ATC | GAT | CCT | AAT | GGT | TAT | GTT | TTA | TTA | CAT | CCA | AAT | CTT | CAG | 1584

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| Phe | Ala | Ile | Asp | Pro | Asn | Gly | Tyr | Val | Leu | Leu | His | Pro | Asn | Leu | Gln |      |
|     |     | 515 |     |     |     |     | 520 |     |     |     |     | 525 |     |     |     |      |
| CCA | AAG | AAC | CCC | AAA | TCT | CAG | GAG | CCA | GTA | ACA | TTG | GAT | TTC | CTT | GAT | 1632 |
| Pro | Lys | Asn | Pro | Lys | Ser | Gln | Glu | Pro | Val | Thr | Leu | Asp | Phe | Leu | Asp |      |
|     | 530 |     |     |     | 535 |     |     |     |     | 540 |     |     |     |     |     |      |
| GCA | GAG | TTA | GAG | AAT | GAT | ATT | AAA | GTG | GAG | ATT | CGA | AAT | AAG | ATG | ATT | 1680 |
| Ala | Glu | Leu | Glu | Asn | Asp | Ile | Lys | Val | Glu | Ile | Arg | Asn | Lys | Met | Ile |      |
| 545 |     |     |     |     | 550 |     |     |     |     | 555 |     |     |     |     | 560 |      |
| GAT | GGG | GAA | AGT | GGA | GAA | AAA | ACA | TTC | AGA | ACT | CTG | GTT | AAA | TCT | CAA | 1728 |
| Asp | Gly | Glu | Ser | Gly | Glu | Lys | Thr | Phe | Arg | Thr | Leu | Val | Lys | Ser | Gln |      |
|     |     |     |     | 565 |     |     |     |     | 570 |     |     |     |     | 575 |     |      |
| GAT | GAG | AGA | TAT | ATT | GAC | AAA | GGA | AAC | AGG | ACA | TAC | ACA | TGG | ACA | CCT | 1776 |
| Asp | Glu | Arg | Tyr | Ile | Asp | Lys | Gly | Asn | Arg | Thr | Tyr | Thr | Trp | Thr | Pro |      |
|     |     |     | 580 |     |     |     |     | 585 |     |     |     |     | 590 |     |     |      |
| GTC | AAT | GGC | ACA | GAT | TAC | AGT | TTG | GCC | TTG | GTA | TTA | CCA | ACC | TAC | AGT | 1824 |
| Val | Asn | Gly | Thr | Asp | Tyr | Ser | Leu | Ala | Leu | Val | Leu | Pro | Thr | Tyr | Ser |      |
|     |     | 595 |     |     |     |     | 600 |     |     |     |     | 605 |     |     |     |      |
| TTT | TAC | TAT | ATA | AAA | GCC | AAA | CTA | GAA | GAG | ACA | ATA | ACT | CAG | GCC | AGA | 1872 |
| Phe | Tyr | Tyr | Ile | Lys | Ala | Lys | Leu | Glu | Glu | Thr | Ile | Thr | Gln | Ala | Arg |      |
|     | 610 |     |     |     |     | 615 |     |     |     |     | 620 |     |     |     |     |      |
| TCA | AAA | AAG | GGC | AAA | ATG | AAG | GAT | TCG | GAA | ACC | CTG | AAG | CCA | GAT | AAT | 1920 |
| Ser | Lys | Lys | Gly | Lys | Met | Lys | Asp | Ser | Glu | Thr | Leu | Lys | Pro | Asp | Asn |      |
| 625 |     |     |     |     | 630 |     |     |     |     | 635 |     |     |     |     | 640 |      |
| TTT | GAA | GAA | TCT | GGC | TAT | ACA | TTC | ATA | GCA | CCA | AGA | GAT | TAC | TGC | AAT | 1968 |
| Phe | Glu | Glu | Ser | Gly | Tyr | Thr | Phe | Ile | Ala | Pro | Arg | Asp | Tyr | Cys | Asn |      |
|     |     |     |     | 645 |     |     |     |     | 650 |     |     |     |     | 655 |     |      |
| GAC | CTG | AAA | ATA | TCG | GAT | AAT | AAC | ACT | GAA | TTT | CTT | TTA | AAT | TTC | AAC | 2016 |
| Asp | Leu | Lys | Ile | Ser | Asp | Asn | Asn | Thr | Glu | Phe | Leu | Leu | Asn | Phe | Asn |      |
|     |     |     | 660 |     |     |     |     | 665 |     |     |     |     | 670 |     |     |      |
| GAG | TTT | ATT | GAT | AGA | AAA | ACT | CCA | AAC | AAC | CCA | TCA | TGT | AAC | GCG | GAT | 2064 |
| Glu | Phe | Ile | Asp | Arg | Lys | Thr | Pro | Asn | Asn | Pro | Ser | Cys | Asn | Ala | Asp |      |
|     |     | 675 |     |     |     |     | 680 |     |     |     |     | 685 |     |     |     |      |
| TTG | ATT | AAT | AGA | GTC | TTG | CTT | GAT | GCA | GGC | TTT | ACA | AAT | GAA | CTT | GTC | 2112 |
| Leu | Ile | Asn | Arg | Val | Leu | Leu | Asp | Ala | Gly | Phe | Thr | Asn | Glu | Leu | Val |      |
|     | 690 |     |     |     |     | 695 |     |     |     |     | 700 |     |     |     |     |      |
| CAA | AAT | TAC | TGG | AGT | AAG | CAG | AAA | AAT | ATC | AAG | GGA | GTG | AAA | GCA | CGA | 2160 |
| Gln | Asn | Tyr | Trp | Ser | Lys | Gln | Lys | Asn | Ile | Lys | Gly | Val | Lys | Ala | Arg |      |
| 705 |     |     |     |     | 710 |     |     |     |     | 715 |     |     |     |     | 720 |      |
| TTT | GTT | GTG | ACT | GAT | GGT | GGG | ATT | ACC | AGA | GTT | TAT | CCC | AAA | GAG | GCT | 2208 |
| Phe | Val | Val | Thr | Asp | Gly | Gly | Ile | Thr | Arg | Val | Tyr | Pro | Lys | Glu | Ala |      |
|     |     |     |     | 725 |     |     |     |     | 730 |     |     |     |     | 735 |     |      |
| GGA | GAA | AAT | TGG | CAA | GAA | AAC | CCA | GAG | ACA | TAT | GAG | GAC | AGC | TTC | TAT | 2256 |
| Gly | Glu | Asn | Trp | Gln | Glu | Asn | Pro | Glu | Thr | Tyr | Glu | Asp | Ser | Phe | Tyr |      |
|     |     |     | 740 |     |     |     |     | 745 |     |     |     |     | 750 |     |     |      |
| AAA | AGG | AGC | CTA | GAT | AAT | GAT | AAC | TAT | GTT | TTC | ACT | GCT | CCC | TAC | TTT | 2304 |
| Lys | Arg | Ser | Leu | Asp | Asn | Asp | Asn | Tyr | Val | Phe | Thr | Ala | Pro | Tyr | Phe |      |
|     |     | 755 |     |     |     |     | 760 |     |     |     |     | 765 |     |     |     |      |
| AAC | AAA | AGT | GGA | CCT | GGT | GCC | TAT | GAA | TCG | GGC | ATT | ATG | GTA | AGC | AAA | 2352 |
| Asn | Lys | Ser | Gly | Pro | Gly | Ala | Tyr | Glu | Ser | Gly | Ile | Met | Val | Ser | Lys |      |
| 770 |     |     |     |     | 775 |     |     |     |     | 780 |     |     |     |     |     |      |
| GCT | GTA | GAA | ATA | TAT | ATT | CAA | GGG | AAA | CTT | CTT | AAA | CCT | GCA | GTT | GTT | 2400 |
| Ala | Val | Glu | Ile | Tyr | Ile | Gln | Gly | Lys | Leu | Leu | Lys | Pro | Ala | Val | Val |      |
| 785 |     |     |     |     | 790 |     |     |     |     | 795 |     |     |     |     | 800 |      |
| GGA | ATT | AAA | ATT | GAT | GTA | AAT | TCC | TGG | ATA | GAG | AAT | TTC | ACC | AAA | ACC | 2448 |
| Gly | Ile | Lys | Ile | Asp | Val | Asn | Ser | Trp | Ile | Glu | Asn | Phe | Thr | Lys | Thr |      |
|     |     |     |     | 805 |     |     |     |     | 810 |     |     |     |     | 815 |     |      |
| TCA | ATC | AGA | GAT | CCG | TGT | GCT | GGT | CCA | GTT | TGT | GAC | TGC | AAA | AGA | AAC | 2496 |
| Ser | Ile | Arg | Asp | Pro | Cys | Ala | Gly | Pro | Val | Cys | Asp | Cys | Lys | Arg | Asn |      |
|     |     |     | 820 |     |     |     |     | 825 |     |     |     |     | 830 |     |     |      |
| AGT | GAC | GTA | ATG | GAT | TGT | GTG | ATT | CTG | GAT | GAT | GGT | GGG | TTT | CTT | CTG | 2544 |
| Ser | Asp | Val | Met | Asp | Cys | Val | Ile | Leu | Asp | Asp | Gly | Gly | Phe | Leu | Leu |      |
|     |     | 835 |     |     |     |     | 840 |     |     |     |     | 845 |     |     |     |      |

| | | | | | | | | | | | | | | | | |
|---|---|---|---|---|---|---|---|---|---|---|---|---|---|---|---|---|
| ATG | GCA | AAT | CAT | GAT | GAT | TAT | ACT | AAT | CAG | ATT | GGA | AGA | TTT | TTT | GGA | 2592 |
| Met | Ala | Asn | His | Asp | Asp | Tyr | Thr | Asn | Gln | Ile | Gly | Arg | Phe | Phe | Gly | |
| | 850 | | | | 855 | | | | | 860 | | | | | | |
| GAG | ATT | GAT | CCC | AGC | TTG | ATG | AGA | CAC | CTG | GTT | AAT | ATA | TCA | GTT | TAT | 2640 |
| Glu | Ile | Asp | Pro | Ser | Leu | Met | Arg | His | Leu | Val | Asn | Ile | Ser | Val | Tyr | |
| 865 | | | | | 870 | | | | | 875 | | | | | 880 | |
| GCT | TTT | AAC | AAA | TCT | TAT | GAT | TAT | CAG | TCA | GTA | TGT | GAG | CCC | GGT | GCT | 2688 |
| Ala | Phe | Asn | Lys | Ser | Tyr | Asp | Tyr | Gln | Ser | Val | Cys | Glu | Pro | Gly | Ala | |
| | | | | 885 | | | | | 890 | | | | | 895 | | |
| GCA | CCA | AAA | CAA | GGA | GCA | GGA | CAT | CGC | TCA | GCA | TAT | GTG | CCA | TCA | GTA | 2736 |
| Ala | Pro | Lys | Gln | Gly | Ala | Gly | His | Arg | Ser | Ala | Tyr | Val | Pro | Ser | Val | |
| | | | 900 | | | | | 905 | | | | | 910 | | | |
| GCA | GAC | ATA | TTA | CAA | ATT | GGC | TGG | TGG | GCC | ACT | GCT | GCT | GCC | TGG | TCT | 2784 |
| Ala | Asp | Ile | Leu | Gln | Ile | Gly | Trp | Trp | Ala | Thr | Ala | Ala | Ala | Trp | Ser | |
| | | 915 | | | | | 920 | | | | | 925 | | | | |
| ATT | CTA | CAG | CAG | TTT | CTC | TTG | AGT | TTG | ACC | TTT | CCA | CGA | CTC | CTT | GAG | 2832 |
| Ile | Leu | Gln | Gln | Phe | Leu | Leu | Ser | Leu | Thr | Phe | Pro | Arg | Leu | Leu | Glu | |
| | 930 | | | | | 935 | | | | | 940 | | | | | |
| GCA | GTT | GAG | ATG | GAG | GAT | GAT | GAC | TTC | ACG | GCC | TCC | CTG | TCC | AAG | CAG | 2880 |
| Ala | Val | Glu | Met | Glu | Asp | Asp | Asp | Phe | Thr | Ala | Ser | Leu | Ser | Lys | Gln | |
| 945 | | | | | 950 | | | | | 955 | | | | | 960 | |
| AGC | TGC | ATT | ACT | GAA | CAA | ACC | CAG | TAT | TTC | TTC | GAT | AAC | GAC | AGT | AAA | 2928 |
| Ser | Cys | Ile | Thr | Glu | Gln | Thr | Gln | Tyr | Phe | Phe | Asp | Asn | Asp | Ser | Lys | |
| | | | | 965 | | | | | 970 | | | | | 975 | | |
| TCA | TTC | AGT | GGT | GTA | TTA | GAC | TGT | GGA | AAC | TGT | TCC | AGA | ATC | TTT | CAT | 2976 |
| Ser | Phe | Ser | Gly | Val | Leu | Asp | Cys | Gly | Asn | Cys | Ser | Arg | Ile | Phe | His | |
| | | | 980 | | | | | 985 | | | | | 990 | | | |
| GGA | GAA | AAG | CTT | ATG | AAC | ACC | AAC | TTA | ATA | TTC | ATA | ATG | GTT | GAG | AGC | 3024 |
| Gly | Glu | Lys | Leu | Met | Asn | Thr | Asn | Leu | Ile | Phe | Ile | Met | Val | Glu | Ser | |
| | | 995 | | | | | 1000 | | | | | 1005 | | | | |
| AAA | GGG | ACA | TGT | CCA | TGT | GAC | ACA | CGA | CTG | CTC | ATA | CAA | GCG | GAG | CAG | 3072 |
| Lys | Gly | Thr | Cys | Pro | Cys | Asp | Thr | Arg | Leu | Leu | Ile | Gln | Ala | Glu | Gln | |
| | | 1010 | | | | | 1015 | | | | | 1020 | | | | |
| ACT | TCT | GAC | GGT | CCA | AAT | CCT | TGT | GAC | ATG | GTT | AAG | CAA | CCT | AGA | TAC | 3120 |
| Thr | Ser | Asp | Gly | Pro | Asn | Pro | Cys | Asp | Met | Val | Lys | Gln | Pro | Arg | Tyr | |
| 1025 | | | | | 1030 | | | | | 1035 | | | | | 1040 | |
| CGA | AAA | GGG | CCT | GAT | GTC | TGC | TTT | GAT | AAC | AAT | GTC | TTG | GAG | GAT | TAT | 3168 |
| Arg | Lys | Gly | Pro | Asp | Val | Cys | Phe | Asp | Asn | Asn | Val | Leu | Glu | Asp | Tyr | |
| | | | | 1045 | | | | | 1050 | | | | | 1055 | | |
| ACT | GAC | TGT | GGT | GGT | GTT | TCT | GGA | TTA | AAT | CCC | TCC | CTG | TGG | TAT | ATC | 3216 |
| Thr | Asp | Cys | Gly | Gly | Val | Ser | Gly | Leu | Asn | Pro | Ser | Leu | Trp | Tyr | Ile | |
| | | | 1060 | | | | | 1065 | | | | | 1070 | | | |
| ATT | GGA | ATC | CAG | TTT | CTA | CTA | CTT | TGG | CTG | GTA | TCT | GGC | AGC | ACA | CAC | 3264 |
| Ile | Gly | Ile | Gln | Phe | Leu | Leu | Leu | Trp | Leu | Val | Ser | Gly | Ser | Thr | His | |
| | | 1075 | | | | | 1080 | | | | | 1085 | | | | |
| CGG | CTG | TTA | TGACCTTCTA AAAACCAAAT CTGCATAGTT AAACTCCAGA | | | | | | | | | | | | | 3313 |
| Arg | Leu | Leu | | | | | | | | | | | | | | |
| | | 1090 | | | | | | | | | | | | | | |

CCCTGCCAAA ACATGAGCCC TGCCCTCAAT TACAGTAACG TAGGGTCAGC TATAAAATCA    3373

GACAAACATT AGCTGGGCCT GTTCCATGGC ATAACACTAA GGCGCAGACT CCTAAGGCAC    3433

CCACTGGCTG CATGTCAGGG TGTCAGATCC TTAAACGTGT GTGAATGCTG CATCATCTAT    3493

GTGTAACATC AAAGCAAAAT CCTATACGTG TCCTCTATTG GAAAATTTGG GCGTTTGTTG    3553

TTGCATTGTT GGT    3566

( 2 ) INFORMATION FOR SEQ ID NO:25:

( i ) SEQUENCE CHARACTERISTICS:
        ( A ) LENGTH: 1091 amino acids
        ( B ) TYPE: amino acid
        ( D ) TOPOLOGY: linear ( i i ) MOLECULE TYPE: protein ( x i ) SEQUENCE DESCRIPTION: SEQ ID NO:25:

| | | | | | | | | | | | | | | |
|---|---|---|---|---|---|---|---|---|---|---|---|---|---|---|
| Met | Ala | Ala | Gly | Cys | Leu | Leu | Ala | Leu | Thr | Leu | Thr | Leu | Phe | Gln | Ser |
| 1 | | | | 5 | | | | | 10 | | | | | 15 |
| Leu | Leu | Ile | Gly | Pro | Ser | Ser | Glu | Glu | Pro | Phe | Pro | Ser | Ala | Val | Thr |
| | | | 20 | | | | | 25 | | | | | 30 | | |
| Ile | Lys | Ser | Trp | Val | Asp | Lys | Met | Gln | Glu | Asp | Leu | Val | Thr | Leu | Ala |
| | | 35 | | | | | 40 | | | | | 45 | | | |
| Lys | Thr | Ala | Ser | Gly | Val | Asn | Gln | Leu | Val | Asp | Ile | Tyr | Glu | Lys | Tyr |
| | 50 | | | | | 55 | | | | | 60 | | | | |
| Gln | Asp | Leu | Tyr | Thr | Val | Glu | Pro | Asn | Asn | Ala | Arg | Gln | Leu | Val | Glu |
| 65 | | | | | 70 | | | | | 75 | | | | | 80 |
| Ile | Ala | Ala | Arg | Asp | Ile | Glu | Lys | Leu | Leu | Ser | Asn | Arg | Ser | Lys | Ala |
| | | | | 85 | | | | | 90 | | | | | 95 | |
| Leu | Val | Ser | Leu | Ala | Leu | Glu | Ala | Glu | Lys | Val | Gln | Ala | Ala | His | Gln |
| | | | 100 | | | | | 105 | | | | | 110 | | |
| Trp | Arg | Glu | Asp | Phe | Ala | Ser | Asn | Glu | Val | Val | Tyr | Tyr | Asn | Ala | Lys |
| | | 115 | | | | | 120 | | | | | 125 | | | |
| Asp | Asp | Leu | Asp | Pro | Glu | Lys | Asn | Asp | Ser | Glu | Pro | Gly | Ser | Gln | Arg |
| | 130 | | | | | 135 | | | | | 140 | | | | |
| Ile | Lys | Pro | Val | Phe | Ile | Glu | Asp | Ala | Asn | Phe | Gly | Arg | Gln | Ile | Ser |
| 145 | | | | | 150 | | | | | 155 | | | | | 160 |
| Tyr | Gln | His | Ala | Ala | Val | His | Ile | Pro | Thr | Asp | Ile | Tyr | Glu | Gly | Ser |
| | | | | 165 | | | | | 170 | | | | | 175 | |
| Thr | Ile | Val | Leu | Asn | Glu | Leu | Asn | Trp | Thr | Ser | Ala | Leu | Asp | Glu | Val |
| | | | 180 | | | | | 185 | | | | | 190 | | |
| Phe | Lys | Lys | Asn | Arg | Glu | Glu | Asp | Pro | Ser | Leu | Leu | Trp | Gln | Val | Phe |
| | | 195 | | | | | 200 | | | | | 205 | | | |
| Gly | Ser | Ala | Thr | Gly | Leu | Ala | Arg | Tyr | Tyr | Pro | Ala | Ser | Pro | Trp | Val |
| | 210 | | | | | 215 | | | | | 220 | | | | |
| Asp | Asn | Ser | Arg | Thr | Pro | Asn | Lys | Ile | Asp | Leu | Tyr | Asp | Val | Arg | Arg |
| 225 | | | | | 230 | | | | | 235 | | | | | 240 |
| Arg | Pro | Trp | Tyr | Ile | Gln | Gly | Ala | Ala | Ser | Pro | Lys | Asp | Met | Leu | Ile |
| | | | | 245 | | | | | 250 | | | | | 255 | |
| Leu | Val | Asp | Val | Ser | Gly | Ser | Val | Ser | Gly | Leu | Thr | Leu | Lys | Leu | Ile |
| | | | 260 | | | | | 265 | | | | | 270 | | |
| Arg | Thr | Ser | Val | Ser | Glu | Met | Leu | Glu | Thr | Leu | Ser | Asp | Asp | Asp | Phe |
| | | 275 | | | | | 280 | | | | | 285 | | | |
| Val | Asn | Val | Ala | Ser | Phe | Asn | Ser | Asn | Ala | Gln | Asp | Val | Ser | Cys | Phe |
| | 290 | | | | | 295 | | | | | 300 | | | | |
| Gln | His | Leu | Val | Gln | Ala | Asn | Val | Arg | Asn | Lys | Lys | Val | Leu | Lys | Asp |
| 305 | | | | | 310 | | | | | 315 | | | | | 320 |
| Ala | Val | Asn | Asn | Ile | Thr | Ala | Lys | Gly | Ile | Thr | Asp | Tyr | Lys | Lys | Gly |
| | | | | 325 | | | | | 330 | | | | | 335 | |
| Phe | Ser | Phe | Ala | Phe | Glu | Gln | Leu | Leu | Asn | Tyr | Asn | Val | Ser | Arg | Ala |
| | | | 340 | | | | | 345 | | | | | 350 | | |
| Asn | Cys | Asn | Lys | Ile | Ile | Met | Leu | Phe | Thr | Asp | Gly | Gly | Glu | Glu | Arg |
| | | 355 | | | | | 360 | | | | | 365 | | | |
| Ala | Gln | Glu | Ile | Phe | Asn | Lys | Tyr | Asn | Lys | Asp | Lys | Lys | Val | Arg | Val |
| | 370 | | | | | 375 | | | | | 380 | | | | |
| Phe | Arg | Phe | Ser | Val | Gly | Gln | His | Asn | Tyr | Glu | Arg | Gly | Pro | Ile | Gln |
| 385 | | | | | 390 | | | | | 395 | | | | | 400 |
| Trp | Met | Ala | Cys | Glu | Asn | Lys | Gly | Tyr | Tyr | Tyr | Glu | Ile | Pro | Ser | Ile |
| | | | | 405 | | | | | 410 | | | | | 415 | |

| | | | | | | | | | | | | | | |
|---|---|---|---|---|---|---|---|---|---|---|---|---|---|---|
| Gly | Ala | Ile | Arg 420 | Ile | Asn | Thr | Gln | Glu 425 | Tyr | Leu | Asp | Val | Leu 430 | Gly | Arg |
| Pro | Met | Val 435 | Leu | Ala | Gly | Asp | Ala 440 | Lys | Gln | Val | Gln 445 | Trp | Thr | Asn |
| Val | Tyr 450 | Leu | Asp | Ala | Leu 455 | Glu | Leu | Gly | Leu | Val 460 | Ile | Thr | Gly | Thr | Leu |
| Pro 465 | Val | Phe | Asn | Ile 470 | Thr | Gly | Gln | Phe | Glu 475 | Asn | Lys | Thr | Asn | Leu | Lys 480 |
| Asn | Gln | Leu | Ile | Leu 485 | Gly | Val | Met | Gly 490 | Val | Asp | Val | Ser | Leu 495 | Glu | Asp |
| Ile | Lys | Arg | Leu 500 | Thr | Pro | Arg | Phe | Thr 505 | Leu | Cys | Pro | Asn | Gly 510 | Tyr | Tyr |
| Phe | Ala | Ile 515 | Asp | Pro | Asn | Gly | Tyr 520 | Val | Leu | Leu | His | Pro 525 | Asn | Leu | Gln |
| Pro | Lys 530 | Asn | Pro | Lys | Ser | Gln 535 | Glu | Pro | Val | Thr | Leu 540 | Asp | Phe | Leu | Asp |
| Ala 545 | Glu | Leu | Glu | Asn | Asp 550 | Ile | Lys | Val | Glu | Ile 555 | Arg | Asn | Lys | Met | Ile 560 |
| Asp | Gly | Glu | Ser | Gly 565 | Glu | Lys | Thr | Phe | Arg 570 | Thr | Leu | Val | Lys | Ser 575 | Gln |
| Asp | Glu | Arg | Tyr 580 | Ile | Asp | Lys | Gly | Asn 585 | Arg | Thr | Tyr | Thr | Trp 590 | Thr | Pro |
| Val | Asn | Gly 595 | Thr | Asp | Tyr | Ser | Leu 600 | Ala | Leu | Val | Leu | Pro 605 | Thr | Tyr | Ser |
| Phe | Tyr 610 | Tyr | Ile | Lys | Ala | Lys 615 | Leu | Glu | Glu | Thr | Ile 620 | Thr | Gln | Ala | Arg |
| Ser 625 | Lys | Lys | Gly | Lys | Met 630 | Lys | Asp | Ser | Glu | Thr 635 | Leu | Lys | Pro | Asp | Asn 640 |
| Phe | Glu | Glu | Ser | Gly 645 | Tyr | Thr | Phe | Ile | Ala 650 | Pro | Arg | Asp | Tyr | Cys 655 | Asn |
| Asp | Leu | Lys | Ile | Ser 660 | Asp | Asn | Asn | Thr | Glu 665 | Phe | Leu | Leu | Asn 670 | Phe | Asn |
| Glu | Phe | Ile 675 | Asp | Arg | Lys | Thr | Pro 680 | Asn | Asn | Pro | Ser | Cys 685 | Asn | Ala | Asp |
| Leu | Ile 690 | Asn | Arg | Val | Leu | Leu 695 | Asp | Ala | Gly | Phe | Thr 700 | Asn | Glu | Leu | Val |
| Gln 705 | Asn | Tyr | Trp | Ser | Lys 710 | Gln | Lys | Asn | Ile | Lys 715 | Gly | Val | Lys | Ala | Arg 720 |
| Phe | Val | Val | Thr | Asp 725 | Gly | Gly | Ile | Thr | Arg 730 | Val | Tyr | Pro | Lys | Glu 735 | Ala |
| Gly | Glu | Asn | Trp 740 | Gln | Glu | Asn | Pro | Glu 745 | Thr | Tyr | Glu | Asp | Ser 750 | Phe | Tyr |
| Lys | Arg | Ser 755 | Leu | Asp | Asn | Asp | Asn 760 | Tyr | Val | Phe | Thr | Ala 765 | Pro | Tyr | Phe |
| Asn | Lys 770 | Ser | Gly | Pro | Gly | Ala 775 | Tyr | Glu | Ser | Gly | Ile 780 | Met | Val | Ser | Lys |
| Ala 785 | Val | Glu | Ile | Tyr | Ile 790 | Gln | Gly | Lys | Leu | Leu 795 | Lys | Pro | Ala | Val | Val 800 |
| Gly | Ile | Lys | Ile | Asp 805 | Val | Asn | Ser | Trp | Ile 810 | Glu | Asn | Phe | Thr | Lys 815 | Thr |
| Ser | Ile | Arg | Asp 820 | Pro | Cys | Ala | Gly | Pro 825 | Val | Cys | Asp | Cys | Lys 830 | Arg | Asn |
| Ser | Asp | Val 835 | Met | Asp | Cys | Val | Ile 840 | Leu | Asp | Asp | Gly | Gly 845 | Phe | Leu | Leu |

| | | | | | | | | | | | | | |
|---|---|---|---|---|---|---|---|---|---|---|---|---|---|
|Met|Ala|Asn|His|Asp|Asp|Tyr|Thr|Asn|Gln|Ile|Gly|Arg|Phe|Phe|Gly|
| |850| | | | |855| | | | |860| | | | |

Glu Ile Asp Pro Ser Leu Met Arg His Leu Val Asn Ile Ser Val Tyr
865                   870                   875                   880

Ala Phe Asn Lys Ser Tyr Asp Tyr Gln Ser Val Cys Glu Pro Gly Ala
                885                   890                   895

Ala Pro Lys Gln Gly Ala Gly His Arg Ser Ala Tyr Val Pro Ser Val
            900                   905                   910

Ala Asp Ile Leu Gln Ile Gly Trp Trp Ala Thr Ala Ala Ala Trp Ser
            915                   920                   925

Ile Leu Gln Gln Phe Leu Leu Ser Leu Thr Phe Pro Arg Leu Leu Glu
    930                   935                   940

Ala Val Glu Met Glu Asp Asp Phe Thr Ala Ser Leu Ser Lys Gln
945                   950                   955                   960

Ser Cys Ile Thr Glu Gln Thr Gln Tyr Phe Phe Asp Asn Asp Ser Lys
                965                   970                   975

Ser Phe Ser Gly Val Leu Asp Cys Gly Asn Cys Ser Arg Ile Phe His
            980                   985                   990

Gly Glu Lys Leu Met Asn Thr Asn Leu Ile Phe Ile Met Val Glu Ser
        995                   1000                  1005

Lys Gly Thr Cys Pro Cys Asp Thr Arg Leu Leu Ile Gln Ala Glu Gln
    1010                  1015                  1020

Thr Ser Asp Gly Pro Asn Pro Cys Asp Met Val Lys Gln Pro Arg Tyr
1025                  1030                  1035                  1040

Arg Lys Gly Pro Asp Val Cys Phe Asp Asn Asn Val Leu Glu Asp Tyr
            1045                  1050                  1055

Thr Asp Cys Gly Gly Val Ser Gly Leu Asn Pro Ser Leu Trp Tyr Ile
            1060                  1065                  1070

Ile Gly Ile Gln Phe Leu Leu Leu Trp Leu Val Ser Gly Ser Thr His
        1075                  1080                  1085

Arg Leu Leu
    1090

( 2 ) INFORMATION FOR SEQ ID NO:26:

( i ) SEQUENCE CHARACTERISTICS:
        ( A ) LENGTH: 34 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:26:

GCGGGGGAGG GGGCATTGAT CTTCGATCGC GAAG             34

( 2 ) INFORMATION FOR SEQ ID NO:27:

( i ) SEQUENCE CHARACTERISTICS:
        ( A ) LENGTH: 156 base pairs
        ( B ) TYPE: nucleic acid
        ( C ) STRANDEDNESS: unknown
        ( D ) TOPOLOGY: unknown ( i i ) MOLECULE TYPE: DNA (genomic)

( i x ) FEATURE:
        ( A ) NAME/KEY: CDS
        ( B ) LOCATION: 1..156

( x i ) SEQUENCE DESCRIPTION: SEQ ID NO:27:

GGT AAT GAA ATG ACT AAC TTA GCC TTT GAA CTA GAC CCC CTA GAG TTA        48
Gly Asn Glu Met Thr Asn Leu Ala Phe Glu Leu Asp Pro Leu Glu Leu

```
            1                   5                                  10                                 15
GAG  GAG  GAA  GAG  GCT  GAG  CTT  GGT  GAG  CAG  AGT  GGC  TCT  GCC  AAG  ACT          96
Glu  Glu  Glu  Glu  Ala  Glu  Leu  Gly  Glu  Gln  Ser  Gly  Ser  Ala  Lys  Thr
                    20                             25                        30

AGT  GTT  AGC  AGT  GTC  ACC  ACC  CCG  CCA  CCC  CAT  GGC  AAA  CGC  ATC  CCC          144
Ser  Val  Ser  Ser  Val  Thr  Thr  Pro  Pro  Pro  His  Gly  Lys  Arg  Ile  Pro
               35                             40                        45

TTC  TTT  AAG  AAG                                                                       156
Phe  Phe  Lys  Lys
          50
```

( 2 ) INFORMATION FOR SEQ ID NO:28:

( i ) SEQUENCE CHARACTERISTICS:
        ( A ) LENGTH: 52 amino acids
        ( B ) TYPE: amino acid
        ( D ) TOPOLOGY: linear ( i i ) MOLECULE TYPE: protein ( x i ) SEQUENCE DESCRIPTION: SEQ ID NO:28:

```
Gly  Asn  Glu  Met  Thr  Asn  Leu  Ala  Phe  Glu  Leu  Asp  Pro  Leu  Glu  Leu
 1                   5                             10                        15

Glu  Glu  Glu  Glu  Ala  Glu  Leu  Gly  Glu  Gln  Ser  Gly  Ser  Ala  Lys  Thr
                    20                             25                        30

Ser  Val  Ser  Ser  Val  Thr  Thr  Pro  Pro  Pro  His  Gly  Lys  Arg  Ile  Pro
               35                             40                        45

Phe  Phe  Lys  Lys
          50
```

( 2 ) INFORMATION FOR SEQ ID NO:29:

( i ) SEQUENCE CHARACTERISTICS:
        ( A ) LENGTH: 180 base pairs
        ( B ) TYPE: nucleic acid
        ( C ) STRANDEDNESS: unknown
        ( D ) TOPOLOGY: unknown ( i i ) MOLECULE TYPE: DNA (genomic)

( i x ) FEATURE:
        ( A ) NAME/KEY: CDS
        ( B ) LOCATION: 1..129

( x i ) SEQUENCE DESCRIPTION: SEQ ID NO:29:

```
TGG  TCC  TTT  GCC  TGC  GCC  TGT  GCC  GCC  TTC  ATC  CTC  CTC  TTT  CTC  GGC          48
Trp  Ser  Phe  Ala  Cys  Ala  Cys  Ala  Ala  Phe  Ile  Leu  Leu  Phe  Leu  Gly
 1                   5                             10                        15

GGT  CTC  GCC  CTC  CTG  CTG  TTC  TCC  CTG  CCT  CGA  ATG  CCC  CGG  AAC  CCA          96
Gly  Leu  Ala  Leu  Leu  Leu  Phe  Ser  Leu  Pro  Arg  Met  Pro  Arg  Asn  Pro
                    20                             25                        30

TGG  GAG  TCC  TGC  ATG  GAT  GCT  GAG  CCC  GAG  CAC  TAACCCTCCT  GCGGCCCTAG            149
Trp  Glu  Ser  Cys  Met  Asp  Ala  Glu  Pro  Glu  His
               35                             40

CGACCCTCAG GCTTCTTCCC AGGAAGCGGG G                                                        180
```

( 2 ) INFORMATION FOR SEQ ID NO:30:

( i ) SEQUENCE CHARACTERISTICS:
        ( A ) LENGTH: 43 amino acids
        ( B ) TYPE: amino acid
        ( D ) TOPOLOGY: linear ( i i ) MOLECULE TYPE: protein ( x i ) SEQUENCE DESCRIPTION: SEQ ID NO:30:

```
Trp  Ser  Phe  Ala  Cys  Ala  Cys  Ala  Ala  Phe  Ile  Leu  Leu  Phe  Leu  Gly
```

(2) INFORMATION FOR SEQ ID NO:31:

(i) SEQUENCE CHARACTERISTICS:
(A) LENGTH: 411 base pairs
(B) TYPE: nucleic acid
(C) STRANDEDNESS: unknown
(D) TOPOLOGY: unknown (ii) MOLECULE TYPE: DNA (genomic)

(ix) FEATURE:
(A) NAME/KEY: CDS
(B) LOCATION: 1..411

(xi) SEQUENCE DESCRIPTION: SEQ ID NO:31:

| CTC | GGC | TCC | AGC | AAA | TCA | GGC | GAT | AAC | TCC | AGT | TCC | AGT | CTG | GGA | GAT | 48 |
| Leu | Gly | Ser | Ser | Lys | Ser | Gly | Asp | Asn | Ser | Ser | Ser | Ser | Leu | Gly | Asp | |
| 1 | | | | 5 | | | | | 10 | | | | | 15 | | |

| GTG | GTG | ACT | GGC | ACC | CGC | CGC | CCC | ACA | CCC | CCT | GCC | AGT | ACA | GAG | CAT | 96 |
| Val | Val | Thr | Gly | Thr | Arg | Arg | Pro | Thr | Pro | Pro | Ala | Ser | Thr | Glu | His | |
| | | | 20 | | | | | 25 | | | | | 30 | | | |

| GTG | CCC | CCC | TAT | GAC | GTG | GTG | CCT | TCC | ATG | AGG | CCC | ATC | ATC | CTG | GTG | 144 |
| Val | Pro | Pro | Tyr | Asp | Val | Val | Pro | Ser | Met | Arg | Pro | Ile | Ile | Leu | Val | |
| | | 35 | | | | | 40 | | | | | 45 | | | | |

| GGA | CCG | TCG | CTC | AAG | GGC | TAC | GAG | GTT | ACA | GAC | ATG | ATG | CAG | AAA | GCT | 192 |
| Gly | Pro | Ser | Leu | Lys | Gly | Tyr | Glu | Val | Thr | Asp | Met | Met | Gln | Lys | Ala | |
| | 50 | | | | | 55 | | | | | 60 | | | | | |

| TTA | TTT | GAC | TTC | TTG | AAG | CAT | CGG | TTT | GAT | GGC | AGG | ATC | TCC | ATC | ACT | 240 |
| Leu | Phe | Asp | Phe | Leu | Lys | His | Arg | Phe | Asp | Gly | Arg | Ile | Ser | Ile | Thr | |
| 65 | | | | | 70 | | | | | 75 | | | | | 80 | |

| CGT | GTG | ACG | GCA | GAT | ATT | TCC | CTG | GCT | AAG | CGC | TCA | GTT | CTC | AAC | AAC | 288 |
| Arg | Val | Thr | Ala | Asp | Ile | Ser | Leu | Ala | Lys | Arg | Ser | Val | Leu | Asn | Asn | |
| | | | | 85 | | | | | 90 | | | | | 95 | | |

| CCC | AGC | AAA | CAC | ATC | ATC | ATT | GAG | CGC | TCC | AAC | ACA | CGC | TCC | AGC | CTG | 336 |
| Pro | Ser | Lys | His | Ile | Ile | Ile | Glu | Arg | Ser | Asn | Thr | Arg | Ser | Ser | Leu | |
| | | | 100 | | | | | 105 | | | | | 110 | | | |

| GCT | GAG | GTG | CAG | AGT | GAA | ATC | GAG | CGA | ATC | TTC | GAG | CTG | GCC | CGG | ACC | 384 |
| Ala | Glu | Val | Gln | Ser | Glu | Ile | Glu | Arg | Ile | Phe | Glu | Leu | Ala | Arg | Thr | |
| | | 115 | | | | | 120 | | | | | 125 | | | | |

| CTT | CAG | TTG | GTC | GCT | CTG | GAT | GCT | GAC | | | | | | | | 411 |
| Leu | Gln | Leu | Val | Ala | Leu | Asp | Ala | Asp | | | | | | | | |
| | 130 | | | | | 135 | | | | | | | | | | |

(2) INFORMATION FOR SEQ ID NO:32:

(i) SEQUENCE CHARACTERISTICS:
(A) LENGTH: 137 amino acids
(B) TYPE: amino acid
(D) TOPOLOGY: linear (ii) MOLECULE TYPE: protein (xi) SEQUENCE DESCRIPTION: SEQ ID NO:32:

| Leu | Gly | Ser | Ser | Lys | Ser | Gly | Asp | Asn | Ser | Ser | Ser | Ser | Leu | Gly | Asp |
| 1 | | | | 5 | | | | | 10 | | | | | 15 | |

| Val | Val | Thr | Gly | Thr | Arg | Arg | Pro | Thr | Pro | Pro | Ala | Ser | Thr | Glu | His |
| | | | 20 | | | | | 25 | | | | | 30 | | |

| Val | Pro | Pro | Tyr | Asp | Val | Val | Pro | Ser | Met | Arg | Pro | Ile | Ile | Leu | Val |
| | | 35 | | | | | 40 | | | | | 45 | | | |

| Gly | Pro | Ser | Leu | Lys | Gly | Tyr | Glu | Val | Thr | Asp | Met | Met | Gln | Lys | Ala |
|---|---|---|---|---|---|---|---|---|---|---|---|---|---|---|---|
| | 50 | | | | | 55 | | | | | 60 | | | | |
| Leu | Phe | Asp | Phe | Leu | Lys | His | Arg | Phe | Asp | Gly | Arg | Ile | Ser | Ile | Thr |
| 65 | | | | | 70 | | | | | 75 | | | | | 80 |
| Arg | Val | Thr | Ala | Asp | Ile | Ser | Leu | Ala | Lys | Arg | Ser | Val | Leu | Asn | Asn |
| | | | | 85 | | | | | 90 | | | | | 95 | |
| Pro | Ser | Lys | His | Ile | Ile | Ile | Glu | Arg | Ser | Asn | Thr | Arg | Ser | Ser | Leu |
| | | | 100 | | | | | 105 | | | | | 110 | | |
| Ala | Glu | Val | Gln | Ser | Glu | Ile | Glu | Arg | Ile | Phe | Glu | Leu | Ala | Arg | Thr |
| | | 115 | | | | | 120 | | | | | 125 | | | |
| Leu | Gln | Leu | Val | Ala | Leu | Asp | Ala | Asp | | | | | | | |
| | 130 | | | | | 135 | | | | | | | | | |